US008088794B2

(12) United States Patent
Kim et al.

(10) Patent No.: US 8,088,794 B2
(45) Date of Patent: Jan. 3, 2012

(54) SUBSTITUTED AMIDE DERIVATIVES AND METHODS OF USE

(75) Inventors: Tae-Seong Kim, Thousand Oaks, CA (US); David Bauer, Sudbury, MA (US); Steven Bellon, Wellesley, MA (US); Alessandro Boezio, Somerville, MA (US); Shon Booker, Thousand Oaks, CA (US); Deborah Choquette, Medford, MA (US); Derin C. D'Amico, Newbury Park, CA (US); Noel D'Angelo, Thousand Oaks, CA (US); Celia Dominguez, Los Angeles, CA (US); Ingrid M. Fellows, Fresno, CA (US); Julie Germain, Medford (CA); Russell Graceffa, Hampton, NH (US); Jean-Christophe Harmange, Andover, MA (US); Satoko Hirai, Cambridge, MA (US); Daniel La, Brookline, MA (US); Matthew Lee, Calabasas, CA (US); Longbin Liu, Thousand Oaks, CA (US); Mark H. Norman, Thousand Oaks, CA (US); Michele Potashman, Cambridge, MA (US); Philip Roveto, San Francisco, CA (US); Aaron C. Siegmund, Ventura, CA (US); Ning Xi, Thousand Oaks, CA (US); Kevin Yang, San Gabriel, CA (US)

(73) Assignee: Amgen Inc., Thousands Oaks, CA (US)

( * ) Notice: Subject to any disclaimer, the term of this patent is extended or adjusted under 35 U.S.C. 154(b) by 0 days.

(21) Appl. No.: 12/945,575

(22) Filed: Nov. 12, 2010

(65) Prior Publication Data
US 2011/0118252 A1 May 19, 2011

Related U.S. Application Data

(62) Division of application No. 11/412,302, filed on Apr. 26, 2006, now Pat. No. 7,858,623.

(60) Provisional application No. 60/675,805, filed on Apr. 27, 2005.

(51) Int. Cl.
*A61K 31/47* (2006.01)
*C07D 453/02* (2006.01)
(52) U.S. Cl. .................................. 514/312; 546/135
(58) Field of Classification Search .................. 546/135; 514/312
See application file for complete search history.

(56) References Cited

U.S. PATENT DOCUMENTS

| 3,755,332 | A | 8/1973 | Wasley et al. |
| 4,916,135 | A | 4/1990 | Effland et al. |
| 5,580,870 | A | 12/1996 | Barker et al. |
| 5,866,572 | A | 2/1999 | Barker et al. |
| 5,965,563 | A | 10/1999 | Buzzetti et al. |
| 6,143,764 | A | 11/2000 | Kubo et al. |
| 6,265,398 | B1 | 7/2001 | Braun et al. |
| 6,313,129 | B1 | 11/2001 | Uckun et al. |
| 6,358,962 | B2 | 3/2002 | Uckun et al. |
| 6,399,602 | B1 | 6/2002 | Barker et al. |
| 6,469,013 | B2 | 10/2002 | Uckun et al. |
| 6,495,556 | B2 | 12/2002 | Uckun et al. |
| 6,573,289 | B1 | 6/2003 | Tasaka et al. |
| 6,897,214 | B2 | 5/2005 | Barker et al. |
| 2003/0165873 | A1 | 9/2003 | Come et al. |
| 2004/0053908 | A1 | 3/2004 | Funahashi et al. |
| 2004/0209905 | A1 | 10/2004 | Kubo et al. |
| 2004/0242603 | A1 | 12/2004 | Fujiwara et al. |
| 2005/0245547 | A1 | 11/2005 | Kim et al. |

FOREIGN PATENT DOCUMENTS

| EP | 860433 A1 | 8/1998 |
| EP | 1411046 A | 4/2004 |
| EP | 1415987 A1 | 5/2004 |
| EP | 1 548 008 A1 | 6/2005 |
| EP | 1548 008 A1 | 6/2005 |
| JP | 63-145272 | 6/1988 |
| JP | 8-193070 | 7/1996 |
| JP | 11-158149 | 6/1999 |
| WO | WO 96/23774 | 8/1996 |
| WO | WO 96/29301 | 9/1996 |
| WO | WO 96/29305 | 9/1996 |
| WO | WO 97/03069 | 1/1997 |
| WO | WO97/22596 | 6/1997 |
| WO | WO98/37079 | 8/1998 |
| WO | WO 99/35132 | 7/1999 |
| WO | WO 99/54309 | 10/1999 |
| WO | WO 99/61428 | 12/1999 |
| WO | WO 00/10981 | 3/2000 |
| WO | WO 00/47212 | 8/2000 |
| WO | WO00/50405 | 8/2000 |

(Continued)

OTHER PUBLICATIONS

Anderson et al., "Involvement of the protein tyrosine kinase p56$^{lck}$ in T cell signaling and thymocyte development," Advances in Immunology, 56:151-178 (1994).
Appleby et al., Defective T cell receptor signaling in mice lacking the thymic isoform of p59$^{fyn}$, Cell, 70:751-763 (1992).
Asami et al., "Purification and characterization of hepatocyte growth factor from injured liver of carbon tetrachloride-treated rats," Journal of Biochemistry, 109:8-13 (1991).
Asano et al., "Silver halide color photographic materials," Abstract 113:181318 (1990).

(Continued)

*Primary Examiner* — Rebecca Anderson
(74) *Attorney, Agent, or Firm* — Olga Mekhovich; Joseph W. Bulock

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

14 Claims, No Drawings

FOREIGN PATENT DOCUMENTS

| WO | WO 00/56720 | 9/2000 |
|---|---|---|
| WO | WO 00/61580 | 10/2000 |
| WO | WO 01/21594 | 3/2001 |
| WO | WO 01/70673 | 9/2001 |
| WO | WO 01/70734 | 9/2001 |
| WO | WO 02/22607 | 3/2002 |
| WO | WO 02/22608 | 3/2002 |
| WO | WO 02/30924 | 4/2002 |
| WO | WO 02/076976 | 10/2002 |
| WO | WO02/098426 | 12/2002 |
| WO | WO03/004472 | 1/2003 |
| WO | WO 03/040108 | 5/2003 |
| WO | WO 03/040109 | 5/2003 |
| WO | WO 03/064413 | 8/2003 |
| WO | WO 03/082272 | 10/2003 |
| WO | WO2004/018430 | 3/2004 |
| WO | WO 2004/029045 | 4/2004 |
| WO | WO2004/030672 | 4/2004 |
| WO | WO2004/037784 | 5/2004 |
| WO | WO2004/043379 | 5/2004 |
| WO | WO2004/046133 | 6/2004 |
| WO | WO 2004/078114 | 9/2004 |
| WO | WO2004/083235 | 9/2004 |
| WO | WO 2004/085425 | 10/2004 |
| WO | WO 2004/098604 | 11/2004 |
| WO | WO2005/005389 | 1/2005 |
| WO | WO2005/021553 | 3/2005 |
| WO | WO2005/030140 | 4/2005 |
| WO | WO2005/037285 | 4/2005 |
| WO | WO2005/070891 | 8/2005 |
| WO | WO2005/080377 | 9/2005 |
| WO | WO2005/117867 | 12/2005 |
| WO | WO2006/004636 | 1/2006 |

OTHER PUBLICATIONS

Boehm et al., "Antiangiogenic therapy of experimental cancer does not induce acquired drug resistance," Nature, 390:404-407 (1997).

Bolen et al., "Leukocyte protein tyrosine kinases: Potential targets for drug discovery," Annu. Rev. Immunology, 15:371-404 (1997).

Bussolino et al., "Hepatocyte growth factor is a potent angiogenic factor which stimulates endothelial cell motility and growth," The Journal of Cell Biology, 119(3):629-641 (1992).

Chan et al., "Isoforms of human HGF and their biological activities," Hepatocyte Growth Factor~Scatter Factor (HGF-SF) and the C-Met Receptor, pp. 67-79, Goldberg and Rosen (Eds.), Birkhauser Verlag Basel, Switzerland (1993).

Chatterjee, A.K., "A note on 4-Aminoquinolines. III. Some 4-(quinolylamino)quinolines," Science and Culture 23:195 (1957).

Cockerill et al., "Indazolylamino quinazolines and pyridopyrimidines as inhibitors of the EGFr and C-erbB-2," Bioorganic & Medicinal Chemistry Letters, 11:1401-1405 (2001).

Di Renzo et al., "Selective expression of the Met/HGF receptor in human central nervous system microglia, Oncogene," 8:219-222 (1992).

Gibson et al., "Epidermal growth factor receptor tyrosine kinase: Structure-activity relationships and antitumor activity of novel quinazolines," Bioorganic & Medicinal Chemistry Letters, 7(21):2723-2728 (1997).

Giordano et al., "Transfer of motogenic and invasive response to scatter factor/hepatocyte growth factor by transfection of human MET protooncogene," Proceedings of the National Academy of Sciences, USA, 90:649-653 (1993).

Goldman et al, "Defective expression of p56lck in an infant with severe combined immunodeficiency," Journal of Clinical Investigations, 102(2):421-429 (1998).

Han et al., "Characterization of the DNF15S2 locus on human chromosome 3: Identification of a gene coding for four kringle domains with homology to hepatocyte growth factor," Biochemistry, 30:9768-9780 (1991).

Igawa et al., "Hepatocyte growth factor is a potent mitogen for cultured rabbit renal tubular epithelial cells," Biochemical and Biophysical Research Communications, 174(2):831-838 (1991).

Jeffers et al., "Hepatocyte growth factor/scatter factor—Met signaling in tumorigenicity and invasion/metastasis," J. Mol. Med., 74:505-513 (1996).

Kane et al., "Signal transduction by the TCR for antigen," Current Opinion in Immunology, 12:242-249 (2000).

Kasai et al., "Flexible coordination networks with fluorinated backbones, remarkable ability for induced-fit enclathration of organic molecules," Journal of American Chemical Society, 122:2140-2141 (2000).

Lempert-Sreter et al., "The synthesis of di(1-isoquinolinyl) and di(4-quinazolinyl) disulfides form 1(2H)-isoquinolinethiones and 4(3H)-quinazolinethiones, respectively, with tosyl chloride and sodium ethoxide," Acta Chemica Hungarica, 112(1):83-87 (1983).

Makisumi, Yasuo, "The Thio-claisen rearrangement of allyl 4-quinolyl sulfides," Tetrahedron Letters, 51:6399-6403 (1966).

Maslankiewicz, M.J., "Reactions of β- and γ-quinolinyl sulfides with a nitrating mixture," Polish Journal of Chemistry, 68(12):2545-2552 (1994).

Matsumoto et al., "Hepatocyte growth factor is a potent stimulator of human melanocyte DNA synthesis and growth," Biochemical and Biophysical Research Communications, 176(1):45-51 (1991).

Matsunaga et al., "$C_{17,20}$-lyase inhibitors, Part 2:Design, synthesis and structure-activity relationships of (2-naphthylmethyl)-1H-imidazoles as novel $C_{17,20}$-lyase inhibitors," Bioorganic & Medicinal Chemistry, 12:4313-4336 (2004).

Maulik et al., "Role of the hepatocyte growth factor receptor, c-Met, in oncogenesis and potential for therapeutic inhibition," Cytokine & Growth Factor Reviews, 13:41-59 (2002).

Montesano et al., "Induction of epithelial tubular morphogenesis in vitro by fibroblast-derived soluble factors," Cell, 66:697-711 (1991).

Nakamura et al., "Partial purification and characterization of hepatocyte growth factor from serum of hepatectomized rats," Biochemical and Biophysical Research Communications, 122(3):1450-1459 (1984).

Naldini et al., "Scatter factor and hepatocyte growth factor are indistinguishable ligands for the MET receptor," EMBO Journal, 10:2867-2878 (1991).

Park et al., "Sequence of MET protooncogene cDNA has features characteristic of the tyrosine kinase family of growth-factor receptors," Proceedings of the National Academy of Sciences, USA, 84:6379-6383 (1987).

Renfrew, Alice G., "Studies in the Quinoline Series. IV. Quinolyl Mercaptans and Sulfides," J. American Chemical Society, 1433-1436 (1946).

Di Renzo et al., "Overexpression of the c-MET/HGF receptor gene in human thyroid carcinomas," Oncogene, 7:2549-2553 (1992).

Rubin et al., "A broad-spectrum human lung fibroblast-derived mitogen is a variant of hepatocyte growth factor," Proceedings of the National Academy of Sciences, USA, 88:415-419 (1991).

Sinyak et al., "The synthesis and biological properties of the derivatives of 4-heterylmercaptoquinazoline," Khimiko-Farmatsevticheskii Zhurnal, 20(2), 168-171 (1986). Abstract 104:199594.

Solbreux et al., "Extrahepatic bile duct growth in mice repeatedly injected with human normal serum, IgA-deficient serum or purified secretory IgA", Hepatology, 13:735-742 (1991).

Soriano et al., "Targeted disruption of the c-src proto-oncogene leads to osteopetrosis in mice," Cell, 64:693-702 (1991).

Stern et al., "Epithelial scatter factor and development of the chick embryonic axis," Development 110:1271-1284 (1990).

Stoker et al., "Scatter factor is a fibroblast-derived modulator of epithelial cell mobility," Nature, 327:239-242 (1987).

Thakore, P.V. et al., "Studies in the synthesis of quinoline derivatives. Part VIII. Synthesis of 4:3'-methylenebis(2,2'-dichloro-4'-methylquinoline) derivatives," Journal of the Indian Chemical Society, 54(12):1204-1206 (1977).

Turner et al., "Signalling through the high-affinity IgE receptor FcεRI," Nature, 402:B24-B30 (1999).

Vicentini et al., "Fgr deficiency results in defective eosinophil recruitment to the lung during allergic airway inflammation," The Journal of Immunology, 168:6446-6454 (2002).

Weidner et al., "Scatter Factor: Molecular characteristics and effect on the invasiveness of epithelial cells," The Journal of Cell Biology, 111:2097-2108 (1990).

Wyszomirski et al., "Conformations of monosubstituted and disubstituted 3,4'-, 3,3'- and 4,4'-diquinolinyl sulfides studied by NMR spectroscopy," Phosphorus, Sulfur, and Silicon, 95-96:415-416 (1994).

Zhang et al., "Synthesis and SAR of potent EGFR/erbB2 dual inhibitors," Bioorganic & Medicinal Chemistry Letters, 14:111-114 (2004).

Breier et al., "The role of vascular endothelial growth factor in blood vessel formation," Trends in Cell Biology, 6:454-456 (1996).

Paolo M. Comoglio, "Structure, biosynthesis and biochemical properties of the HGF receptor in normal and malignant cells," Hepatocyte Growth Factor-Scatter Factor (HGF-SF) and the C-*Met* Receptor, eds. Goldberg and Rosen, Birkhauser Verlag Basel, Switzerland, 131-165 (1993).

Connell et al., "Patent focus on cancer chemotherapeutics. II Angiogenesis agents: Apr. 2000-Sep. 2000" Expert Opinion on Therapeutic Patents, 11(1):77-114 (2001).

Kubo et al., "Synthesis and Structure-Activity Relationship for New Series of 4-Phenoxyquinoline Derivatives as Specific Inhibitors of Platelet-Derived Growth Factor Receptor Tyrosine Kinase," Bioorganic & Medicinal Chemistry 11, 5117-5133 (2003).

Kamel et al., "New 4-substituted phenoxyquinolines of possible antimicrobial activity", Egyptian Journal of Pharmaceutical Sciences, 38(1-3), 61-69 (1997).

Wright et al., "Anilinoquinazoline Inhibitors of Fructose 1,6-Bisphosphatase Bind at a Novel Allosteric Site: Synthesis, In Vitro Characterization, and X-ray Crystallography," Journal of Medicinal Chemistry, (45), 3865-3877 (2002).

Steck et al., "Pyridazines. VI. Some 6-Substituted 3(2H)pyridazinones (1)" Journal of Heterocyclic Chemistry, 11 (5), 755-761, (1974).

Okushima et al., "A Novel Class of Cardiotonics. Synthesis and Pharmacological Properties of [4-(Substituted-amino)phenyl] pyridazinones and Related Derivatives," Journal of Medicinal Chemistry 30(7) 1157-1161 (1987).

Okushima et al., "A new class of cardiotonics. Structure-activity relationships of pyridazinones and pharmacological properties of MCI-154," database accession No. 1993:93799 compounds with RN 145917-30-2 Chemical Abstracts Service; Research and Development Review—Mitsubishi Kasei Corporation 1992, 6(2) 1 page.

A.H. Abadi and H.A. Al-Khamees, "3-Cyano-4,6 disubstituted-2(1H)-imino or oxopyridines: New Antineoplastic Agents with High Selectivity Towards Leukemia Cell Lines," Arch. Pharm. Pharm. Med. Chem 331 (10), 319-324, (1998).

Omar et al., "Synthesis of some new 4-substituted anilinoquinolines of expected biological activity" Chemical Abstracts Service, Database accession No. 1999-458494 Egyptian Journal of Pharmaceutical Sciences , Volume Date 1997, 38(4-6), (1998) 1 page.

SEQUENCE LISTING

<160> NUMBER OF SEQ ID NOS: 2

<210> SEQ ID NO 1
<211> LENGTH: 39
<212> TYPE: DNA
<213> ORGANISM: Homo sapiens

<400> SEQUENCE: 1
attgacggat ccatgctaaa tccagagctg gtccaggca                39

<210> SEQ ID NO 2
<211> LENGTH: 37
<212> TYPE: DNA
<213> ORGANISM: Homo sapiens

<400> SEQUENCE: 2
acaacagaat tcaatacgga gcgacacatt ttacgtt                 37

US 8,088,794 B2

SUBSTITUTED AMIDE DERIVATIVES AND METHODS OF USE

RELATED APPLICATION

This application is a divisional patent application of, and claims the benefit of, U.S. patent application Ser. No. 11/412,302, filed 26 Apr. 2006, now U.S. Pat. No. 7,858,623, which in turn claims the benefit of U.S. Provisional Application Ser. No. 60/675,805, filed 27 Apr. 2005, both specifications of which are hereby incorporated herein by reference in their entireties.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins, which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerates tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants, which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors, which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Base1, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Base1, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met proto-oncogene have been postulated to play a role in microglial reactions to CNS injuries (Oncogene, 8:219-222 (1993)).

Metastatic SCC cells overexpress c-Met and have enhanced tumoregenesis and metastasis in vivo [G. Gong et al., Oncogene, 23:6199-6208 (2004)]. C-Met is required for tumor cell survival [N. Shinomiya et al., Cancer Research, 64:7962-7970 (2004)]. For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Kirin Japanese patent application JP11158149, published 28 Nov. 1997, describes substituted phenyl compounds. Kirin publication WO 00/43366 describes substituted phenyl compounds. Kirin publication WO 03/000660 describes substituted phenyl compounds. Substituted quinolines are described in U.S. Pat. No. 6,143,764. WO 02/32872 describes substituted quinolines. Patent Application WO 00/47212 describes substituted quinazoline derivatives. Patent Application WO 98/37079 describes substituted N-heterocyclic compounds. Kubo et al, Biorg. Med. Chem., 11:5117-33 (2003) describes phenoxyquinoline derivatives. Patent Application WO 04/46133, published 3 Jun. 2004, describes amino-heterocycles for treating pain. Patent Application WO 03/004472, published 16 Jan. 2003, describes pyrazine-2- carboxamides. JP63145272, published 17 Jun. 1988, describes 4,5-dihydro-6-(4-substituted phenyl)-3(2H)-pyridazinones. Kamel, et al., Egyptian J. of Pharm. Sci., 38:61-69 (1997) describes 4-substituted phenoxyquinolines. Patent Application WO 04/18430, published 4 Mar. 2004, describes quinoline derivatives. Patent Application WO 02/32872, published 25 Apr. 2002, describes urea derivatives. Patent Application WO 04/37784, published 6 May 2004, describes substituted pyrrolidones. Patent Application WO 00/50405 published 31 Aug. 2000, describes quinoline-6-carboxamides. Patent Application WO 04/083235, published 30 Sep. 2004, describes azaheterocyclyl aromatic compounds.

Compounds of the current invention have not been described as inhibitors of c-Met such as for the treatment of cancer.

DESCRIPTION OF THE INVENTION

A class of compounds useful in treating cancer and angiogenesis is defined by Formula I

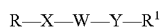

enantiomers, diastereomers, salts solvates, and N-oxides thereof wherein
R is

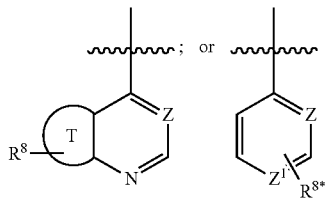

T is selected from phenyl, 5-6-membered heteroaryl, or 5-6 membered heterocyclyl;
Z is selected from N or $CR^7$;
$Z^1$ is selected from N or $CR^7$;
W is a substituted or unsubstituted phenyl, a substituted or unsubstituted benzomorpholinyl, a substituted or unsubstituted 6-membered nitrogen containing heteroaryl; a substituted or unsubstituted $c_{3-7}$cycloalkyl, $c_{1-6}$alky and $c_{1-6}$alkynyl;
X is selected from O, S, S(=O), $SO_2$, $NR^2$ and $CR^3R^4$;
Y is selected from $-NR^aC(=O)-(CR^3R^4)_p-$, $-NR^aC(=S)-(CR^3R^4)_p-$, $-NR^a-(CR^3R^4)_p-$, $-NR^a-(CR^3R^4)_pC(=O)-$, $-NR^a-(CR^3R^4)_pC(=S)-$, $-NR^aS(=O)_t-$, $-NR^aS(=O)_t-(CR^3R^4)_p-$, $-C(=O)NR^a-(CR^3R^4)_p-$, and $-NR^a-(CR^1R^4)_p-S(=O)_t-$, and where W is benzomorpholinyl Y may further include $-C(=O)$;
$R^a$ is selected from H, alkyl, heterocyclyl, aryl, arylalkyl, heterocyclylalkyl, cycloalkyl, cycloalkylalkyl, alkenyl and alkynyl; wherein $R^a$ is optionally substituted;
$R^1$ is a partially unsaturated or saturated ring selected from

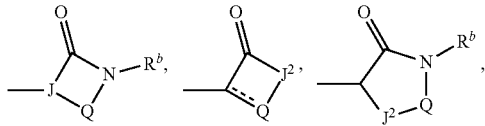

-continued

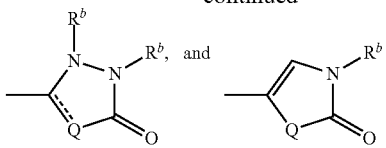

wherein J is N or $CR^{4a}$;
$J^2$ is O or $CR^{4a}R^{4a}$;
Q is a 1-5 membered saturated or partially unsaturated alkly chain, or a 2-5 membered saturated or partially unsaturated heteroalkyl chain;
$R^1$ is optionally fused with an optionally substituted phenyl or an optionally substituted 5-6 membered heterocyclyl ring;
wherein $R^1$ is optionally substituted with one or more substituents independently selected from H, halo, hydroxyl, $R^{5a}R^aN-$, $R^{5a}R^aN-C_{1-6}$ alkyl, $R^5(S=O)-C_{1-6}$ alky, $NR^5R^{5a}-(C=O)-C_{1-6}$ alky, optionally substituted alkyl, alkenyl hydroxyalkyl, $C_{1-6}$ alkoxy-$C_{1-6}$ alkyl, alkenylalkyl, $C_{1-6}$ alkylthio-$C_{1-3}$ alkyl, $-C_{1-6}$ alkyl-$NR^a-C(=O)-OR^5$, $-C_{1-3}$ alkyl-$NR^a-(C=O)-R^5$, $-C_{1-3}$ alkyl-$C(=O)-C_{1-3}$ alkyl, aminoalkyl, hydroxy-substituted aminoalkyl, hydroxy-substituted haloalkyl, (heterocyclo)hydroxyalkyl, halo$C_{1-6}$-alkyl, azidoalkyl, optionally substituted aryl-$C_{1-6}$ alkyl, optionally substituted 5-6-membered heterocyclyl-$C_{1-6}$ alkyl, optionally substituted $C_{1-6}$-alkyl, optionally substituted $C_{3-7}$ cycloalkyl, optionally substituted 5-6 membered heterocyclyl, optionally substituted 5-10 membered heteroaryl, optionally, optionally substituted $C_{3-6}$ cycloalkyl, substituted heteroarylalkyl, optionally substituted arylalkyl, and optionally substituted $C_{6-10}$ aryl;
$R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;
$R^3$ and $R^4$ are each independently selected from H, alkyl, aryl, heterocyclyl, arylalkyl, heterocyclylalkyl, haloalkyl, cycloalkyl, cycloalkylalkyl, $R^6$ and alkyl substituted with $R^6$; alternatively $R^3$ and $R^4$, together with the carbon atom they are attached to, form an optionally substituted 3-6 membered ring;
$R^{3a}$ is absent or is selected from H, alkyl, aryl, heterocyclyl, arylalkyl, heterocyclylalkyl, cycloalkyl, cycloalkylalkyl, $R^6$ and alkyl substituted with $R^6$;
$R^{4a}$ is absent or is selected from H, halo, $-OR^5-NR^aR^5$, alkyl, aryl, heterocyclyl, arylalkyl, heterocyclylalkyl, cycloalkyl, cycloalkylalkyl, $R^6$ and alkyl substituted with $R^6$;
$R^5$ is independently selected at each occurrence from H, alkyl, haloalkyl, hydroxyalkyl, alkoxyalkyl, alkylaminoalkyl, alkylthioalkyl, arylalkyl, heterocyclylalkyl, cycloalkylalkyl, aryl, heterocyclyl, alkenyl, alkynyl and cycloalkyl;
$R^{5a}$ is independently selected at each occurrence from H, alkyl, haloalkyl, arylalkyl aminoalkyl, heterocyclylalkyl, cycloalkylalkyl, aryl, heterocyclyl, alkenyl, alkynyl and cycloalkyl;
or when $R^5$ and $R^a$, or $R^{5a}$ and $R^a$ is bonded to the same nitrogen atom, $R^a$ and $R^5$, or $R^a$ and $R^{5a}$ may independently optionally combine to form a heterocyclo ring.
$R^6$ is selected from cyano, $-OR^2$, $-SR^2$, halo, $-SO_2R^2$, $-C(=O)R^2$, $-SO_2NR^2R^5$, $-NR^5C(=O)OR^2$, $-NR^5C(=O)NR^5R^2$, $-NR^5C(=O)R^2$, $-CO_2R^2$, $-C(=O)NR^2R^5$ and $-NR^2R^5$;
$R^7$ is selected from H, halo, cyano, $-C(=O)NR^aR^5$ and alkyl;

R[8] is one or more substituents independently selected at each occurrence from H, cyano, hydroxyl, halo, optionally substituted heterocyclyl, —C(=O)NR[a]R[5], —OC(=O)NR[a]R[5], —NR[a]C(=O)OR[5], —NR[a]C(=O)—R[5], R[5]R[a]N—O$_2$S—, R[5]O$_2$S—, R[5]O$_2$SR[a]N—, R[5]R[a]N—, alkyl, aminoalkyl, alkylaminoalkyl, alkoxyalkyl, phenylalkyl, heterocyclylalkyl, alkoxy, haloalkoxy, alkylaminoalkoxy, arylalkoxy, heterocyclylalkoxy, cycloalkylalkoxy, heterocyclyl(hydroxyalkoxy), cycloalkyl(hydroxyalkoxy), aryl(hydroxyalkoxy), alkoxyalkoxy, aryloxyalkoxy, heterocyclyloxyalkoxy, cycloalkyloxyalkoxy, aryloxy, heterocyclyloxy, cycloalkyloxy; aryl and heteroaryl, alternatively where R[8] comprises an NR[a]R[5] moiety R[a] and R[5], together with the nitrogen atom they are attached to, may optionally form a substituted or unsubstituted 4-6 membered ring;

R[8]* is one or more substituents independently selected at each occurrence from H, cyano, hydroxyl, halo, optionally substituted heterocyclyl, —NR[a]C(=O)NR[a]R[5], NR[a]C(=NR[b])—NR[5], NR[a]C(=S)NR[a]R[5], —OC(=O)NR[a]R[5], —NR[a]C(=O)OR[5], NR[a]C(=O)—R[5], R[5]R[a]N—O$_2$S—, R[5]O$_2$S—, R[5]O$_2$SR[a]N—, R[5]R[a]N—, alkyl, aminoalkyl, alkylaminoalkyl, alkoxyalkyl, phenylalkyl, heterocyclylalkyl, alkoxy, haloalkoxy, alkylaminoalkoxy, arylalkoxy, heterocyclylalkoxy, cycloalkylalkoxy, heterocyclyl(hydroxyalkoxy), cycloalkyl(hydroxyalkoxy), aryl(hydroxyalkoxy), alkoxyalkoxy, aryloxyalkoxy, heterocyclyloxyalkoxy, cycloalkyloxyalkoxy, aryloxy, heterocyclyloxy, and cycloalkyloxy; alternatively where R[8a] comprises an NR[a]R[5] moiety R[a] and R[5], together with the nitrogen atom they are attached to, may optionally form a substituted or unsubstituted 4-6 membered ring;

p is 0, 1, 2, or 3; and
t is 0, 1 or 2;

wherein each alkyl, aryl, heteroaryl, cycloalkyl, alkenyl, alkynyl, heterocyclyl, and alkoxy moiety of any R, R[1], R[2], R[3], R, R[5], R[7], R[8], R[8]*, and R[a] is optionally independently substituted with one or more groups independently selected at each occurrence from halo, oxo, —NR[a]R[5], —OR[5a], —CO$_2$R[5], —C(=O)R[5], (C$_1$-C$_6$)alkylamino, —NH—N=NH, (C$_1$-C$_6$)alkyl, (C$_1$-C$_6$)alkynyl, (C$_3$-C$_6$)cycloalkyl, (C$_1$-C$_6$)haloalkyl, di(C$_1$-C$_6$)alkylamino, (C$_1$-C$_6$)alkylamino-(C$_1$-C$_6$)alkyl, (C$_1$-C$_6$)hydroxyalkylamino, (C$_1$-C$_6$)alkylamino-(C$_1$-C$_6$)alkylamino, phenyl, heterocyclic, heteroaryl, —(CR[3]R[4])$_p$alkyl-S(=O)-alkyl, and —(CR[3]R[4])$_p$alkyl-S(O)$_2$-alkyl.

The invention also relates to compounds wherein
R is selected from

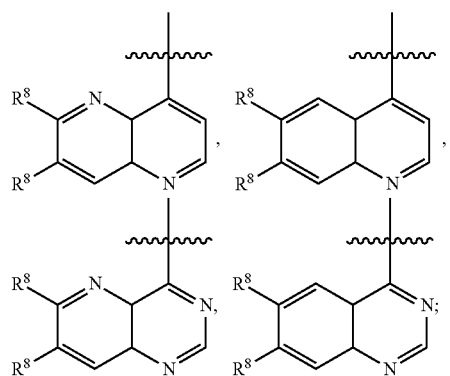

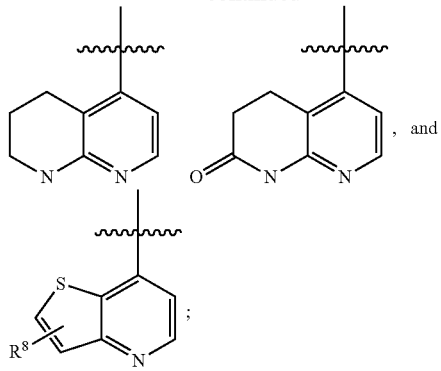

R[8] is independently selected from H, cyano, hydroxy, —C(=O)NR[a]R[5a], 5-6 membered heterocyclyl, —NR[a]C(=O)—R[5a], R[5a]R[a]N—O$_2$S—, R[5a]O$_2$SR[a]N—, R[5a]R[a]N—, C$_{1-6}$-alkyl, amino-C$_{1-6}$-alkyl, C$_{1-6}$-alkylamino-C$_{1-6}$-alkyl, alkoxy-C$_{1-6}$-alkyl, phenyl-C$_{1-6}$-alkyl, heterocyclyl-C$_{1-6}$-alkyl, C$_{1-6}$-alkoxy, halo-C$_{1-6}$-alkoxy, C$_{1-6}$-alkylamino-C$_{1-6}$-alkoxy, aryl-C$_{1-6}$-alkoxy, 5-6-membered heterocyclyl-C$_{1-6}$-alkoxy, C$_{3-6}$-cycloalkyl-C$_{1-6}$-alkoxy, 5-6-membered heterocyclyl(hydroxyl-C$_{1-6}$-alkoxy), C$_{3-6}$-cycloalkyl(hydroxyl-C$_{1-6}$-alkoxy), phenyl(hydroxyl-C$_{1-6}$-alkoxy), C$_{1-6}$-alkoxy-C$_{1-6}$-alkoxy, phenyloxy-C$_{1-6}$-alkoxy, 5-6 membered heterocyclyloxy-C$_{1-6}$alkoxy, C$_{3-6}$-cycloalkyloxy-C$_{1-6}$-alkoxy, phenyloxy, 5-6-membered heterocyclyloxy, and C$_{3-6}$-cycloalkyloxy;

R[a] is selected from H, C$_{1-6}$-alkyl, 5-6 membered heterocyclyl, phenyl, phenyl-C$_{1-4}$-alkyl, 5-6 membered heterocyclyl-C$_{1-6}$-alkyl, C$_{3-6}$-cycloalkyl, C$_{3-6}$-cycloalkyl-C$_{1-6}$-alkyl, C$_{2-6}$-alkenyl and C$_{2-6}$-alkynyl; and R[5a] is selected from H, C$_{1-6}$-alkyl, C$_{1-6}$-haloalkyl, phenyl-C$_{1-6}$-alkyl, 5-6 membered heterocyclyl-C$_{1-6}$-alkyl, C$_{3-6}$-cycloalkyl-C$_{1-6}$-alkyl, phenyl, 5-6 membered heterocyclyl, C$_{2-6}$-alkenyl, C$_{2-6}$-alkynyl and C$_{3-6}$-cycloalkyl;

in conjunction with any of the above or below embodiments.

The invention also relates to compounds wherein
R[8] is independently selected from H, cyano, aminocarbonyl, C$_{1-3}$-alkylaminocarbonyl, C$_{1-6}$-alkyl, C$_{1-6}$-alkoxy, C$_{1-3}$-alkylamino-C$_{1-3}$-alkoxy, 5-6 membered heterocyclyl-C$_{1-3}$-alkoxy, C$_{4-6}$-cycloalkyl-C$_{1-3}$-alkoxy, 5-6 membered heterocyclyl-C$_{1-3}$-(hydroxyalkoxy), C$_{3-6}$-cycloalkyl-C$_{1-3}$-(hydroxyalkoxy), C$_{1-2}$-alkoxy-C$_{1-3}$-alkoxy, phenyloxy-C$_{1-3}$alkoxy, 5-6 membered heterocyclyloxy-C$_{1-3}$-alkoxy, cycloalkyloxy-C$_{1-3}$-alkoxy, 5-6 membered heterocyclyloxy, and C$_{3-6}$-cycloalkyloxy; in conjunction with any of the above or below embodiments.

The invention also relates to compounds wherein
R[8] is independently selected from H, methyl, cyano, aminocarbonyl, methylaminocarbonyl, methoxy, dimethylaminopropoxy, 3-(morpholin-4-yl)ethoxy, 3-(pyrrolidin-1-yl)propoxy, 2-hydroxy-3-(morpholin-4-yl)propoxy, 3-(1,2,4-triazol-1-yl)propoxy, 3-(4-methylpiperazin-1-yl)propoxy, 3-(piperidin-4-yl)propoxy, dimethylaminoethoxy and diethylaminoethoxy; in conjunction with any of the above or below embodiments.

The invention also relates to compounds wherein
R is selected from 6,7-dimethoxy-4-quinolinyl, 6-methoxy-7-(dimethylaminopropoxy)-4-quinolinyl, 6-methoxy-7-(3-(morpholin-4-yl)propoxy)-4-quinolinyl, 6-methoxy-7-(3-(pyrrolidin-1-yl)propoxy)-4-quinolinyl, 6-methoxy-7-(2-hydroxy-3-(morpholin-4-yl)propoxy)-4-quinolinyl, 6-methoxy-7-(3-(1,2,4-triazol-1-yl)propoxy)-4-quinolinyl, 6-methoxy-7-(3-(4-methylpiperazin-1-yl)propoxy)-

4-quinolinyl, 6-methoxy-7-(3-(piperidin-4-yl)propoxy)-4-quinolinyl, 6,7-dimethoxy-4-quinazolinyl and 6-methoxy-7-(dimethylaminopropoxy)-4-quinazolinyl; in conjunction with any of the above or below embodiments.

The invention also relates to compounds wherein

W is selected from substituted or unsubstituted phenyl, substituted or unsubstituted pyridyl, substituted or unsubstituted pyrimidinyl, substituted or unsubstituted pyridazinyl and substituted or unsubstituted pyrazinyl; in conjunction with any of the above or below embodiments.

The invention also relates to compounds wherein

W is substituted or unsubstituted phenyl; in conjunction with any of the above or below embodiments.

The invention also relates to compounds wherein

W is substituted or unsubstituted pyridyl; in conjunction with any of the above or below embodiments.

The invention also relates to compounds wherein

X is O; in conjunction with any of the above or below embodiments.

The invention also relates to compounds wherein

Y is selected from —NHC(=O)—, —NHC(=O)—(CH$_2$)$_p$—, —NH—(CH$_2$)$_p$—, and —NH—(CH$_2$)$_p$C(=O)—; and wherein p is 0 or 1; in conjunction with any of the above or below embodiments.

The invention also relates to compounds wherein

Y is —NHC(=O)—; in conjunction with any of the above or below embodiments.

The invention also relates to compounds wherein p is 1; in conjunction with any of the above or below embodiments.

The invention also relates to compounds wherein $R^1$ is selected from

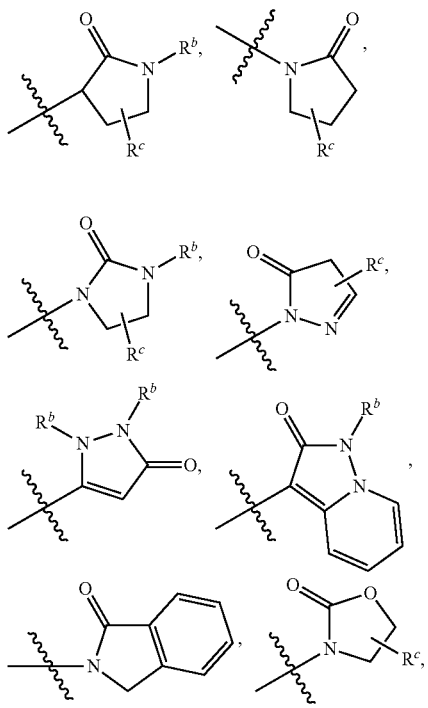

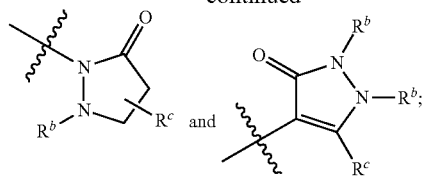

$R^b$ is independently selected at each occurrence from H, optionally substituted arylalkyl, optionally substituted 5-6-membered heterocyclyl-C$_{1-3}$ alkyl, optionally substituted C$_{1-6}$-alkyl, optionally substituted 5-6 membered heterocyclyl, optionally substituted C$_{6-10}$ aryl, optionally substituted C$_{6-10}$ heteroaryl, optionally substituted C$_{3-6}$ cycloalkyl, and R$^a$R$^{5a}$N—C$_{1-3}$alkyl;

$R^c$ is one or more substituents selected from H, methyl, isopropyl, tert-butyl, bromo, fluoro, hydroxyl, R$^{5a}$R$^a$N—, R$^{5a}$R$^a$N—C$_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-C$_{1-2}$-alkyl, optionally substituted phenyl, and optionally substituted 5-6-membered heterocyclyl; C$_{6-10}$ aryl, nitrile, —C(=O)OR$^{5a}$, —C(=O)NR$^{5a}$R$^a$, —C(=O)R$^{5a}$ and optionally substituted heteroaryl R$^a$ is selected from H, C$_{1-6}$-alkyl, optionally substituted 5-6 membered heterocyclyl, optionally substituted phenyl, optionally substituted phenyl-C$_{1-6}$-alkyl, optionally substituted 5-6 membered heterocyclyl-C$_{1-6}$-alkyl, C$_{3-6}$-cycloalkyl, C$_{3-6}$-cycloalkyl-C$_{1-6}$-alkyl, C$_{2-6}$-alkenyl and C$_{2-6}$-alkynyl; and R$^{5a}$ is selected from H, C$_{1-6}$-alkyl, C$_{1-6}$-haloalkyl, phenyl-C$_{1-6}$-alkyl, 5-6 membered heterocyclyl-C$_{1-6}$-alkyl, C$_{3-6}$-cycloalkyl-C$_{1-6}$-alkyl, R$^a$C(=O)—, optionally substituted phenyl, optionally substituted 5-6-membered heterocyclyl, C$_{2-6}$-alkenyl, C$_{2-6}$-alkynyl and C$_{3-6}$-cycloalkyl; or wherein two adjacent R$^c$ substituents, two adjacent R$^b$ substituents or R$^c$ together with an adjacent R$^b$ together form an optionally substituted fused ring; or wherein two R$^c$ substituents, together form an optionally substituted spiro ring; in conjunction with any of the above or below embodiments.

The invention also relates to compounds wherein

R$^b$ is selected from H, optionally substituted benzyl, C$_{1-3}$ alkylaryl, C$_{1-3}$ alkylheteroaryl, methyl, ethyl, isopropyl, butyl, sec-butyl, isobutyl, methoxymethyl, —(C$_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

R$^c$ is one or more substituents selected from H, methyl, isopropyl, tert-butyl, bromo, fluoro, hydroxyl, R$^{5a}$R$^a$N—, R$^{5a}$R$^a$N—C$_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^a$, —C(=O)NR$^{5a}$R$^a$, —C(=O)R$^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein $R^1$ is selected from

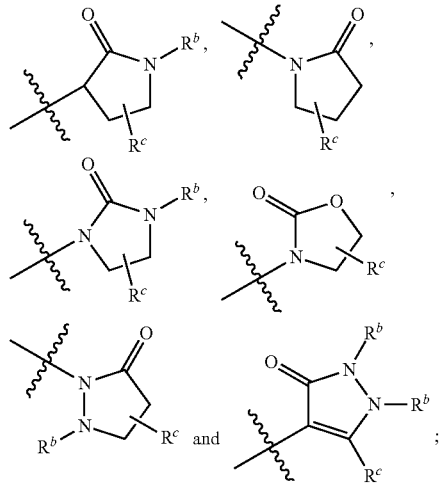

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^a$, —C(=O)NR$^{5a}$R$^a$, C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused ring; or wherein two $R^c$ substituents, together form an optionally substituted spiro ring; in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —$(C_{1-6})$alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl, 1-naphthy, nitrile, —C(=O)OR$^{5a}$, —C(=O)NR$^{5a}$R$^a$, and —C(=O)R$^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein R$^1$ is selected from

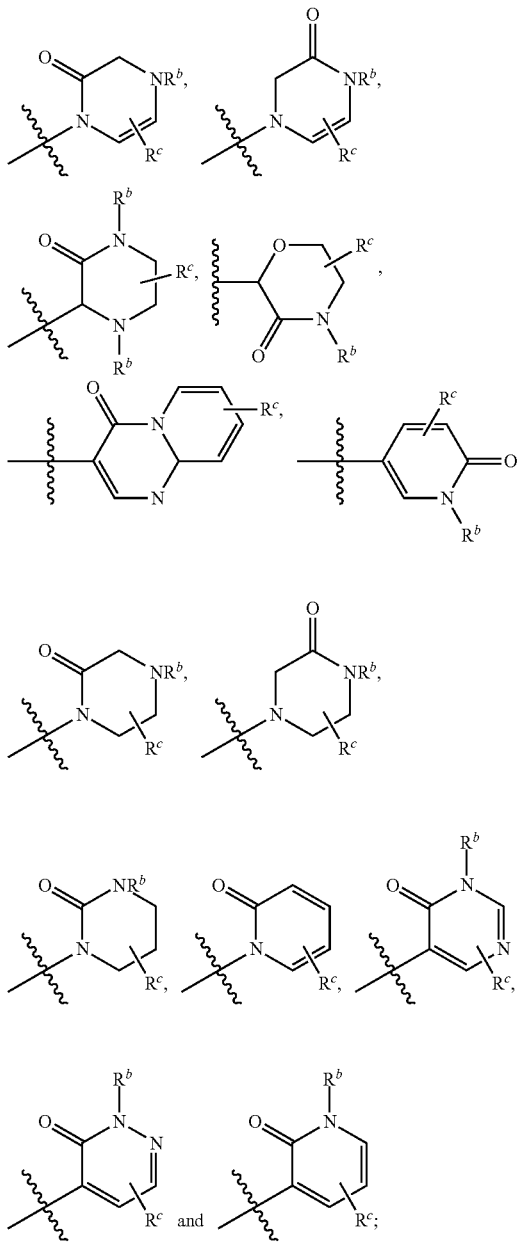

R$^b$ is independently selected at each occurrence from H, optionally substituted arylalkyl, optionally substituted 5-6-membered heterocyclyl-C$_{1-3}$ alkyl, optionally substituted C$_{1-6}$-alkyl, optionally substituted 5-6 membered heterocyclyl, optionally substituted C$_{6-10}$ ary, optionally substituted C$_{6-10}$ heteroaryl, optionally substituted C$_{3-6}$ cycloalkyl, and R$^a$R$^{5a}$N—C$_{1-3}$alkyl;

R$^c$ is one or more substituents selected from H, methyl, isopropyl, tert-butyl, bromo, fluoro, hydroxyl, R$^{5a}$R$^a$N—, R$^{5a}$R$^a$N—C$_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-C$_{1-2}$-alkyl, optionally substituted phenyl, and optionally substituted 5-6-membered heterocyclyl; C$_{6-10}$ aryl, nitrile, —C(=O)OR$^{5a}$, —C(=O)NR$^a$R$^a$, —C(=O)R$^{5a}$ and optionally substituted heteroaryl R$^a$ is selected from H, C$_{1-6}$-alkyl, optionally substituted 5-6 membered heterocyclyl, optionally substituted phenyl, optionally substituted phenyl-C$_{1-6}$-alkyl, optionally substituted 5-6 membered heterocyclyl-C$_{1-6}$-alkyl, C$_{3-6}$-cycloalkyl, C$_{3-6}$-cycloalkyl-C$_{1-6}$-alkyl, C$_{2-6}$-alkenyl and C$_{2-6}$-alkynyl; and R$^{5a}$ is selected from H, C$_{1-6}$-alkyl, C$_{1-6}$-haloalkyl, phenyl-C$_{1-6}$alkyl, 5-6 membered heterocyclyl-C$_{1-6}$-alkyl, C$_{3-6}$-cycloalkyl-C$_{1-6}$-alkyl, R$^a$C(=O)—, optionally substituted phenyl, optionally substituted 5-6-membered heterocyclyl, C$_{2-6}$-alkenyl, C$_{2-6}$-alkynyl and C$_{3-6}$-cycloalkyl; or wherein two adjacent R$^c$ substituents, two adjacent R$^b$ substituents or R$^c$ together with an adjacent R$^b$ together form an optionally substituted fused ring; or wherein two R$^c$ substituents, together form an optionally substituted spiro ring; in conjunction with any of the above or below embodiments.

The invention also relates to compounds wherein

R$^b$ is selected from H, optionally substituted benzyl, C$_{1-3}$ alkylaryl, C$_{1-3}$ alkylheteroaryl, methyl, ethyl, isopropyl, butyl, sec-butyl, isobutyl, methoxymethyl, —(C$_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

R$^c$ is one or more substituents selected from H, methyl, isopropyl, tert-butyl, bromo, fluoro, hydroxyl, R$^{5a}$R$^a$N—, R$^{5a}$R$^a$N—C$_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-C$_{1-2}$-alkyl, optionally substituted phenyl, and optionally substituted 5-6-membered heterocyclyl; C$_{6-10}$ aryl, nitrile, —C(=O)OR$^{5a}$, —C(=O)NR$^{5a}$R$^a$, —C(=O)R$^{5a}$ and optionally substituted heteroaryl R$^{5a}$ is selected from H, methyl, ethyl, isopropyl, butyl, sec-butyl, isobutyl, phenylmethyl, optionally substituted 5-6 membered heterocyclyl-C$_{1-2}$-alkyl, optionally substituted phenyl, and optionally substituted 5-6-membered heterocyclyl; or wherein two R$^c$ substituents, two R$^b$ substituents or R$^c$ together with R$^b$ together form an optionally substituted fused phenyl ring; or wherein two R$^c$ substituents, together form an optionally substituted 3-6 membered spiro ring; in conjunction with any of the above or below embodiments.

The invention also relates to compounds wherein $R^1$ is selected from

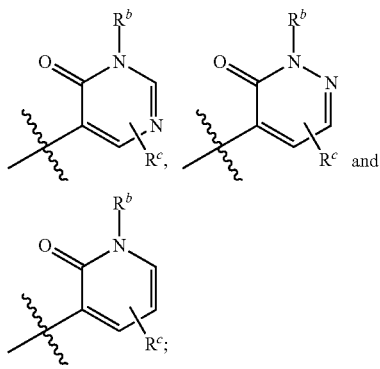

wherein $R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^a R^{5a} N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, C(=O)R$^{5a}$ and optionally substituted heteroraryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused ring; or wherein two $R^c$ substituents, together form an optionally substituted spiro ring; in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —($C_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroraryl $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds of Formula II

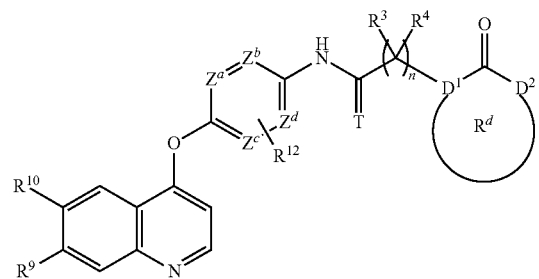

II wherein

T is O or S;

$R^3$ and $R^4$ is each independently selected from H, $C_{1-2}$-alkyl, phenyl, 5-6-membered heterocyclyl, phenyl-$C_{1-2}$-alkyl, 5-6-membered heterocyclyl-$C_{1-3}$-alkyl, $C_{3-6}$cycloalkyl, and $C_{3-6}$-cycloalkyl-$C_{1-2}$-alkyl; alternatively $R^3$ and $R^4$, together with the atom they are attached to, form an optionally substituted 4-6 membered ring;

$R^9$ and $R^{10}$ is independently selected from H, cyano, hydroxy, —C(=O)NR$^a$R$^{5a}$, 5-6 membered heterocyclyl, —NR$^a$C(=O)—R$^{1a}$, $R^{5a}R^aN$—$O_2S$—, $R^{5a}O_2SR^aN$—, $R^{5a}R^aN$—, $C_{1-6}$-alkyl, amino-$C_{1-6}$-alkyl, $C_{1-6}$-alkylamino-$C_{1-6}$-alkyl, alkoxy-$C_{1-6}$-alkyl, hydroxy-, aryl-$C_{1-6}$-alkyl, heterocyclyl-$C_{1-6}$-alkyl, $C_{1-6}$-alkoxy, halo-$C_{1-6}$-alkoxy, $C_{1-6}$-alkylamino-$C_{1-6}$-alkoxy, aryl-$C_{1-6}$-alkoxy, 5-6-membered heterocyclyl, —$C_{1-6}$alkoxy, $C_{3-6}$-cycloalkyl-$C_{1-6}$-alkoxy, 5-6-membered heterocyclyl(hydroxyl-$C_{1-6}$-alkoxy), $C_{3-6}$-cycloalkyl(hydroxyl-$C_{1-6}$-alkoxy), phenyl(hydroxyl-$C_{1-6}$-alkoxy), $C_{1-6}$-alkoxy-$C_{1-6}$-alkoxy, phenyloxy-$C_{1-6}$-alkoxy, 5-6 membered heterocyclyloxy-$C_{1-6}$-alkoxy, $C_{3-6}$-cycloalkyloxy-$C_{1-6}$-alkoxy, phenyloxy, 5-6-membered heterocyclyloxy, and $C_{3-6}$-cycloalkyloxy; each of $Z^a$, $Z^b$, $Z^c$ and $Z^d$ is independently selected from N or CH; provided no more than 2 of $Z^a$, $Z^b$, $Z^c$ and $Z^d$ are N;

n is 0, 1, 2 or 3;

$D^1$ is selected from N or $CR^{11}$;

$D^2$ is selected from $NR^{13}$, O, or $CHR^{11}$; provided either $D^1$ is N or $D^2$ is $NR^{13}$;

ring $R^d$ including

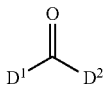

forms an optionally substituted optionally benzo-fused 4-7 membered heterocyclic moiety, $R^{11}$ is selected from H, halo, $C_{1-4}$-alkyl, $C_{1-4}$-haloalkyl, $C_{1-4}$-hydroxyalkyl, $-NH_2$, $-OR^{12}$ alkoxycarbonyl, $-CO_2H$, $-CONR^3R^{5a}$, $(C_1-C_3)$alkylamino, di$(C_1-C_6)$alkylamino, $(C_1-C_3)$hydroxyalkylamino, $(C_1-C_3)$alkylamino-$(C_1-C_3)$alkylamino, $C_{1-3}$-alkoxy-$C_{1-3}$-alkyl, $C_{1-3}$-alkylamino-$C_{1-3}$-alkyl, $C_{1-3}$-alkylthio-$C_{1-3}$-alkyl, optionally substituted phenyl-$C_{1-3}$-alkyl, 5-6 membered heterocyclyl-$C_{1-3}$-alkyl, $C_{3-6}$-cycloalkyl-$C_{1-3}$-alkyl, optionally substituted phenyl, optionally substituted 5-6 membered heterocyclyl, and $C_{3-6}$-cycloalkyl;

$R^a$ is selected from H, alkyl, heterocyclyl, aryl, arylalkyl, heterocyclylalkyl, cycloalkyl, cycloalkylalkyl, alkenyl and alkynyl;

$R^{5a}$ is selected from H, alkyl, haloalkyl, arylalkyl, heterocyclylalkyl, cycloalkylalkyl, aryl, heterocyclyl, alkenyl, alkynyl and cycloalkyl;

$R^{12}$ is selected from H, halo, $C_{1-2}$-alkyl and methoxy;

$R^{13}$ is selected from H, alkyl, haloalkyl, optionally substituted phenylalkyl, optionally substituted 5-10 membered heterocyclylalkyl, cycloalkylalkyl, optionally substituted phenyl or naphthyl, optionally substituted 5-10 membered heterocyclyl and cycloalkyl.

The invention also relates to compounds wherein $R^9$ and $R^{10}$ are independently selected from H, cyano, aminocarbonyl, $C_{1-3}$-alkylaminocarbonyl, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-3}$-alkoxy, cycloalkyloxy-$C_{1-3}$-alkoxy, 5-6 membered heterocyclyloxy, and $C_{3-6}$-cycloalkyloxy; in conjunction with any of the above or below embodiments.

The invention also relates to compounds wherein $R^9$ is independently selected from H, methyl, cyano, aminocarbonyl, methylaminocarbonyl, methoxy, dimethylaminopropoxy, 3-(morpholin-4-yl)ethoxy, 3-(pyrrolidin-1-yl)propoxy, 2-hydroxy-3-(morpholin-4-yl)propoxy, 3-(1,2,4-triazol-1-yl)propoxy, 3-(4-methylpiperazin-1-yl)propoxy, 3-(piperidin-4-yl)propoxy, dimethylaminoethoxy and diethylaminoethoxy; in conjunction with any of the above or below embodiments.

The invention also relates to compounds wherein $R^{10}$ is methoxy; in conjunction with any of the above or below embodiments.

The invention also relates to compounds wherein $Z^a$ is CH; wherein $Z^b$ is CH; wherein $Z^c$ is CF; and wherein $Z^d$ is CH; in conjunction with any of the above or below embodiments.

The invention also relates to compounds wherein
$Z^a$ is N;
$Z^a$ is CH;
$Z^c$ is CH;
$Z^d$ is CH; and
$R^{12}$ is H; in conjunction with any of the above or below embodiments.

The invention also relates to compounds wherein
$Z^a$ is CH;
$Z^b$ is N;
$Z^c$ is CH;
$Z^d$ is CH; and
$R^{12}$ is H; in conjunction with any of the above or below embodiments.

The invention also relates to compounds wherein
$Z^a$ is CH;
$Z^b$ is N;
$Z^c$ is CH;
$Z^d$ is N; and
$R^{12}$ is H; in conjunction with any of the above or below embodiments.

The invention also relates to compounds wherein $R^d$ is

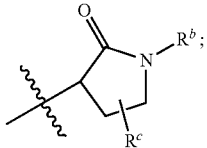

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, $-C(=O)OR^{5a}$, $-C(=O)NR^{5a}R^a$, $-C(=O)R^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;
in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —($C_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

$R^c$ is one or more substituents selected from H, methyl, isopropyl, tert-butyl, bromo, fluoro, hydroxyl, R$^{5a}$R$^a$N—, R$^{5a}$R$^a$N—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroraryl $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or two $R^c$ substituents, two $R^b$ substituents or $R^c$ together with $R^b$ together form an optionally substituted fused phenyl ring; or two $R^c$ substituents, together form an optionally substituted 3-6 membered spiro ring; in conjunction with any of the above or below embodiments.

The invention also relates to compounds wherein
$R^d$ is

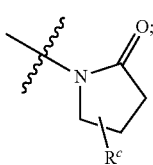

wherein
$R^c$ is one or more substituents selected from H, methyl, isopropyl, tert-butyl, bromo, fluoro, hydroxyl, R$^{5a}$R$^a$N—, R$^{5a}$R$^a$N—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroraryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, R$^a$C(=O)—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;
in conjunction with any of the above or below embodiments.

The invention also relates to compounds wherein $R^c$ is one or more substituents selected from H, methyl, isopropyl, tert-butyl, bromo, fluoro, hydroxyl, R$^{5a}$R$^a$N—, R$^{5a}$R$^a$N—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein R$^a$ is selected from H, methyl, ethyl, isopropyl, butyl, sec-butyl, isobutyl, phenyl, and phenylmethyl; and wherein R$^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroraryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroraryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring;
in conjunction with any of the above or below embodiments.

The invention also relates to compounds wherein
$R^d$ is

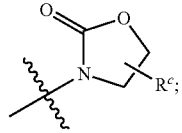

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC$(=O)—, optionally substituted phenyl, optionally substituted 5-6-membered heterocyclyl, $C_{2-6}$-alkenyl, $C_{2-4}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments.

The invention also relates to compounds wherein $R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or two $R^c$ substituents, two $R^b$ substituents or $R^c$ together with $R^b$ together form an optionally substituted fused phenyl ring; or two $R^c$ substituents, together form an optionally substituted 3-6 membered spiro ring;

in conjunction with any of the above or below embodiments.

The invention also relates to compounds wherein $R^d$ is

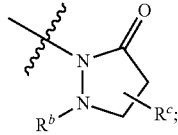

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC$(=O)—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —(C$_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, optionally substituted benzyl, and;

$R^a$ is selected from H, methyl, ethyl, isopropyl, butyl, sec-butyl, isobutyl, phenyl, and phenylmethyl; and $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein $R^d$ is

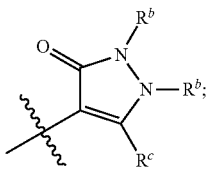

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —($C_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —C(=O)OR$^{5a}$, —C(=O)NR$^{5a}$R$^a$, and —C(=O)R$^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein $R^d$ is

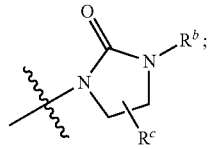

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}$R$^a$, —C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments. The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —$(C_{1-6})$alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl,1-naphthy, nitrile, —$C(=O)OR^{5a}$, —$C(=O)NR^{5a}R^a$, and —$C(=O)R^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring;

in conjunction with any of the above or below embodiments. The invention also relates to compounds wherein $R^d$ is

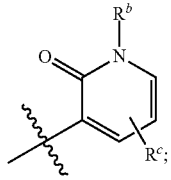

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —$C(=O)OR^{5a}$, —$C(=O)NR^{5a}R^a$, —$C(=O)R^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments. The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —$(C_{1-6})$alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylmethyl, pyridyl, thienyl, optionally substituted phenyl, 1-naphthy, nitrile, —$C(=O)OR^{5a}$, —$C(=O)NR^{5a}R^a$, and —$C(=O)R^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —$C(=O)OR^{5a}$, —$C(=O)NR^{5a}R^a$, —$C(=O)R^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein $R^d$ is

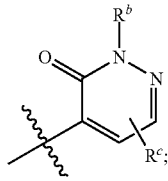

$R^b$ is independently selected at each occurrence from H, optionally substituted arylalkyl, optionally substituted 5-6-membered heterocyclyl-$C_{1-3}$ alkyl, optionally substituted $C_{1-6}$-alkyl, optionally substituted 5-6 membered heterocyclyl, optionally substituted $C_{6-10}$ ary, optionally substituted $C_{6-10}$ heteroaryl, optionally substituted $C_{3-6}$ cycloalkyl, and $R^aR^{5a}N$—$C_{1-3}$alkyl;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}R^a$, —C(=O)R$^{5a}$ and optionally substituted heteroaryl $R^a$ is selected from H, $C_{1-6}$-alkyl, optionally substituted 5-6 membered heterocyclyl, optionally substituted phenyl, optionally substituted phenyl-$C_{1-6}$-alkyl, optionally substituted 5-6 membered heterocyclyl-$C_{1-6}$-alkyl, $C_{3-6}$-cycloalkyl, $C_{3-6}$-cycloalkyl-$C_{1-6}$-alkyl, $C_{2-6}$-alkenyl and $C_{2-6}$-alkynyl; and $R^{5a}$ is selected from H, $C_{1-6}$-alkyl, $C_{1-6}$-haloalkyl, phenyl-$C_{1-6}$-alkyl, 5-6 membered heterocyclyl-$C_{1-6}$-alkyl, $C_{3-6}$-cycloalkyl-$C_{1-6}$-alkyl, $R^aC(=O)$—, optionally substituted phenyl, optionally substituted 5-6-membered heterocyclyl, $C_{2-6}$-alkenyl, $C_{2-6}$-alkynyl and $C_{3-6}$-cycloalkyl; or wherein two adjacent $R^c$ substituents, two adjacent $R^b$ substituents or $R^c$ together with an adjacent $R^b$ together form an optionally substituted fused phenyl ring; or wherein two $R^c$ substituents, together form an optionally substituted spiro ring;

in conjunction with any of the above or below embodiments.

The invention also relates to compounds wherein $R^b$ is selected from H, optionally substituted benzyl, $C_{1-3}$ alkylaryl, $C_{1-3}$ alkylheteroaryl, methyl, ethyl, isopropyl, butyl, sec-butyl, isobutyl, methoxymethyl, —($C_{1-6}$)alkyl, 2-hydroxy 2-methylbutyl, 2-hydroxy-2-methylpropyl, 2-hydroxypropyl, 1-(1-hydroxycyclopropyl)methyl, ethylaminomethyl, piperidin-1-ylmethyl, pyrrolidin-1-ylm-ethyl, pyridyl, thienyl, optionally substituted phenyl,1-naphthy, nitrile, —C(=O)OR$^{5a}$, —C(=O)NR$^{5a}R^a$, and —C(=O)R$^{5a}$;

$R^c$ is one or more substituents selected from H, methyl, isopropyl, tert-butyl, bromo, fluoro, hydroxyl, $R^{5a}R^aN$—, $R^{5a}R^aN$—$C_{1-3}$ alkyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, and optionally substituted benzyl; wherein $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; $C_{6-10}$ aryl, nitrile, —C(=O)OR$^{5a}$, —C(=O)NR$^{5a}R^a$, —C(=O)R$^{5a}$ and optionally substituted heteroaryl $R^a$ is selected from H, methyl, ethyl, isopropyl, butyl, sec-butyl, isobutyl, phenyl, and phenylmethyl; and wherein $R^{5a}$ is selected from H, methyl, ethyl, isopropyl, butyl, sec-butyl, isobutyl, phenylmethyl, optionally substituted 5-6 membered heterocyclyl-$C_{1-2}$-alkyl, optionally substituted phenyl, and optionally substituted 5-6-membered heterocyclyl; or wherein two $R^c$ substituents, two $R^b$ substituents or $R^c$ together with $R^b$ together form an optionally substituted fused phenyl ring; or wherein two $R^c$ substituents, together form an optionally substituted 3-6 membered spiro ring; in conjunction with any of the above or below embodiments.

The invention also relates to compounds wherein n is 0 or 1; in conjunction with any of the above or below embodiments;

T is O; in conjunction with any of the above or below embodiments; and $R^3$ and $R^4$ are both H; in conjunction with any of the above or below embodiments.

The invention also relates to compounds wherein

R is

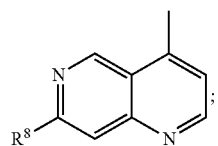

in conjunction with any of the above or below embodiments.

The invention also relates to compounds

R is

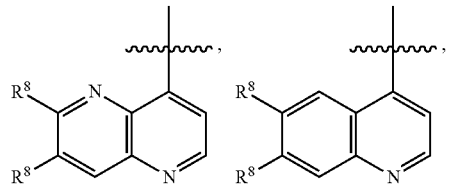

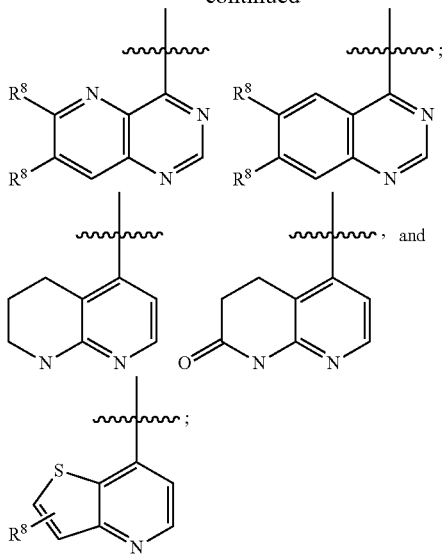

$R^{8a}$ is $C_{1-3}$ alkyl or H; in conjunction with any of the above or below embodiments.

The invention also relates to compounds wherein R is

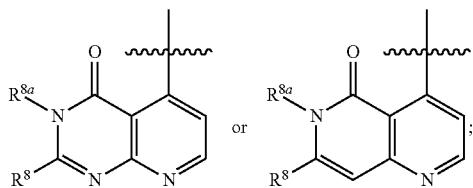

$R^{8a}$ is $C_{1-3}$ alkyl or H; in conjunction with any of the above or below embodiments.

The invention also relates to compounds and pharmaceutically acceptable salts and solvates thereof selected from N-(4-(6,7-dimethoxyquinolin-4-yloxy)-3-fluorophenyl)-1-methyl-3-oxo-2-phenyl-5-(pyridin-4-yl)-2,3-dihydro-1H-pyrazole-4-carboxamide;

N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide;

N-(4-(6,7-dimethoxyquinolin-4-yloxy)-3-fluorophenyl)-5-((ethyl(methyl)amino)methyl)-1-methyl-3-oxo-2-phenyl-2,3-dihydro-1H-pyrazole-4-carboxamide;

N-(4-(6,7-dimethoxyquinolin-4-yloxy)-3-fluorophenyl)-5-((dimethylamino)methyl)-1-methyl-3-oxo-2-phenyl-2,3-dihydro-1H-pyrazole-4-carboxamide;

5-(aminomethyl)-N-(3-fluoro-4-(7-methoxyquinolin-4-yloxy)phenyl)-1-methyl-3-oxo-2-phenyl-2,3-dihydro-1H-pyrazole-4-carboxamide;

tert-butyl (4-((3-fluoro-4-(7-methoxyquinolin-4-yloxy)phenyl)carbamoyl)-1-methyl-3-oxo-2-phenyl-2,3-dihydro-1H-pyrazol-5-yl)methylcarbamate;

N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide;

N-(3-fluoro-4-(7-methoxyquinolin-4-yloxy)phenyl)-1-methyl-3-oxo-2-phenyl-5-(pyrrolidin-1-ylmethyl)-2,3-dihydro-1H-pyrazole-4-carboxamide;

N-(3-fluoro-4-(7-methoxyquinolin-4-yloxy)phenyl)-5-methyl-3-oxo-2-phenyl-1-((tetrahydrofuran-2-yl)methyl)-2,3-dihydro-1H-pyrazole-4-carboxamide;

5-((ethyl(methyl)amino)methyl)-N-(3-fluoro-4-(7-methoxyquinolin-4-yloxy)phenyl)-1-methyl-3-oxo-2-phenyl-2,3-dihydro-1H-pyrazole-4-carboxamide;

2-benzyl-N-(5-(7-methoxyquinolin-4-yloxy)pyridin-2-yl)-1-methyl-3-oxo-5-(pyridin-4-yl)-2,3-dihydro-1H-pyrazole-4-carboxamide;

2-benzyl-N-(3-fluoro-4-(7-methoxyquinolin-4-yloxy)phenyl)-1-methyl-3-oxo-5-(pyridin-4-yl)-2,3-dihydro-1H-pyrazole-4-carboxamide;

(S)-N-(5-(7-methoxyquinolin-4-yloxy)pyridin-2-yl)-1-methyl-3-oxo-2-(1-phenylethyl)-5-(pyridin-4-yl)-2,3-dihydro-1H-pyrazole-4-carboxamide;

(S)-N-(3-fluoro-4-(7-methoxyquinolin-4-yloxy)phenyl)-1-methyl-3-oxo-2-(1-phenylethyl)-5-(pyridin-4-yl)-2,3-dihydro-1H-pyrazole-4-carboxamide;

N-(5-(7-methoxyquinolin-4-yloxy)pyridin-2-yl)-1-methyl-3-oxo-2-phenyl-5-(pyridin-4-yl)-2,3-dihydro-1H-pyrazole-4-carboxamide;

N-(3-fluoro-4-(7-methoxyquinolin-4-yloxy)phenyl)-1-methyl-3-oxo-2-phenyl-5-(pyridin-4-yl)-2,3-dihydro-1H-pyrazole-4-carboxamide;

N-(5-(6,7-dimethoxyquinolin-4-yloxy)pyridin-2-yl)-1-methyl-3-oxo-2-phenyl-5-(pyridin-4-yl)-2,3-dihydro-1H-pyrazole-4-carboxamide;

N-(3-fluoro-4-(7-methoxyquinolin-4-yloxy)phenyl)-1-methyl-3-oxo-2-phenyl-5-(pyridin-2-yl)-2,3-dihydro-1H-pyrazole-4-carboxamide;

N-(5-(7-methoxyquinolin-4-yloxy)pyridin-2-yl)-1-methyl-3-oxo-2-phenyl-5-(pyridin-2-yl)-2,3-dihydro-1H-pyrazole-4-carboxamide;

N-(3-fluoro-4-(7-methoxyquinolin-4-yloxy)phenyl)-1-methyl-3-oxo-2-phenyl-5-(tetrahydro-2H-pyran-4-yl)-2,3-dihydro-1H-pyrazole-4-carboxamide;

N-(5-(7-methoxyquinolin-4-yloxy)pyridin-2-yl)-1-methyl-3-oxo-2-phenyl-5-(tetrahydro-2H-pyran-4-yl)-2,3-dihydro-1H-pyrazole-4-carboxamide;

1-Methyl-N-(5-((7-(methyloxy)-4-quinolinyl)oxy)-2-pyridinyl)-5-(2-methyl-1,3-thiazol-4-yl)-3-oxo-2-phenyl-2,3-dihydro-1H-pyrazole-4-carboxamide;

N-(5-((6,7-bis(methyloxy)-4-quinolinyl)oxy)-2-pyridinyl)-1-methyl-5-(5-methyl-3-isoxazolyl)-3-oxo-2-phenyl-2,3-dihydro-1H-pyrazole-4-carboxamide;

1-methyl-5-(5-methyl-3-isoxazolyl)-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-1-methyl-5-(5-methyl-3-isoxazolyl)-3-oxo-2-phenyl-2,3-dihydro-1H-pyrazole-4-carboxamide;

1-methyl-N-(5-((7-(methyloxy)-4-quinoinyl)oxy)-2-pyridinyl)-3-oxo-2-phenyl-5-(2-pyrazinyl)-2,3-dihydro-1H-pyrazole-4-carboxamide;

N-(3-fluoro-4-((7-(methyloxy)-4-quinolinyl)oxy)phenyl)-1-methyl-3-oxo-2-phenyl-5-(2-pyrazinyl)-2,3-dihydro-1H-pyrazole-4-carboxamide;

N-(5-((6,7-bis(methyloxy)-4-quinolinyl)oxy)-2-pyridinyl)-1-methyl-3-oxo-2-phenyl-5-(2-pyrazinyl)-2,3-dihydro-1H-pyrazole-4-carboxamide;

N-(5-((6,7-bis(methyloxy)-4-quinolinyl)oxy)-2-pyridinyl)-1-methyl-5-(2-methyl-1,3-thiazol-4-yl)-3-oxo-2-phenyl-2,3-dihydro-1H-pyrazole-4-carboxamide;

N-(3-fluoro-4-((7-(methyloxy)-4-quinolinyl)oxy)phenyl)-1-methyl-5-(2-methyl-1,3-thiazol-4-yl)-3-oxo-2-phenyl-2,3-dihydro-1H-pyrazole-4-carboxamide;

N-(4-(6,7-dimethoxyquinolin-4-yloxy)-3-fluorophenyl)-N,1,5-trimethyl-3-oxo-2-phenyl-2,3-dihydro-1H-pyrazole-4-carboxamide;

2-(3-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide;

2-(3-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide;

N-(4-(6,7-dimethoxyquinolin-4-yloxy)-3-fluorophenyl)-1,5-dimethyl-3-oxo-2-p-tolyl-2,3-dihydro-1H-pyrazole-4-carboxamide;

N-(4-(6,7-dimethoxyquinolin-4-yloxy)-3-fluorophenyl)-2-(4-fluorophenyl)-1,5-dimethyl-3-oxo-2,3-dihydro-1H-pyrazole-4-carboxamide;

N-(5-(6,7-dimethoxyquinolin-4-yloxy)pyridine-2-yl)-1,5-dimethyl-3-oxo-2-p-tolyl-2,3-dihydro-1H-pyrazole-4-carboxamide;

N-(5-(6,7-dimethoxyquinolin-4-yloxy)pyridin-2-yl)-2-(4-fluorophenyl)-1,5-dimethyl-3-oxo-2,3-dihydro-1H-pyrazole-4-carboxamide;

2-(3-chlorophenyl)-N-(5-(7-methoxyquinolin-4-yloxy)pyridin-2-yl)-1,5-dimethyl-3-oxo-2,3-dihydro-1H-pyrazole-4-carboxamide;

N-(5-(7-methoxyquinolin-4-yloxy)pyridin-2-yl)-1,5-dimethyl-3-oxo-2-p-tolyl-2,3-dihydro-1H-pyrazole-4-carboxamide;

2-(2-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide;

2-(2-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide;

2-(2-chlorophenyl)-N-(3-fluoro-4-(7-methoxyquinolin-4-yloxy)phenyl)-1,5-dimethyl-3-oxo-2,3-dihydro-1H-pyrazole-4-carboxamide;

N-(3-fluoro-4-(7-methoxyquinolin-4-yloxy)phenyl)-2-(4-fluorophenyl)-1,5-dimethyl-3-oxo-2,3-dihydro-1H-pyrazole-4-carboxamide;

2-(3-chlorophenyl)-N-(3-fluoro-4-(7-methoxyquinolin-4-yloxy)phenyl)-1,5-dimethyl-3-oxo-2,3-dihydro-1H-pyrazole-4-carboxamide;

N-(6-(6,7-dimethoxyquinolin-4-yloxy)pyridin-3-yl)-1,5-dimethyl-3-oxo-2-phenyl-2,3-dihydro-1H-pyrazole-4-carboxamide;

N-(2-chloro-4-(6,7-dimethoxyquinolin-4-yloxy)phenyl)-1,5-dimethyl-3-oxo-2-phenyl-2,3-dihydro-1H-pyrazole-4-carboxamide;

2-benzyl-N-(4-(6,7-dimethoxyquinolin-4-yloxy)-3-fluorophenyl)-1,5-dimethyl-3-oxo-2,3-dihydro-1H-pyrazole-4-carboxamide;

2-benzyl-N-(5-(6,7-dimethoxyquinolin-4-yloxy)pyridin-2-yl)-1,5-dimethyl-3-oxo-2,3-dihydro-1H-pyrazole-4-carboxamide;

N-(5-(7-methoxyquinolin-4-yloxy)pyridin-2-yl)-1-methyl-3-oxo-2-phenyl-2,3-dihydro-1H-pyrazole-4-carboxamide;

N-(4-(6,7-dimethoxyquinolin-4-yloxy)-3-fluorophenyl)-1-(2-hydroxy-2-methylpropyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-3-oxo-1-(2-oxobutyl)-2-phenyl-2,3-dihydro-1H-pyrazole-4-carboxamide;

N-(3-fluoro-4-(7-methoxyquinolin-4-yloxy)phenyl)-5-methyl-1-(3-methyl-2-oxobutyl)-3-oxo-2-phenyl-2,3-dihydro-1H-pyrazole-4-carboxamide;

(R)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide;

N-(3-fluoro-4-(7-methoxyquinolin-4-yloxy)phenyl)-1-((2R,3R)-3-hydroxybutan-2-yl)-5-methyl-3-oxo-2-phenyl-2,3-dihydro-1H-pyrazole-4-carboxamide;

1-((2R,3R)-3-hydroxybutan-2-yl)-N-(5-(7-methoxyquinolin-4-yloxy)pyridin-2-yl)-5-methyl-3-oxo-2-phenyl-2,3-dihydro-1H-pyrazole-4-carboxamide;

(S)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

(R)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

(S)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

(R)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-1-(((3-methyl-2-oxooxazolidin-5-yl)methyl)-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-(methylamino)propyl)-5-methyl-3-oxo-2-phenyl-2,3-dihydro-1H-pyrazole-4-carboxamide;

1-(3-chloro-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-2-methylbutyl)-5-methyl-3-oxo-2-phenyl-2,3-dihydro-1H-pyrazole-4-carboxamide;

1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-morpholinopropyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-1-(oxazolidin-5-ylmethyl)-3-oxo-2-phenyl-2,3-dihydro-1H-pyrazole-4-carboxamide;

(S)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide;

1-(3-amino-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

1-(2-hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-2-methylpropyl)-5-methyl-3-oxo-2-phenyl-2,3-dihydro-1H-pyrazole-4-carboxamide;

(R)-1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide;

1-(3-(dimethylamino)-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

(R-N-(3-fluoro-4-(7-methoxyquinolin-4-yloxy)phenyl)-1-(2-hydroxypropyl)-5-methyl-3-oxo-2-phenyl-2,3-dihydro-1H-pyrazole-4-carboxamide;

(R-N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide;

1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide;

N-(5-(6,7-dimethoxyquinolin-4-yloxy)pyridin-2-yl)-1-(2-hydroxy-2-methylpropyl)-5-methyl-3-oxo-2-phenyl-2,3-dihydro-1H-pyrazole-4-carboxamide;

(R)-2-(3-chlorophenyl)-N-(3-fluoro-4-(7-methoxyquinolin-4-yloxy)phenyl)-1-(2-hydroxypropyl)-5-methyl-3-oxo-2,3-dihydro-1H-pyrazole-4-carboxamide;

(R)-2-(3-chlorophenyl)-1-(2-hydroxypropyl)-N-(5-(7-methoxyquinolin-4-yloxy)pyridin-2-yl)-5-methyl-3-oxo-2,3-dihydro-1H-pyrazole-4-carboxamide;

(R)-N-(3-fluoro-4-(7-methoxyquinolin-4-yloxy)phenyl)-2-(4-fluorophenyl)-1-(2-hydroxypropyl)-5-methyl-3-oxo-2,3-dihydro-1H-pyrazole-4-carboxamide 1-(2-hydroxy-2-methylpropyl)-N-(5-(1-oxo-7-methoxyquinolin-4-yloxy)pyridin-2-yl)-5-methyl-3-oxo-2-phenyl-2,3-dihydro-1H-pyrazole-4-carboxamide;

N-(3-Fluoro-4-(7-hydroxyquinolin-4-yloxy)phenyl)-1-(2-hydroxy-2-methylpropyl)-5-methyl-3-oxo-2-phenyl-2,3-dihydro-1H-pyrazole-4-carboxamide;

1-(2-hydroxy-2-methylpropyl)-N-(5-(7-hydroxyquinolin-4-yloxy)pyridin-2-yl)-5-methyl-3-oxo-2-phenyl-2,3-dihydro-1H-pyrazole-4-carboxamide;

N-(4-(6-Ethyl-7-methoxyquinolin-4-yloxy)-3-fluorophenyl)-1,5-dimethyl-3-oxo-2-phenyl-2,3-dihydro-1H-pyrazole-4-carboxamide;

N-(3-Fluoro-4-(7-methoxyquinolin-4-yloxy)phenyl)-1,5-dimethyl-3-oxo-2-phenyl-2,3-dihydro-1H-pyrazole-4-carboxamide;

N-(3-fluoro-4-(7-Methoxyquinolin-4-yloxy)phenyl)-1,2-dimethyl-3-oxo-5-phenyl-2,3-dihydro-1H-pyrazole-4-carboxamide;

N-(5-(7-Methoxyquinolin-4-yloxy)pyridin-2-yl)-1,2-dimethyl-3-oxo-5-phenyl-2,3-dihydro-1H-pyrazole-4-carboxamide;

N-(4-(6,7-Dimethoxyquinolin-4-yloxy)-3-fluorophenyl)-1,2-dimethyl-3-oxo-5-phenyl-2,3-dihydro-1H-pyrazole-4-carboxamide;

N-(5-(7-Methoxyquinolin-4-yloxy)pyridin-2-yl)-1,5-dimethyl-3-oxo-2-phenyl-2,3-dihydro-1H-pyrazole-4-carboxamide;

(R)-1-(2-Hydroxypropyl)-N-(5-(7-methoxyquinolin-4-yloxy)pyridin-2-yl)-2-methyl-3-oxo-5-phenyl-2,3-dihydro-1H-pyrazole-4-carboxamide;

(R)-N-(3-Fluoro-4-(7-methoxyquinolin-4-yloxy)phenyl)-1-(2-hydroxypropyl)-2-methyl-3-oxo-5-phenyl-2,3-dihydro-1H-pyrazole-4-carboxamide (S)-N-(3-fluoro-4-(6-methoxyquinolin-4-yloxy)phenyl)-1-(2-hydroxypropyl)-5-methyl-3-oxo-2-phenyl-2,3-dihydro-1H-pyrazole-4-carboxamide;

1-(2-aminoethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide 1-(2-(1,3-dioxo-1,3-dihydro-2H-isoindol-2-yl)ethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-(2-aminoethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

5-methyl-N-(5-((7-(methyloxy)-4-quinolinyl)oxy)-2-pyridinyl)-3-oxo-2-phenyl-1-(phenylmethyl)-2,3-dihydro-1H-pyrazole-4-carboxamide 1-benzyl-N-(3-fluoro-4-(7-methoxyquinolin-4-yloxy)phenyl)-5-methyl-3-oxo-2-phenyl-2,3-dihydro-1H-pyrazole-4-carboxamide;

5-methyl-1-(2-(methyloxy)ethyl)-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-5-methyl-1-(2-(methyloxy)ethyl)-3-oxo-2-phenyl-2,3-dihydro-1H-pyrazole-4-carboxamide;

1-(2-hydroxyethyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

1-((2R)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

(S)-1-(2-(dimethylamino)propyl)-N-(3-fluoro-4-(7-methoxyquinolin-4-yloxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-3-oxo-2-phenyl-1-(2-(1-pyrrolidinyl)ethyl)-2,3-dihydro-1H-pyrazole-4-carboxamide;

1-((2S)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-1-((2S)-2-fluoropropyl)-5-methyl-3-oxo-2-phenyl-2,3-dihydro-1H-pyrazole-4-carboxamide;

1-((2S)-2-(acetylamino)propyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-((2S)-2-aminopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-((2S)-2-azidopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-1-(2-hydroxyethyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-3-oxo-2-phenyl-1-propyl-2,3-dihydro-1H-pyrazole-4-carboxamide;

N-(4-((6,7-bis(methyloxy)-4-quinolinyl)oxy)-3-fluorophenyl)-1-((2R)-2-hydroxypropyl)-5-methyl-3-oxo-2-phenyl-2,3-dihydro-1H-pyrazole-4-carboxamide;

N-(4-((6,7-bis(methyloxy)-4-quinolinyl)oxy)-3-fluorophenyl)-1-((2S)-2-hydroxypropyl)-5-methyl-3-oxo-2-phenyl-2,3-dihydro-1H-pyrazole-4-carboxamide;

5-methyl-N-(5-((7-(methyloxy)-4-quinolinyl)oxy)-2-pyridinyl)-1-(2-methylpropyl)-3-oxo-2-phenyl-2,3-dihydro-1H-pyrazole-4-carboxamide;

5-methyl-N-(5-((7-(methyloxy)-4-quinolinyl)oxy)-2-pyridinyl)-3-oxo-2-phenyl-1-propyl-2,3-dihydro-1H-pyrazole-4-carboxamide;

N-(3-fluoro-4-((7-(methyloxy)-4-quinolinyl)oxy)phenyl)-5-methyl-3-oxo-1-(2-oxopropyl)-2-phenyl-2,3-dihydro-1H-pyrazole-4-carboxamide;

1-(2,3-dihydroxy-2-methylpropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-1-(2-hydroxypropyl)-5-methyl-3-oxo-2-phenyl-2,3-dihydro-1H-pyrazole-4-carboxamide;

N-(4-((6,7-bis(methyloxy)-4-quinazolinyl)oxy)-3-fluorophenyl)-1-(2-hydroxy-2-methylpropyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-1-(2-methyl-2-propen-1-yl)-3-oxo-2-phenyl-2,3-dihydro-1H-pyrazole-4-carboxamide;

N-(4-((6,7-bis(methyloxy)-4-quinolinyl)oxy)-3-fluorophenyl)-1-((2S)-2-hydroxypropyl)-5-methyl-3-oxo-2-phenyl-2,3-dihydro-1H-pyrazole-4-carboxamide;

N-(4-((6,7-bis(methyloxy)-4-quinolinyl)oxy)-3-fluorophenyl)-5-methyl-3-oxo-1-(2-oxopropyl)-2-phenyl-2,3-dihydro-1H-pyrazole-4-carboxamide;

N-(4-((6,7-bis(methyloxy)-4-quinolinyl)oxy)-3-fluorophenyl)-1-(2,3-dihydroxy-2-methylpropyl)-5-methyl-3-oxo-2-phenyl-2,3-dihydro-1H-pyrazole-4-carboxamide;

N-(4-((6,7-bis(methyloxy)-4-quinolinyl)oxy)-3-fluorophenyl)-5-methyl-1-(2-methyl-2-propen-1-yl)-3-oxo-2-phenyl-2,3-dihydro-1H-pyrazole-4-carboxamide;

N-(5-((6,7-bis(methyloxy)-4-quinolinyl)oxy)-2-pyridinyl)-5-methyl-3-oxo-2-phenyl-1-propyl-2,3-dihydro-1H-pyrazole-4-carboxamide;

N-(4-((6,7-bis(methyloxy)-4-quinolinyl)oxy)-3-fluorophenyl)-5-methyl-3-oxo-2-phenyl-2,3-dihydro-1H-pyrazole-4-carboxamide;

N-(5-((6,7-bis(methyloxy)-4-quinolinyl)oxy)-2-pyridinyl)-5-methyl-3-oxo-2-phenyl-1-(2-propen-1-yl)-2,3-dihydro-1H-pyrazole-4-carboxamide;

N-(4-((6,7-bis(methyloxy)-1-oxido-4-quinolinyl)oxy)-3-fluorophenyl)-5-methyl-3-oxo-2-phenyl-1-(2-propen-1-yl)-2,3-dihydro-1H-pyrazole-4-carboxamide;

N-(4-((6,7-bis(methyloxy)-4-quinolinyl)oxy)-3-fluorophenyl)-5-methyl-3-oxo-2-phenyl-1-(phenylmethyl)-2,3-dihydro-1H-pyrazole-4-carboxamide;

4-(6,7-Dimethoxyquinolin-4-yloxy)-3-fluoro-N-(5-oxo-1-phenyl-2,5-dihydro-1H-pyrazol-3-yl)benzamide;

4-(6,7-Dimethoxyquinolin-4-yloxy)-N-(((1,2-dimethyl-5-oxo-3-phenyl-2,5-dihydro-1H-pyrazol-4-yl)methyl)-3-fluorobenzamide;

4-(6,7-Dimethoxyquinolin-4-yloxy)-N-(2,3-dimethyl-5-oxo-1-phenyl-2,5-dihydro-1H-pyrazol-4-yl)-3-fluorobenzamide 4-(6,7-Dimethoxyquinolin-4-yloxy)-N-((2,3-dimethyl-5-oxo-1-phenyl-2,5-dihydro-1H-pyrazol-4-yl)methyl)-3-fluorobenzamide;

1-Benzyl-N-(5-(7-methoxyquinolin-4-yloxy)pyridin-2-yl)-2-oxo-1,2-dihydropyrazolo[1,5-a]pyridine-3-carboxamide;

4-((5-(6,7-Dimethoxyquinolin-4-yloxy)pyridin-2-ylamino)methyl)-1,5-dimethyl-2-phenyl-1,2-dihydropyrazol-3-one;

N-(3-fluoro-4-(2-(3-methyl-1,2,4-oxadiazol-5-yl)thieno[3,2-b]pyridin-7-yloxy)phenyl)-1-(2-hydroxy-2-methylpropyl)-5-methyl-3-oxo-2-phenyl-2,3-dihydro-1H-pyrazole-4-carboxamide;

N-(3-fluoro-4-((2-(1-methyl-1H-imidazol-5-yl)thieno[3,2-b]pyridin-7-yl)oxy)phenyl)-1-(2-hydroxy-2-methylpropyl)-5-methyl-3-oxo-2-phenyl-2,3-dihydro-1H-pyrazole-4-carboxamide;

N-(3-fluoro-4-((2-(1-methyl-1H-imidazol-5-yl)thieno[3,2-b]pyridin-7-yl)oxy)phenyl)-1-((2R)-2-hydroxypropyl)-5-methyl-3-oxo-2-phenyl-2,3-dihydro-1H-pyrazole-4-carboxamide;

N-(3-fluoro-4-(7H-pyrrolo[2,3-d]pyrimidin-4-yloxy)phenyl)-1-(2-hydroxy-2-methylpropyl)-5-methyl-3-oxo-2-phenyl-2,3-dihydro-1H-pyrazole-4-carboxamide;

N-(3-fluoro-4-(1H-pyrrolo[2,3-b]pyridin-4-yloxy)phenyl)-1-(2-hydroxy-2-methylpropyl)-5-methyl-3-oxo-2-phenyl-2,3-dihydro-1H-pyrazole-4-carboxamide;

Methyl(6-((4-(((1-(2-hydroxy-2-methylpropyl)-5-methyl-3-oxo-2-phenyl-2,3-dihydro-1H-pyrazol-4-yl)carbonyl)amino)phenyl)oxy)-1H-benzimidazol-2-yl)carbamate;

N-(4-(2-(azetidine-1-carbonyl)thieno[3,2-b]pyridin-7-yloxy)-3-fluorophenyl)-5-methyl-3-oxo-2-phenyl-1-propyl-2,3-dihydro-1H-pyrazole-4-carboxamide;

7-(2-fluoro-4-(1-(2-hydroxy-2-methylpropyl)-5-methyl-3-oxo-2-phenyl-2,3-dihydro-1H-pyrazole-4-carboxamido)phenoxy)-N-methylthieno[3,2-b]pyridine-2-carboxamide;

N-(3-fluoro-4-(2-(1-methylpiperazine-4-carbonyl)thieno[3,2-b]pyridin-7-yloxy)phenyl)-1-(2-hydroxy-2-methylpropyl)-5-methyl-3-oxo-2-phenyl-2,3-dihydro-1H-pyrazole-4-carboxamide;

N-(2-(dimethylamino)ethyl)-7-(2-fluoro-4-(1-(2-hydroxy-2-methylpropyl)-5-methyl-3-oxo-2-phenyl-2,3-dihydro-1H-pyrazole-4-carboxamido)phenoxy)thieno[3,2-b]pyridine-2-carboxamide;

N-(4-(2-(3-(dimethylamino)pyrrolidine-1-carbonyl)thieno[3,2-b]pyridin-7-yloxy)-3-fluorophenyl)-1-(2-hydroxy-2-methylpropyl)-5-methyl-3-oxo-2-phenyl-2,3-dihydro-1H-pyrazole-4-carboxamide;

7-(2-fluoro-4-(1-(2-hydroxy-2-methylpropyl)-5-methyl-3-oxo-2-phenyl-2,3-dihydro-1H-pyrazole-4-carboxamido)phenoxy)-N,N-dimethylthieno[3,2-b]pyridine-2-carboxamide;

7-(2-fluoro-4-(1-(2-hydroxy-2-methylpropyl)-5-methyl-3-oxo-2-phenyl-2,3-dihydro-1H-pyrazole-4-carboxamido)phenoxy)thieno[3,2-b]pyridine-2-carboxamide;

N-(2-(dimethylamino)ethyl)-7-(2-fluoro-4-(1-(2-hydroxy-2-methylpropyl)-5-methyl-3-oxo-2-phenyl-2,3-dihydro-1H-pyrazole-4-carboxamido)phenoxy)-N-methylthieno[3,2-b]pyridine-2-carboxamide;

7-(2-fluoro-4-(1-(2-hydroxy-2-methylpropyl)-5-methyl-3-oxo-2-phenyl-2,3-dihydro-1H-pyrazole-4-carboxamido)phenoxy)-N-(2-methoxyethyl)thieno[3,2-b]pyridine-2-carboxamide;

N-(4-(2-(azetidine-1-carbonyl)thieno[3,2-b]pyridin-7-yloxy)-3-fluorophenyl)-1-(2-hydroxy-2-methylpropyl)-5-methyl-3-oxo-2-phenyl-2,3-dihydro-1H-pyrazole-4-carboxamide;

N-cyclopropyl-7-(2-fluoro-4-(1-(2-hydroxy-2-methylpropyl)-5-methyl-3-oxo-2-phenyl-2,3-dihydro-1H-pyrazole-4-carboxamido)phenoxy)thieno[3,2-b]pyridine-2-carboxamide 7-(2-fluoro-4-(5-methyl-3-oxo-2-phenyl-1-propyl-2,3-dihydro-1H-pyrazole-4-carboxamido)phenoxy)thieno[3,2-b]pyridine-2-carboxamide;

N-(3-fluoro-4-(6-(pyrrolidine-1-carboxamido)pyrimidin-4-yloxy)phenyl)-1-(2-hydroxy-2-methylpropyl)-5-methyl-3-oxo-2-phenyl-2,3-dihydro-1H-pyrazole-4-carboxamide;

N-(3-fluoro-4-(6-(pyrrolidine-1-carboxamido)pyrimidin-4-yloxy)phenyl)-5-methyl-3-oxo-2-phenyl-1-propyl-2,3-dihydro-1H-pyrazole-4-carboxamide;

N-(6-(4-(1,5-dimethyl-3-oxo-2-phenyl-2,3-dihydro-1H-pyrazole-4-carboxamido)-2-fluorophenoxy)pyrimidin-4-yl)morpholine-4-carboxamide;

N-(6-(2-fluoro-4-(5-methyl-3-oxo-2-phenyl-1-propyl-2,3-dihydro-1H-pyrazole-4-carboxamido)phenoxy)pyrimidin-4-yl)morpholine-4-carboxamide;

N-(6-(2-fluoro-4-(5-methyl-3-oxo-2-phenyl-1-propyl-2,3-dihydro-1H-pyrazole-4-carboxamido)phenoxy)pyrimidin-4-yl)piperidine-1-carboxamide;

N-(6-(2-fluoro-4-(5-methyl-3-oxo-2-phenyl-1-propyl-2,3-dihydro-1H-pyrazole-4-carboxamido)phenoxy)pyrimidin-4-yl)-4-methylpiperazine-1-carboxamide;

(R)-N-(4-(6-(3-(dimethylamino)pyrrolidine-1-carboxamido)pyrimidin-4-yloxy)-3-fluorophenyl)-5-methyl-3-oxo-2-phenyl-1-propyl-2,3-dihydro-1H-pyrazole-4-carboxamide;

(R)-N-(4-(6-aminopyrimidin-4-yloxy)-3-fluorophenyl)-1-(2-hydroxypropyl)-5-methyl-3-oxo-2-phenyl-2,3-dihydro-1H-pyrazole-4-carboxamide;

N-(3-fluoro-4-(2-(pyrrolidine-1-carboxamido)pyridin-4-yloxy)phenyl)-1,5-dimethyl-3-oxo-2-phenyl-2,3-dihydro-1H-pyrazole-4-carboxamide;

N-(4-(4-(1,5-dimethyl-3-oxo-2-phenyl-2,3-dihydro-1H-pyrazole-4-carboxamido)-2-fluorophenoxy)pyridin-2-yl)piperidine-1-carboxamide;

(R)-N-(4-(2-(3-(dimethylamino)pyrrolidine-1-carboxamido)pyridin-4-yloxy)-3-fluorophenyl)-1,5-dimethyl-3-oxo-2-phenyl-2,3-dihydro-1H-pyrazole-4-carboxamide;

N-(3-fluoro-4-(2-(pyrrolidine-1-carboxamido)pyridin-4-yloxy)phenyl)-1-(2-hydroxy-2-methylpropyl)-5-methyl-3-oxo-2-phenyl-2,3-dihydro-1H-pyrazole-4-carboxamide;

N-(3-fluoro-4-(2-(pyrrolidine-1-carboxamido)pyridin-4-yloxy)phenyl)-5-methyl-3-oxo-2-phenyl-1-propyl-2,3-dihydro-1H-pyrazole-4-carboxamide;

N-(4-(4-(1,5-dimethyl-3-oxo-2-phenyl-2,3-dihydro-1H-pyrazole-4-carboxamido)-2-fluorophenoxy)pyridin-2-yl)morpholine-4-carboxamide;

N-(4-(2-fluoro-4-(1-(2-hydroxy-2-methylpropyl)-5-methyl-3-oxo-2-phenyl-2,3-dihydro-1H-pyrazole-4-carboxamido)phenoxy)pyridin-2-yl)piperidine-1-carboxamide;

5-methyl-N-(4-((7-(methyloxy)-4-quinolinyl)methyl)phenyl)-3-oxo-2-phenyl-1-propyl-2,3-dihydro-1H-pyrazole-4-carboxamide;

N-(4-(hydroxy(7-methoxyquinolin-4-yl)methyl)phenyl)-5-methyl-3-oxo-2-phenyl-1-propyl-2,3-dihydro-1H-pyrazole-4-carboxamide;

1,5-dimethyl-N-(5-((7-(methyloxy)-4-quinolinyl)oxy)-2-pyrimidinyl)-3-oxo-2-phenyl-2,3-dihydro-1H-pyrazole-4-carboxamide;

5-methyl-N-(4-((7-(methyloxy)-4-quinolinyl)sulfinyl)phenyl)-3-oxo-2-phenyl-1-propyl-2,3-dihydro-1H-pyrazole-4-carboxamide 1-(2-hydroxy-2-methylpropyl)-5-methyl-N-(4-((7-(methyloxy)-4-quinolinyl)thio)phenyl)-3-oxo-2-phenyl-2,3-dihydro-1H-pyrazole-4-carboxamide 5-methyl-N-(4-((7-(methyloxy)-4-quinolinyl)thio)phenyl)-3-oxo-2-phenyl-1-propyl-2,3-dihydro-1H-pyrazole-4-carboxamide 5-methyl-N-(3-((7-(methyloxy)-4-quinolinyl)oxy)propyl)-3-oxo-2-phenyl-1-propyl-2,3-dihydro-1H-pyrazole-4-carboxamide;

5-methyl-N-(trans-4-((7-(methyloxy)-4-quinolinyl)oxy)cyclohexyl)-3-oxo-2-phenyl-1-propyl-2,3-dihydro-1H-pyrazole-4-carboxamide;

5-methyl-N-(cis-4-((7-(methyloxy)-4-quinolinyl)oxy)cyclohexyl)-3-oxo-2-phenyl-1-propyl-2,3-dihydro-1H-pyrazole-4-carboxamide;

1-(2-hydroxy-2-methylpropyl)-5-methyl-N-(trans-4-((7-(methyloxy)-4-quinolinyl)oxy)cyclohexyl)-3-oxo-2-phenyl-2,3-dihydro-1H-pyrazole-4-carboxamide 5-methyl-N-(4-((7-(methyloxy)-4-quinolinyl)amino)phenyl)-3-oxo-2-phenyl-1-propyl-2,3-dihydro-1H-pyrazole-4-carboxamide;

5-methyl-N-(5-((7-(methyloxy)-4-quinolinyl)oxy)-2-pyrimidinyl)-3-oxo-2-phenyl-1-propyl-2,3-dihydro-1H-pyrazole-4-carboxamide;

N-(3-fluoro-4-((7-(methyloxy)-4-quinolinyl)amino)phenyl)-1-(2-hydroxy-2-methylpropyl)-5-methyl-3-oxo-2-phenyl-2,3-dihydro-1H-pyrazole-4-carboxamide;

1-(2-hydroxy-2-methylpropyl)-5-methyl-4-((7-((7-(methyloxy)-4-quinolinyl)oxy)-2,3-dihydro-4H-1,4-benzoxazin-4-yl)carbonyl)-2-phenyl-1,2-dihydro-3H-pyrazol-3-one;

1-(2-hydroxy-2-methylpropyl)-5-methyl-N-(4-((7-(methyloxy)-4-quinolinyl)amino)phenyl)-3-oxo-2-phenyl-2,3-dihydro-1H-pyrazole-4-carboxamide;

N-(4-(6,7-dimethoxyquinolin-4-yloxy)-3-fluorophenyl)-3-hydroxy-2-(1-oxoisoindolin-2-yl)propanamide;

N-(4-(6,7-dimethoxyquinolin-4-yloxy)-3-fluorophenyl)-2-(1-oxoisoindolin-2-yl)acetamide;

N-(4-(6,7-dimethoxyquinolin-4-yloxy)-3-fluorophenyl)-2-oxo-1,5-diphenyl-1,2-dihydropyridine-3-carboxamide;

N-(5-((6,7-bis(methyloxy)-4-quinolinyl)oxy)-2-pyridinyl)-6-oxo-1-(phenylmethyl)-1,1',2',3',6,6'-hexahydro-3,4'-bipyridine-5-carboxamide;

N-(5-((6,7-bis(methyloxy)-4-quinolinyl)oxy)-2-pyridinyl)-6-oxo-1-(phenylmethyl)-1,6-dihydro-3,3'-bipyridine-5-carboxamide;

N-(5-((6,7-bis(methyloxy)-4-quinolinyl)oxy)-2-pyridinyl)-6'-oxo-1'-(phenylmethyl)-1',6'-dihydro-2,3'-bipyridine-5'-carboxamide N-(5-((6,7-bis(methyloxy)-4-quinolinyl)oxy)-2-pyridinyl)-2-oxo-1-(phenylmethyl)-5-(2-thienyl)-1,2-dihydro-3-pyridinecarboxamide;

N-(5-((6,7-bis(methyloxy)-4-quinolinyl)oxy)-2-pyridinyl)-2-oxo-1-(phenylmethyl)-5-(2-pyrazinyl)-1,2-dihydro-3-pyridinecarboxamide;

N-(5-((6,7-bis(methyloxy)-4-quinolinyl)oxy)-2-pyridinyl)-5-methyl-2-oxo-1-(phenylmethyl)-1,2-dihydro-3-pyridinecarboxamide;

N-(4-((6,7-bis(methyloxy)-4-quinolinyl)oxy)-3-fluorophenyl)-5-bromo-1-(3-methylphenyl)-2-oxo-1,2-dihydro-3-pyridinecarboxamide;

N-(4-((6,7-bis(methyloxy)-4-quinolinyl)oxy)-3-fluorophenyl)-5-(1-methyl-1H-pyrazol-4-yl)-2-oxo-1-phenyl-1,2-dihydro-3-pyridinecarboxamide;

N-(3-fluoro-4-((6-(methyloxy)-7-((3-(4-morpholinyl)propyl)oxy)-4-quinolinyl)oxy)phenyl)-2-oxo-5-phenyl-1-(phenylmethyl)-1,2-dihydro-3-pyridinecarboxamide;

1,1-dimethylethyl 5-(((5-((6,7-bis(methyloxy)-4-quinolinyl)oxy)-2-pyridinyl)amino)carbonyl)-6-oxo-1-(phenylmethyl)-1,3',6,6'-tetrahydro-3,4'-bipyridine-1'(2'H)-carboxylate;

N-(4-((6,7-bis(methyloxy)-4-quinolinyl)oxy)-3-fluorophenyl)-2-oxo-1-(phenylmethyl)-5-(2-pyrimidinyl)-1,2-dihydro-3-pyridinecarboxamide;

N-(4-((6,7-bis(methyloxy)-4-quinolinyl)oxy)-3-fluorophenyl)-2-oxo-1-phenyl-5-(1H-pyrazol-4-yl)-1,2-dihydro-3-pyridinecarboxamide;

1-benzyl-5-bromo-N-(2-chloro-4-(6,7-dimethoxyquinolin-4-yloxy)phenyl)-2-oxo-1,2-dihydropyridine-3-carboxamide;

N-(5-(7-methoxyquinolin-4-yloxy)pyridin-2-yl)-2-oxo-1-phenyl-5-(pyridin-3-yl)-1,2-dihydropyridine-3-carboxamide;

N-(5-(7-methoxyquinolin-4-yloxy)pyridin-2-yl)-2-oxo-1-phenyl-5-(pyrazin-2-yl)-1,2-dihydropyridine-3-carboxamide;

N-(5-(6,7-dimethoxyquinolin-4-yloxy)pyridin-2-yl)-2-oxo-1-phenyl-5-(pyridin-3-yl)-1,2-dihydropyridine-3-carboxamide;

N-(5-(6,7-dimethoxyquinolin-4-yloxy)pyridin-2-yl)-2-oxo-1-phenyl-5-(pyrazin-2-yl)-1,2-dihydropyridine-3-carboxamide;

N-(5-(6,7-dimethoxyquinolin-4-yloxy)pyridin-2-yl)-2-oxo-1-phenyl-5-(thiophen-2-yl)-1,2-dihydropyridine-3-carboxamide;

5-benzyl-N-(5-(6,7-dimethoxyquinolin-4-yloxy)pyridin-2-yl)-2-oxo-1-phenyl-1,2-dihydropyridine-3-carboxamide;

tert-butyl 4-(5-((5-(6,7-dimethoxyquinolin-4-yloxy)pyridin-2-yl)carbamoyl)-6-oxo-1-phenyl-1,6-dihydropyridin-3-yl)-5,6-dihydropyridine-1(2H)-carboxylate;

5-bromo-N-(2-chloro-4-(6,7-dimethoxyquinolin-4-yloxy)phenyl)-2-oxo-1-phenyl-1,2-dihydropyridine-3-carboxamide;

N-(5-(6,7-dimethoxyquinolin-4-yloxy)pyridin-2-yl)-4-(2-methoxyethylamino)-2-oxo-1-phenyl-1,2-dihydropyridine-3-carboxamide;

N-(5-(6,7-dimethoxyquinolin-4-yloxy)pyridin-2-yl)-2-oxo-1-phenyl-4-(tetrahydro-2H-pyran-4-ylamino)-1,2-dihydropyridine-3-carboxamide;

N-(5-(6,7-dimethoxyquinolin-4-yloxy)pyridin-2-yl)-2-oxo-1-phenyl-4-(phenylamino)-1,2-dihydropyridine-3-carboxamide;

N-(5-(6,7-dimethoxyquinolin-4-yloxy)pyridin-2-yl)-4-(4-methylpiperazin-1-yl)-2-oxo-1-phenyl-1,2-dihydropyridine-3-carboxamide;

N-(5-(6,7-dimethoxyquinolin-4-yloxy)pyridin-2-yl)-4-(methylamino)-2-oxo-1-phenyl-1,2-dihydropyridine-3-carboxamide;

N-(5-(6,7-dimethoxyquinolin-4-yloxy)pyridin-2-yl)-4-(dimethylamino)-2-oxo-1-phenyl-1,2-dihydropyridine-3-carboxamide;

4-(2-methoxyethylamino)-N-(5-(7-methoxyquinolin-4-yloxy)pyridin-2-yl)-2-oxo-1-phenyl-1,2-dihydropyridine-3-carboxamide;

N-(3-fluoro-4-(7-methoxyquinolin-4-yloxy)phenyl)-4-(2-methoxyethylamino)-2-oxo-1-phenyl-1,2-dihydropyridine-3-carboxamide N-(4-((6,7-bis(methyloxy)-4-quinolinyl)oxy)-3-fluorophenyl)-1-cyclopentyl-6-oxo-5-(2-oxo-1-pyrrolidinyl)-1,6-dihydro-3-pyridinecarboxamide;

1-benzyl-N-(5-(6,7-dimethoxyquinolin-4-yloxy)pyridin-2-yl)-4-(2-methoxyethylamino)-2-oxo-1,2-dihydropyridine-3-carboxamide;

1-benzyl-N-(5-(6,7-dimethoxyquinolin-4-yloxy)pyridin-2-yl)-4-(dimethylamino)-2-oxo-1,2-dihydropyridine-3-carboxamide;

1-benzyl-N-(5-(6,7-dimethoxyquinolin-4-yloxy)pyridin-2-yl)-4-(methylamino)-2-oxo-1,2-dihydropyridine-3-carboxamide;

1-benzyl-N-(5-(6,7-dimethoxyquinolin-4-yloxy)pyridin-2-yl)-2-oxo-4-(phenylamino)-1,2-dihydropyridine-3-carboxamide;

1-benzyl-N-(5-(6,7-dimethoxyquinolin-4-yloxy)pyridin-2-yl)-2-oxo-4-(pyridin-4-ylamino)-1,2-dihydropyridine-3-carboxamide;

1-benzyl-N-(5-(6,7-dimethoxyquinolin-4-yloxy)pyridin-2-yl)-4-(4-methylpiperazin-1-yl)-2-oxo-1,2-dihydropyridine-3-carboxamide;

1-benzyl-N-(5-(6,7-dimethoxyquinolin-4-yloxy)pyridin-2-yl)-2-oxo-4-(tetrahydro-2H-pyran-4-ylamino)-1,2-dihydropyridine-3-carboxamide;

1-benzyl-N-(5-(6,7-dimethoxyquinolin-4-yloxy)pyridin-2-yl)-2-oxo-4-(4-(trifluoromethyl)phenylamino)-1,2-dihydropyridine-3-carboxamide;

1-cyclopentyl-N-(4-(6,7-dimethoxyquinolin-4-yloxy)-3-fluorophenyl)-6-oxo-5-(2-oxopyrrolidin-1-yl)-1,6-dihydropyridine-3-carboxamide;

N-(3-fluoro-4-(2-(pyrrolidine-1-carboxamido)pyridin-4-yloxy)phenyl)-3-oxo-2-phenyl-2,3-dihydropyridazine-4-carboxamide;

6-((diethylamino)methyl)-N-(4-(6,7-dimethoxyquinolin-4-yloxy)-3-fluorophenyl)-3-oxo-2-phenyl-2,3-dihydropyridazine-4-carboxamide;

6-((dimethylamino)methyl)-N-(3-fluoro-4-(7-methoxyquinolin-4-yloxy)phenyl)-3-oxo-2-phenyl-2,3-dihydropyridazine-4-carboxamide;

N-(3-fluoro-4-(7-methoxyquinolin-4-yloxy)phenyl)-6-methyl-3-oxo-2-phenyl-2,3-dihydropyridazine-4-carboxamide;

N-(5-(6,7-dimethoxyquinolin-4-yloxy)pyridin-2-yl)-6-methyl-3-oxo-2-phenyl-2,3-dihydropyridazine-4-carboxamide;

2-benzyl-N-(5-(6,7-dimethoxyquinolin-4-yloxy)pyridin-2-yl)-6-methyl-3-oxo-2,3-dihydropyridazine-4-carboxamide;

N-(3-fluoro-4-(7-methoxyquinolin-4-yloxy)phenyl)-3-oxo-2-phenyl-2,3-dihydropyridazine-4-carboxamide;

N-(2-chloro-4-(6,7-dimethoxyquinolin-4-yloxy)phenyl)-6-methyl-3-oxo-2-phenyl-2,3-dihydropyridazine-4-carboxamide;

(R)-N-(4-(6,7-dimethoxyquinolin-4-yloxy)-3-fluorophenyl)-6-(((3-(dimethylamino)pyrrolidin-1-yl)methyl)-3-oxo-2-phenyl-2,3-dihydropyridazine-4-carboxamide;

3-benzyl-N-(4-(6,7-dimethoxyquinolin-4-yloxy)-3-fluorophenyl)-2-oxoimidazolidine-1-carboxamide;

N-(4-(6,7-dimethoxyquinolin-4-yloxy)-3-fluorophenyl)-5-((dimethylamino)methyl)-2-oxo-3-phenyl-tetrahydropyrimidine-1(2H)-carboxamide;

N-(3-Fluoro-4-(7-methoxyquinolin-4-yloxy)phenyl)-3-oxo-4-phenylmorpholine-2-carboxamide;

N-(5-(7-methoxyquinolin-4-yloxy)pyridin-2-yl)-1-methyl-3-oxo-2-phenyl-2,3-dihydro-1H-pyrazole-4-carboxamide; and N-(3-Fluoro-4-(7-methoxyquinolin-4-yloxy)phenyl)-3-oxo-4-phenylmorpholine-2-carboxamide.

INDICATIONS

Compounds of the present invention would be useful for, but not limited to, the prevention or treatment of angiogenesis related diseases. The compounds of the invention have kinase inhibitory activity, such as VEGFR/KDR and/or c-Met inhibitory activity. The compounds of the invention are useful in therapy as antineoplasia agents or to minimize deleterious effects of VEGF and/or HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, lck, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

DEFINITIONS

"Angiogenesis" is defined as any alteration of an existing vascular bed or the formation of new vasculature, which benefits tissue perfasion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-II" includes any sub formulas.

The compounds of the invention are endowed with kinase inhibitory activity, such as KDR and/or c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR and/or c-Met.

The present invention comprises a pharmaceutical composition comprising a therapeutically effective amount of a compound of Formulas I-II in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of Formula I-II.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AI, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphirin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-SN, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin 1, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including
N-(4-chlorophenyl)-4-(4-pyridinylmethyl)-1-phthalazinamine;
4-[4-[[[[4-chloro-3-(trifluoromethyl)phenyl]amino]carbonyl]amino]phenoxy]-N-methyl-2-pyridinecarboxamide;
N-[2-(diethylamino)ethyl]-5-[(5-fluoro-1,2-dihydro-2-oxo-3H-indol-3-ylidene)methyl]-2,4-dimethyl-1H-pyrrole-3-carboxamide;
3-[(4-bromo-2,6-difluorophenyl)methoxy]-5-[[[[4-(1-pyrrolidinyl)butyl]amino]carbonyl]amino]-4-isothiazolecarboxamide;
N-(4-bromo-2-fluorophenyl)-6-methoxy-7-[(1-methyl-4-piperidinyl)methoxy]-4-quinazolinamine;
3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;
N-[5-[[[5-(1,1-dimethylethyl)-2-oxazolyl]methyl]thio]-2-thiazolyl]-4-piperidinecarboxamide;
N-[3-chloro-4-[(3-fluorophenyl)methoxy]phenyl]-6-[5-[[[2-(methylsulfonyl)ethyl]amino]methyl]-2-furanyl]-4-quinazolinamine
4-[(4-Methyl-1-piperazinyl)methyl]-N-[4-methyl-3-[[4-(3-pyridinyl)-2-pyrimidinyl]amino]-phenyl]benzamide
N-(3-chloro-4-fluorophenyl)-7-methoxy-6-[3-(4-morpholinyl)propoxy]-4-quinazolinamine
N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;
2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;
N-[3-(Azetidin-3-ylmethoxy)-5-trifluoromethyl-phenyl]-2-(4-fluoro-benzylamino)-nicotinamide.
6-fluoro-N-(4-(1-methylethyl)phenyl)-2-((4-pyridinylmethyl)amino)-3-pyridinecarboxamide;
2-((4-pyridinylmethyl)amino)-N-(3-(((2S)-2-pyrrolidinylmethyl)oxy)-5-(trifluoromethyl)phenyl)-3-pyridinecarboxamide;
N-(3-(1,1-dimethylethyl)-1H-pyrazol-5-yl)-2-((4-pyridinylmethyl)amino)-3-pyridinecarboxamide;
N-(3,3-dimethyl-2,3-dihydro-1-benzofuran-6-yl)-2-((4-pyridinylmethyl)amino)-3-pyridinecarboxamide;
N-(3-((((2S)-1-methyl-2-pyrrolidinyl)methyl)oxy)-5-(trifluoromethyl)phenyl)-2-((4-pyridinylmethyl)amino)-3-pyridinecarboxamide;
2-((4-pyridinylmethyl)amino)-N-(3-((2-(1-pyrrolidinyl)ethyl)oxy)-4-(trifluoromethyl)phenyl)-3-pyridinecarboxamide;
N-(3,3-dimethyl-2,3-dihydro-1H-indol-6-yl)-2-((4-pyridinylmethyl)amino)-3-pyridinecarboxamide;
N-(4-(pentafluoroethyl)-3-(((2S)-2-pyrrolidinylmethyl)oxy)phenyl)-2-((4-pyridinylmethyl)amino)-3-pyridinecarboxamide;
N-(3-((3-azetidinylmethyl)oxy)-5-(trifluoromethyl)phenyl)-2-((4-pyridinylmethyl)amino)-3-pyridinecarboxamide;
N-(3-(4-piperidinyloxy)-5-(trifluoromethyl)phenyl)-2-((2-(3-pyridinyl)ethyl)amino)-3-pyridinecarboxamide;
N-(4,4-dimethyl-1,2,3,4-tetrahydro-isoquinolin-7-yl)-2-(1H-indazol-6-ylamino)-nicotinamide;
2-(1H-indazol-6-ylamino)-N-[3-(1-methylpyrrolidin-2-ylmethoxy)-5-trifluoromethyl-phenyl]-nicotinamide;
N-[1-(2-dimethylamino-acetyl)-3,3-dimethyl-2,3-dihydro-1H-indol-6-yl]-2-(1H-indazol-6-ylamino)-nicotinamide;
2-(1H-indazol-6-ylamino)-N-[3-(pyrrolidin-2-ylmethoxy)-5-trifluoromethyl-phenyl]-nicotinamide;
N-(1-acetyl-3,3-dimethyl-2,3-dihydro-1H-indol-6-yl)-2-(1H-indazol-6-ylamino)-nicotinamide;
N-(4,4-dimethyl-1-oxo-1,2,3,4-tetrahydro-isoquinolin-7-yl)-2-(1H-indazol-6-ylamino)-nicotinamide;
N-[4-(tert-butyl)-3-(3-piperidylpropyl)phenyl][2-(1H-indazol-6-ylamino)(3-pyridyl)]carboxamide;
N-[5-(tert-butyl)isoxazol-3-yl][2-(1H-indazol-6-ylamino)(3-pyridyl)]carboxamide; and
N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070);

ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering A G, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering A G, Germany); ZK Angio, (Schering A G, Germany); ZK 229561, (Novartis, Switzerland, and Schering A G, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT I (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I-II.

Also included in the family of compounds of Formula I-II are the pharmaceutically acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of Formula I-II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-II include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-II. When a basic group and an acid group are present in the same molecule, a compound of Formula I-II may also form internal salts.

GENERAL SYNTHETIC PROCEDURES

The compounds of the invention can be synthesized according to the following procedures of Schemes 1-10, wherein the substituents are as defined for Formulas I-II, above, except where further noted.

The following abbreviations are used throughout the specification:

HOAc—acetic acid
MeCN, $CH_3CN$—acetonitrile
$NH_3$—ammonia
$NH_4Cl$—ammonium chloride
Ar—argon
HBTA—O-benzotriazol-1-yl-N,N,N',N'-tetramethyluronium hexafluorophosphate
HATU—O-(7-azabenzotriazol-1-yl)-N,N,N',N'-tetramethyluronium hexafluorophosphate
PyBop—benzotriazol-1-yl-oxy-tripyrrolidino-phosphonium hexafluorophosphate
$Pd_2(dba)_3$—bis(dibenzylideneacetone) palladium
BINAP—2,2'-bis(diphenylphosphino)-1,1'-binaphthyl
TEAC—bis(tetra-ethylammonium)carbonate
$BBr_3$—boron tribromide
BSA—bovine serum albumin
$Br_2$—bromine
BOC—butyloxycarbonyl
$Cs_2CO_3$—cesium carbonate
$CHCl_3$—chloroform
$CDCl_3$—chloroform deuterated
Cu—copper
CuI—copper(I) iodide
$Et_2O$—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
$H_2$—hydrogen
$H_2O_2$—hydrogen peroxide
Fe—iron
LiHMDS—lithium bis(trimethylsilyl)-amide
LDA—Lithium diisopropylamide
MCPBA—meta-chloroperbenzoic acid
$MgSO_4$—magnesium sulfate
MeOH, $CH_3OH$—methanol
MeI—methyl iodide
$CH_2Cl_2$, DCM—methylene chloride
NMP—N-methylpyrrolidinone
ML, ml—milliliter
$N_2$—nitrogen
Pd/C—palladium on carbon
$Pd(OAc)_2$—palladium acetate
$Pd(OH)_2$—palladium hydroxide
$Pd(PPh_3)_4$— palladium tetrakis triphenylphosphine
$Pd(dppf)C_{12}$—1,1-bis(diphenylphosphino)ferrocene palladium chloride
PBS—phosphate buffered saline
$POCl_3$—phosphorous oxychloride
$K_2CO_3$—potassium carbonate
KOH—potassium hydroxide
RT—room temperature
$NaHCO_3$—sodium bicarbonate
$NaBH_4$—sodium borohydride
$NaBH_3CN$—sodium cyanoborohydride
NaOtBu—sodium tert-butoxide
NaOH—sodium hydroxide
$NaClO_2$—sodium chlorite
NaCl—sodium chloride
$NaHPO_4$—sodium biphospate
NaH—sodium hydride
NaI—sodium iodide
$Na_2SO_4$—sodium sulfate
TBTU—O-benzotriazol-1-yl-N,N,N',N'-tetramethyluronium tetrafluoroborate
THF—tetrahydrofuran
$Et_3N$, TEA—triethylamine
TFA—trifluoroacetic acid
$P(t-bu)_3$—tri(tert-butyl)phosphine
$H_2O$—water Scheme 1

R-halo + HX—W—$NO_2$ $\xrightarrow[\text{base}]{\text{DMAP}}$ R—X—W—$NO_2$ $\xrightarrow{\text{reduction}}$
1             2                                    3

R—X—W—$NH_2$
4

HATU $\downarrow R^1$—OH

R—X—W—Y—$R^1$
5

Substituted compounds 5, where Y is —NH—C(=O)—, can be prepared by the process outlined in Scheme 1. The halo substituted ring R-halo 1, is condensed with an alcohol 2 (where X is O) is heated, preferably in the presence of a catalyst such as DMAP, solvent such as dioxane, and base, such as pyridine to form the ether 3. Preferably the reaction is heated above RT, more preferably above 75° C., even more preferably at about 110° C. The nitro compound 3 is reduced to the amine 4 such as by treatment with Fe, HCl and an alcohol such as MeOH, in an appropriate solvent such as THF. The amine 4 is coupled with a carboxylic acid derivative $R^1$—OH, such as a carboxylic acid or anhydride, in the presence of a coupling agent such as HATU, or with PyBOP and base such as DIEA, to yield the desired compounds 5.

Scheme 2

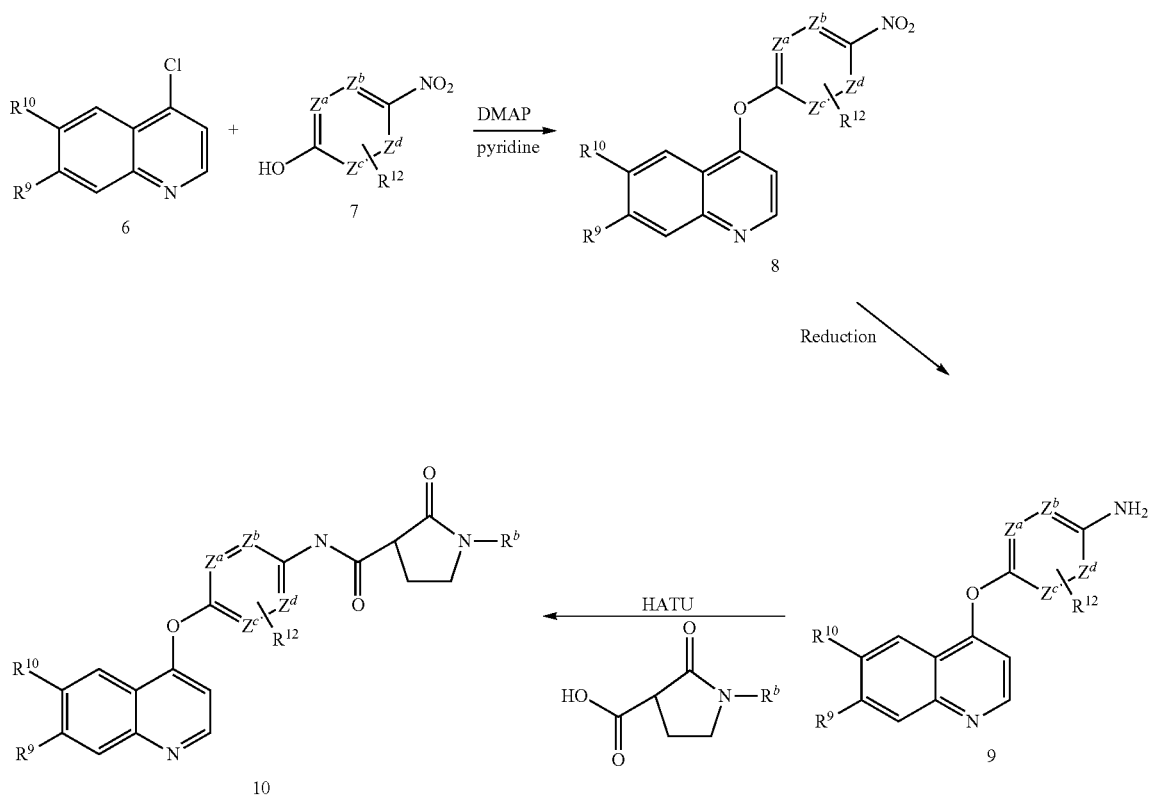

Alternatively, compounds of the invention where X is O and $R^1$ is 2-oxopyrrolyl can be prepared by the method described in Scheme 2. The halo substituted quinoline derivative 6, is condensed with alcohol 7 is heated, preferably in the presence of a catalyst such as DMAP, solvent such as dioxane, and base, such as pyridine to form ether 8. Preferably the reaction is heated above RT, more preferably above 75° C., even more preferably at about 110° C. The nitro compound 8 is reduced to the amine 9 such as by treatment with Fe, HCl and an alcohol such as MeOH, in an appropriate solvent such as THF. The amine 9 is coupled with a carboxylic acid, in the presence of a coupling agent such as HATU to yield the desired compounds 10.

Scheme 3

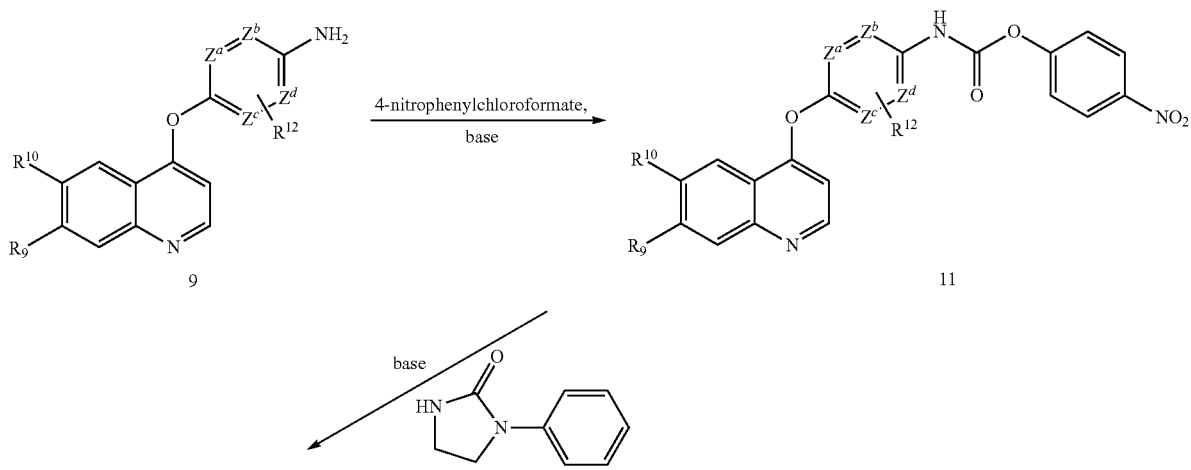

-continued

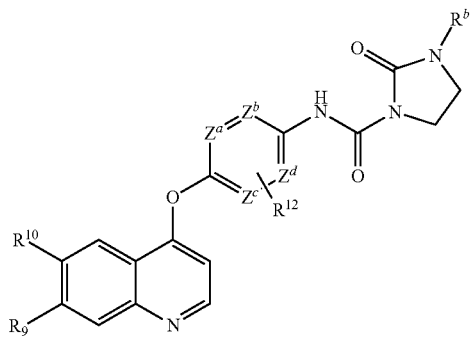

12

Alternatively, compounds of the invention where $R^1$ is 2-oxoimidazolyl can be prepared by the method described in Scheme 3. The amine 9 can be activated such as with a chloroformate to form the caarbamate 11. The substituted imidazolidin-2-one is treated with base, such as NaH, in an appropriate solvent such as DMF and added to the carbamate 11 to provide the desired compounds 12.

Compounds of the invention where $R^1$ is 2-oxopyrrolyl can be prepared by the method described in Scheme 4. The N-protected 2-oxopyrrolidine 13 is alkylated such as by treatment with base, e.g. LDA, in a suitable solvent such as THF, followed by addition of a compound with an appropriate leaving group, such as a halo substituent. The reaction temperature is preferably below RT, preferably at about 0° C. Following deprotection, such as by treatment with TFA, where the amine is protected with a BOC group, the free amine 15 is treated with a chloroformate in the presence of base, such as TEA, to form the active ester 16. Treatment with the ester 16 with an amine yields the desired amides 17.

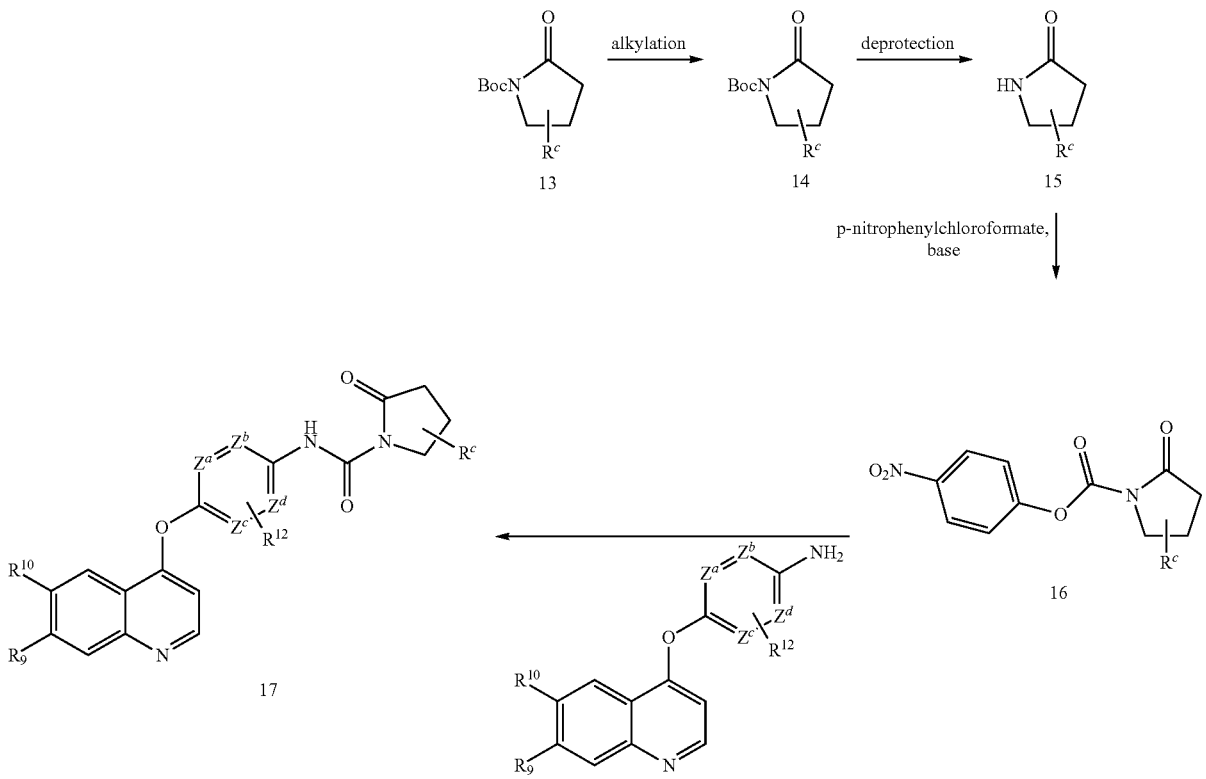

Scheme 5

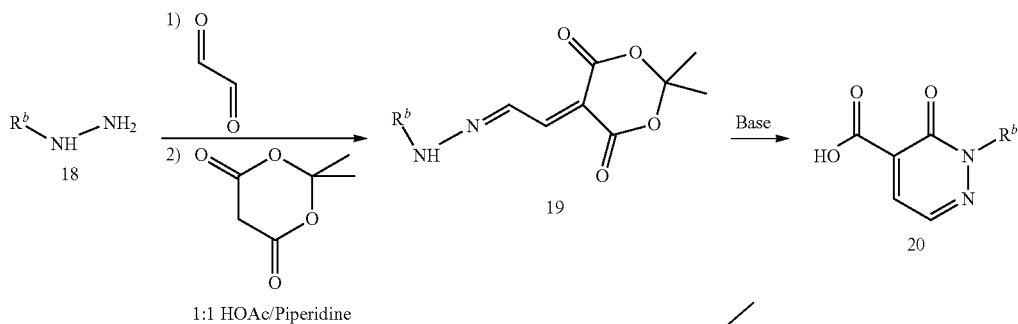

1:1 HOAc/Piperidine

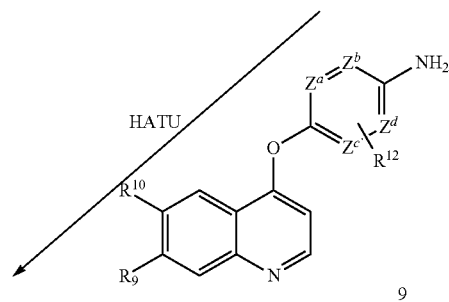

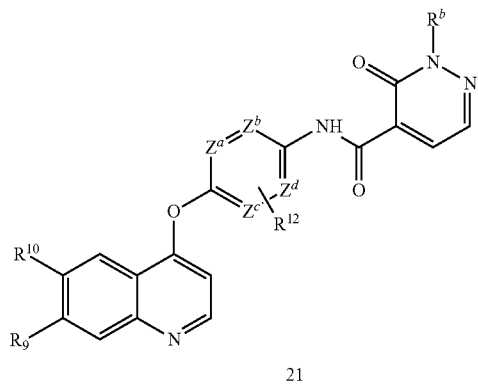

Substituted pyridazines 21 of the invention can be prepared by the method described in Scheme 5. Hydrazines 18 are reacted with oxaldehyde then with 2,2-dimethyl-1,3-dioxane-4,6-dione followed by acid, such as acetic acid, and piperidines, to form the diaza butadiene-4-ylidene 19. Cyclization, such as by treatment with base, e.g. sodium methoxide, yields the pyridazine carboxylic acid 20. The reaction is heated at a temperature above RT, preferably at about reflux. Formation of the desired amides 21 from the pyridazine 20 is by the coupling procedure described above, or with PyBOP and base such as DIEA.

Scheme 6

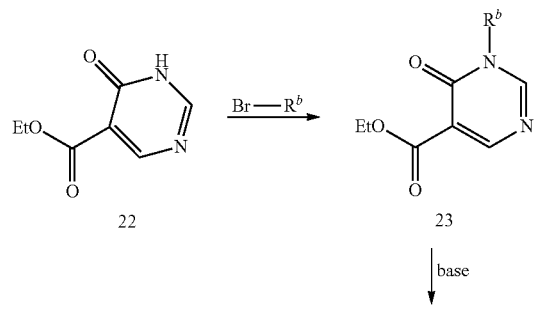

-continued

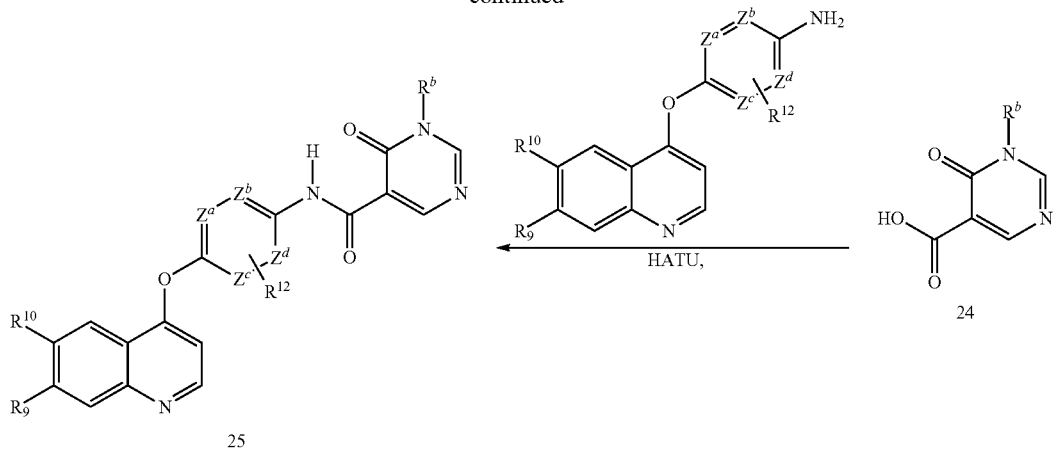

Substituted pyrimidines 25 of the invention can be prepared by the method described in Scheme 6. Alkylation of the oxo-1,6-dihydropyrimidine ester 22, such as by reaction with the appropriate halide in the presence of base, e.g. $K_2CO_3$, and a solvent such as DMF, provided the substituted pyrimidines 23. De-esterification of 23, such as by treatment with base, e.g. NaOH, provides the carboxylic acid 24, which can be coupled via the methods described above to provide the amides 25.

Substituted oxazolidine acetamides 28 of the invention can be prepared by the method described in Scheme 7. Treatment of the amine 9 with an activated acetyl compound, e.g. chloroacetyl chloride, such as in the presence of base, e.g. $NaHCO_3$, provides the chloroacetamide 26. The reaction is held at a temperature below RT, preferably at about 0° C. Treatment of the acetamide 26 with an amino-alcohol, at a temperature above RT, preferably above 50° C., more preferably at about 80° C., provides the substituted acetamide 27. Cyclization of the acetamide 27, such as by treatment with Scheme 7

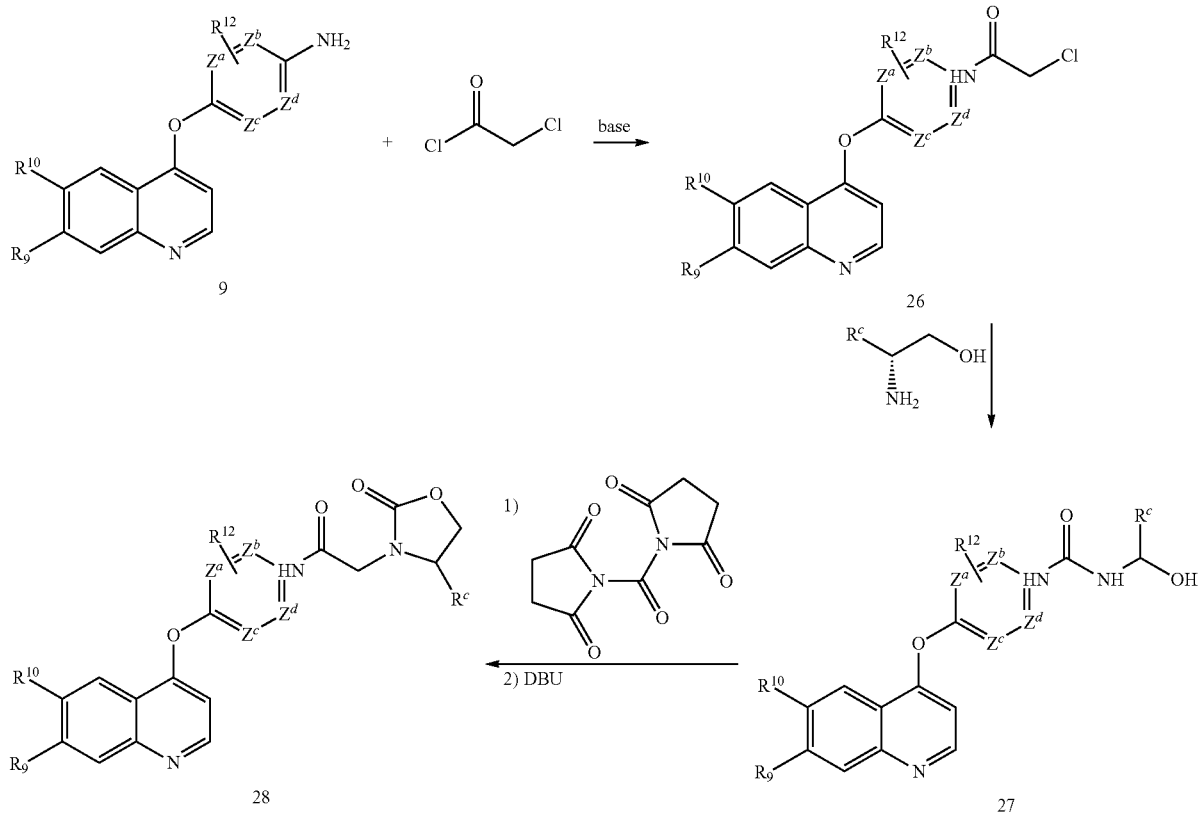

1-(2,5-dioxopyrrolidine-1-carbonyl)pyrrolidine-2,5-dione and DBU, yields the desired oxazoldine acetamides 28.

Scheme 8

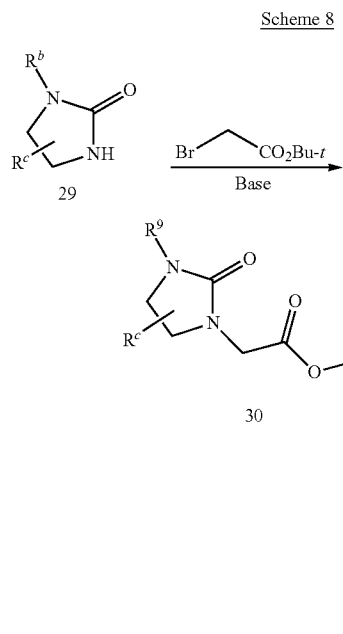

Imidazolidine acetic acids 31 of the invention can be prepared by the method described in Scheme 8. Alkylation of the imidazolidine 29, such as by treatment with base, e.g. NaH, followed by addition of the appropriate haloacetic acid ester provides the desired substituted imidazolidine 30. De-esterification of 30 such as by treatment with base, e.g. NaOH, provides the desired acetic acid 31, which can be coupled with an amine to provide the acetamides of the invention.

Scheme 9

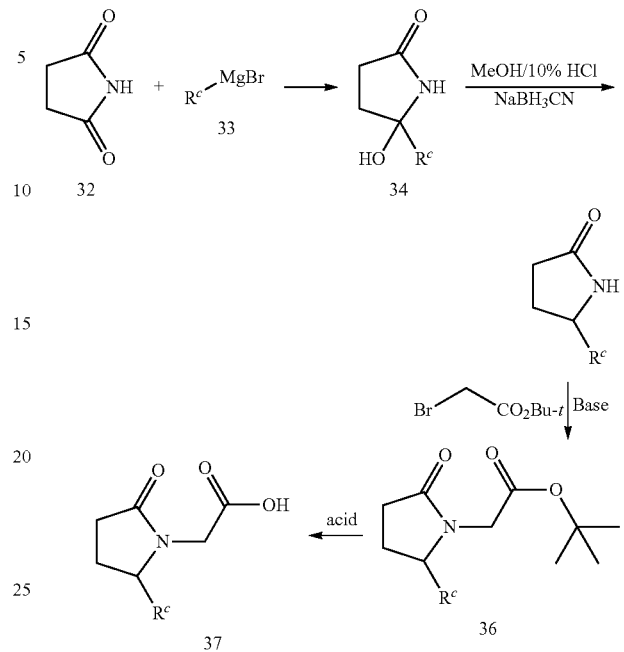

Similarly, pyrrolyl acetic acids 37 of the invention can be prepared by the method described in Scheme 9. Substituted hydroxyl-pyrroles 34, formed such as by Grignard reactions with pyrrolidine-2,5-dione and substituted magnesium bromides, are reduced, such with NaBH$_3$CN and acid, e.g. HCl, to provide the pyrrolidones 35. Alkylation of the pyrrolidone, such as with treatment with base, e.g. NaH, followed by addition of 2-haloacetates, provides the desired pyrrolidinyl acetates 36. De-esterification of 36, such as by treatment with acid, e.g. HCl, provides the desired pyrrolidinyl acetic acid 37 which can be treated with an amine as described above to provide the acetamides of the invention.

Scheme 10

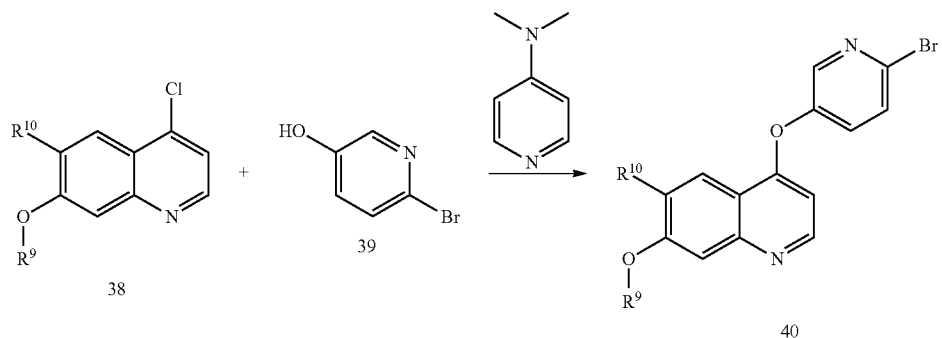

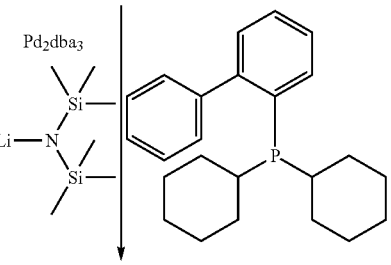

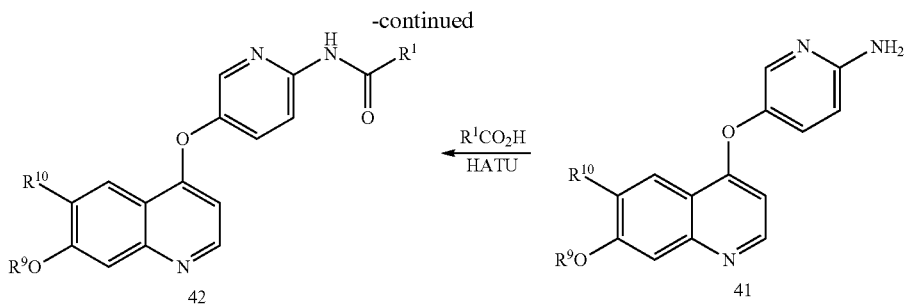

-continued

Alternatively, compounds of the invention where W is pyridyl can be prepared by the method described in Scheme 10. The halo substituted quinoline derivative 38, is condensed with alcohol 39, preferably in the presence of a catalyst such as DMAP, solvent such as dioxane, and base, such as pyridine to form ether 40. Preferably the reaction is heated above RT, more preferably above about 75° C., even more preferably at about 105° C. The halo compound 40 is converted to the amine 41 such as by treatment with LiHMDS, 2-(dicyclohexylphosphino)biphenyl and a palladium catalyst, such as $Pd_2(dba)_3$. Preferably the reaction is heated above RT, more preferably at about 65° C. The amine 41 is coupled with a carboxylic acid, in the presence of a coupling agent such as HBTU to yield the desired compounds 42.

The starting compounds defined in Schemes 1-10 may also be present with functional groups in protected form if necessary and/or in the form of salts, provided a salt-forming group is present and the reaction in salt form is possible. If so desired, one compound of Formula I can be converted into another compound of Formula I or a N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with hydrogen peroxide, oxone, or a peracid, e.g. mCPBA, in an inert solvent, e.g. $CH_2Cl_2$, or a mixture of $H_2O$ and an alcohol such as MeOH or EtOH, at a temperature between about −10-35° C., such as about 0° C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3, E. Gross and J. Meienhofer editors, Academic Press, London and New York (1981), in "Methoden der Organischen Chemie" (Methods of Organic Chemistry), Houben Weyl, 4$^{th}$ edition, Volume 15/1, Georg Thieme Verlag, Stuttgart (1974), in H.-D. Jakubke and H. Jescheit, "Aminosäuren, Peptide, Proteine" (Amino acids, Peptides, Proteins), Verlag Chemie, Weinheim, Deerfield Beach, and Basel (1982), and in Jochen Lehmann, "Chemie der Kohlenhydrate: Monosaccharide und Derivate" (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example, a dihalogenide of a compound of Formula I) may also be converted into a salt with one acid molecule per compound (for example, a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150° C., for example at about −80° C. to about 60° C., at RT, at about −20° C. to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example $H_2O$, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials, which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups, which do not participate in the reaction, should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

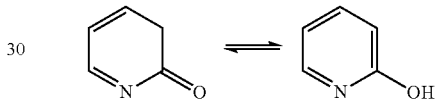

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, "Comprehensive Organic Transformations", VCH Publishers (1989); T. W. Greene and P. G. M. Wuts, "Protective Groups in Organic Synthesis", 3$^{rd}$ edition, John Wiley and Sons (1999); L. Fieser and M. Fieser, "Fieser and Fieser's Reagents for Organic Synthesis", John Wiley and Sons (1994); A. Katritzky and A. Pozharski, "Handbook of Heterocyclic Chemistry", 2$^{nd}$ edition (2001); M. Bodanszky, A. Bodanszky, "The Practice of Peptide Synthesis", Springer-Verlag, Berlin Heidelberg (1984); J. Seyden-Penne, "Reductions by the Alumino- and Borohydrides in Organic Synthesis", 2$^{nd}$ edition, Wiley-VCH, (1997); and L. Paquette, editor, "Encyclopedia of Reagents for Organic Synthesis", John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

These detailed descriptions fall within the scope, and serve to exemplify, the above-described General Synthetic Procedures, which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, CH$_2$Cl$_2$ and toluene were obtained from the Aldrich Chemical Company, EMD among others.

EXAMPLE 1

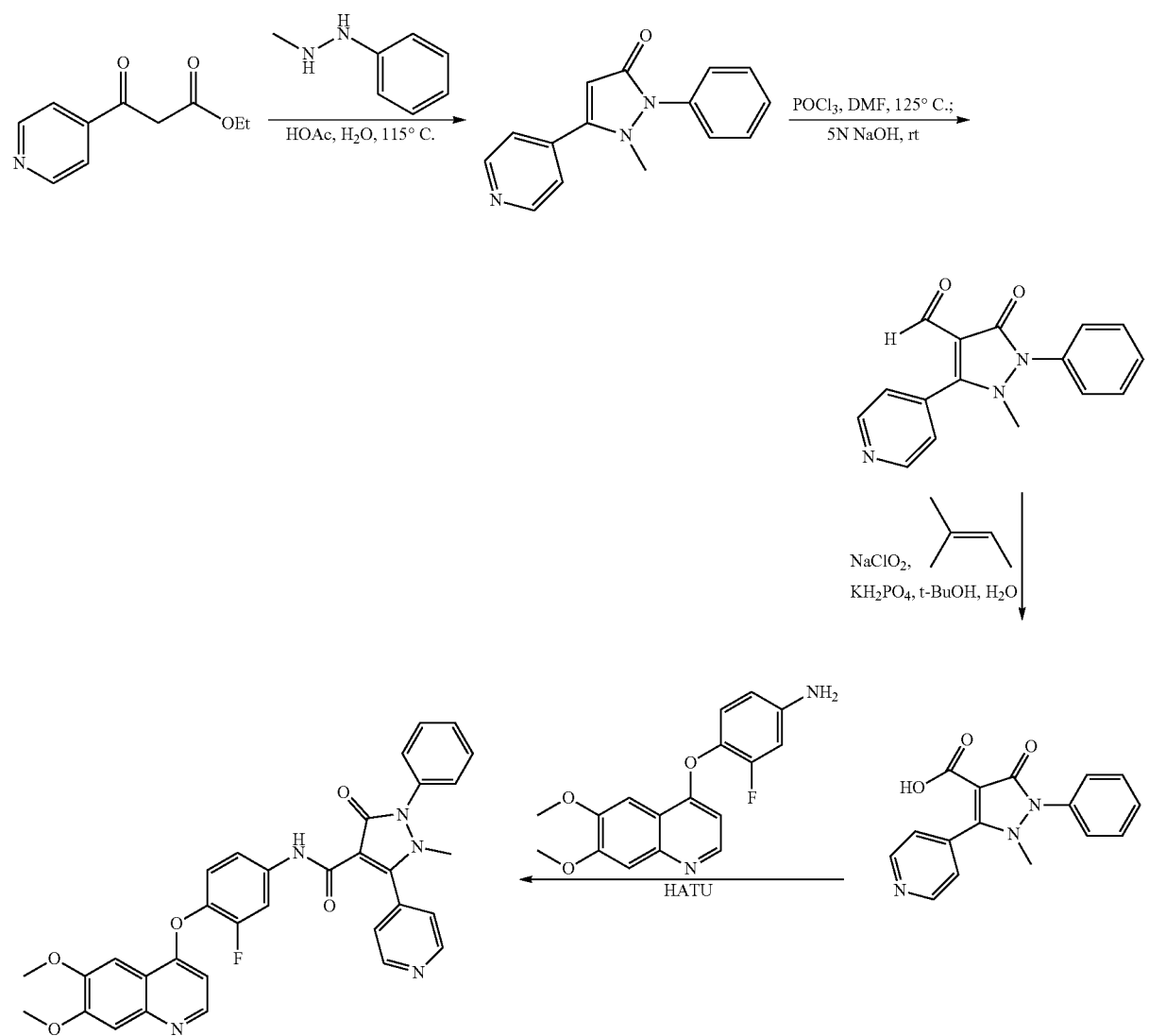

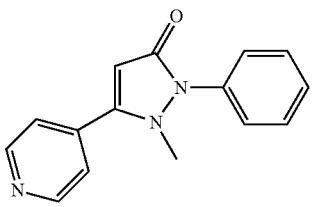

Step 1: 1-methyl-2-phenyl-5-(pyridin-4-yl)-1,2-dihydropyrazol-3-one. thyl isonicotinoylacetate (3.01 g, 16 mmol) and 1-methyl-2-phenylhydrazine (2.03 g, 17 mmol) were suspended in water (50 ml) and glacial acetic acid (1.35 ml, 23 mmol) was added. The flask was fitted with a reflux condenser and placed in a preheated oil bath (115 C) and stirred. After 4 hours, the reaction cooled to room temperature and extracted with EtOAc (2×100 ml; 50 ml), 10:1 DCM/MeOH (110 ml), and EtOAc again. The organic phases were combined, dried over sodium sulfate, filtered, and concentrated. The crude material was purified on silica gel (DCM->20:1->10:1 DCM/MeOH->10:1->4:1 DCM/2 N ammonia in MeOH). Fractions with product collected, concentrated, and repurified on silica gel using DCM->20:1 DCM/MeOH->5:1 DCM/2 N ammonia in MeOH). The fractions with product were collected and concentrated to give 1-methyl-2-phenyl-5-(pyridin-4-yl)-1,2-dihydropyrazol-3-one (3.31 g, 70% purity, 9.2 mmol, 59%). MS (ESI pos. ion) m/z: 252 (MH+). Calc'd exact mass for $C_{15}H_{13}N_3O$: 251.

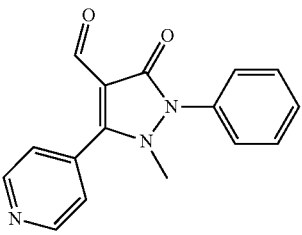

Step 2: 1-methyl-3-oxo-2-phenyl-5-(pyridin-4-yl)-2,3-dihydro-1H-pyrazole-4-carbaldehyde. To a 25 ml round-bottom flask with stirbar was added N,N-dimethylformamide (10.0 ml, 130 mmol). The flask was cooled in an ice water bath, and phosphorous oxychloride (4.2 ml, 45 mmol) was added. The reaction was warmed to room temperature and stirred under nitrogen. After 50 minutes, this was transferred, first via syringe and then pipette, to a solution of 1-methyl-2-phenyl-5-(pyridin-4-yl)-1,2-dihydropyrazol-3-one (3.31 g, 13 mmol) in DMF (18 ml). The flask was placed in a preheated oil bath (120 C), stirred for 12 minutes, and then cooled to room temperature. The reaction was poured into a aqueous solution of 5 N NaOH (40 ml) and diluted with ice water (~75 ml). More ice and water were added. The aqueous phase was extracted with chloroform and the organic extracts were dried over sodium sulfate, filtered, and concentrated. DMF present, so the crude material was diluted with chloroform and washed with water. The aqueous extractions were extracted with chloroform, and the organic layers were combined, dried over sodium sulfate, filtered, and concentrated to give the crude product. MS (ESI pos. ion) m/z: 280 (MH+). Calc'd exact mass for $C_{16}H_{13}N_3O_2$: 279. Material taken to next step without further purification.

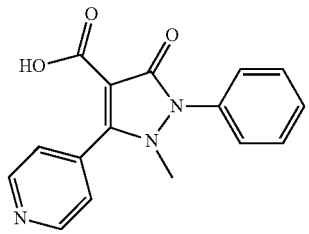

Step 3: 1-methyl-3-oxo-2-phenyl-5-(pyridin-4-yl)-2,3-dihydro-1H-pyrazole-4-carboxylic acid. The crude 1-methyl-3-oxo-2-phenyl-5-(pyridin-4-yl)-2,3-dihydro-1H-pyrazole-4-carbaldehyde was dissolved in t-BuOH (~70 ml) and 2-methyl-2-butene (25 ml, 236 mmol) was added, followed by sodium chlorite (2.43 g, 27 mmol) in water (30 ml) with ~5 ml water rinse. Then, potassium phosphate monobasic (10.35 g, 76 mmol) was added as a suspension in water (~70 ml), and the reaction was stirred at room temperature. After 9 hours, the reaction was poured into water (400 ml) and the aqueous phase was then extracted with EtOAc, DCM, and 10:1 DCM/MeOH exhaustively until most of the product had been extracted. The organic extracts were combined, dried over sodium sulfate, filtered, and concentrated to give desired 1-methyl-3-oxo-2-phenyl-5-(pyridin-4-yl)-2,3-dihydro-1H-pyrazole-4-carboxylic acid (1.98 g, 6.7 mmol, 52% yield over two steps). MS (ESI pos. ion) m/z: 296 (MH+). Calc'd exact mass for $C_{16}H_{13}N_3O_3$: 295.

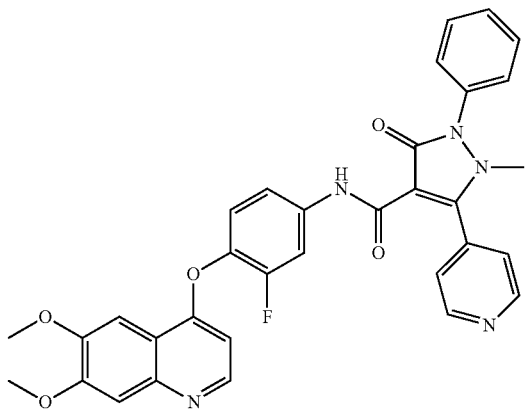

Step 4. N-(4-(6,7-dimethoxyquinolin-4-yloxy)-3-fluorophenyl)-1-methyl-3-oxo-2-phenyl-5-(pyridin-4-yl)-2,3-dihydro-1H-pyrazole-4-carboxamide. 4-(6,7-dimethoxyquinolin-4-yloxy)-3-fluorobenzenamine (628.9 mg, 2.001 mmol) and 1-methyl-3-oxo-2-phenyl-5-(pyridin-4-yl)-2,3-dihydro-1H-pyrazole-4-carboxylic acid (520 mg, 1.76 mmol) (1.679 g of a 30% by weight solution of acid in DMF) was dissolved in DCM (20 ml) and HATU (1.042 g, 2.740 mmol) was added. The reaction was stirred under nitrogen at room temperature overnight, and then filtered. The filtered solid was washed with dichloromethane, and the filtrate was concentrated and purified on silica gel (DCM->50:1->25:1->10:1 DCM/MeOH). The fractions with product were collected, concentrated, and purified on silica gel (30:1->20:1->10:1 DCM/MeOH). Fractions with product collected, concentrated, and purified again on silica gel (25:1->20:1 DCM/MeOH). Fractions with pure product collected and concentrated to give desired N-(4-(6,7-dimethoxyquinolin-4-yloxy)-3-fluorophenyl)-1-methyl-3-oxo-2-phenyl-5-(pyridin-4-yl)-2,3-dihydro-1H-pyrazole-4-carboxamide (225.9 mg, 0.382 mmol, 22% yield). MS (ESI pos. ion) m/z: 592 (MH+). Calc'd exact mass for $C_{33}H_{26}FN_5O_5$: 591. $^1$H NMR (400 MHz, CDCl$_3$): 10.96 (s, 1H), 8.88 (d, J=4.0 Hz, 2H), 8.48 (d, J=6.0 Hz, 1H), 7.83 (d, J=12 Hz, 1H), 7.65-7.47 (m, 8H), 7.41 (s, 1H), 7.30 (d, J=10.0 Hz, 1H), 7.16 (t, J=8.0 Hz, 1H), 6.40 (d, J=5.2 Hz, 1H), 4.05 (s, 6H), 3.20 (s, 3H).

EXAMPLE 2

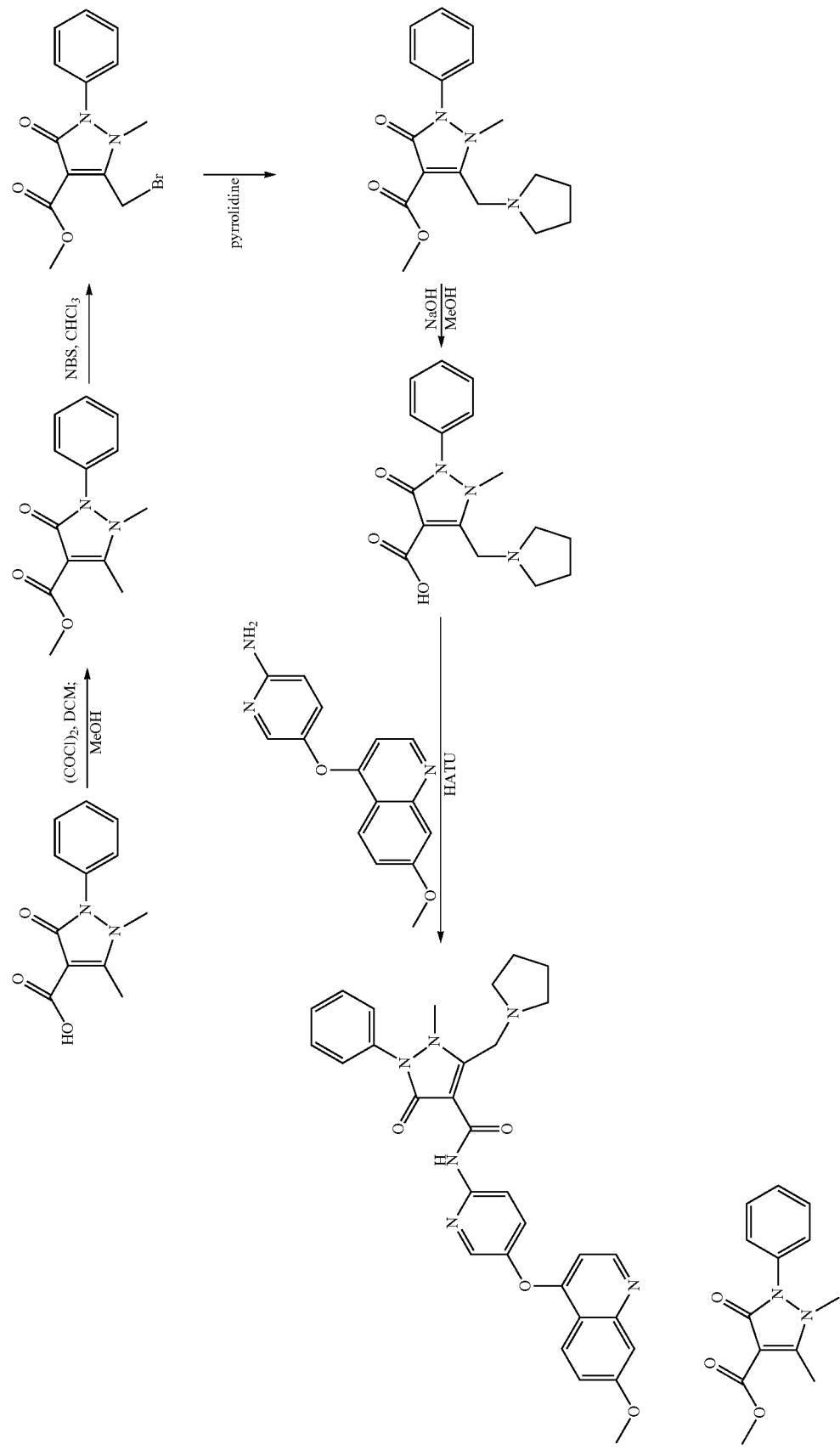

Step 1: Methyl 1,5-dimethyl-3-oxo-2-phenyl-2,3-dihydro-1H-pyrazole-4-carboxylate. 2,3-dimethyl-5-oxo-1-phenyl-2,5-dihydro-1H-pyrazole-4-carboxylic acid (7.55 g, 33 mmol) was dissolved in dichlormethane (145 ml) and oxalyl chloride (4.1 ml, 46 mmol) was added via syringe over about 10 minutes, resulting in vigorous bubbling. After stirring at room temperature for about 30 minutes, the reaction was cautiously quenched with MeOH (100 ml). The methanol was added slowly at first as vigorous gas evolution was observed. The reaction was stirred at room temperature for 1 hour, concentrated, and then partitioned between dichlormethane (125 ml) and saturated sodium bicarbonate (125 ml). More dichlormethane and saturated sodium bicarbonate were added, and the layers of the biphasic, homogeneous solution were separated. The aqueous phase was extracted with dichlormethane (3×100 ml), and the organic phases were collected, dried over sodium sulfate, filtered, and concentrated to give desired methyl 1,5-dimethyl-3-oxo-2-phenyl-2,3-dihydro-1H-pyrazole-4-carboxylate (7.82 g, 79% purity by HPLC, 25 mmol, 77% yield). MS (ESI pos. ion) m/z: 247 (MH+). Calc'd exact mass for $C_{13}H_{14}N_2O_3$: 246.

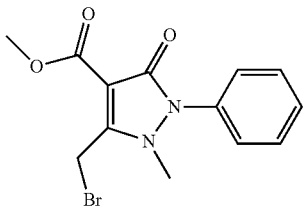

Step 2: Methyl 5-(bromomethyl)-1-methyl-3-oxo-2-phenyl-2,3-dihydro-1H-pyrazole-4-carboxylate. Methyl 1,5-dimethyl-3-oxo-2-phenyl-2,3-dihydro-1H-pyrazole-4-carboxylate (7.82 g, 31.8 mmol) was dissolved in CHCl$_3$ (150 ml) and n-bromosuccimide (6.91 g, 38.8 mmol) was added. The reaction was stirred at room temperature, and after 1.5 hours, more NBS (6.23 g, 35.2 mmol) was added. After another hour of stirring, the reaction was filtered, and the solid was washed with chloroform. The filtrate was concentrated, treated with dichlormethane, and refiltered. The filtrate was again concentrated, and filtered through silica gel (~3 inches, dichlormethane/MeOH). The fractions with product collected, concentrated, and purified on silica gel (dichlormethane/MeOH) to give the desired methyl 5-(bromomethyl)-1-methyl-3-oxo-2-phenyl-2,3-dihydro-1H-pyrazole-4-carboxylate (4.11 g, 82% purity, 10.4 mmol, 33% yield). MS (ESI pos. ion) m/z: 325, 327 (MH+). Calc'd exact mass for $C_{13}H_{13}Br^{79.0}N_2O_3$: 324. Calc'd exact mass for $C_{13}H_{13}Br^{81.0}N_2O_3$: 326.

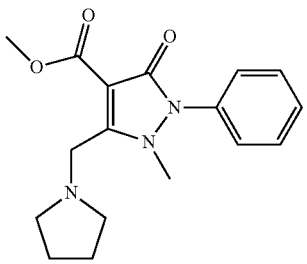

Step 3: Methyl 1-methyl-3-oxo-2-phenyl-5-(pyrrolidin-1-ylmethyl)-2,3-dihydro-1H-pyrazole-4-carboxylate. Methyl 5-(bromomethyl)-1-methyl-3-oxo-2-phenyl-2,3-dihydro-1H-pyrazole-4-carboxylate (1.266 g, 3.9 mmol) was dissolved in dichlormethane (30 ml) and pyrrolidine (0.40 ml, 4.8 mmol) was added via syringe. The reaction was stirred under nitrogen at room temperature. After about 20 minutes, more pyrrolidine (0.090 ml, 1.1 mmol) was added, and stirring was continued for 3.5 hours. The reaction was concentrated and purified on silica gel (dichlormethane, MeOH, 2 N ammonia in MeOH) to give the desired methyl 1-methyl-3-oxo-2-phenyl-5-(pyrrolidin-1-ylmethyl)-2,3-dihydro-1H-pyrazole-4-carboxylate (1.182 g, 70% purity by HPLC, 2.62 mmol, 67% yield). MS (ESI pos. ion) m/z: 316 (MH+). Calc'd exact mass for $C_{17}H_{21}N_3O_3$: 315.

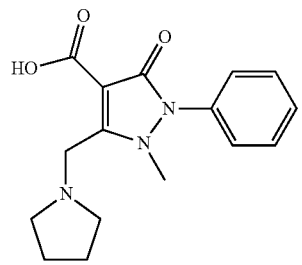

Step 4: 1-methyl-3-oxo-2-phenyl-5-(pyrrolidin-1-ylmethyl)-2,3-dihydro-1H-pyrazole-4-carboxylic acid. Methyl 1-methyl-3-oxo-2-phenyl-5-(pyrrolidin-1-ylmethyl)-2,3-dihydro-1H-pyrazole-4-carboxylate (1.182 g, 3.7 mmol) was dissolved in MeOH (17 ml) and sodium hydroxide (4.2 ml, 1.0 M, 4.2 mmol) and solid sodium hydroxide (282 mg, 7.05 mmol) were added. The reaction was stirred at room temperature for 3 hours, and then stirred at 90° C. for 1 hour. The reaction was then cooled to room temperature and treated with aq. 10% HCl to lower the pH to around 2. The reaction was concentrated, treated with 1:1 dichlormethane/MeOH, and filtered. The filtrate was concentrated to give the desired methyl 1-methyl-3-oxo-2-phenyl-5-(pyrrolidin-1-ylmethyl)-2,3-dihydro-1H-pyrazole-4-carboxylate (1.342 g, 77% purity by HPLC, 3.43 mmol, 93% yield). MS (ESI pos. ion) m/z: 302 (MH+). Calc'd exact mass for $C_{16}H_{19}N_3O_3$: 301.

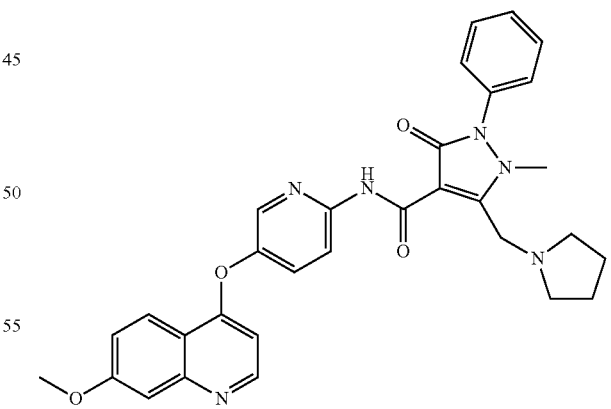

Step 5: N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide. 5-(7-methoxy-quinolin-4-yloxy)pyridin-2-amine (549 mg, 2.05 mmol) and 1-methyl-3-oxo-2-phenyl-5-(pyrrolidin-1-ylmethyl)-2,3-dihydro-1H-pyrazole-4-carboxylic acid (696 mg, 2.31 mmol) were suspended in dichlormethane (10 ml) and N-ethyl-N-isopropylpropan-2-amine (0.70 ml, 4.0 mmol), DMF (0.5 ml) and more dichlormethane (5 ml) were added. Finally, HATU (1.004 g, 2.641 mmol) was added, and the reaction was stirred under nitrogen at room temperature. After stirring for 2.5 weeks, the reaction was filtered and the solid was washed with DCM and MeOH. The filtrate was concentrated and purified on silica gel (~3 inches, dichloromethane, MeOH, 2 N ammonia in MeOH) to give the desired N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide (90.6 mg, 0.165 mmol, 8%). MS (ESI pos. ion) m/z: 551 (MH+). Calc'd exact mass for $C_{31}H_{30}N_6O_4$: 550. $^1$H NMR (400 MHz, CDCl$_3$): 11.44 (s, 1H), 8.61 (d, J=6.0 Hz, 1H), 8.38 (d, J=9.2 Hz, 1H), 8.30-8.21 (m, 2H), 7.62-7.37 (m, 7H), 7.24 (d, J=8.0 Hz, 1H), 6.43 (d, J=6.4 Hz, 1H), 4.35 (s, 2H), 3.98 (s, 3H), 3.57 (s, 3H), 2.73 (s, 4H), 1.84 (s, 4H).

EXAMPLE 3

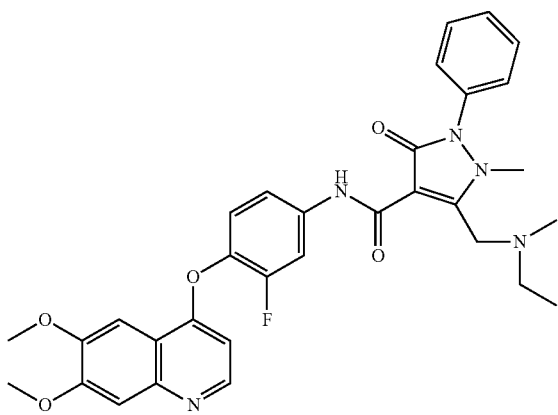

N-(4-(6,7-dimethoxyquinolin-4-yloxy)-3-fluorophenyl)-5-((ethyl(methyl)amino)methyl)-1-methyl-3-oxo-2-phenyl-2,3-dihydro-1H-pyrazole-4-carboxamide: MS (ESI pos. ion) m/z 586 (MH+) Calc'd exact mass for $C_{32}H_{32}FN_5O_5$ 585. $^1$H NMR (300 MHz, CDCl$_3$) 11.08 (s, 1H). 8.49 (d, J=5.26 Hz, 1 H) 7.93 (d, =12.42 Hz, 1 H); 7.68-7.25 (m, 8 H), 7.18 (t, J=17.25 Hz, 1 H) 6.43 (d, =6.14 Hz, 1 H) 4.21 (s, 2 H) 4.06 (s, 3 H) 3.57 (s, 3 H) 2.62 (q, J=7.16 Hz, 2 H) 2.36 (s, 3 H) 1.14 (t, =7.09 Hz, 3 H).

EXAMPLE 4

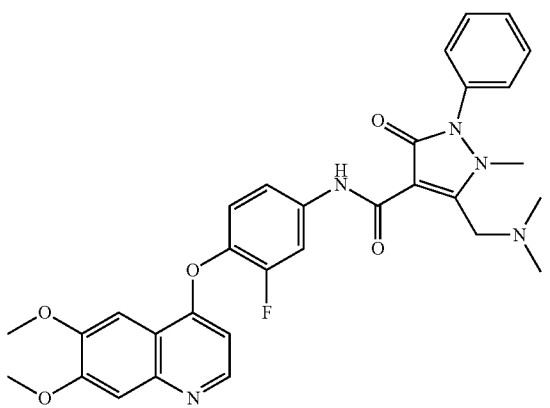

N-(4-(6,7-dimethoxyquinolin-4-yloxy)-3-fluorophenyl)-5-((dimethylamino)methyl)-1-methyl-3-oxo-2-phenyl-2,3-dihydro-1H-pyrazole-4-carboxamide: MS (ESI pos. ion) m/z 572 (MH+) Calc'd exact mass for $C_{31}H_{30}FN_5O_5$ 571.6. $^1$H NMR (300 MHz, CDCl$_3$) 11.06 (1 H, s), 8.49 (1 H, d, =5.3 Hz), 7.93 (1 H, d, =12.4 Hz), 7.66-7.28 (8 H, m), 7.18 (1 H, t, =8.8 Hz), 6.44 (2 H, d, =5.5 Hz), 4.16 (2 H, s), 4.11-3.99 (6 H, m), 3.56 (3 H, s), 2.41 (6 H, s).

EXAMPLE 5

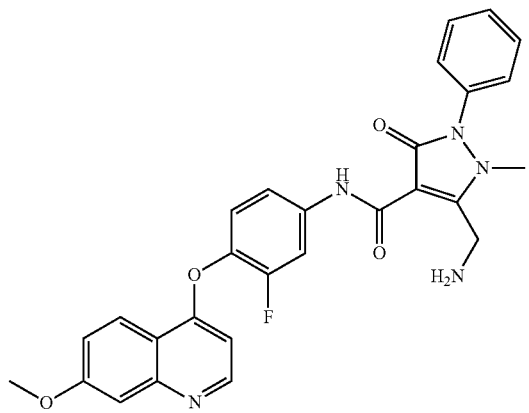

5-(aminomethyl)-N-(3-fluoro-4-(7-methoxyquinolin-4-yloxy)phenyl)-1-methyl-3-oxo-2-phenyl-2,3-dihydro-1H-pyrazole-4-carboxamide: MS (ESI pos. ion) m/z: 514 (MH+). Calc'd exact mass for $C_{28}H_{24}FN_5O_4$: 513. $^1$H NMR (400 MHz, CDCl$_3$): 10.93 (s, 1H), 8.61 (d, J=5.5 Hz, 1H), 8.29 (d, J=8.0 Hz, 1H), 7.93 (d, J=13.0H, 1H), 7.62-7.48 (m, 3H), 7.44 (s, 1H), 7.39 (d, J=8.0 Hz, 2H), 7.35-7.16 (m, 3H), 6.43 (d, J=5.0 Hz, 1H), 4.30 (s, 2H), 3.98 (s, 3H), 3.51 (s, 3H), 2.0 (br s, 3H).

EXAMPLE 6

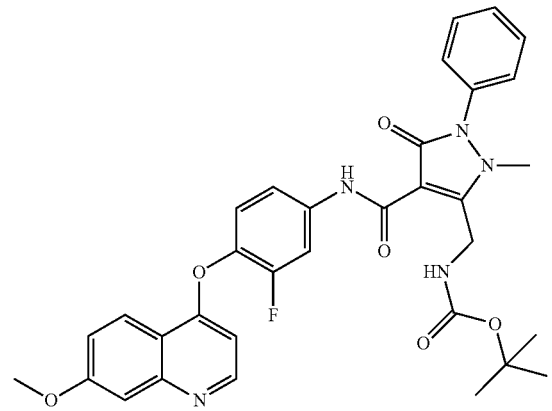

tert-butyl (4-((3-fluoro-4-(7-methoxyquinolin-4-yloxy)phenyl)carbamoyl)-1-methyl-3-oxo-2-phenyl-2,3-dihydro-1H-pyrazol-5-yl)methylcarbamate: MS (ESI pos. ion) m/z: 614 (MH+). Calc'd exact mass for $C_{33}H_{32}FN_5O_6$: 613.

EXAMPLE 7

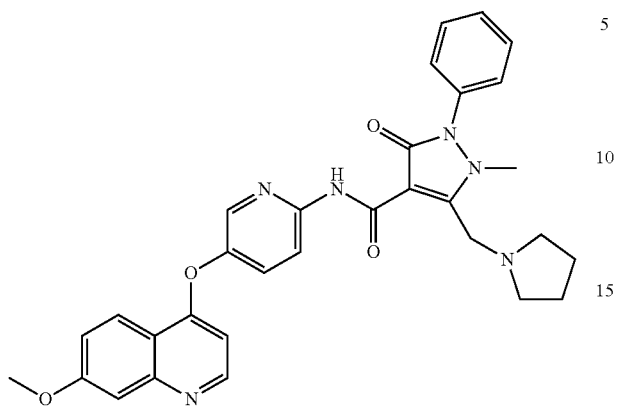

N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide: MS (ESI pos. ion) m/z: 551 (MH+). Calc'd exact mass for $C_{31}H_{30}N_6O_4$: 550. $^1$H NMR (400 MHz, CDCl$_3$) 11.44 (s, 1H), 8.61 (d, J=5.0 Hz, 1H), 8.38 (d, J=9.0 Hz, 1H), 8.28-8.22 (m, 2H), 7.56 (t, J=7.0 Hz, 2H), 7.53-7.45 (m, 2H), 7.41 (dt, J=8.0 Hz, 2.0 Hz, 3H), 7.26-7.21 (m, 1H), 6.43 (d, J=5.0 Hz, 1H), 4.35 (s, 2H), 3.98 (s, 3H), 3.57 (s, 3H), 2.78-2.69 (m, 4H), 1.89-1.81 (m, 4H).

EXAMPLE 8

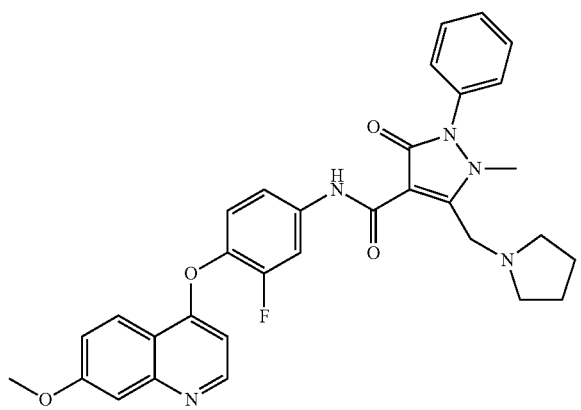

N-(3-fluoro-4-(7-methoxyquinolin-4-yloxy)phenyl)-1-methyl-3-oxo-2-phenyl-5-(pyrrolidin-1-ylmethyl)-2,3-dihydro-1H-pyrazole-4-carboxamide: MS (ESI pos. ion) m/z: 568 (MH+). Calc'd exact mass for $C_{32}H_{30}FN_5O_4$: 567. $^1$H NMR (400 MHz, CDCl$_3$): 11.06 (s, 1H), 8.60 (d, J=5.0 Hz, 1H), 8.28 (d, J=9.0 Hz, 1H), 7.93 (d, J=12.0 Hz, 1H), 7.59 (t, J=8.0 Hz, 2H), 7.51 (d, J=7.0 Hz, 1H), 7.40 (t, J=9.0 Hz, 3H), 7.33-7.21 (m, 2H), 7.17 (t, J=8.0 Hz, 1H), 6.41 (d, J=5.0 Hz, 1H), 4.35 (s, 2H), 3.98 (s, 3H), 3.58 (s, 3H), 2.75-2.70 (m, 4H), 1.86-1.81 (m, 4H).

EXAMPLE 9

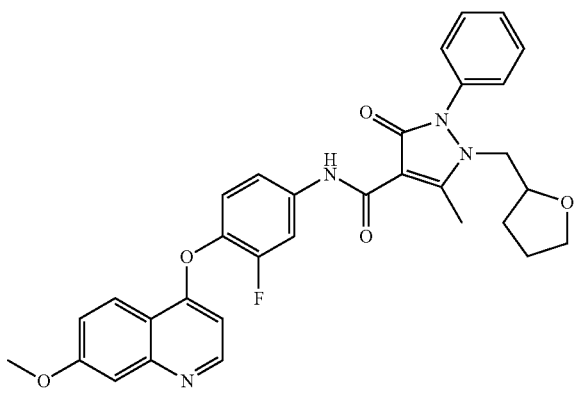

N-(3-fluoro-4-(7-methoxyquinolin-4-yloxy)phenyl)-5-methyl-3-oxo-2-phenyl-1-((tetrahydrofuran-2-yl)methyl)-2,3-dihydro-1H-pyrazole-4-carboxamide: MS (ESI pos. ion) m/z: 569 (MH+). Calc'd exact mass for $C_{32}H_{29}FN_4O_5$: 568; $^1$H NMR (400 MHz, CDCl$_3$): 10.94 (s, 1H), 8.76 (d, J=7.0 Hz, 1H), 8.46 (d, J=9.0 Hz, 1H), 8.07 (d, J=12.0 Hz, 1H), 7.79-7.76 (m, 1H), 7.64 7.59 (m, 3H), 7.48 (d, J=9.0 Hz, 2H), 7.41-7.31 (m, 2H), 7.30-7.24 (m, 1H), 6.80 (d, J=7.0 Hz, 1H), 4.09 (s, 3H), 4.08-4.01 (m, 1H), 3.87 (dd, J=15.0 Hz, 3.5 Hz, 1H), 3.75-3.64 (m, 3H), 2.51 (s, 3H), 2.01-1.91 (m, 1H), 1.84 (quintet, J=6.0 Hz, 2H), 1.56-1.47 (m, 1H).

EXAMPLE 10

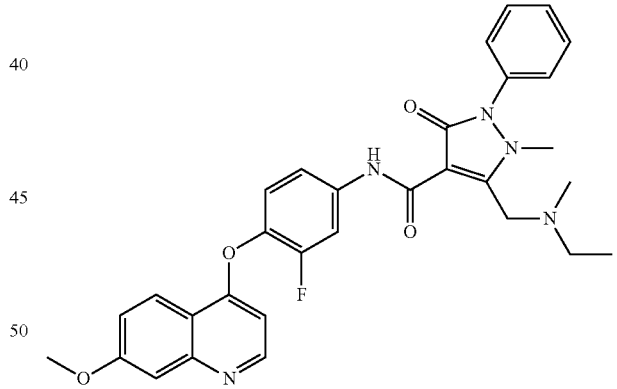

5-((ethyl(methyl)amino)methyl)-N-(3-fluoro-4-(7-methoxyquinolin-4-yloxy)phenyl)-1-methyl-3-oxo-2-phenyl-2,3-dihydro-1H-pyrazole-4-carboxamide: MS (ESI pos. ion) m/z: 556 (MH+). Calc'd exact mass for $C_{31}H_{30}FN_5O_4$: 555. $^1$H NMR (400 MHz, CDCl$_3$): 11.06 (s, 1H), 8.59 (d, J=5.0 Hz, 1H), 8.28 (d, J=9.0 Hz, 1H), 7.92 (d, J=12.0 Hz, 1H), 7.59 (t, J=7.0 Hz, 2H), 7.53-7.48 (m, 1H), 7.43-7.36 (m, 3H), 7.31 (d, J=9.0 Hz, 1H), 7.23 (d, J=10.0 Hz, 1H), 7.17 (t, J=9.0 Hz, 1H), 6.41 (d, J=5.0 Hz, 1H), 4.22 (s, 2H), 3.98 (s, 3H), 3.58 (s, 3H), 2.63 (quartet, J=7.0 Hz, 2H), 2.37 (s, 3H), 1.15 (t, J=7.0 Hz, 3H).

EXAMPLE 11

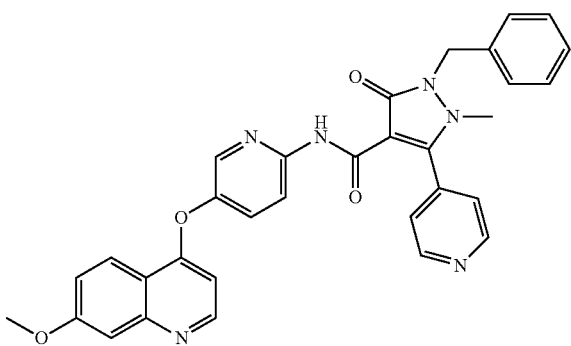

2-benzyl-N-(5-(7-methoxyquinolin-4-yloxy)pyridin-2-yl)-1-methyl-3-oxo-5-(pyridin-4-yl)-2,3-dihydro-1H-pyrazole-4-carboxamide MS (ESI pos. ion) m/z 559 (MH+). Calc'd exact mass for $C_{32}H_{26}N_6O_4$ 558.

EXAMPLE 12

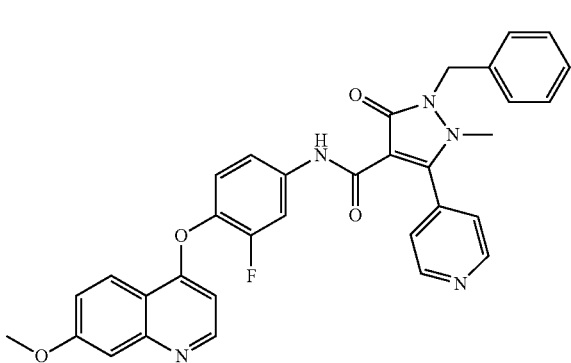

2-benzyl-N-(3-fluoro-4-(7-methoxyquinolin-4-yloxy)phenyl)-1-methyl-3-oxo-5-(pyridin-4-yl)-2,3-dihydro-1H-pyrazole-4-carboxamide: MS (ESI pos. ion) m/z 576 (MH+). Calc'd exact mass for $C_{33}H_{26}FN_5O_4$ 575.

EXAMPLE 13

(S)-N-(5-(7-methoxyquinolin-4-yloxy)pyridin-2-yl)-1-methyl-3-oxo-2-(1-phenylethyl)-5-(pyridin-4-yl)-2,3-dihydro-1H-pyrazole-4-carboxamide: MS (ESI pos. ion) m/z: 573 (MH+). Calc'd exact mass for $C_{33}H_{28}N_6O_4$: 572. $^1$H NMR (400 MHz, CDCl$_3$): 11.52 (s, 1H), 8.98 (d, J=6.0 Hz, 2H), 8.84 (d, J=6.0 Hz, 1H), 8.41 (d, J=9.0 Hz, 1H), 8.37 (d, J=3.0 Hz, 1H), 8.31 (d, J=9.0 Hz, 1H), 7.81 (d, J=5.0 Hz, 2H), 7.78 (d, J=2.0 Hz, 1H), 7.60 (dd, J=9.0 Hz, 2.0 Hz, 1H), 7.50-7.38 (m, 6H), 6.76 (d, J=7.0 Hz, 1H), 6.17 (quartet, J=8.0 Hz, 1H), 4.08 (s, 3H), 3.13 (s, 3H), 2.02 (d, J=7.0 Hz, 3H).

EXAMPLE 14

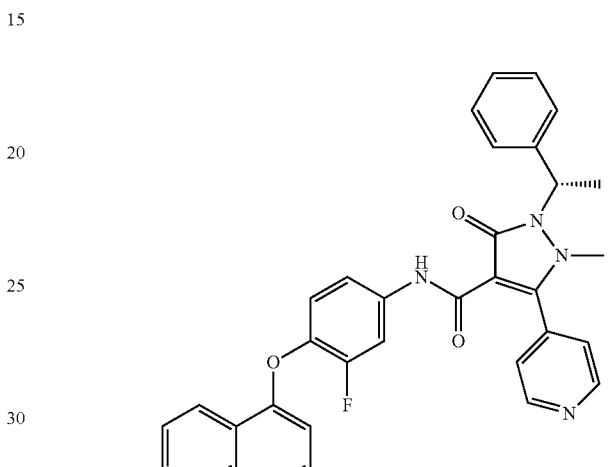

(S)-N-(3-fluoro-4-(7-methoxyquinolin-4-yloxy)phenyl)-1-methyl-3-oxo-2-(1-phenylethyl)-5-(pyridin-4-yl)-2,3-dihydro-1H-pyrazole-4-carboxamide: MS (ESI pos. ion) m/z: 590 (MH+). Calc'd exact mass for $C_{34}H_{28}FN_5O_4$: 589.

EXAMPLE 15

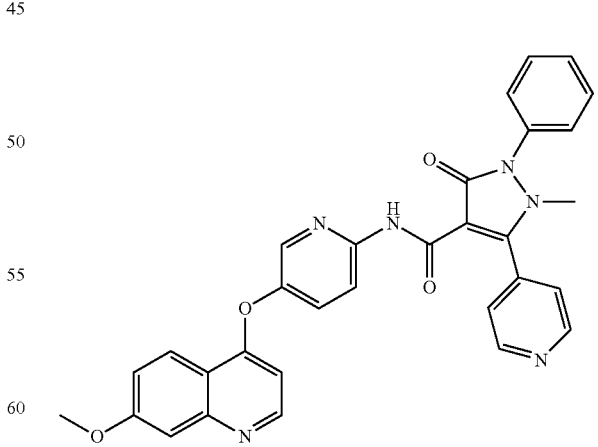

N-(5-(7-methoxyquinolin-4-yloxy)pyridin-2-yl)-1-methyl-3-oxo-2-phenyl-5-(pyridin-4-yl)-2,3-dihydro-1H-pyrazole-4-carboxamide: MS (ESI pos. ion) m/z: 545 (MH+). Calc'd exact mass for $C_{31}H_{24}N_6O_4$: 544.

EXAMPLE 16

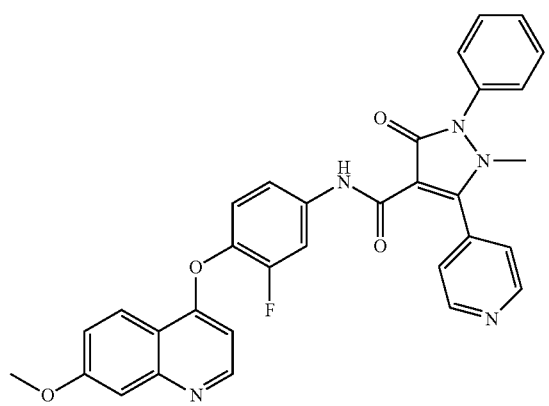

N-(3-fluoro-4-(7-methoxyquinolin-4-yloxy)phenyl)-1-methyl-3-oxo-2-phenyl-5-(pyridin-4-yl)-2,3-dihydro-1H-pyrazole-4-carboxamide: MS (ESI pos. ion) m/z: 562 (MH+). Calc'd exact mass for $C_{32}H_{24}FN_5O_4$: 561.

EXAMPLE 17

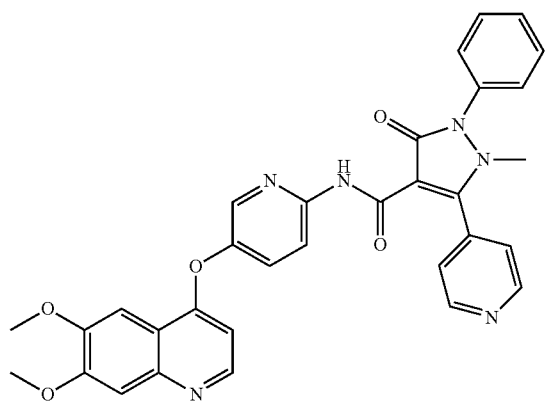

N-(5-(6,7-dimethoxyquinolin-4-yloxy)pyridin-2-yl)-1-methyl-3-oxo-2-phenyl-5-(pyridin-4-yl)-2,3-dihydro-1H-pyrazole-4-carboxamide: MS (ESI pos. ion) m/z: 575 (MH+). Calc'd exact mass for $C_{32}H_{26}N_6O_5$: 574.

EXAMPLE 18

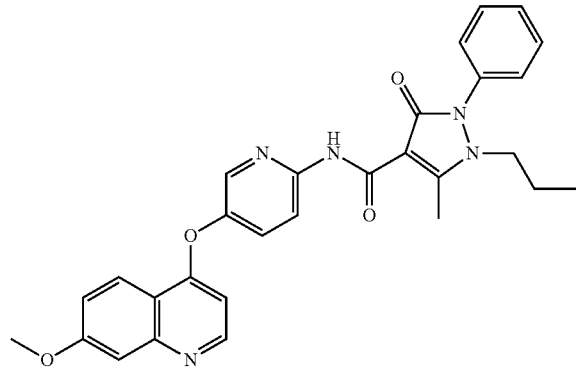

N-(5-(7-methoxyquinolin-4-yloxy)pyridin-2-yl)-5-methyl-3-oxo-2-phenyl-1-propyl-2,3-dihydro-1H-pyrazole-4-carboxamide: MS (ESI pos. ion) m/z: 510 (MH+). Calc'd exact mass for $C_{29}H_{27}N_5O_4$: 509. $^1$HNMR (300 MHz, CDCl$_3$): 0.81 (t, 3H), 1.54 (m, 2H), 2.82 (s, 3H), 3.75 (m, 2H), 4.0 (s, 3H), 6.45 (d, 1H), 7.31 (d, 2H), 7.41-7.52 (m, 6H), 8.30 (d, 2H), 8.40 (d, 1H), 8.60 (d, 1H).

EXAMPLE 19

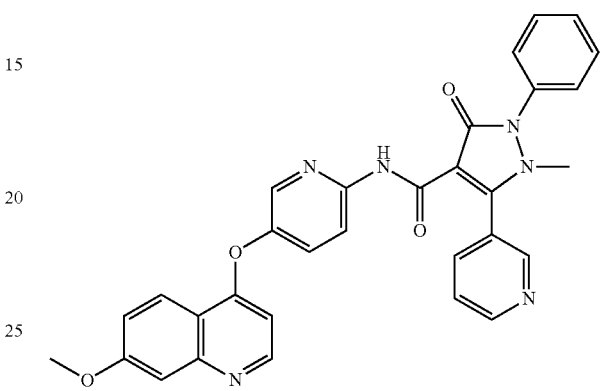

N-(5-(7-methoxyquinolin-4-yloxy)pyridin-2-yl)-1-methyl-3-oxo-2-phenyl-5-(pyridin-3-yl)-2,3-dihydro-1H-pyrazole-4-carboxamide: MS (ESI pos. ion) m/z: 545 (MH+). Calc'd exact mass for $C_{31}H_{24}N_6O_4$: 544. $^1$HNMR (300 MHz, CDCl$_3$): 3.42 (s, 3H), 3.89 (s, 3H), 4.37-4.49 (m, 1H), 5.22 (s, 1H), 6.34 (d, J=5.26 Hz, 1H), 7.15 (dd, J=9.21, 2.48 Hz, 1H), 7.20 (s, 2H), 7.28-7.50 (m, 7H), 8.15 (d, J=6.14 Hz, 1H), 8.17 (s, 1H), 8.29 (d, J=9.06 Hz, 1H), 8.52 (d, J=5.26 Hz, 1H), 11.55 (s, 1H).

EXAMPLE 20

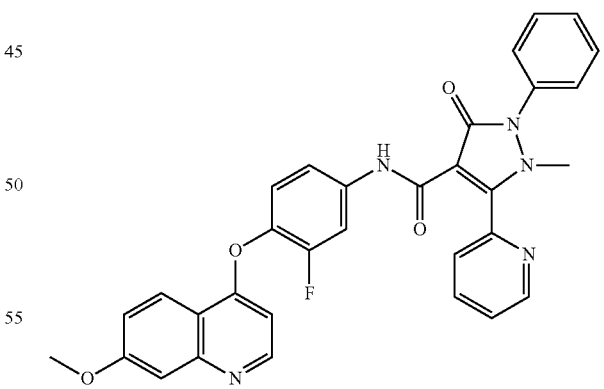

N-(3-fluoro-4-(7-methoxyquinolin-4-yloxy)phenyl)-1-methyl-3-oxo-2-phenyl-5-(pyridin-2-yl)-2,3-dihydro-1H-pyrazole-4-carboxamide: MS (ESI pos. ion) m/z: 562 (MH+). Calc'd exact mass for $C_{32}H_{24}FN_5O_4$: 561. $^1$HNMR (300 MHz, CDCl$_3$): 2.80 (s, 1H), 3.34 (s, 3H), 3.96 (s, 3H), 6.39 (d, J=5.12 Hz, 1H), 7.11-7.32 (m, 4H), 7.40-7.64 (m, 6H), 7.79-8.01 (m, 3H), 8.25 (d, J=9.21 Hz, 1H), 8.57 (d, J=5.26 Hz, 1H), 8.80 (d, J=4.53 Hz, 1H), 11.12 (s, 1H).

EXAMPLE 21

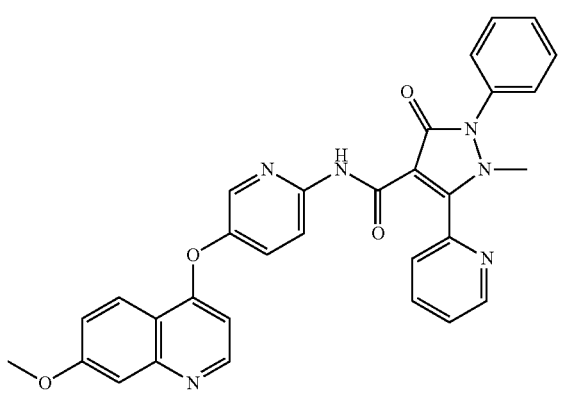

N-(5-(7-methoxyquinolin-4-yloxy)pyridin-2-yl)-1-methyl-3-oxo-2-phenyl-5-(pyridin-2-yl)-2,3-dihydro-1H-pyrazole-4-carboxamide: MS (ESI pos. ion) m/z: 545 (MH+). Calc'd exact mass for $C_{31}H_{24}N_6O_4$: 544. $^1$HNMR (300 MHz, CDCl$_3$): 3.24 (s, 3H), 3.88 (s, 3H), 6.32 (d, J=5.26 Hz, 1H), 7.13 (dd, J=9.13, 2.41 Hz, 1H), 7.20 (s, 1H), 7.31-7.53 (m, 7H), 7.80-7.90 (m, 2H), 8.10-8.23 (m, 3H), 8.50 (d, J=5.26 Hz, 1H), 8.72 (d, J=4.82 Hz, 1H), 11.39 (s, 1H).

EXAMPLE 22

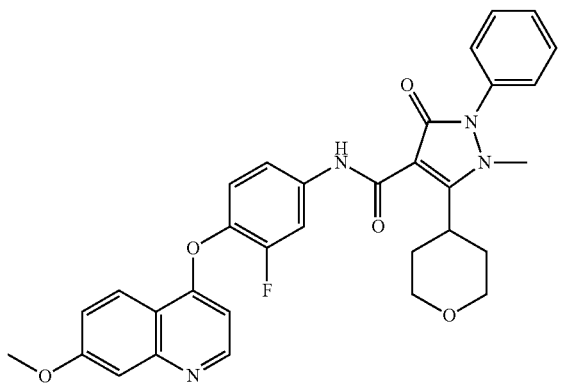

N-(3-fluoro-4-(7-methoxyquinolin-4-yloxy)phenyl)-1-methyl-3-oxo-2-phenyl-5-(tetrahydro-2H-pyran-4-yl)-2,3-dihydro-1H-pyrazole-4-carboxamide: MS (ESI pos. ion) m/z: 569 (MH+). Calc'd exact mass for $C_{32}H_{29}FN_4O_5$: 568. $^1$HNMR (300 MHz, CDCl$_3$): 1.83 (d, J=10.96 Hz, 2H), 2.33 (qd, J=12.57, 4.38 Hz, 2H), 3.49 (s, 3H), 3.63 (t, J=1.03 Hz, 2H), 3.96 (s, 3H), 4.15 (dd, J=11.40, 3.80 Hz, 2H), 4.47-4.60 (m, 1H), 5.29 (s, 1H), 6.40 (dd, J=5.19, 0.80 Hz, 1H), 7.14-7.42 (m, 4H), 7.46-7.60 (m, 3H), 7.92 (dd, J=12.50, 2.27 Hz, 1H), 8.27 (d, J=9.21 Hz, 1H), 8.59 (d, J=5.26 Hz, 1H), 11.25 (s, 1H).

EXAMPLE 23

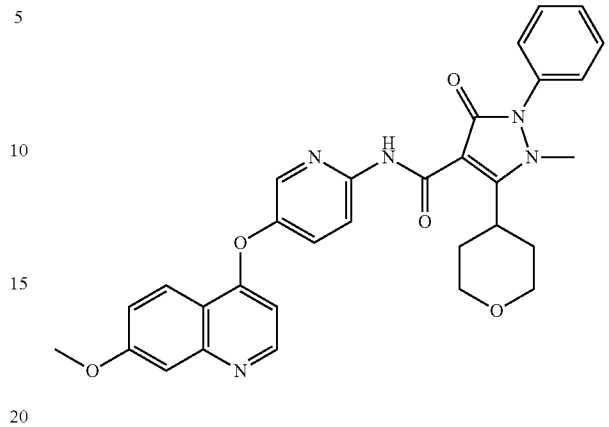

N-(5-(7-methoxyquinolin-4-yloxy)pyridin-2-yl)-1-methyl-3-oxo-2-phenyl-5-(tetrahydro-2H-pyran-4-yl)-2,3-dihydro-1H-pyrazole-4-carboxamide: MS (ESI pos. ion) m/z: 552 (MH+). Calc'd exact mass for $C_{31}H_{29}N_5O_5$: 551. $^1$HNMR (300 MHz, CDCl$_3$): 1.76 (d, J=10.67 Hz, 2H), 2.19-2.35 (m, 2H), 3.42 (s, 3H), 3.50-3.60 (m, 2H), 3.89 (s, 3H), 4.07 (dd, J=11.55, 3.80 Hz, 2H), 4.37-4.49 (m, 1H), 5.22 (s, 1H), 6.34 (d, J=5.26 Hz, 1H), 7.15 (dd, J=9.21, 2.48 Hz, 1H), 7.28-7.50 (m, 5H), 8.15 (d, J=6.14 Hz, 1H), 8.17 (s, 1H), 8.29 (d, J=9.06 Hz, 1H), 8.52 (d, J=5.26 Hz, 1H), 11.55 (s, 1H).

EXAMPLE 24

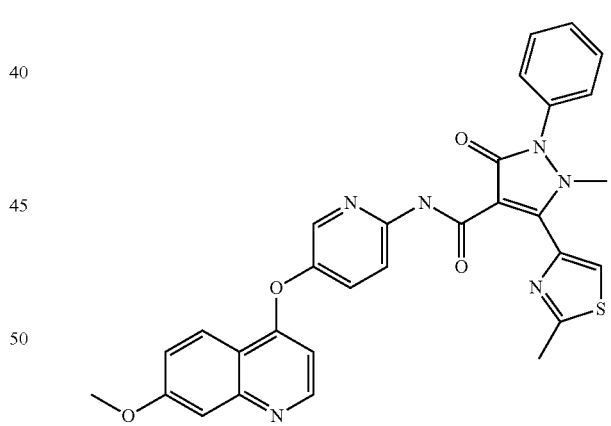

1-Methyl-N-(5-((7-(methyloxy)-4-quinolinyl)oxy)-2-pyridinyl)-5-(2-methyl-1,3-thiazol-4-yl)-3-oxo-2-phenyl-2,3-dihydro-1H-pyrazole-4-carboxamide: MS (ESI pos. ion) m/z: 565 (MH$^+$). Calc'd exact mass for $C_{30}H_{24}N_6O_4S$: 564. $^1$H NMR (400 MHz, DMSO-d$_6$) 11.51 (s, 1H), 8.62 (d, J=5.18 Hz, 1 H), 8.32-8.36 (m, 2 H), 8.29 (d, J=9.09 Hz, 1 H), 8.22 (d, J=9.09 Hz, 1 H), 7.77 (dd, J=9.16, 2.84 Hz, 1 H), 7.61-7.68 (m, 2 H), 7.53-7.60 (m, 3 H), 7.42 (d, J=2.40 Hz, 1 H), 7.30 (dd, J=9.09, 2.40 Hz, 1 H), 6.53 (d, J=5.18 Hz, 1 H), 3.94 (s, 3 H), 3.28-3.33 (m, 3 H), 2.78 (s, 3 H):

EXAMPLE 25

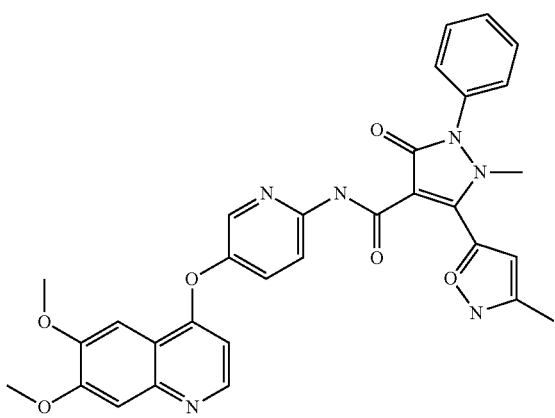

N-(5-((6,7-bis(methyloxy)-4-quinolinyl)oxy)-2-pyridinyl)-1-methyl-5-(5-methyl-3-isoxazolyl)-3-oxo-2-phenyl-2,3-dihydro-1H-pyrazole-4-carboxamide: MS (ESI pos. ion) m/z: 579 (MH$^+$). Calc'd exact mass for $C_{31}H_{26}N_6O_6$: 578.

EXAMPLE 26

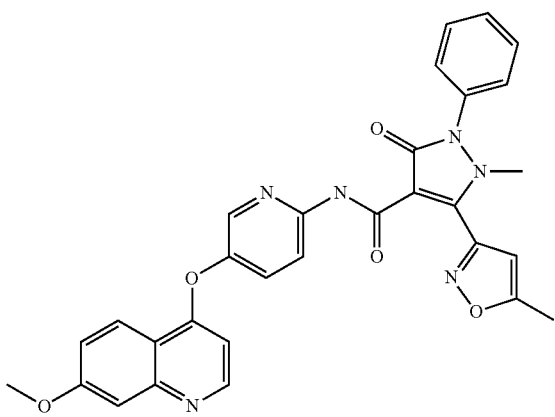

1-methyl-5-(5-methyl-3-isoxazolyl)-N-(5-((7-(methyloxy)-4-quinolinyl)oxy)-2-pyridinyl)-3-oxo-2-phenyl-2,3-dihydro-1H-pyrazole-4-carboxamide: MS (ESI pos. ion) m/z: 549 (MH$^+$). Calc'd exact mass for $C_{30}H_{24}N_6O_5$: 548.

EXAMPLE 27

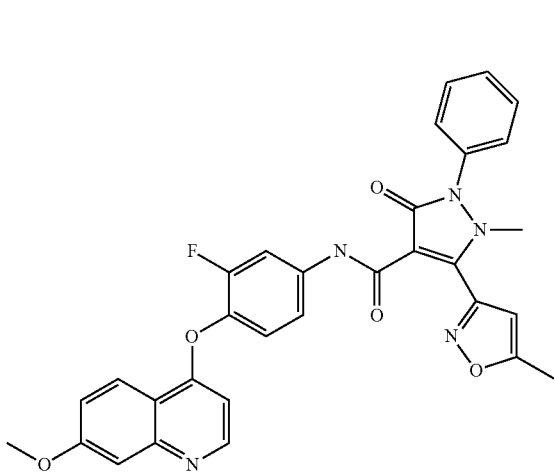

N-(3-fluoro-4-((7-(methyloxy)-4-quinolinyl)oxy)phenyl)-1-methyl-5-(5-methyl-3-isoxazolyl)-3-oxo-2-phenyl-2,3-dihydro-1H-pyrazole-4-carboxamide: MS (ESI pos. ion) m/z: 566 (MH$^+$). Calc'd exact mass for $C_{31}H_{24}FN_5O_5$: 565.

EXAMPLE 28

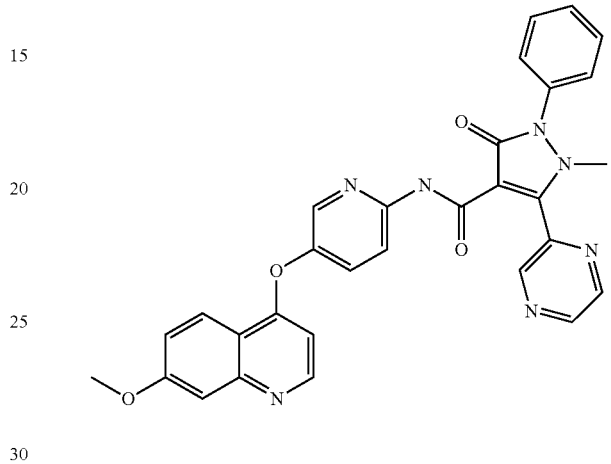

1-methyl-N-(5-((7-(methyloxy)-4-quinolinyl)oxy)-2-pyridinyl)-3-oxo-2-phenyl-5-(2-pyrazinyl)-2,3-dihydro-1H-pyrazole-4-carboxamide: MS (ESI pos. ion) m/z: 546 (MH$^+$). Calc'd exact mass for $C_{30}H_{23}N_7O_4$: 545.

EXAMPLE 29

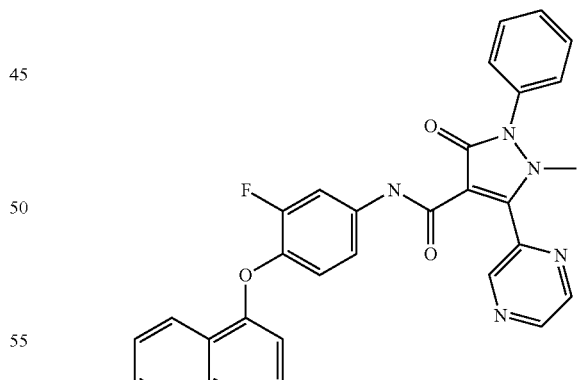

N-(3-fluoro-4-((7-(methyloxy)-4-quinolinyl)oxy)phenyl)-1-methyl-3-oxo-2-phenyl-5-(2-pyrazinyl)-2,3-dihydro-1H-pyrazole-4-carboxamide: MS (ESI pos. ion) m/z: 563.2 (MH$^+$). Calc'd exact mass for $C_{31}H_{23}FN_6O_4$: 562.

EXAMPLE 30

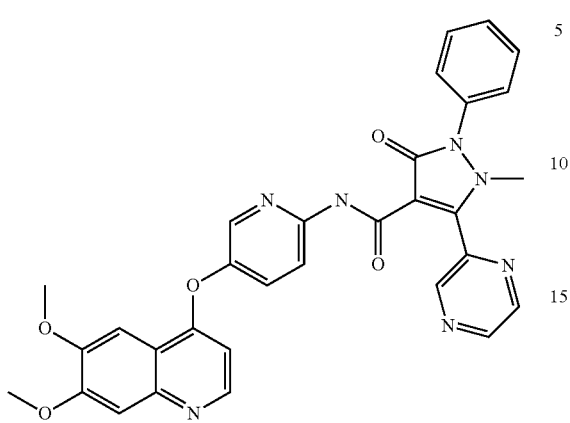

N-(5-((6,7-bis(methyloxy)-4-quinolinyl)oxy)-2-pyridinyl)-1-methyl-3-oxo-2-phenyl-5-(2-pyrazinyl)-2,3-dihydro-1H-pyrazole-4-carboxamide: MS (ESI pos. ion) m/z: 576 (MH+). Calc'd exact mass for $C_{31}H_{25}N_7O_5$: 575. $^1$H NMR (400 MHz, DMSO-$d_6$) 11.28 (s, 1 H), 9.11 (d, J=1.14 Hz, 1 H), 8.87-8.90 (m, 1 H), 8.85 (d, J=2.53 Hz, 1 H), 8.48 (d, J=5.31 Hz, 1 H), 8.34 (d, J=2.91 Hz, 1 H), 8.22 (d, J=9.09 Hz, 1 H), 7.74 (dd, J=8.97, 2.91 Hz, 1 H), 7.64-7.69 (m, 2 H), 7.57-7.63 (m, 3 H), 7.52 (s, 1 H), 7.40 (s, 1 H), 6.52 (d, J=5.31 Hz, 1 H), 3.94 (d, J=5.31 Hz, 6 H), 3.30 (s, 3H).

EXAMPLE 31

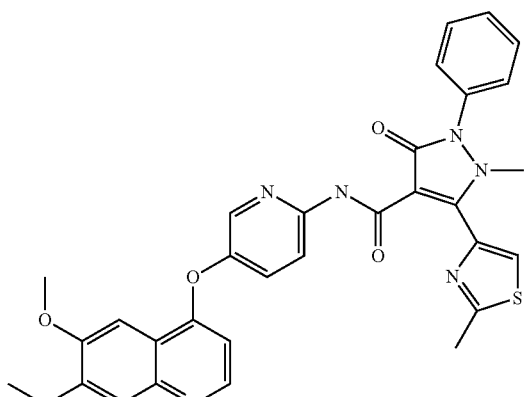

N-(5-((6,7-bis(methyloxy)-4-quinolinyl)oxy)-2-pyridinyl)-1-methyl-5-(2-methyl-1,3-thiazol-4-yl)-3-oxo-2-phenyl-2,3-dihydro-1H-pyrazole-4-carboxamide: MS (ESI pos. ion) m/z: 595 (MH+). Calc'd exact mass for $C_{31}H_{26}N_6O_5S$: 594.

EXAMPLE 32

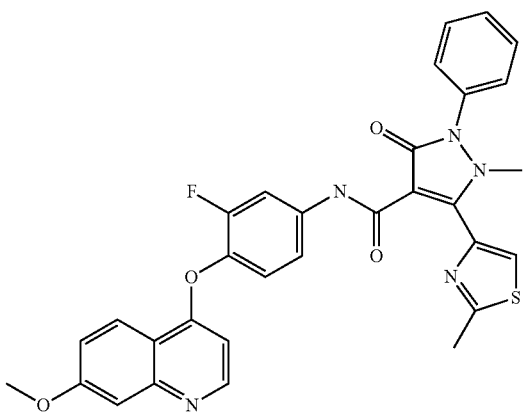

N-(3-fluoro-4-((7-(methyloxy)-4-quinolinyl)oxy)phenyl)-1-methyl-5-(2-methyl-1,3-thiazol-4-yl)-3-oxo-2-phenyl-2,3-dihydro-1H-pyrazole-4-carboxamide: MS (ESI pos. ion) m/z: 582 (MH+). Calc'd exact mass for $C_{31}H_{24}FN_5O_4S$: 581.

EXAMPLE 33

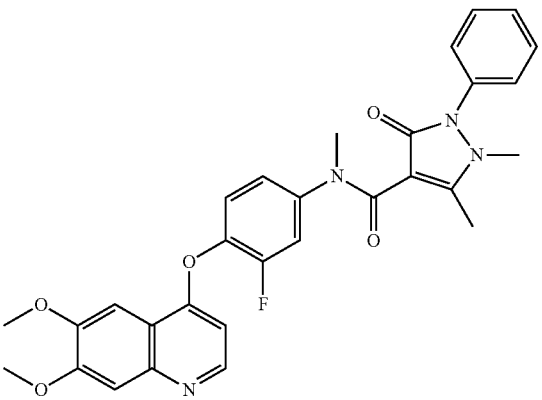

N-(4-(6,7-dimethoxyquinolin-4-yloxy)-3-fluorophenyl)-N,1,5-trimethyl-3-oxo-2-phenyl-2,3-dihydro-1H-pyrazole-4-carboxamide: MS (ESI pos. ion) m/z 543 (MH+) Calc'd exact mass for $C_{30}H_{27}FN_4O_5$ 543. $^1$H NMR (300 MHz, CDCl$_3$) 8.28 (1 H, d, 5.3 Hz), 7.56 (1 H, s), 7.33-7.53 (4 H, m), 7.24-7.10 (5 H, m), 6.26 (1 H, d, =5.4 Hz), 4.06 (6 H, s), 3.52 (3 H, s), 3.22 (3 H, s), 2.54 (3 H, s).

EXAMPLE 34

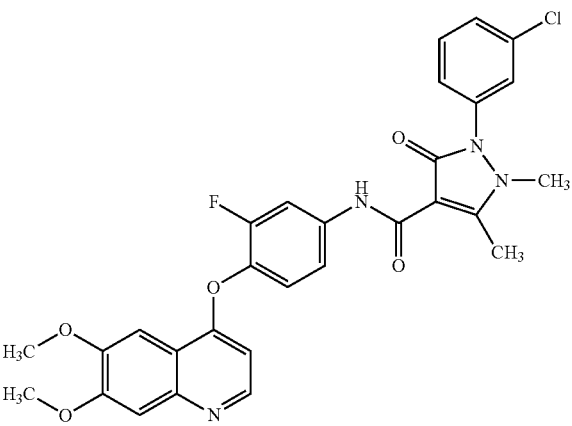

2-(3-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide: MS (ESI pos. ion) m/z: 563 (MH+). Calc'd exact mass for $C_{29}H_{24}ClFN_4O_5$: 562.

EXAMPLE 35

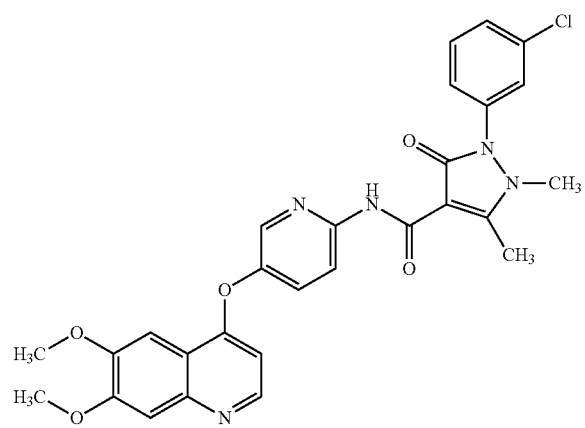

2-(3-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide: MS (ESI pos. ion) m/z: 546 (MH+). Calc'd exact mass for $C_{28}H_{24}ClN_5O_5$: 545.

EXAMPLE 36

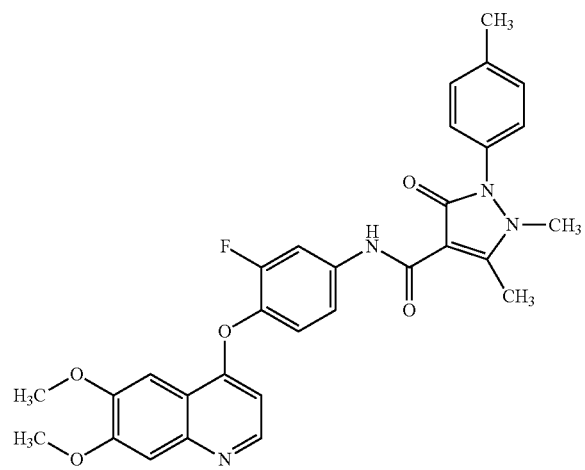

N-(4-(6,7-dimethoxyquinolin-4-yloxy)-3-fluorophenyl)-1,5-dimethyl-3-oxo-2-p-tolyl-2,3-dihydro-1H-pyrazole-4-carboxamide: MS (ESI pos. ion) m/z: 543 (MH+). Calc'd exact mass for $C_{30}H_{27}FN_4O_5$: 542. $^1$H NMR (400 MHz, DMSO-$d_6$) 11.00 (s, 1 H), 8.48 (d, J=5.31 Hz, 1 H), 7.98 (dd, J=13.20, 2.21 Hz, 1 H), 7.53 (s, 1 H), 7.29-7.45 (m, 7 H), 6.47 (d, J=5.43 Hz, 1 H), 3.95 (s, 6 H), 3.35 (s, 3 H), 2.70 (s, 3 H), 2.40 (s, 3 H).

EXAMPLE 37

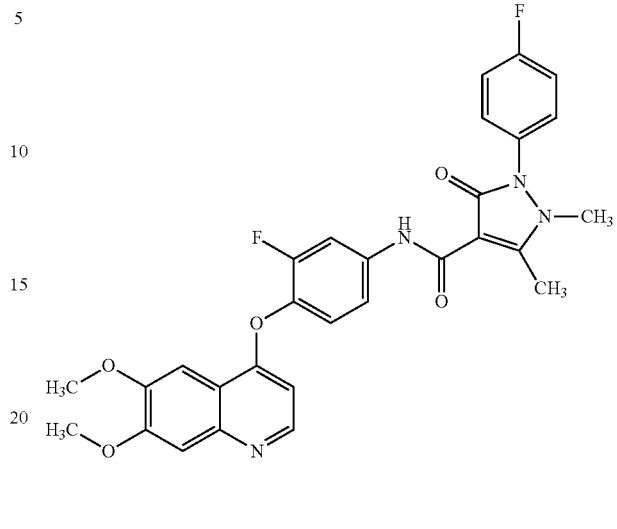

N-(4-(6,7-dimethoxyquinolin-4-yloxy)-3-fluorophenyl)-2-(4-fluorophenyl)-1,5-dimethyl-3-oxo-2,3-dihydro-1H-pyrazole-4-carboxamide: MS (ESI pos. ion) m/z: 547 (MH+). Calc'd exact mass for $C_{29}H_{24}F_2N_4O_5$: 546. $^1$H NMR (400 MHz, DMSO-$d_6$) 10.94 (s, 1 H), 8.48 (d, J=5.18 Hz, 1 H), 7.98 (dd, J=13.07, 2.34 Hz, 1 H), 7.32-7.55 (m, 8 H), 6.47 (d, J=5.05 Hz, 1 H), 3.95 (s, 6 H), 3.37 (s, 3 H), 2.70 (s, 3 H).

EXAMPLE 38

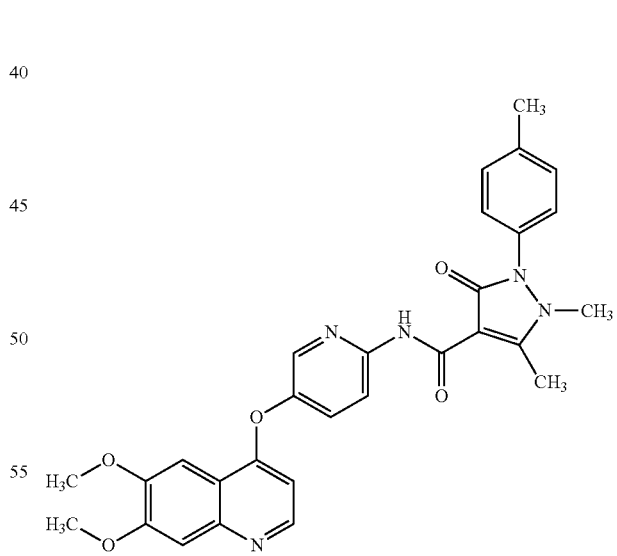

N-(5-(6,7-dimethoxyquinolin-4-yloxy)pyridine-2-yl)-1,5-dimethyl-3-oxo-2-p-tolyl-2,3-dihydro-1H-pyrazole-4-carboxamide: MS (ESI pos. ion) m/z: 526 (MH+). Calc'd exact mass for $C_{29}H_{27}N_5O_5$: 525.

EXAMPLE 39

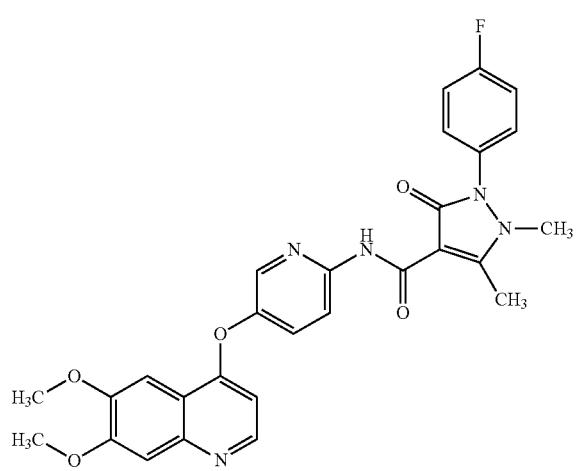

N-(5-(6,7-dimethoxyquinolin-4-yloxy)pyridin-2-yl)-2-(4-fluorophenyl)-1,5-dimethyl-3-oxo-2,3-dihydro-1H-pyrazole-4-carboxamide: MS (ESI pos. ion) m/z: 530 (MH+). Calc'd exact mass for $C_{28}H_{24}FN_5O_5$: 529.

EXAMPLE 40

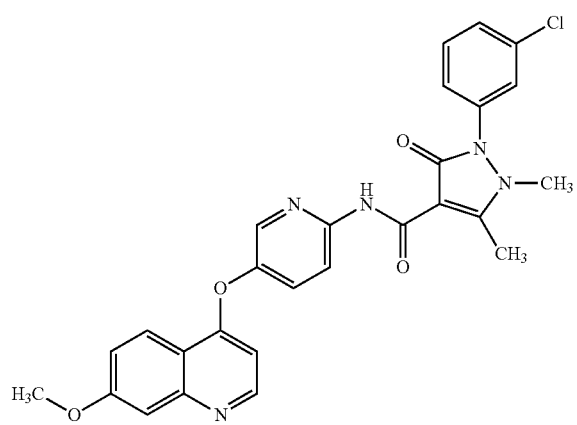

2-(3-chlorophenyl)-N-(5-(7-methoxyquinolin-4-yloxy)pyridin-2-yl)-1,5-dimethyl-3-oxo-2,3-dihydro-1H-pyrazole-4-carboxamide: MS (ESI pos. ion) m/z: 516 (MH+). Calc'd exact mass for $C_{27}H_{22}ClN_5O_4$: 515. $^1$H NMR (400 MHz, DMSO-$d_6$) 11.15 (s, 1 H), 8.62 (d, J=5.30 Hz, 1 H), 8.32-8.39 (m, 2 H), 8.22 (d, J=9.22 Hz, 1 H), 7.81 (dd, J=8.97, 3.03 Hz, 1 H), 7.57-7.66 (m, 3 H), 7.41-7.46 (m, 2 H), 7.30 (dd, J=9.16, 2.59 Hz, 1 H), 6.54 (d, J=5.18 Hz, 1 H), 3.94 (s, 3 H), 3.40 (s, 3 H), 2.73 (s, 3 H).

EXAMPLE 41

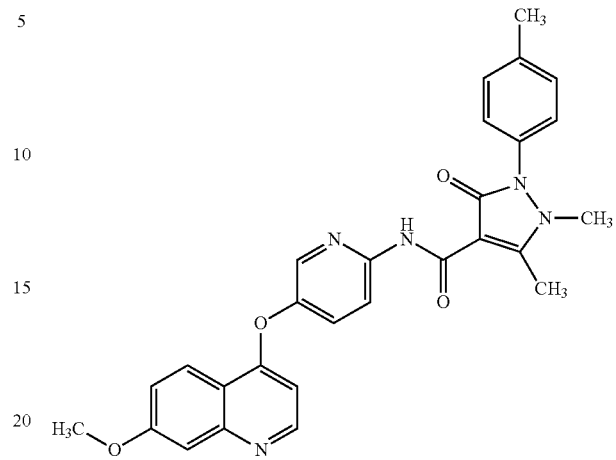

N-(5-(7-methoxyquinolin-4-yloxy)pyridin-2-yl)-1,5-dimethyl-3-oxo-2-p-tolyl-2,3-dihydro-1H-pyrazole-4-carboxamide: MS (ESI pos. ion) m/z: 496 (MH+). Calc'd exact mass for $C_{28}H_{25}N_5O_4$: 495. $^1$H NMR (400 MHz, DMSO-$d_6$) 11.29 (s, 1 H), 8.62 (d, J=4.93 Hz, 1 H), 8.30-8.40 (m, 2 H), 8.22 (d, J=9.22 Hz, 1 H), 7.80 (d, J=9.60 Hz, 1 H), 7.26-7.46 (m, 6 H), 6.53 (d, J=4.93 Hz, 1 H), 3.94 (s, 3 H), 3.35 (s, 3 H), 2.71 (s, 3 H), 2.40 (s, 3 H).

EXAMPLE 42

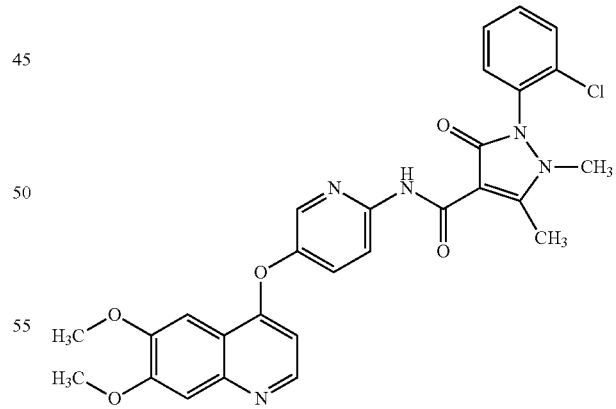

2-(2-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide: MS (ESI pos. ion) m/z: 546 (MH+). Calc'd exact mass for $C_{28}H_{24}ClN_5O_5$: 545.

EXAMPLE 43

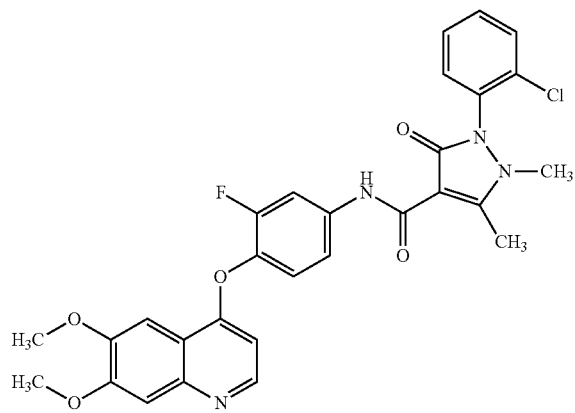

2-(2-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide: MS (ESI pos. ion) m/z: 563 (MH+). Calc'd exact mass for $C_{29}H_{24}ClFN_4O_5$: 562.

EXAMPLE 44

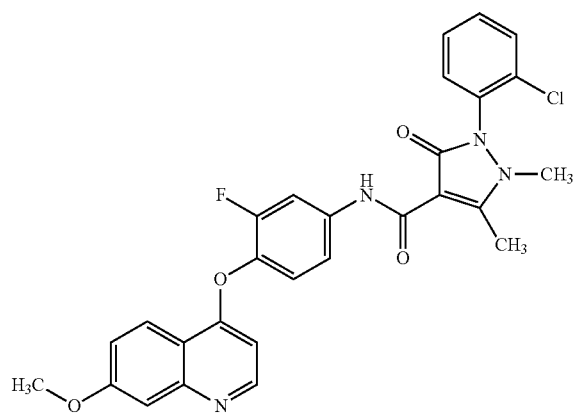

2-(2-chlorophenyl)-N-(3-fluoro-4-(7-methoxyquinolin-4-yloxy)phenyl)-1,5-dimethyl-3-oxo-2,3-dihydro-1H-pyrazole-4-carboxamide: MS (ESI pos. ion) m/z: 533 (MH+). Calc'd exact mass for $C_{28}H_{22}ClFN_4O_4$: 532. $^1$H NMR (400 MHz, DMSO-$d_6$) 10.88 (s, 1 H), 8.61 (d, J=5.18 Hz, 1 H), 8.23 (d, J=9.09 Hz, 1 H), 7.99 (dd, J=13.07, 1.71 Hz, 1 H), 7.77 (d, J=7.71 Hz, 1 H), 7.55-7.72 (m, 3 H), 7.37-7.47 (m, 2 H), 7.26-7.38 (m, 2 H), 6.48 (d, J=5.18 Hz, 1 H), 3.94 (s, 3 H), 3.34 (s, 3 H), 2.71 (s, 3 H).

EXAMPLE 45

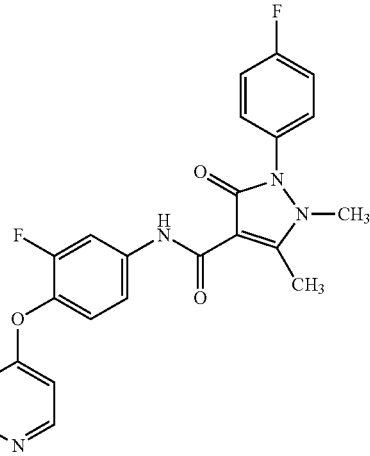

N-(3-fluoro-4-(7-methoxyquinolin-4-yloxy)phenyl)-2-(4-fluorophenyl)-1,5-dimethyl-3-oxo-2,3-dihydro-1H-pyrazole-4-carboxamide: MS (ESI pos. ion) m/z: 517 (MH+). Calc'd exact mass for $C_{28}H_{22}F_2N_4O_4$: 516. $^1$H NMR (400 MHz, DMSO-$d_6$) 10.95 (s, 1 H), 8.61 (d, J=5.18 Hz, 1 H), 8.23 (d, J=9.09 Hz, 1 H), 7.99 (dd, J=12.88, 1.89 Hz, 1 H), 7.27-7.57 (m, 8 H), 6.48 (d, J=5.18 Hz, 1 H), 3.94 (s, 3 H), 3.36 (s, 3 H), 2.70 (s, 3 H).

EXAMPLE 46

2-(3-chlorophenyl)-N-(3-fluoro-4-(7-methoxyquinolin-4-yloxy)phenyl)-1,5-dimethyl-3-oxo-2,3-dihydro-1H-pyrazole-4-carboxamide: MS (ESI pos. ion) m/z: 533 (MH+). Calc'd exact mass for $C_{28}H_{22}ClFN_4O_4$: 532. $^1$H NMR (400 MHz, DMSO-$d_6$) 10.85 (s, 1 H), 8.62 (d, J=5.18 Hz, 1 H), 8.24 (d, J=9.09 Hz, 1 H), 7.99 (dd, J=13.01, 2.40 Hz, 1 H), 7.57-7.66 (m, 3 H), 7.29-7.47 (m, 5 H), 6.49 (d, J=5.05 Hz, 1 H), 3.95 (s, 3 H), 3.41 (s, 3 H), 2.72 (s, 3 H).

EXAMPLE 47

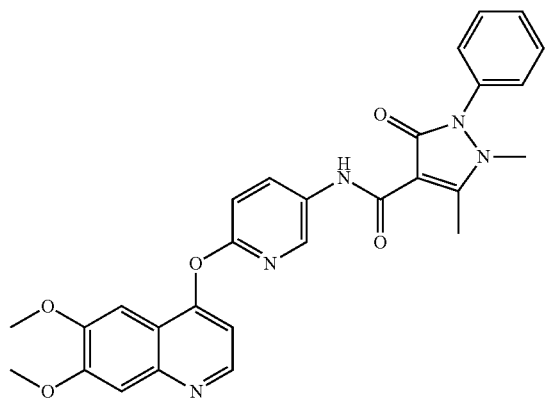

N-(6-(6,7-dimethoxyquinolin-4-yloxy)pyridin-3-yl)-1,5-dimethyl-3-oxo-2-phenyl-2,3-dihydro-1H-pyrazole-4-carboxamide: MS (ESI pos. ion) m/z: 512 (MH+). Calc'd exact mass for $C_{28}H_{25}N_5O_5$: 511 1H NMR (400 MHz, DMSO-$d_6$) 10.86 (s, 1 H), 8.56 (d, J=5.05 Hz, 1 H), 8.50 (d, J=2.65 Hz, 1 H), 8.27 (dd, J=2.9, 5.81 Hz, 1 H), 7.7-7.38 (3 m, 7 H).7.31 (d, J=8.72 Hz, 1 H), 6.84 (d, J=5.18 Hz, 1 H), 3.95 (s, 3 H), 3.89 (s, 3 H), 3.38 (s, 3 H), 2.71 (s, 3 H).

EXAMPLE 48

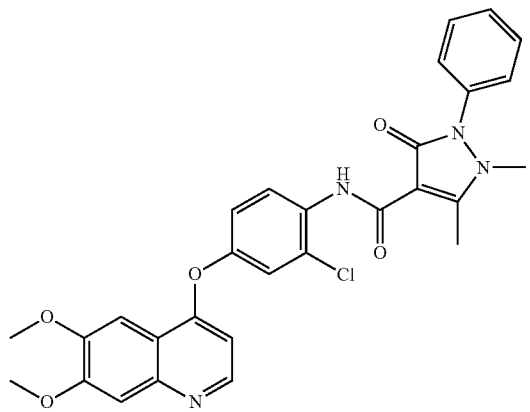

N-(2-chloro-4-(6,7-dimethoxyquinolin-4-yloxy)phenyl)-1,5-dimethyl-3-oxo-2-phenyl-2,3-dihydro-1H-pyrazole-4-carboxamide: MS (ESI pos. ion) m/z: 545 (MH+). Calc'd exact mass for $C_{29}H_{25}ClN_4O_5$: 544 1H NMR (400 MHz, CDCl$_3$) 11.12 (s, 1 H), 8.70 (d, J=8.79 Hz, 1 H), 8.50 (d, J=5.37 Hz, 1H), 7.43-7.63 (m, 5 H), 7.38 (d, J=7.32 Hz, 2H), 7.11 (dd, J=9.28, 1.95 Hz, 1 H), 6.55 (d, J=3.91 Hz, 1 H), 4.07 (s, 3 H), 4.04 (s, 3 H), 3.48 (s, 1 H), 3.37 (s, 3 H), 2.81 (s, 3 H)

EXAMPLE 49

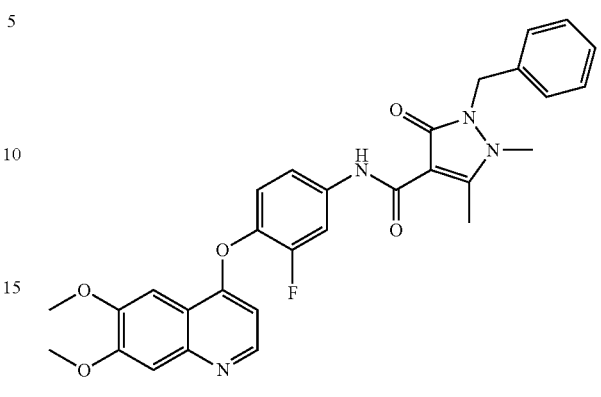

2-benzyl-N-(4-(6,7-dimethoxyquinolin-4-yloxy)-3-fluorophenyl)-1,5-dimethyl-3-oxo-2,3-dihydro-1H-pyrazole-4-carboxamide: MS (ESI pos. ion) m/z: 543 (MH+). Calc'd exact mass for $C_{30}H_{27}FN_4O_5$ 542 1H NMR (400 MHz, CDCl$_3$) 10.98 (s, 1 H), 8.50 (d, J=5.37 Hz, 1H), 7.97 (d, J=12.70 Hz, 1 H), 7.61 (s, 1 H), 7.53 (s, 1 H), 7.42-7.29 (m, 4 H), 7.24-7.15 (m, 3 H), 6.49 (s, 1 H), 5.18 (s, 2 H), 4.07 (s, 6 H), 3.40 (s, 3 H), 2.67 (s, 3H)

EXAMPLE 50

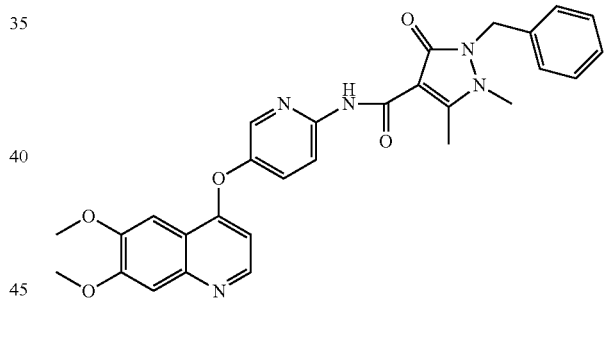

2-benzyl-N-(5-(6,7-dimethoxyquinolin-4-yloxy)pyridin-2-yl)-1,5-dimethyl-3-oxo-2,3-dihydro-1H-pyrazole-4-carboxamide: MS (ESI pos. ion) m/z: 526 (MH+). Calc'd exact mass for $C_{29}H_{27}N_5O_5$: 525 1H NMR (400 MHz, CDCl$_3$) 11.43 (s, 1 H), 8.51 (d, J=5.37 Hz, 1H,), 8.40 (d, J=8.79 Hz, 1 H), 8.29 (s, 1H), 7.67-7.12 (m, 8 H), 6.53-6.44 (m, 1 H), 5.18 (s, 2 H), 4.07 (s, 3 H), 3.40 (s, 6 H), 2.66 (s, 3 H)

EXAMPLE 51

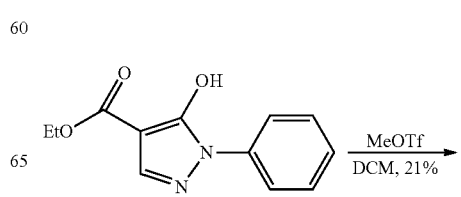

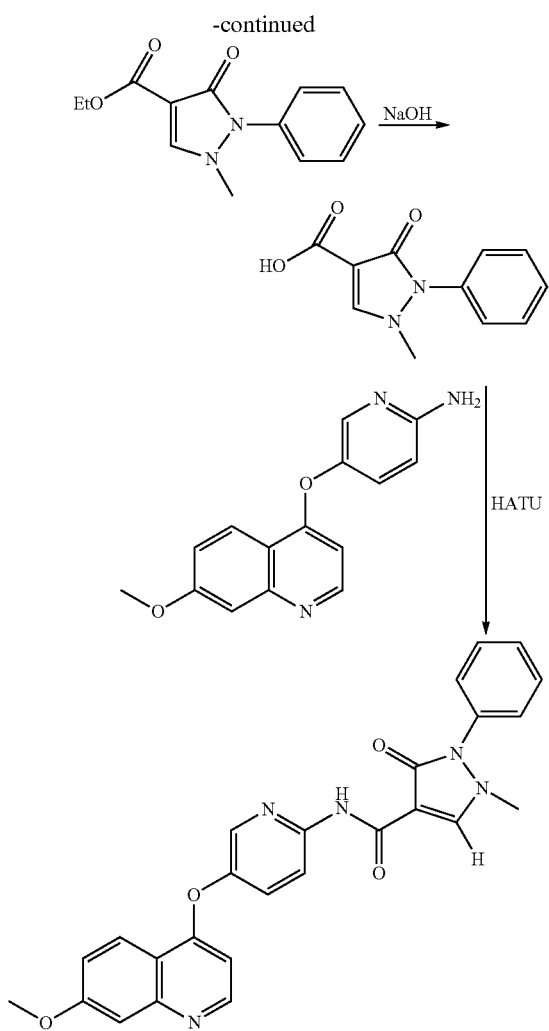

N-(5-(7-methoxyquinolin-4-yloxy)pyridin-2-yl)-1-methyl-3-oxo-2-phenyl-2,3-dihydro-1H-pyrazole-4-carboxamide

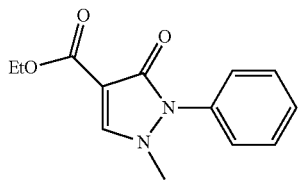

Step 1: Ethyl 1-methyl-3-oxo-2-phenyl-2,3-dihydro-1H-pyrazole-4-carboxylate. To a solution of ethyl 3-oxo-2-phenyl-2,3-dihydro-1H-pyrazole-4-carboxylate (1000 mg, 5.0 mmol) in dichloromethane (10 mL) was added methyl trifluoromethanesulfonate (1200 mg, 7.3 mmol). The red solution was stirred at room temperature. After 14 h, the mixture was partitioned between dichloromethane and NaHCO₃ (sat). The aqueous was extracted with dichloromethane (2×). The combined organic was dried over Na₂SO₄, concentrated and purified on silica. The product was triturated with EtOAc-hexane-CHCl₃ to give the pure product as crystals (260 mg, 21%). Calc'd for $C_{12}H_{12}N_2O_3$, 232.08; MS (ESI pos. ion) m/z: 233 (MH+). ¹H NMR (400 MHz, CHLOROFORM-d): 1.36 (t, J=7.04 Hz, 3 H), 3.39 (s, 3 H), 4.32 (q, J=7.17 Hz, 2 H), 7.32 (d, J=7.43 Hz, 2 H), 7.42 (t, J=7.34 Hz, 1 H), 7.50 (t, J=7.73 Hz, 2 H), 7.99 (s, 1 H).

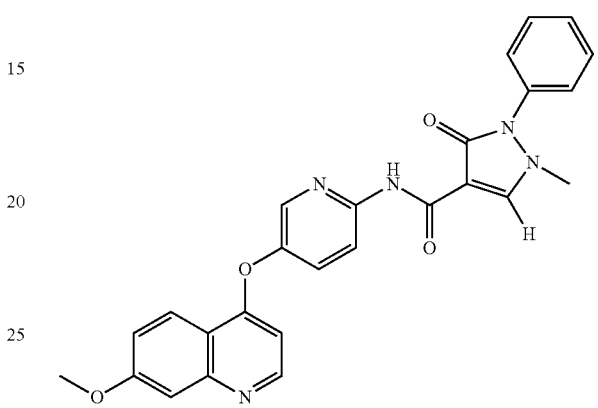

Step 2: N-(5-(7-methoxyquinolin-4-yloxy)pyridin-2-yl)-1-methyl-3-oxo-2-phenyl-2,3-dihydro-1H-pyrazole-4-carboxamide. A solution of ethyl 1-methyl-3-oxo-2-phenyl-2,3-dihydro-1H-pyrazole-4-carboxylate (260 mg, 1056 μmol) in MeOH was treated with NaOH (1000 μl, 5000 μmol) in H₂O (3 mL). The mixture was heated to 60° C. for 30 min and then cooled to room temperature. Then, the mixture was neutralized with aq. HCl (5 N, 1.1 mL) and concentrated to dryness. The residue was further dried with (azeotrope distillation with toluene, 3×5 mL). The resulting carboxylic acid was mixed with 5-(7-methoxyquinolin-4-yloxy)pyridin-2-amine (282 mg, 1054 μmol), Et₃N (500 μl, 3587 μmol), and HATU (401 mg, 1054 mmol) in DMF (4 mL)-dichloromethane (5 mL) and was stirred at 60° C. for 2 h. Upon cooling to room temperature, the mixture was diluted with EtOAc containing 10% MeOH (30 mL) and washed with H₂O. The organic layer was dried over Na₂SO₄, concentrated, and eluded on silica (1-10% 2N NH₃-MeOH in CHCl₃). The product was further purified on preparative HPLC to afford a white powder (100 mg, 20%).

Calc'd for $C_{26}H_{21}N_5O_4$: 467.16; MS (ESI pos. ion) m/z: 468 (MH+). ¹H NMR (400 MHz, DMSO-d₆) 3.49 (s, 3 H) 3.95 (s, 3 H) 6.55 (d, J 5.1, 1 H) 7.30 (dd, J 2.0, 9.0, 1 H) 7.42 (s, 1 H) 7.59 (s, 17 H) 7.50-7.60 (m, 5 H), 7.84 (dd, J 2.8, 9.2, 1 H), 8.22 (d, J 9.2, 1 H), 8.34-8.38 (m, 2 H) 8.62 (d, J 5.3, 1 H) 8.69 (s, 1 H) 10.86 (s, 1 H).

EXAMPLE 52

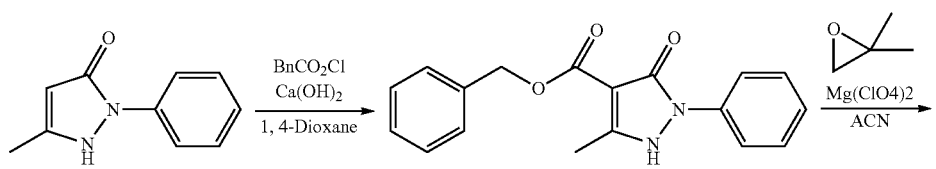

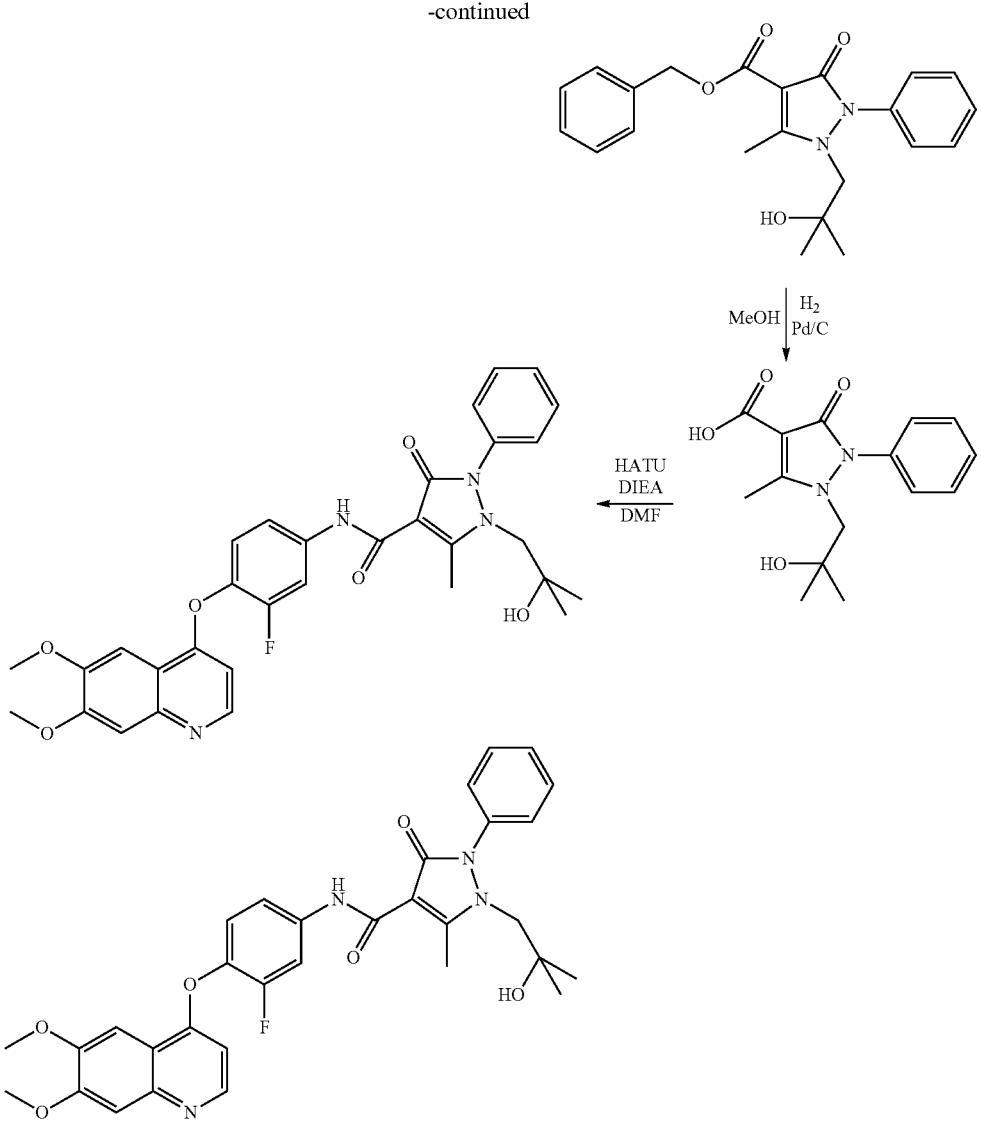

N-(4-(6,7-dimethoxyquinolin-4-yloxy)-3-fluorophenyl)-1-(2-hydroxy-2-methylpropyl)-5-methyl-3-oxo-2-phenyl-2,3-dihydro-1H-pyrazole-4-carboxamide

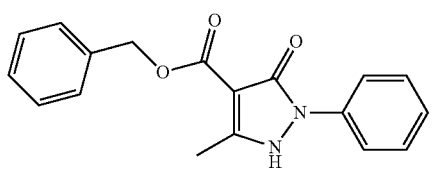

Step 1: Benzyl 5-methyl-3-oxo-2-phenyl-2,3-dihydro-1H-pyrazole-4-carboxylate. A suspension of 3-methyl-1-phenyl-1H-pyrazol-5-ol (10.0 g, 57 mmol) and calcium hydroxide (8.5 g, 115 mmol) in dry 1,4-dioxane (100 mL) was heated to 50° C. for 20 min. The suspension was chilled to 10° C. and benzyl chloroformate (8.2 ml, 57 mmol) added. The resultant was heated to 90° C. for 3 h, cooled to 25° C. and then, chilled (0° C.) 1 M HCl (200 mL) was added. The mixture was stirred at 25° C. overnight. A solid collected by filtration was washed with cold EtOH (2×25 mL) and ether (50 mL), dried at 80° C. (sand bath) exposed to air for 4 h to give the title compound (14.0 g, 79% yield) as an off-white solid. MS (ESI pos. ion) m/z: 309 (MH+). Calc'd exact mass for $C_{18}H_{16}N_2O_3$ 308.

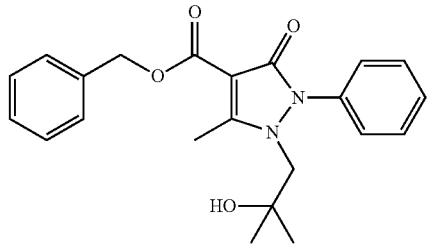

Step 2: Benzyl 1-(2-hydroxy-2-methylpropyl)-5-methyl-3-oxo-2-phenyl-2,3-dihydro-1H-pyrazole-4-carboxylate. To a stirring suspension of benzyl 5-hydroxy-3-methyl-1-phenyl-1H-pyrazole-4-carboxylate (3380 mg, 11 mmol) in chlorobenzene (30 mL) at 10° C. under nitrogen was added trimethylaluminum (16 mL, 33 mmol, 2M in toluene). Internal temperature reached 27° C. At 25° C., 1,2-epoxy-2-methylpropane (1000 mg, 16 mmol) was added. The reaction mixture was stirred for 3 h at 25° C., and then diluted with THF (500 mL). The resultant was chilled to 10° C., and sodium sulfate decahydrate (2 g) was added. After 1 hr, another 2 g of sodium sulfate decahydrate added. After 2 h, the gel was filtered through a bed of celite and washed with EtOAc (3×100 mL). The filtrate was then washed with aq. 1 M HCl (50 mL) and brine. The organic layer was dried over MgSO4. and concentrated. The residue was purified on 120 g silica chromatography (30>90% EtOAc/hex). To give the title compound (1.11 g, 27% yield) as an amorphous solid. MS (ESI pos. ion) m/z: 381 (MH+). Calc'd exact mass for $C_{22}H_{24}N_2O_4$ 380.

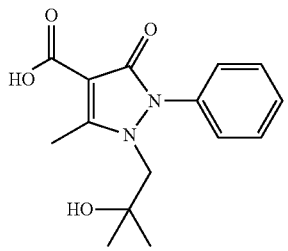

Step 3: 1-(2-hydroxy-2-methylpropyl)-5-methyl-3-oxo-2-phenyl-2,3-dihydro-1H-pyrazole-4-carboxylic acid. To a stirring solution of benzyl 1-(2-hydroxy-2-methylpropyl)-5-methyl-3-oxo-2-phenyl-2,3-dihydro-1H-pyrazole-4-carboxylate (300 mg, 789 μmol) in MeOH (10 mL) was purged with argon for 10 min. To this solution was added Pd/C (40 mg), and the mixture was stirred for 3 h under balloon of hydrogen. Reaction was monitored by LCMS. The reaction mixture was filtered through a bed of celite and concentrated under reduced pressure to give the title compound (220 mg, 96.1% yield) as an off-white solid. MS (ESI pos. ion) m/z: 291 (MH+). Calc'd exact mass for $C_{15}H_{18}N_2O_4$ 290.

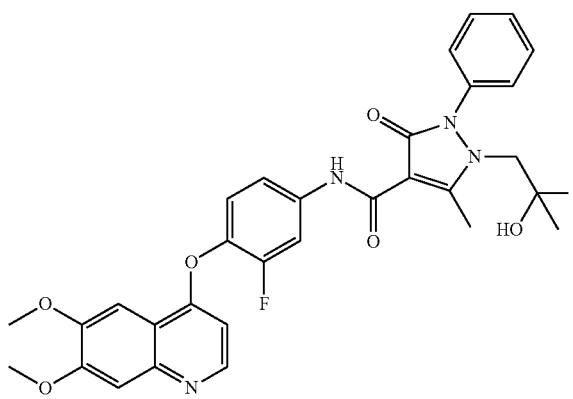

Step 4: N-(4-(6,7-dimethoxyquinolin-4-yloxy)-3-fluorophenyl)-1-(2-hydroxy-2-methylpropyl)-5-methyl-3-oxo-2-phenyl-2,3-dihydro-1H-pyrazole-4-carboxamide. To a stirring solution of 1-(2-hydroxy-2-methylpropyl)-5-methyl-3-oxo-2-phenyl-2,3-dihydro-1H-pyrazole-4-carboxylic acid (104 mg, 358 μmol) and diisopropylethylamine (62 μl, 358 μmol) in DMF (1 mL) was added HATU (136 mg, 358 μmol) and stirred at 37° C. under nitrogen for 15 min. To this was added 3-fluoro-4-(7-methoxyquinolin-4-yloxy)benzenamine (98 mg, 344 mmol) and stirred overnight at 37° C. The reaction mixture was diluted with dichloromethane (10 mL) and washed with 1M NaOH (20 mL), and extracted with dichloromethane (3×5 mL). Combined organics layer was washed with brine and then dried with MgSO4. Residual DMF was removed with repeated azeotroping with toluene (4×5 mL) under reduced pressure. The residue was purified on 12 g silica (10>30% of 6% 2 M NH$_3$ in MeOH/DCM). Final material was lyophilized from 50% ACN/water to give the title compound (155 mg, 74% yield) as a white fluffy solid. MS (ESI pos. ion) m/z: 587 (MH+). Calc'd exact mass for $C_{32}H_{31}FN_4O_6$ 587. $^1$H NMR (400 MHz, CHLOROFORM-d) 10.88 (1 H, s), 8.47 (1 H, d, J=5.3 Hz), 7.92 (1 H, dd, J=12.5, 2.0 Hz), 7.59 (1 H, s), 7.54 (2 H, t, J=7.7 Hz), 7.40-7.49 (2 H, m), 7.30 (3 H, d, J=7.8 Hz), 7.17 (1 H, t, J=8.7 Hz), 6.45 (1 H, d, J=5.3 Hz), 4.06 (3 H, s), 4.05 (3 H, s), 3.88 (2 H, s), 2.89 (3 H, s), 2.01 (1 H, s), 1.15(6 H, s)

EXAMPLE 53

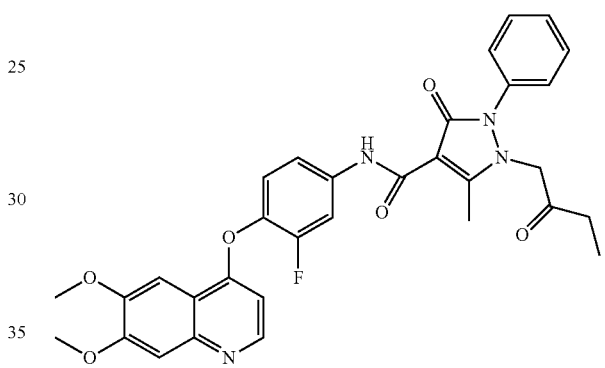

N-(3-fluoro-4-(7-methoxyquinolin-4-yloxy)phenyl)-5-methyl-3-oxo-1-(2-oxobutyl)-2-phenyl-2,3-dihydro-1H-pyrazole-4-carboxamide: MS (ESI pos. ion) m/z: 555 (MH+). Calc'd exact mass for $C_{31}H_{27}FN_4O_5$: 554. $^1$H NMR (400 MHz, CHLOROFORM-d) 10.86 (1 H, s), 8.60 (1 H, d, J=5.3 Hz), 8.28 (1 H, d, J=9.2 Hz), 7.65-8.00 (2 H, m), 7.41-7.58 (4 H, m), 7.28-7.35 (3 H, m), 7.23 (1 H, dd, J=9.2, 2.3 Hz), 7.17 (1 H, t, J=8.7 Hz), 6.44 (1 H, d, J=5.3 Hz), 4.51 (2 H, s), 3.97 (3 H, s), 2.68 (3 H, s), 2.26 (2 H, q, J=7.2 Hz), 1.01 (3 H, t, J=7.2 Hz).

EXAMPLE 54

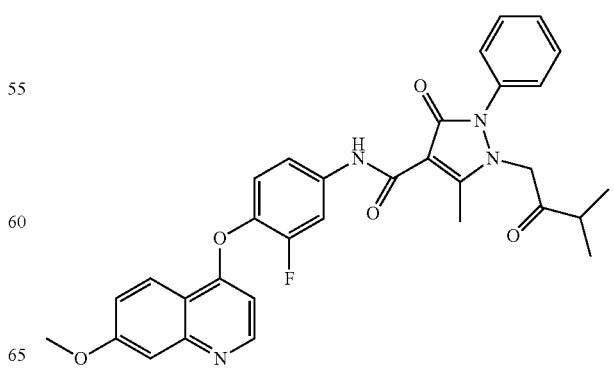

N-(3-fluoro-4-(7-methoxyquinolin-4-yloxy)phenyl)-5-methyl-1-(3-methyl-2-oxobutyl)-3-oxo-2-phenyl-2,3-dihydro-1H-pyrazole-4-carboxamide: MS (ESI pos. ion) m/z: 569 (MH+). Calc'd exact mass for $C_{32}H_{29}FN_4O_5$: 568. $^1$H NMR (400 MHz, CHLOROFORM-d) 10.88 (1 H, s), 8.59 (1 H, d, J=5.3 Hz), 8.21-8.30 (2 H, m), 7.97-8.03 (1 H, m), 7.87-7.95 (2 H, m), 7.71 (1 H, t, J=7.4 Hz), 7.44-7.57 (3 H, m), 7.41 (1 H, d, J=2.2 Hz), 7.26-7.34 (3 H, m), 7.23 (1 H, dd, J=9.2, 2.3 Hz), 7.17 (1 H, t, J=8.7 Hz), 6.42 (1 H, d, J=5.3 Hz), 4.58 (2 H, s), 3.97 (3 H, s), 2.67 (3 H, s), 2.38-2.52 (1 H, m), 2.26 (3 H, s), 0.96 (6 H, d, J=6.8 Hz).

EXAMPLE 55

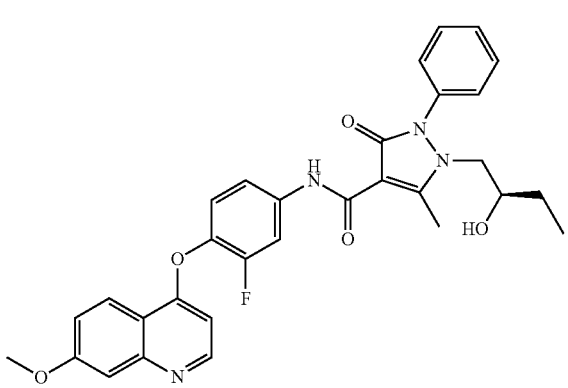

(R)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide: MS (ESI pos. ion) m/z: 557 (MH+). Calc'd exact mass for $C_{31}H_{29}FN_4O_5$: 556. $^1$H NMR (400 MHz, CHLOROFORM-d) 10.90 (1 H, s), 8.50 (1 H, d, J=5.3 Hz), 8.30 (1 H, d, J=9.2 Hz), 7.95 (1 H, dd, J=12.5, 2.0 Hz), 7.39-7.53 (3 H, m), 7.36 (1 H, d, J=2.2 Hz), 7.11-7.31 (6 H, m), 6.42 (3 H, d, J=5.3 Hz), 3.95 (3 H, s), 3.79-3.90 (1 H, m), 3.70 (1 H, dd, J=1.6 Hz), 3.56-3.66 (1 H, m), 2.85 (3 H, s), 1.60-1.82 (1 H, m), 1.27-1.43 (2 H, m), 0.83 (3 H, t, J=7.3 Hz)

EXAMPLE 56

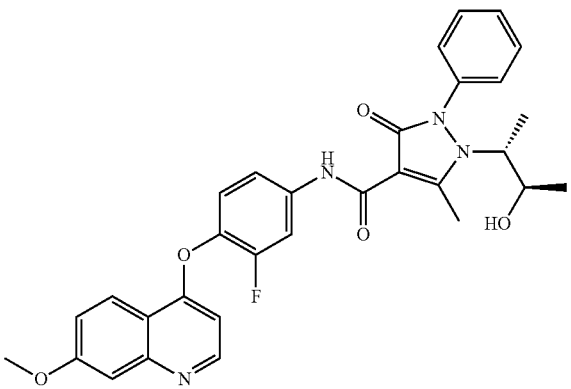

N-(3-fluoro-4-(7-methoxyquinolin-4-yloxy)phenyl)-1-((2R,3R)-3-hydroxybutan-2-yl)-5-methyl-3-oxo-2-phenyl-2,3-dihydro-1H-pyrazole-4-carboxamide: MS (ESI pos. ion) m/z: 557 (MH+). Calc'd exact mass for $C_{31}H_{29}FN_4O_5$: 556. $^1$H NMR (400 MHz, CHLOROFORM-d) 10.94 (1 H, s), 8.54 (1 H, d, J=5.1 Hz), 8.27 (1 H, d, J=9.0 Hz), 7.90 (1 H, dd, J=12.3, 2.0 Hz), 7.43-7.57 (3 H, m), 7.37-7.40 (1 H, m), 7.31 (2 H, d, J=7.6 Hz), 7.25-7.28 (1 H, m), 7.23 (1 H, dd, J=9.2, 2.2 Hz), 7.16 (1 H, t, J=8.7 Hz), 6.40 (1 H, d, J=5.1 Hz), 3.77-4.05 (6 H, m), 2.89 (3 H, s), 1.63-1.91 (2 H, m), 1.50 (3 H, d, J=7.0 Hz), 1.11 (3 H, d, J=6.3 Hz)

EXAMPLE 57

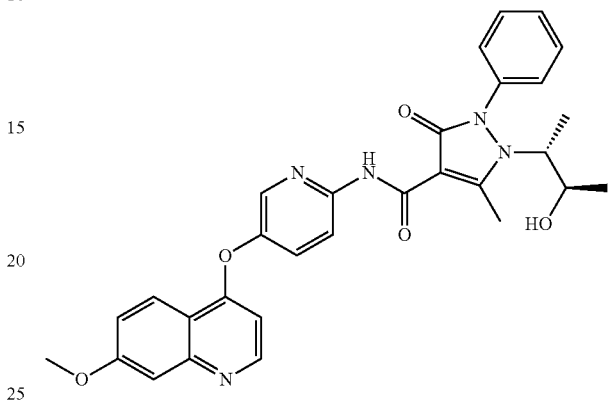

1-((2R,3R)-3-hydroxybutan-2-yl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 540 (MH+). Calc'd exact mass for $C_{30}H_{29}N_5O_5$: 539. $^1$H NMR (400 MHz, CHLOROFORM-d) 11.30 (1 H, s), 8.59 (1 H, d, J=5.3 Hz), 8.36 (1 H, d, J=9.0 Hz), 8.21-8.26 (2 H, m), 7.43-7.56 (4 H, m), 7.41 (1 H, d, J=2.5 Hz), 7.30-7.35 (2 H, m), 7.23 (1 H, dd, J=9.2, 2.5 Hz), 6.42 (1 H, d, J=5.3 Hz), 3.97-4.05 (1 H, m), 3.97 (3 H, s), 3.84-3.93 (1 H, m), 3.49 (1 H, s), 2.90 (3 H, s), 1.50 (3 H, d, J=7.2 Hz), 1.12 (3 H, d, J=6.3 Hz)

EXAMPLE 58

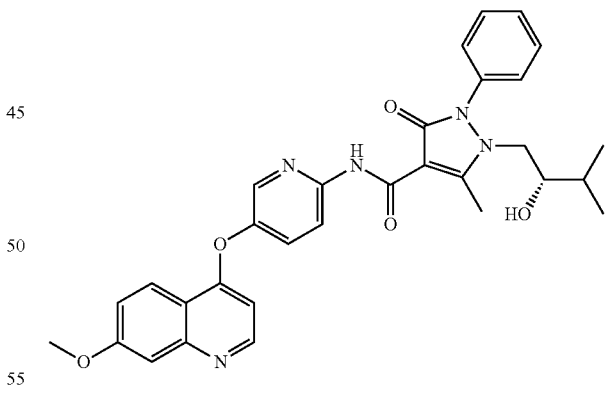

(S)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 554 (MH+). Calc'd exact mass for $C_{31}H_{31}N_5O_5$: 553. $^1$H NMR (400 MHz, DMSO-$d_6$) 11.29 (1 H, s), 8.63 (1 H, d, J=5.1 Hz), 8.37 (1 H, d, J=9.0 Hz), 8.32 (1 H, d, J=2.9 Hz), 8.22 (1 H, d, J=9.2 Hz), 7.80 (1 H, dd, J=9.0, 2.9 Hz), 7.60 (2 H, t, J=7.5 Hz), 7.51 (1 H, t, J=7.3 Hz), 7.40-7.47 (3 H, m), 7.30 (1 H, dd, J=9.2, 2.5 Hz), 6.54 (1 H, d, J=5.3 Hz), 5.10 (1 H, d, J=5.9 Hz), 3.87-3.98 (4 H, m), 3.71 (1 H, d), 3.10-3.21 (1 H, m), 2.76 (3 H, s), 1.33-1.46 (1 H, m), 0.64 (3 H, d, J=6.8 Hz), 0.58 (3 H, d, J=6.8 Hz)

EXAMPLE 59

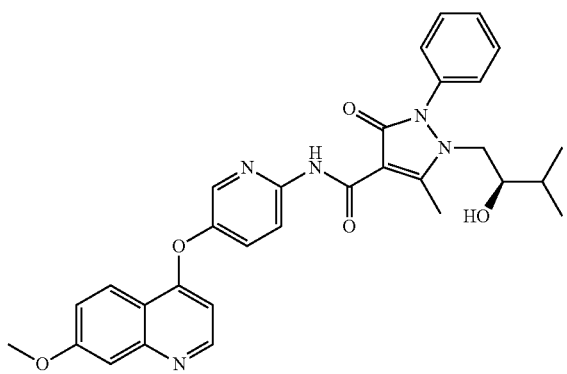

(R)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 554 (MH+). Calc'd exact mass for $C_{31}H_{31}N_5O_5$: 553. $^1$H NMR (400 MHz, DMSO-$d_6$) 11.30 (1 H, s), 8.63 (1 H, d, J=5.1 Hz), 8.37 (1 H, d, J=9.0 Hz), 8.33 (1 H, d, J=2.7 Hz), 8.22 (1 H, d, J=9.2 Hz), 7.80 (1 H, dd, J=9.1, 2.8 Hz), 7.60 (2 H, t, J=7.5 Hz), 7.51 (1 H, t, J=7.3 Hz), 7.39-7.47 (3 H, m), 7.30 (1 H, dd, J=9.2, 2.5 Hz), 6.54 (1 H, d, J=5.1 Hz), 5.11 (1 H, d, J=5.9 Hz), 3.85-3.97 (4 H, m), 3.71 (2 H, s), 3.10-3.21 (2 H, m), 2.76 (3 H, s), 1.32-1.47 (1 H, m), 0.64 (3 H, d, J=6.7 Hz), 0.58 (3 H, d, J=6.8 Hz)

EXAMPLE 60

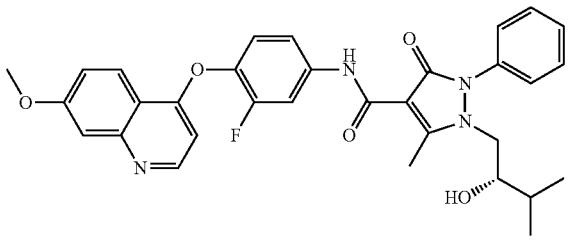

(S)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide: MS (ESI pos. ion) m/z: 571 (MH+). Calc'd exact mass for $C_{32}H_{31}FN_4O_5$: 570. $^1$H NMR (400 MHz, CHLOROFORM-d) 10.93 (1 H, s), 8.47 (1 H, d, J=5.3 Hz), 8.31 (1 H, d, J=9.2 Hz), 7.89-8.03 (1 H, m), 7.39-7.50 (3 H, m), 7.34 (1 H, d, J=2.0 Hz), 7.19-7.31 (3 H, m), 7.08 (2 H, d, J=7.2 Hz), 6.45 (1 H, d, J=5.3 Hz), 3.95 (3 H, s), 3.86 (1 H, dd, J=14.9 Hz), 3.64-3.77 (1 H, m), 3.44-3.48 (4 H, m), 3.33-3.42 (1 H, m), 2.82 (9 H, s), 1.46-1.61 (3 H, m), 0.80 (3 H, d, J=6.7 Hz), 0.72 (3 H, d, J=6.8 Hz)

EXAMPLE 61

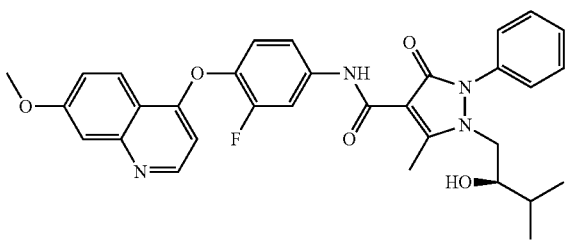

(R)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide: MS (ESI pos. ion) m/z: 571 (MH+). Calc'd exact mass for $C_{32}H_{31}FN_4O_5$: 570. $^1$H NMR (400 MHz, CHLOROFORM-d) 0.73 (d, J=6.85 Hz, 3 H) 0.81 (d, J=6.85 Hz, 3 H) 1.43-1.65 (m, 1 H) 2.83 (s, 3 H) 3.39-3.45 (m, 1 H) 3.94 (s, 3 H) 7.05 (d, J=7.04 Hz, 2 H) 7.20-7.28 (m, 3 H) 7.34 (d, J=2.35 Hz, 1H) 7.38-7.46 (m, 3 H) 7.97 (dd, J=12.42, 1.66 Hz, 1 H) 8.31 (d, J=9.19 Hz, 1 H) 8.47 (d, J=5.28 Hz, 1 H) 10.93 (s, 1 H)

EXAMPLE 62

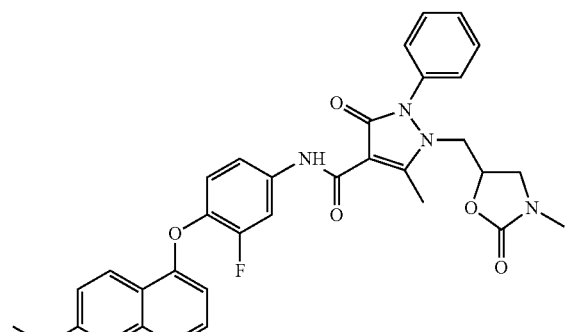

N-(3-fluoro-4-(7-methoxyquinolin-4-yloxy)phenyl)-5-methyl-1-((3-methyl-2-oxooxazolidin-5-yl)methyl)-3-oxo-2-phenyl-2,3-dihydro-1H-pyrazole-4-carboxamide: MS (ESI pos. ion) m/z: 598 (MH+). Calc'd exact mass for $C_{32}H_{28}FN_5O_6$: 597. $^1$H NMR (400 MHz, CHLOROFORM-d) 10.77 (1 H, s), 8.61 (1 H, d, J=5.7 Hz), 8.28 (1 H, d, J=9.2 Hz), 7.91 (1 H, dd, J=12.3, 2.2 Hz), 7.68 (1 H, d, J=2.0 Hz), 7.58 (2 H, t, J=7.6 Hz), 7.48 (1 H, t, J=7.5 Hz), 7.38 (2 H, d, J=7.4 Hz), 7.33 (1 H, d, J=8.8 Hz), 7.23-7.30 (1 H, m), 7.17 (1 H, t, J=8.6 Hz), 6.49 (1 H, d, J=5.5 Hz), 4.42-4.55 (1 H, m), 4.14 (1 H, dd, J=15.7, 8.4 Hz), 4.04 (3 H, s), 3.91 (1 H, dd, J=15.7, 3.3 Hz), 3.52 (1 H, t, J=8.9 Hz), 3.06 (1 H, dd, J=9.2, 5.9 Hz), 2.77-2.93 (6 H, m), 2.67 (4 H, s)

EXAMPLE 63

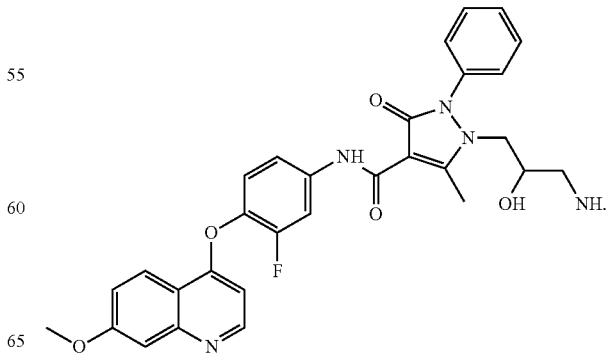

N-(3-fluoro-4-(7-methoxyquinolin-4-yloxy)phenyl)-1-(2-hydroxy-3-(methylamino)propyl)-5-methyl-3-oxo-2-phenyl-2,3-dihydro-1H-pyrazole-4-carboxamide: MS (ESI pos. ion) m/z: 609 (MH+). Calc'd exact mass for $C_{31}H_{30}FN_5O_5$: 608. $^1$H NMR (400 MHz, DMSO-$d_6$) 11.00 (1 H, s), 8.62 (1 H, d, J=5.3 Hz), 8.23 (1 H, d, J=9.2 Hz), 7.97 (1 H, s), 7.59 (2 H, t, J=7.5 Hz), 7.26-7.54 (7 H, m), 6.49 (1 H, d, J=5.1 Hz), 5.15 (1 H, s), 3.79-4.00 (5 H, m), 3.35-3.59 (3 H, m), 2.75 (3 H, s), 2.29 (2 H, d, J=5.5 Hz), 2.07 (3 H, s), 0.99-1.16 (1 H, m)

EXAMPLE 64

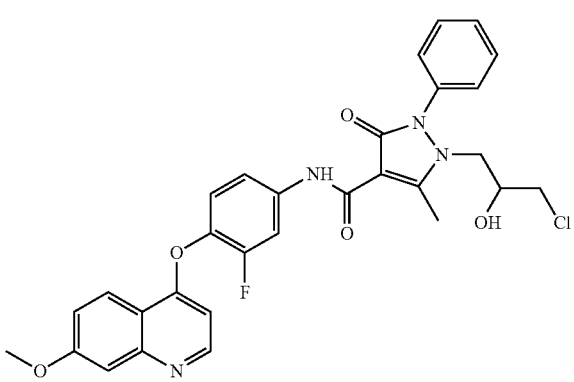

1-(3-chloro-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide: MS (ESI pos. ion) m/z: 577 (MH+). Calc'd exact mass for $C_{30}H_{26}ClFN_4O_5$: 576

EXAMPLE 65

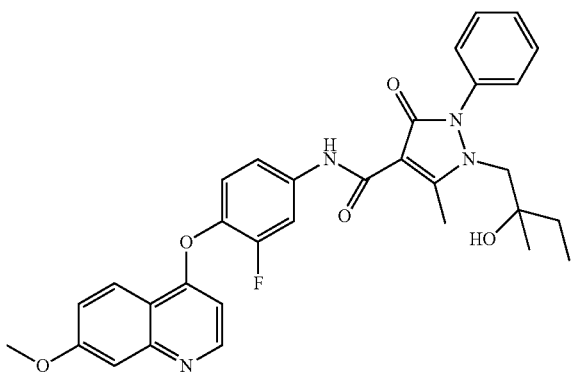

N-(3-fluoro-4-(7-methoxyquinolin-4-yloxy)phenyl)-1-(2-hydroxy-2-methylbutyl)-5-methyl-3-oxo-2-phenyl-2,3-dihydro-1H-pyrazole-4-carboxamide: MS (ESI pos. ion) m/z: 571 (MH+). Calc'd exact mass for $C_{32}H_{31}FN_4O_5$: 570. $^1$H NMR (400 MHz, DMSO-$d_6$) 10.90 (1 H, s), 8.63 (1 H, d, J=5.1 Hz), 8.24 (1 H, d, J=9.0 Hz), 7.99 (1 H, dd, J=13.0, 2.2 Hz), 7.64 (1 H, s), 7.59 (2 H, t, J=7.5 Hz), 7.51 (1 H, t, J=7.4 Hz), 7.41-7.47 (4 H, m), 7.36-7.41 (1 H, m), 7.32 (1 H, dd, J=9.1, 2.4 Hz), 6.50 (1 H, d, J=5.3 Hz), 4.55-4.65 (1 H, m), 4.30 (1 H, dd, J=16.0, 9.2 Hz), 4.02 (1 H, dd, J=15.9, 2.6 Hz), 3.95 (3 H, s), 3.43 (1 H, t, J=9.1 Hz), 3.07 (1H, dd, J=9.4, 5.5 Hz), 2.76 (3 H, s)

EXAMPLE 66

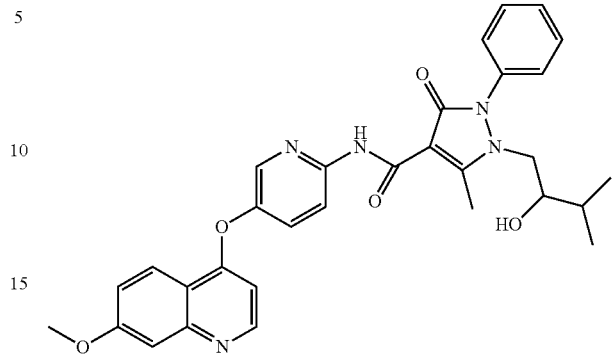

1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 554 (MH+). Calc'd exact mass for $C_{31}H_{31}N_5O_5$: 553. $^1$H NMR (400 MHz, DMSO-$d_6$) 11.30 (1 H, s), 8.63 (1 H, d, J=5.3 Hz), 8.30-8.42 (2H, m), 8.22 (1 H, d, J=9.2 Hz), 7.81 (1 H, dd, J=9.1, 2.8 Hz), 7.60 (2 H, t, J=7.5 Hz), 7.51 (1 H, t, J=7.3 Hz), 7.39-7.47 (3 H, m), 7.30 (1 H, dd, J=9.2, 2.5 Hz), 6.54 (1 H, d, J=5.3 Hz), 5.11 (1 H, d, J=5.7 Hz), 3.86-3.98 (4 H, m), 3.66-3.75 (1 H, m), 3.09-3.20 (1 H, m), 2.76 (3 H, s), 1.34-1.45 (1 H, m), 0.64 (3 H, d, J=6.7 Hz), 0.58 (3 H, d, J=6.7 Hz)

EXAMPLE 67

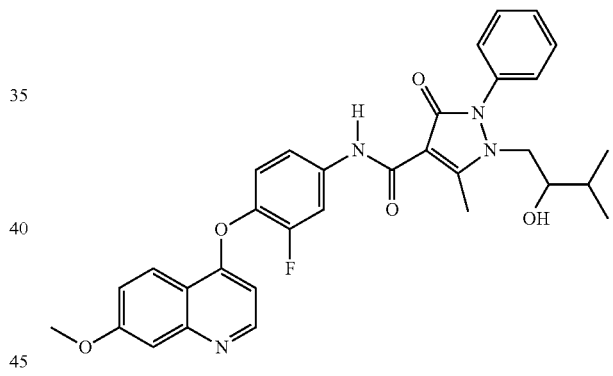

N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide: MS (ESI pos. ion) m/z: 571 (MH+). Calc'd exact mass for $C_{32}H_{31}FN_4O_5$: 570.

EXAMPLE 68

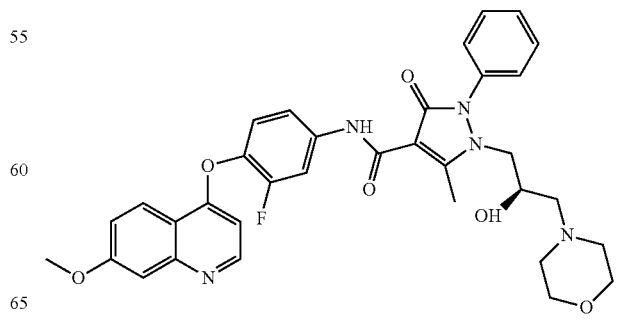

N-(3-fluoro-4-(7-methoxyquinolin-4-yloxy)phenyl)-1-(2-hydroxy-3-morpholinopropyl)-5-methyl-3-oxo-2-phenyl-2,3-dihydro-1H-pyrazole-4-carboxamide: MS (ESI pos. ion) m/z: 628 (MH+). Calc'd exact mass for $C_{34}H_{34}FN_5O_6$: 627.

EXAMPLE 69

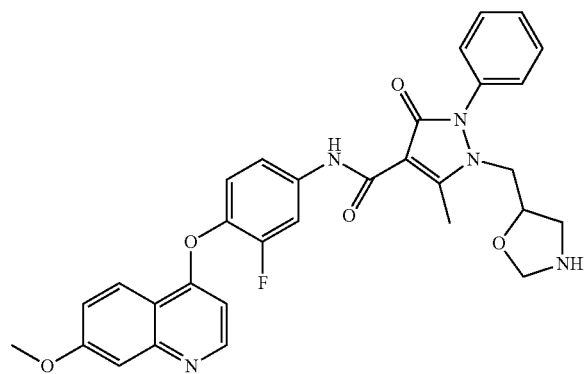

N-(3-fluoro-4-(7-methoxyquinolin-4-yloxy)phenyl)-5-methyl-1-(oxazolidin-5-ylmethyl)-3-oxo-2-phenyl-2,3-dihydro-1H-pyrazole-4-carboxamide: MS (ESI pos. ion) m/z: 584 (MH+). Calc'd exact mass for $C_{31}H_{26}FN_5O_6$: 583. $^1$H NMR (400 MHz, DMSO-$d_6$) 11.30 (1 H, s), 8.63 (1 H, d, J=5.3 Hz), 8.30-8.42 (2 H, m), 8.22 (1 H, d, J=9.2 Hz), 7.81 (1 H, dd, J=9.1, 2.8 Hz), 7.60 (2 H, t, J=7.5 Hz), 7.51 (1 H, t, J=7.3 Hz), 7.39-7.47 (3 H, m), 7.30 (1 H, dd, J=9.2, 2.5 Hz), 6.54 (1 H, d, J=5.3 Hz), 5.11 (1 H, d, J=5.7 Hz), 3.86-3.98 (4 H, m), 3.66-3.75 (1 H, m), 3.09-3.20 (1 H, m), 2.76 (3H, s), 1.34-1.45 (1 H, m), 0.64 (3 H, d, J=6.7 Hz), 0.58 (3 H, d, J=6.7 Hz)

EXAMPLE 70

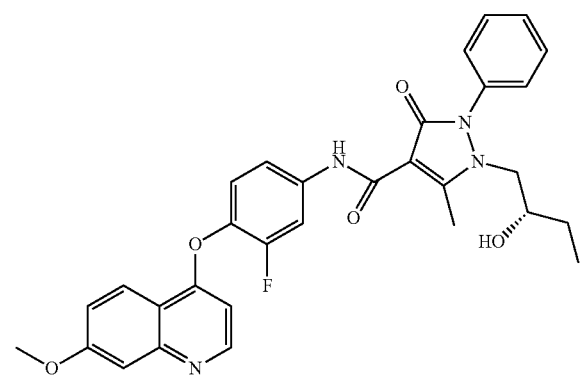

(S)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide: MS (ESI pos. ion) m/z: 557 (MH+). Calc'd exact mass for $C_{31}H_{29}FN_4O_5$: 556.

EXAMPLE 71

1-(3-amino-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide: MS (ESI pos. ion) m/z: 558 (MH+). Calc'd exact mass for $C_{30}H_{28}FN_5O_5$: 557. $^1$H NMR (400 MHz, DMSO-$d_6$) 10.93 (1 H, s), 8.55 (1 H, d, J=5.3 Hz), 8.16 (1 H, d, J=9.0 Hz), 7.92 (1 H, dd, J=12.9, 2.3 Hz), 7.51 (2 H, t, J=7.5 Hz), 7.43 (1 H, t, J=7.4 Hz), 7.32-7.38 (4 H, m), 7.21-7.31 (2 H, m), 6.42 (1 H, d, J=5.1 Hz), 5.05 (1 H, s), 3.81-3.90 (4 H, m), 3.69-3.77 (1 H, m), 2.67-2.72 (3 H, m), 2.23-2.31 (2 H, m)

EXAMPLE 72

1-(2-hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 540 (MH+). Calc'd exact mass for $C_{30}H_{29}N_5O_5$: 539. $^1$H NMR (400 MHz, CHLOROFORM-d) 11.23 (1 H, s), 8.58 (1 H, d, J=5.1 Hz), 8.37 (1 H, d, J=8.8 Hz), 8.20-8.27 (2 H, m), 7.50 (3 H, d, J=7.8 Hz), 7.38-7.44 (2 H, m), 7.26-7.34 (2 H, m), 7.23 (1 H, d, J=8.8 Hz), 6.43 (1 H, d, J=4.9 Hz), 3.97 (3 H, s), 3.88 (2 H, s), 2.88 (3 H, s), 2.51 (1 H, s), 1.14 (6 H, s)

EXAMPLE 73

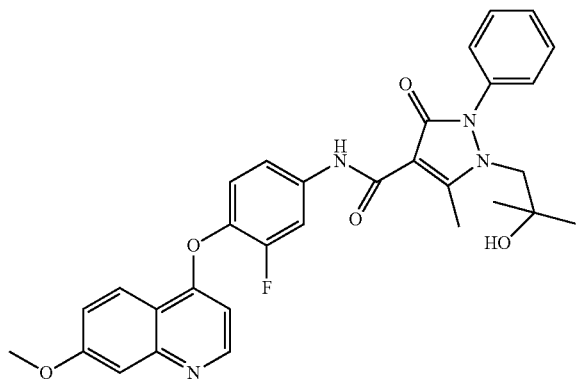

N-(3-fluoro-4-(7-methoxyquinolin-4-yloxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 557 (MH+). Calc'd exact mass for $C_{31}H_{29}N_4O_5$: 556. $^1$H NMR (400 MHz, CHLOROFORM-d) 10.88 (1 H, s), 8.56 (1 H, d, J=5.3 Hz), 8.27 (1 H, d, J=9.2 Hz), 7.92 (1 H, dd, J=12.5, 2.0 Hz), 7.54 (2 H, t, J=7.6 Hz), 7.38-7.49 (2 H, m), 7.29 (3 H, d, J=8.0 Hz), 7.23 (1 H, dd, J=9.2, 2.3 Hz), 7.17 (1 H, t, J=8.7 Hz), 6.42 (1 H, d, J=5.3 Hz), 3.97 (3 H, s), 3.88 (2 H, s), 2.89 (3 H, s), 1.82 (1 H, s), 1.15 (6 H, s)

EXAMPLE 74

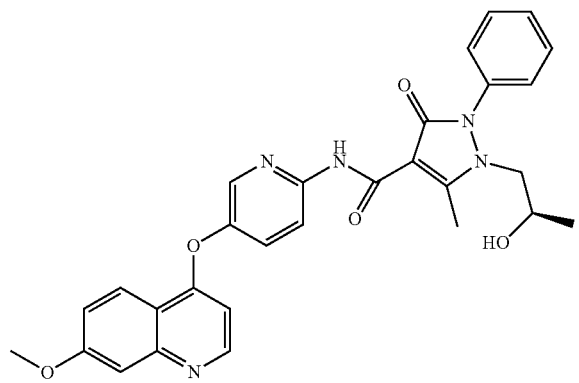

(R)-1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 526 (MH+). Calc'd exact mass for $C_{29}H_{27}N_5O_5$: 525. $^1$H NMR (400 MHz, CHLOROFORM-d) 11.20 (1 H, s), 8.55 (1 H, d, J=5.3 Hz), 8.37 (1 H, d, J=9.0 Hz), 8.21-8.28 (2 H, m), 7.46-7.56 (3 H, m), 7.37-7.45 (2 H, m), 7.21-7.31 (4 H, m), 6.45 (1 H, d, J=5.3 Hz), 3.89-4.01 (4 H, m), 3.78-3.88 (1 H, m), 3.66 (1 H, dd, J=14.8, 2.2 Hz), 2.83 (3 H, s), 1.08 (3 H, d, J=6.1 Hz)

EXAMPLE 75

1-(3-(dimethylamino)-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide: MS (ESI pos. ion) m/z: 586 (MH+). Calc'd exact mass for $C_{32}H_{32}FN_5O_5$: 585. $^1$H NMR (400 MHz, CHLOROFORM-d) 10.88 (1 H, s), 8.58 (1 H, s), 8.23-8.33 (1 H, m), 7.85-7.97 (1 H, m), 7.11-7.61 (11 H, m), 6.37-6.46 (1 H, m), 3.97 (3 H, s), 3.79 (4 H, s), 3.48 (1 H, s), 2.87 (3 H, s), 2.11-2.20 (7 H, m), 1.92-2.02 (2 H, m).

EXAMPLE 76

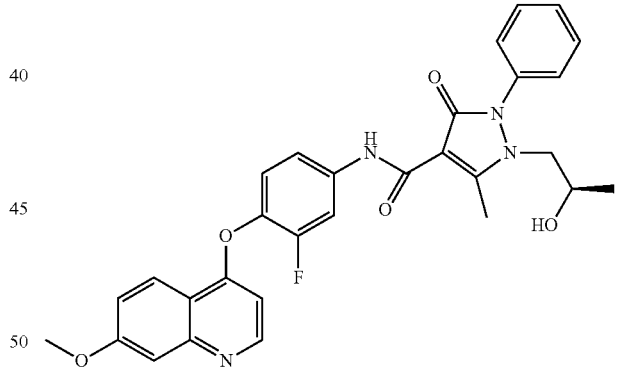

(R)-N-(3-fluoro-4-(7-methoxyquinolin-4-yloxy)phenyl)-1-(2-hydroxypropyl)-5-methyl-3-oxo-2-phenyl-2,3-dihydro-1H-pyrazole-4-carboxamide: MS (ESI pos. ion) m/z: 543 (MH+). Calc'd exact mass for $C_{30}H_{27}FN_4O_5$: 542. $^1$H NMR (400 MHz, CHLOROFORM-d) 10.89 (1 H, s), 8.48 (1 H, d, J=5.3 Hz), 8.29 (1 H, d, J=9.2 Hz), 7.95 (1 H, dd, J=12.4, 1.7 Hz), 7.38-7.51 (1 H, m), 7.35 (1 H, d, J=2.0 Hz), 7.17-7.29 (3 H, m), 7.14 (2 H, d, J=7.6 Hz), 6.42 (1 H, d, J=5.3 Hz), 3.97-4.08 (1 H, m), 3.95 (3 H, s), 3.78-3.92 (2 H, m), 3.64 (1 H, d, J=112.9 Hz), 2.84 (3 H, s), 1.17-1.27 (4 H, m), 1.09 (3 H, d, J=5.9 Hz).

EXAMPLE 77

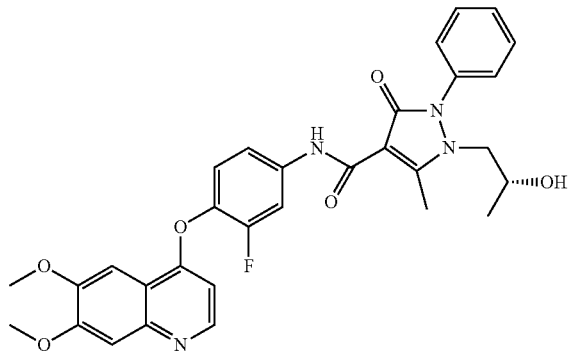

(R)-N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide: MS (ESI pos. ion) m/z: 573 (MH+). Calc'd exact mass for $C_{31}H_{29}FN_4O_6$: 572. $^1$H NMR (400 MHz, CHLOROFORM-d) 10.88 (1 H, s), 8.45 (1 H, d, J=5.5 Hz), 7.93 (1 H, dd, J=12.5, 2.3 Hz), 7.60 (1 H, s), 7.53 (2H, t, J=7.5 Hz), 7.45 (1 H, t, J=7.4 Hz), 7.41 (1 H, s), 7.27-7.33 (3 H, m), 7.19 (1 H, t, J=8.6 Hz), 6.46 (1 H, d, J=5.3 Hz), 4.07 (3 H, s), 4.04 (3 H, s), 3.79-3.96 (2 H, m), 3.63-3.74 (1 H, m), 2.86 (3 H, s), 1.10 (3 H, d, J=6.1 Hz)

EXAMPLE 78

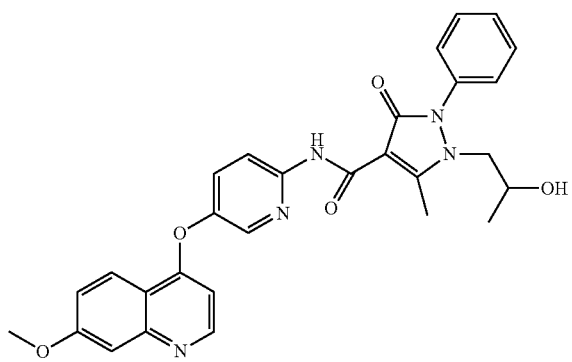

1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide: MS (ESI pos. ion) m/z: 526 (MH+). Calc'd exact mass for $C_{29}H_{27}N_5O_5$: 525. $^1$H NMR (400 MHz, DMSO-$d_6$) 11.27 (1 H, s), 8.62 (1 H, d, J=5.3 Hz), 8.36 (1 H, d, J=9.0 Hz), 8.32 (1 H, d, J=2.7 Hz), 8.22 (1 H, d, J=9.0 Hz), 7.80 (1 H, dd, J=9.0, 2.9 Hz), 7.59 (2 H, t, J=7.5 Hz), 7.51 (1 H, t, J=7.4 Hz), 7.39-7.45 (4 H, m), 7.30 (1 H, dd, J=9.1, 2.4 Hz), 6.54 (1 H, d, J=5.3 Hz), 5.08 (1 H, d, J=5.3 Hz), 3.94 (3 H, s), 3.88 (1 H, dd, J=15.2, 8.9 Hz), 3.55-3.69 (2 H, m), 2.77 (3 H, s)

EXAMPLE 79

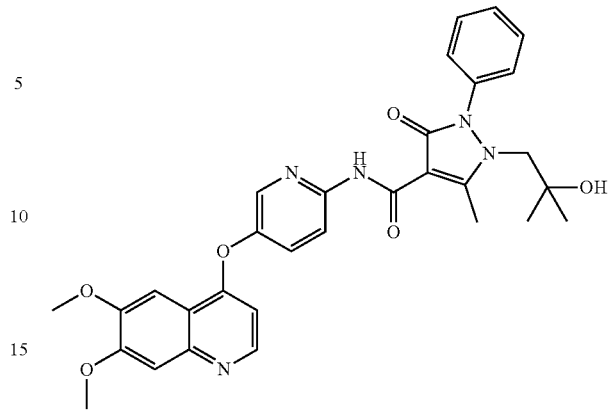

N-(5-(6,7-dimethoxyquinolin-4-yloxy)pyridin-2-yl)-1-(2-hydroxy-2-methylpropyl)-5-methyl-3-oxo-2-phenyl-2,3-dihydro-1H-pyrazole-4-carboxamide: MS (ESI pos. ion) m/z: 570 (MH+). Calc'd exact mass for $C_{31}H_{31}N_5O_6$: 569. $^1$H NMR (400 MHz, DMSO-$d_6$) 11.25 (s, 1 H), 8.49 (d, J=5.2 Hz, 1 H), 8.36 (d, J=9.0 Hz, 1 H), 8.32 (d, J=2.7 Hz, 1 H), 7.79 (dd, J=9.0, 3.0 Hz, 1 H), 7.66-7.29 (m, 7 H), 6.54 (d, J=5.2 Hz, 1 H), 4.85 (s, 1 H), 3.95 (s, 3 H), 3.94 (s, 3 H), 3.86 (s, 2 H), 2.81 (s, 3 H), 0.96 (s, 6 H).

EXAMPLE 80

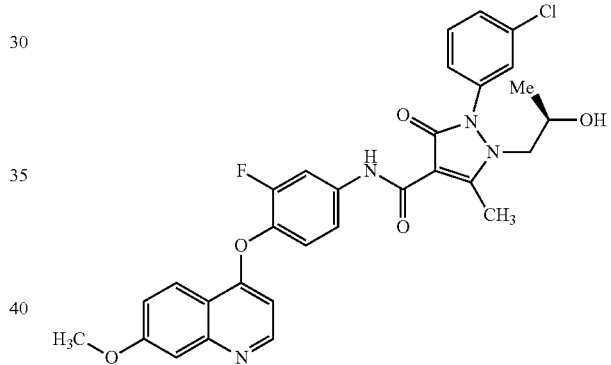

(R)-2-(3-chlorophenyl)-N-(3-fluoro-4-(7-methoxyquinolin-4-yloxy)phenyl)-1-(2-hydroxypropyl)-5-methyl-3-oxo-2,3-dihydro-1H-pyrazole-4-carboxamide: MS (ESI pos. ion) m/z: 577 (MH+). Calc'd exact mass for $C_{30}H_{26}ClFN_4O_5$: 576.

EXAMPLE 81

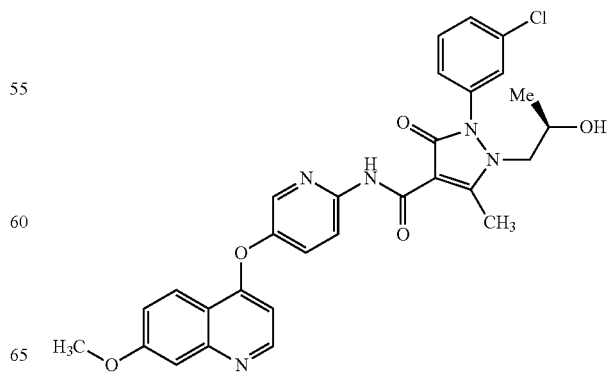

(R)-2-(3-chlorophenyl)-1-(2-hydroxypropyl)-N-(5-(7-methoxyquinolin-4-yloxy)pyridin-2-yl)-5-methyl-3-oxo-2,3-dihydro-1H-pyrazole-4-carboxamide: MS (ESI pos. ion) m/z: 560 (MH+). Calc'd exact mass for $C_{29}H_{26}ClN_5O_5$: 559.

EXAMPLE 82

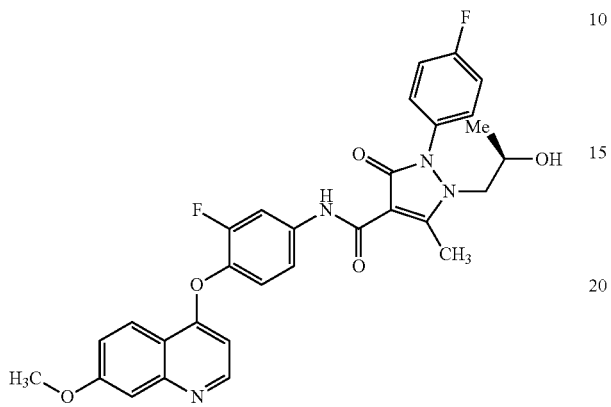

(R)-N-(3-fluoro-4-(7-methoxyquinolin-4-yloxy)phenyl)-2-(4-fluorophenyl)-1-(2-hydroxypropyl)-5-methyl-3-oxo-2,3-dihydro-1H-pyrazole-4-carboxamide: MS (ESI pos. ion) m/z: 561 (MH+). Calc'd exact mass for $C_{30}H_{26}F_2N_4O_5$: 560.

EXAMPLE 83

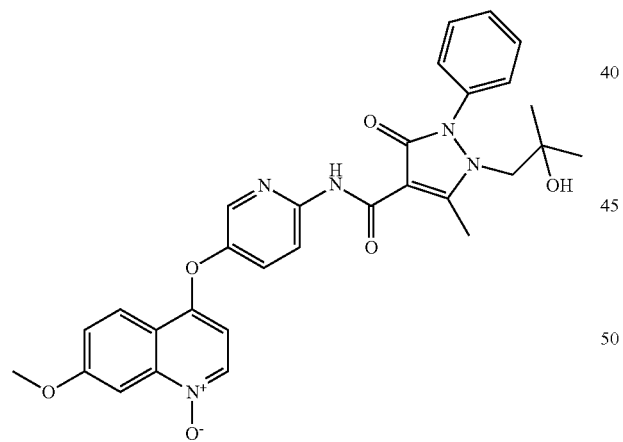

1-(2-hydroxy-2-methylpropyl)-N-(5-(1-oxo-7-methoxyquinolin-4-yloxy)pyridin-2-yl)-5-methyl-3-oxo-2-phenyl-2,3-dihydro-1H-pyrazole-4-carboxamide: A mixture of m-CPBA (151 mg, 675 μmol) and 1-(2-hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (280 mg, 519 μmol) in dichloromethane (10 mL) was stirred at room temperature for 14 h. More m-CPBA (151 mg, 675 μmol) was added, and the mixture was stirred for 24 h. The product fraction was purified from preparative HPLC to give the title compound as a white solid (25 mg, 8.7%). Calc'd for $C_{30}H_{29}N_5O_6$, 555; MS (ESI pos. ion) m/z: 556 (MH+). ¹HNMR (400 MHz, CDCl₃): 11.3 (1H, s), 8.60 (1H, d, J 6.7), 8.42 (1H, d, J 9.0), 8.32 (1H, d, J 9.4), 8.23 (1H, s), 8.00 (1H, s), 7.54-7.50 (3H, m), 7.44-7.40 (2H, m), 7.30 (2H, m), 6.52 (1H, d, J 7.1), 4.06 (3H, s), 3.88 (2H, s), 2.87 (3H, s), 1.15 (6H, s).

EXAMPLE 84

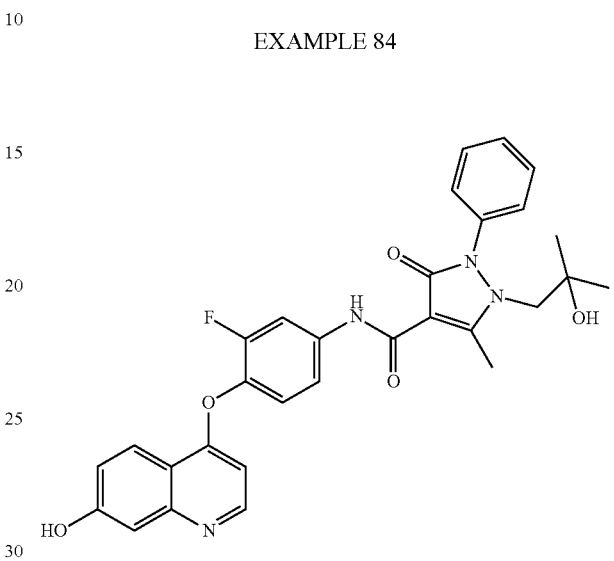

N-(3-Fluoro-4-(7-hydroxyquinolin-4-yloxy)phenyl)-1-(2-hydroxy-2-methylpropyl)-5-methyl-3-oxo-2-phenyl-2,3-dihydro-1H-pyrazole-4-carboxamide: Calc'd for $C_{30}H_{27}FN_4O_5$: 542; MS (ESI pos. ion) m/z: 543 (MH+). ¹HNMR (400 MHz, DMSO-d₆): 10.95 (1H, s, NH), 10.39 (1H, s, OH), 8.56 (1H, d, J5.4), 8.18 (1H, d, J 7.2), 7.96 (1H, d, J 7.9), 7.58-7.22 (8H, m), 6.42 (1H, d, J4.0), 5.75 (1H, s), 4.83 (1H, s, OH), 3.87 (2H, s, CH2), 2.80 (3H, s), 0.96 (6H, s).

EXAMPLE 85

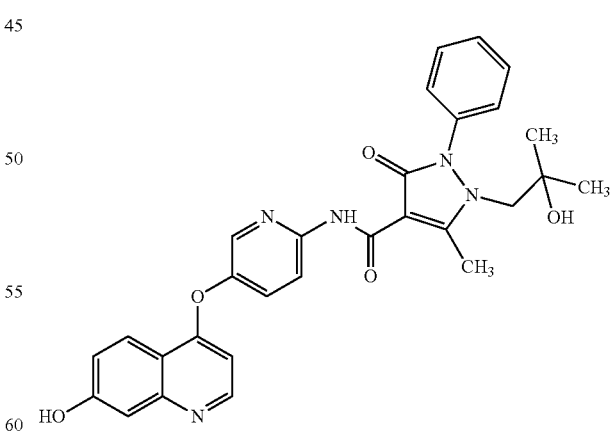

1-(2-hydroxy-2-methylpropyl)-N-(5-(7-hydroxyquinolin-4-yloxy)pyridin-2-yl)-5-methyl-3-oxo-2-phenyl-2,3-dihydro-1H-pyrazole-4-carboxamide: Calc'd for $C_{29}H_{27}N_5O_5$: 525; MS (ESI pos. ion) m/z: 526 (MH+).

EXAMPLE 86

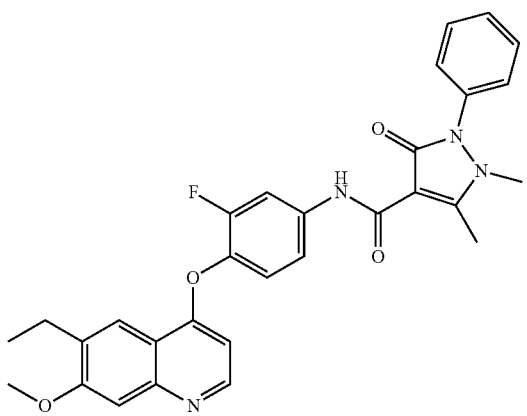

N-(4-(6-Ethyl-7-methoxyquinolin-4-yloxy)-3-fluorophenyl)-1,5-dimethyl-3-oxo-2-phenyl-2,3-dihydro-1H-pyrazole-4-carboxamide: Calc'd for $C_{30}H_{27}FN_4O_4$: 526; MS (ESI pos. ion) m/z: 527 (MH+). $^1$HNMR (400 MHz, CDCl$_3$): 10.88 (1H), 8.54 (1H, d, J=5.1), 8.09 (1H, s), 7.92 (1H, dd, J 2.0, 13.8), 7.57 (2H, t, J 7.5), 7.48 (1H, t, J 7.2), 7.37 (2H, m,), 7.32 (1H, d), 7.17 (1H, t, J 8.8), 6.39 (1H, d, 4.9), 3.99 (3H, s), 3.38 (3H, s), 2.84 (2H, m) 2.81 (3H, s), 1.32 (3H, t, J 7.5).

EXAMPLE 87

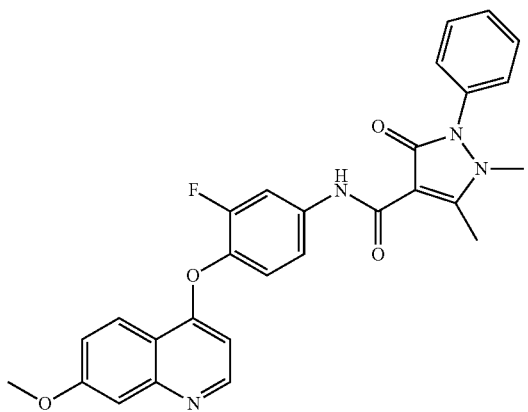

N-(3-Fluoro-4-(7-methoxyquinolin-4-yloxy)phenyl)-1,5-dimethyl-3-oxo-2-phenyl-2,3-dihydro-1H-pyrazole-4-carboxamide: Calc'd for $C_{28}H_{23}FN_4O_4$: 498; MS (ESI pos. ion) m/z: 499 (MH+). $^1$HNMR (400 MHz, CDCl$_3$): 10.88 (1H), 8.58 (1H, d, J=5.7), 8.27 (1H, d, J=9.2), 7.92 (1H, dd, J 2.1, 12.5), 7.57 (2H, t, J 7.8), 7.48 (1H, t, J 7.4), 7.41 (ds, J 2.4), 7.37 (2H, J 7.6), 7.29 (1H, d), 7.22 (1H, dd, J 2.4, 9.2), 7.17 (2H, t, J 8.6), 6.41 (1H, d, 5.3), 3.97 (3H, s), 3.38 (3H, s), 2.80 (3H, s).

EXAMPLE 88

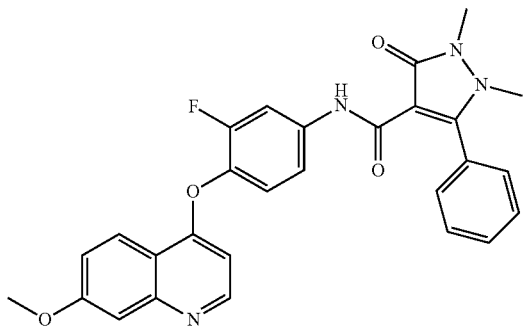

N-(3-fluoro-4-(7-Methoxyquinolin-4-yloxy)phenyl)-1,2-dimethyl-3-oxo-5-phenyl-2,3-dihydro-1H-pyrazole-4-carboxamide: A mixture of HATU (458 mg, 1206 μmol), 1,2-dimethyl-3-oxo-5-phenyl-2,3-dihydro-1H-pyrazole-4-carboxylic acid (140 mg, 603 μmol), 3-fluoro-4-(7-methoxyquinolin-4-yloxy)benzenamine (258 mg, 908 μmol), and Triethylamine (254 μL, 1809 mmol) in DMF (2 mL) was stirred at 60° C. overnight. The mixture was diluted with EtOAc (10 mL). The mixture was transferred to a separatory funnel with EtOAc (20 mL) and was washed with NaOH (1N, 10 mL), H$_2$O (2×10 mL), NaHCO$_3$ (sat), NaCl (sat), and dried over Na$_2$SO$_4$. The residue after concentration was purified on silica gel and the product was triturated with EtOAc-hexane (1:2) to afford a pink solid (106 mg, 35%). Calc'd for $C_{28}H_{23}FN_4O_4$: 498; MS (ESI pos. ion) m/z: 499 (MH+). $^1$HNMR (CDCl$_3$, 400 MHz): 11.04 (1H, s), 8.56 (1H, d, J 5.3), 7.88 (1H, d, J 14.7), 7.55-7.40 (5H, m), 7.47 (1H, s), 7.35 (1H, d), 7.22 (1H, d, J9.1), 7.13 (1H, t, J 8.8), 6.36 (1H, d, J 5.3), 3.96 (3H, s), 3.62 (3H, s), 3.41 (3H, s).

EXAMPLE 89

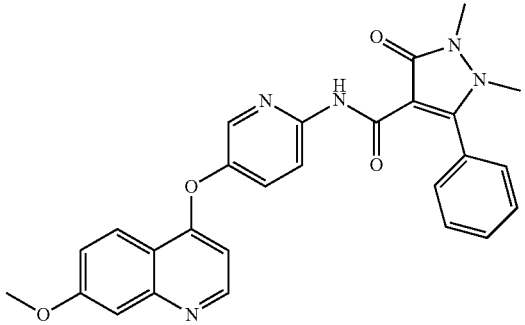

N-(5-(7-Methoxyquinolin-4-yloxy)pyridin-2-yl)-1,2-dimethyl-3-oxo-5-phenyl-2,3-dihydro-1H-pyrazole-4-carboxamide: Calc'd for $C_{27}H_{23}N_5O_4$: 481; MS (ESI pos. ion) m/z: 482 (MH+). $^1$HNMR (CDCl$_3$, 400 MHz): 11.46 (1H, s), 8.58 (1H, d, J 5.3), 8.30 (1H, d, J 9.0), 8.25-8.21 (2H, m), 7.56-7.40 (7H), 7.22 (1H, dd, J 2.3, 9.0), 6.39 (1H, d, J 5.3), 3.97 (3H, s), 3.62 (3H, s), 3.40 (3H, s).

EXAMPLE 90

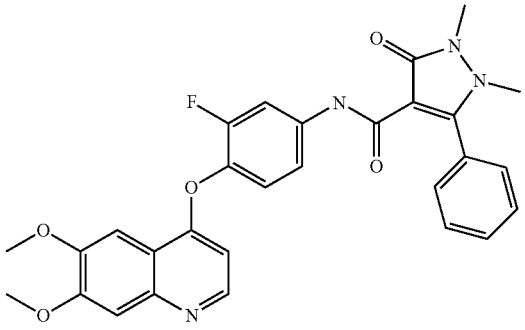

N-(4-(6,7-Dimethoxyquinolin-4-yloxy)-3-fluorophenyl)-1,2-dimethyl-3-oxo-5-phenyl-2,3-dihydro-1H-pyrazole-4-carboxamide: Calc'd for $C_{27}H_{23}N_5O_4$: 528; MS (ESI pos. ion) m/z: 529 (MH+). $^1$HNMR (CDCL$_3$, 400 MHz): 11.05 (1H, s), 8.46 (1H, d, J 5.2), 7.88 (1H, dd, J 2.2, 12.5), 7.53-7.58 (4H, m), 7.47-7.49 (2H, m), 7.40 (1H, s), 7.32 (1H, d, 8), 7.14 (1H, t, J 8.7), 6.39 (1H, d, J 5.1), 4.05 (3H, s), 4.04 (3H, s), 3.62 (3H, s), 3.41 (3H, s).

EXAMPLE 91

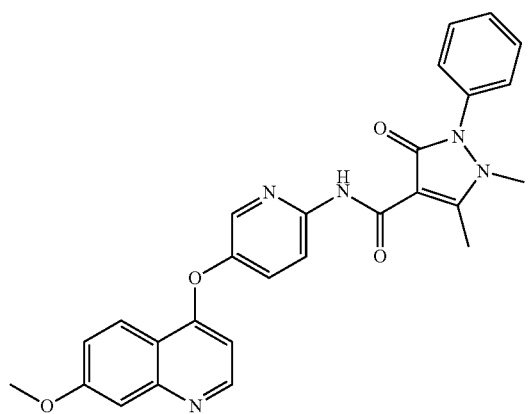

N-(5-(7-Methoxyquinolin-4-yloxy)pyridin-2-yl)-1,5-dimethyl-3-oxo-2-phenyl-2,3-dihydro-1H-pyrazole-4-carboxamide: Calc'd for $C_{27}H_{23}N_5O_4$: 481; MS (ESI pos. ion) m/z: 482 (MH+). $^1$H NMR (CDCl$_3$, 400 MHz): 11.27 (1H, s), 8.60 (1H, d, J 5.1), 8.38 (1H, d, J 9.0), 8.23 (2H, m), 7.53 (3H, m), 7.47 (1H, m), 7.41 (1H, d), 7.37 (2H, d, J 7.4), 7.23 (1H, dd, J 2.4, 9.7), 6.42 (1H, d, J 5.1), 3.97 (3H, s), 3.37 (3H, s), 2.80 (3H, s).

EXAMPLE 92

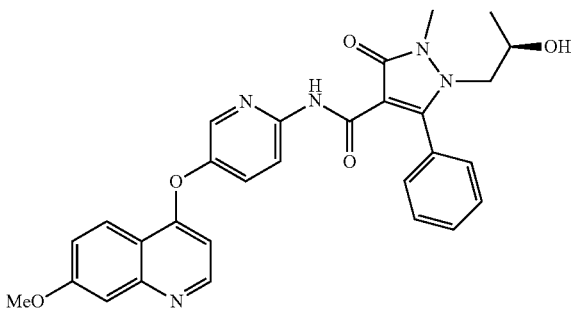

(R)-1-(2-Hydroxypropyl)-N-(5-(7-methoxyquinolin-4-yloxy)pyridin-2-yl)-2-methyl-3-oxo-5-phenyl-2,3-dihydro-1H-pyrazole-4-carboxamide: Calc'd for $C_{29}H_{27}N_5O_5$: 525; MS (ESI pos. ion) m/z: 526 (MH+). $^1$HNMR (CDCl$_3$, 400 MHz): 11.28 (1H, s), 8.53 (1H, d, J 5.1), 8.24-8.21 (3H, m), 7.49-7.39 (7H, m), 7.22 1H, bd, J 9.2), 6.38 (1H, d, J5.1), 4.7 (1H, b), 3.96 (4H, bs), 3.75 (2H, m), 3.63 (3H, s), 1.04 (3H, d, J6.3).

EXAMPLE 93

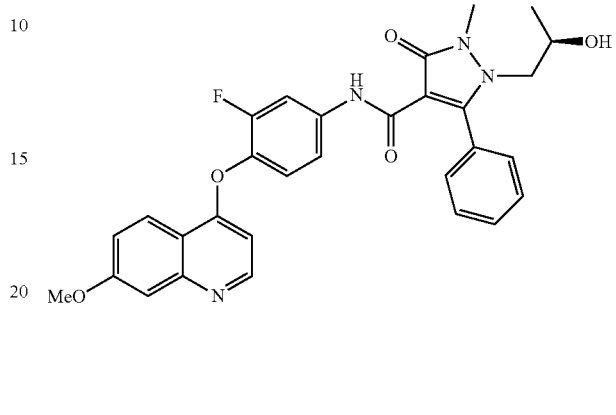

(R)-N-(3-Fluoro-4-(7-methoxyquinolin-4-yloxy)phenyl)-1-(2-hydroxypropyl)-2-methyl-3-oxo-5-phenyl-2,3-dihydro-1H-pyrazole-4-carboxamide: Calc'd for $C_{30}H_{27}FN_4O_5$: 542; MS (ESI pos. ion) m/z: 543 (MH+). $^1$HNMR (CDCl$_3$, 400 MHz): 11.05 (1H, s), 8.55 (1H, d, J 5.3), 8.26 (1H, d, J 9.2), 7.86 (1H, d, J 12.5), 7.53-7.45 (5H, m), 7.39 (1H, d, J 2.3), 7.32 (1H, d, J 9.7), 7.77 (1H, dd, J 9.2, 2.6), 7.14 (1H, t, J 8.8), 6.37 (1H, J 5.3), 3.96 (3H, s), 3.90 (1H, m), 3.76 (2H, d, J 6.0), 3.62 (3H, s), 1.94 (1H, d, J 4.3), 1.04 (3H, d, J 6.2).

EXAMPLE 94

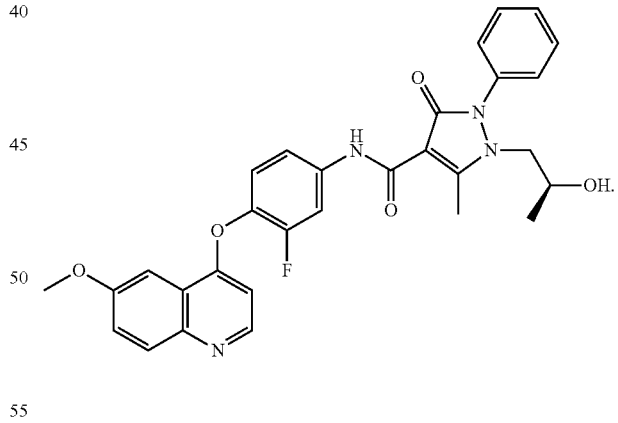

(S)-N-(3-fluoro-4-(6-methoxyquinolin-4-yloxy)phenyl)-1-(2-hydroxypropyl)-5-methyl-3-oxo-2-phenyl-2,3-dihydro-1H-pyrazole-4-carboxamide: MS (ESI pos. ion) m/z: 543 (MH+). Calc'd exact mass for $C_{30}H_{27}FN_4O_5$: 542. $^1$HNMR (300 MHz, CDCl$_3$): 1.01 (d, J=5.85 Hz, 3H), 2.72-2.79 (m, 3H), 3.55 (d, J=12.28 Hz, 1H), 3.69-3.93 (m, 3H), 6.44 (d, J=4.53 Hz, 1H), 7.02 (d, J=6.72 Hz, 2H), 7.04 (s, 2H), 7.27-7.40 (m, 4H), 7.56 (d, J=2.78 Hz, 1H), 7.78-7.91 (m, 2H), 8.31 (d, J=5.26 Hz, 1H), 10.80 (s, 1H).

131
EXAMPLE 95
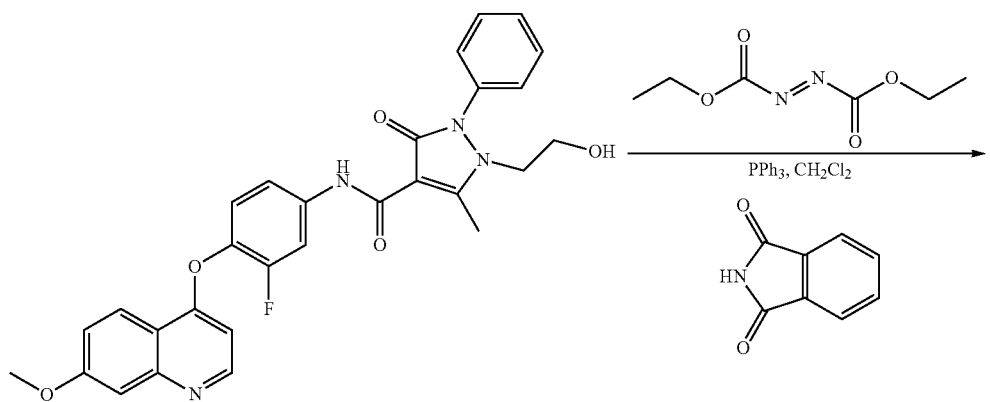
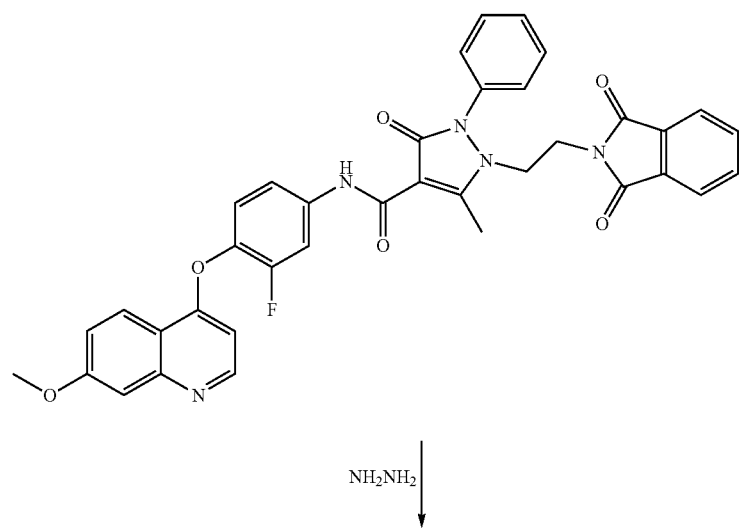
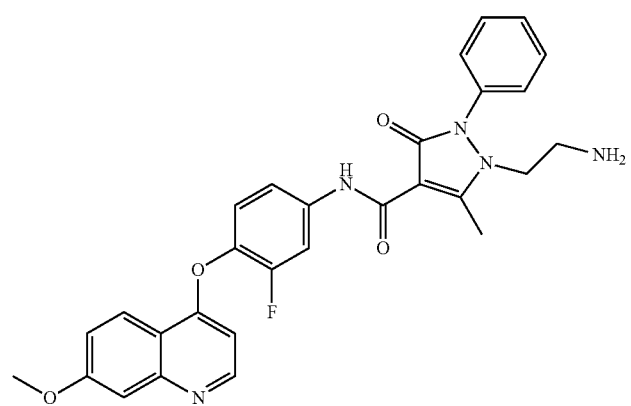

-continued

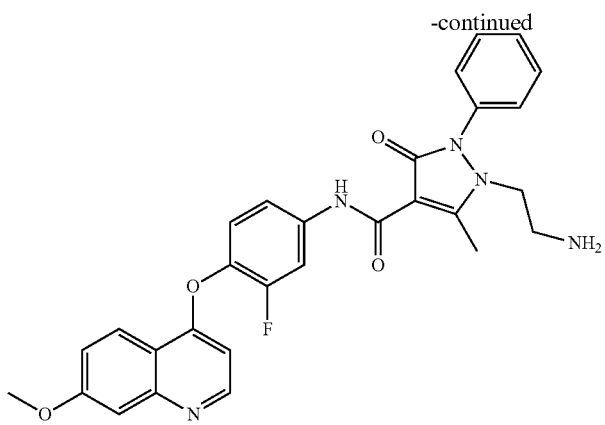

1-(2-aminoethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide

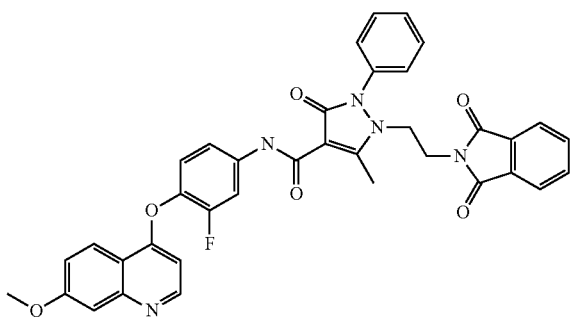

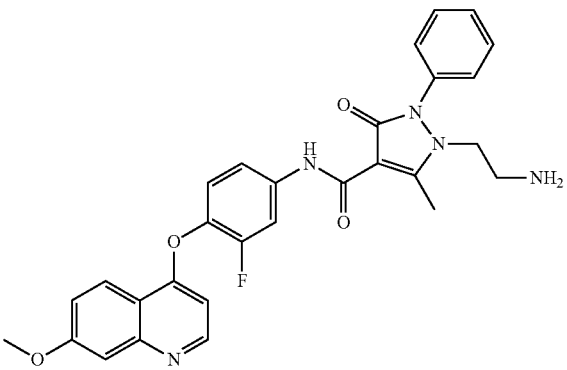

Step 1: 1-(2-(1,3-dioxo-1,3-dihydro-2H-isoindol-2-yl)ethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide. To a solution of N-(3-fluoro-4-(7-methoxyquinolin-4-yloxy)phenyl)-1-(2-hydroxyethyl)-5-methyl-3-oxo-2-phenyl-2,3-dihydro-1H-pyrazole-4-carboxamide (0.20 g, 0.38 mmol) and phthalimide (0.11 g, 0.76 mmol) in 10 mL of $CH_2Cl_2$ was added triphenyl phosphine (0.13 ml, 0.57 mmol), followed by diethyl azodicarboxylate (0.089 ml, 0.57 mmol) via a syringe. The reaction mixture was stirred at RT for 16 hours. The resulting solution was concentrated in vacuo, and the residue was purified by silica gel chromatography (EtOAc to 10% MeOH/EtOAc) to give the title compound as a light yellow solid (0.22 g, 88% yield). MS (ESI pos. ion) m/z: 658 (MH+). Calc'd exact mass for $C_{37}H_{28}FN_5O_6$: 657. $^1$H NMR (300 MHz, MeOH) 8.53 (1 H, d, J=5.5 Hz), 8.28 (1 H, d, J=9.0 Hz), 7.80-7.91 (5 H, m), 7.50 (1 H, s), 7.48 (2 H, d, J=3.0 Hz), 7.26-7.36 (6 H, m), 6.49 (1 H, dd, J=5.4, 1.0 Hz), 4.27 (2 H, t, J=5.5 Hz), 3.97 (3 H, s), 3.74 (2 H, t, J=5.5 Hz), 2.68 (3 H, s).

Step 2: 1-(2-aminoethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide. To a solution of 1-(2-(1,3-dioxoisoindolin-2-yl)ethyl)-N-(3-fluoro-4-(7-methoxyquinolin-4-yloxy)phenyl)-5-methyl-3-oxo-2-phenyl-2,3-dihydro-1H-pyrazole-4-carboxamide (0.20 g, 0.30 mmol) in 1:1 H2O/EtOH was added hydrazine (0.049 g, 1.5 mmol). The reaction was heated to 50° C. for 8 hours and then cooled to RT. The reaction mixture was then diluted with 20 mL of satd. NaHCO3 aq. solution and 60 mL of EtOAc. The organic phase was separated and washed with 30 mL of brine, dried over Na2SO4 and concentrated in vacuo. The residue was washed with 20% hexane in EtOAc to give the title compound as a light yellow solid (0.13 g, 81% yield).

MS (ESI pos. ion) m/z: 528 (MH+). Calc'd exact mass for $C_{29}H_{26}FN_5O_4$: 527. $^1$H NMR (300 MHz, MeOH) 8.54 (1 H, d, J=5.5 Hz), 8.30 (1 H, d, J=9.2 Hz), 7.93-7.97 (1 H, m), 7.54-7.66 (3 H, m), 7.44-7.51 (2 H, m), 7.27-7.38 (4 H, m), 6.50 (1 H, dd, J=5.5, 0.9 Hz), 3.92-4.02 (5 H, m), 2.83 (3 H, s), 2.68 (2 H, t, J=6.7 Hz).

EXAMPLE 96

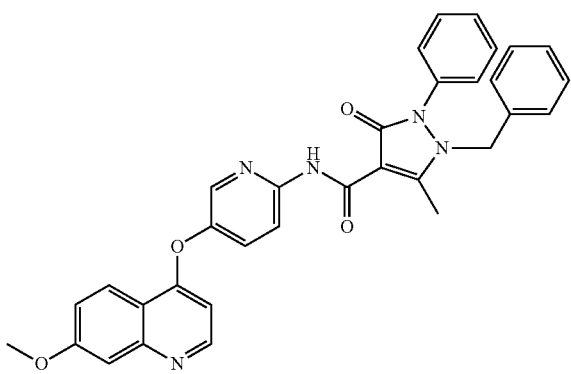

5-methyl-N-(5-((7-(methyloxy)-4-quinolinyl)oxy)-2-pyridinyl)-3-oxo-2-phenyl-1-(phenylmethyl)-2,3-dihydro-1H-pyrazole-4-carboxamide: MS (ESI pos. ion) m/z: 558 (MH+). Calc'd exact mass for $C_{33}H_{27}N_5O_4$: 557. $^1$H NMR (300 MHz, CHLOROFORM-d) 11.40 (1 H, s), 8.80 (1 H, d, J=6.4 Hz), 8.49 (1 H, d, J=9.2 Hz), 8.39 (1 H, d, J=9.4 Hz), 8.27 (1 H, d, J=2.6 Hz), 7.95 (1 H, d, J=2.1 Hz), 7.41-7.58 (5 H, m), 7.31 (1 H, d, J=2.3 Hz), 7.23-7.30 (4 H, m), 6.86-6.91 (1 H, m), 6.85 (1 H, s), 6.73 (1 H, d, J=6.6 Hz), 4.98 (2 H, s), 4.07 (3 H, s), 2.84 (3 H, s).

EXAMPLE 97

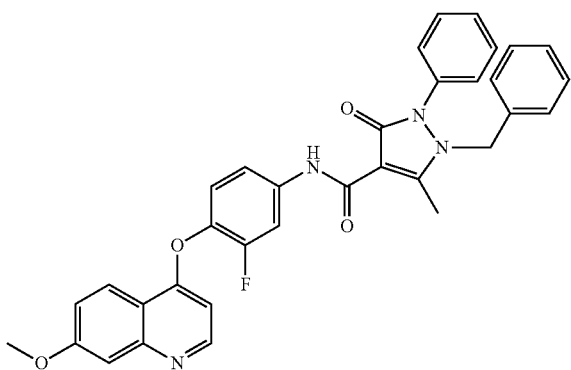

1-benzyl-N-(3-fluoro-4-(7-methoxyquinolin-4-yloxy)phenyl)-5-methyl-3-oxo-2-phenyl-2,3-dihydro-1H-pyrazole-4-carboxamide: MS (ESI pos. ion) m/z: 575 (MH+). Calc'd exact mass for $C_{34}H_{27}FN_4O_4$: 574. $^1$H NMR (300 MHz, CHLOROFORM-d) 11.02 (1 H, s), 8.78 (1 H, s), 8.41 (1 H, d, J=9.4 Hz), 8.03 (1 H, dd, J=12.5, 1.8 Hz), 7.89 (1 H, s), 7.20-7.54 (11 H, m), 6.80-6.91 (2 H, m), 6.75 (1 H, s), 4.99 (2 H, s), 4.06 (3 H, s), 2.85 (3 H, s).

EXAMPLE 98

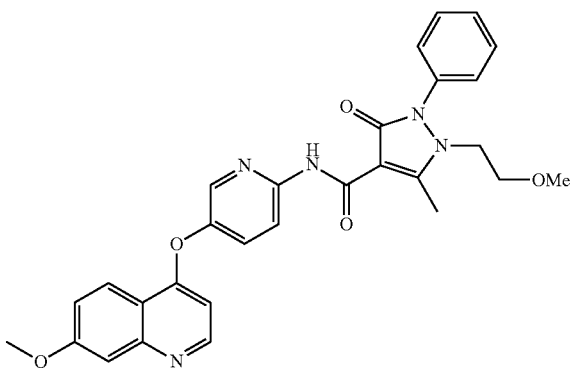

5-methyl-1-(2-(methyloxy)ethyl)-N-(5-((7-(methyloxy)-4-quinolinyl)oxy)-2-pyridinyl)-3-oxo-2-phenyl-2,3-dihydro-1H-pyrazole-4-carboxamide: MS (ESI pos. ion) m/z: 526 (MH+). Calc'd exact mass for $C_{29}H_{27}N_5O_5$: 525. $^1$H NMR (300 MHz, MeOH) 8.81 (1 H, d, J=6.8 Hz), 8.46-8.59 (2 H, m), 8.34 (1 H, d, J=2.4 Hz), 7.84 (1 H, dd, J=9.2, 2.8 Hz), 7.43-7.64 (7 H, m), 7.00 (1 H, d, J=6.8 Hz), 4.06-4.15 (5 H, m), 3.25-3.40 (5 H, m), 2.82 (3 H, s).

EXAMPLE 99

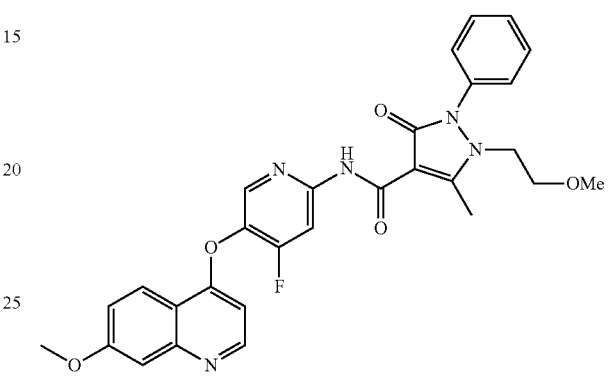

N-(3-fluoro-4-((7-(methyloxy)-4-quinolinyl)oxy)phenyl)-5-methyl-1-(2-(methyloxy)ethyl)-3-oxo-2-phenyl-2,3-dihydro-1H-pyrazole-4-carboxamide: MS (ESI pos. ion) m/z: 543 (MH+). Calc'd exact mass for $C_{30}H_{27}FN_4O_5$: 542. $^1$H NMR (300 MHz, CHLOROFORM-d) 10.90(1 H, s), 8.59 (1 H, d, J=5.3 Hz), 8.27 (1 H, d, J=9.2 Hz), 7.93 (1 H, dd, J=12.5, 2.4 Hz), 7.52-7.59 (1 H, m), 7.14-7.48 (8 H, m), 6.41 (1 H, dd, J=5.3, 0.9 Hz), 3.94-4.02 (5 H, m), 3.34 (2 H, t, J=5.0 Hz), 3.25 (3 H, s), 2.83 (3 H, s).

EXAMPLE 100

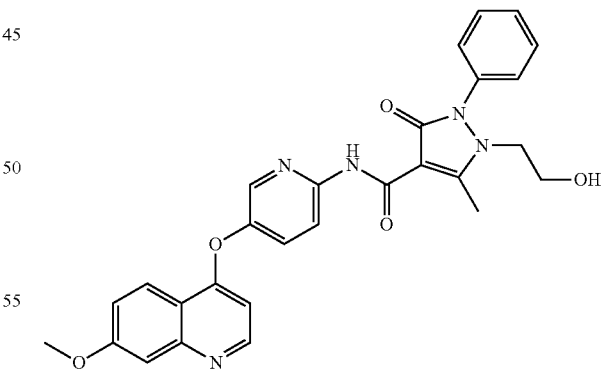

1-(2-hydroxyethyl)-5-methyl-N-(5-((7-(methyloxy)-4-quinolinyl)oxy)-2-pyridinyl)-3-oxo-2-phenyl-2,3-dihydro-1H-pyrazole-4-carboxamide: MS (ESI pos. ion) m/z: 512 (MH+). Calc'd exact mass for $C_{28}H_{25}N_5O_5$: 511. $^1$H NMR (300 MHz, MeOH) 8.81 (1 H, d, J=6.8 Hz), 8.44-8.58 (2 H, m), 8.33 (1 H, s), 7.83 (1 H, d, J=9.0 Hz), 7.43-7.64 (7 H, m), 7.00 (1 H, d, J=6.6 Hz), 4.08 (3 H, s), 4.03 (2 H, t, J=4.4 Hz), 3.51 (2 H, t, J=4.3 Hz), 2.84 (3 H, s).

EXAMPLE 101

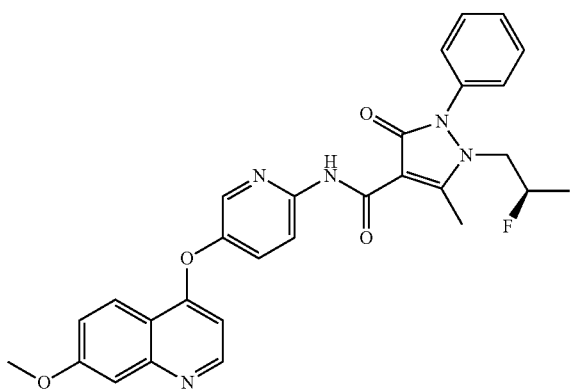

1-((2R)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide: MS (ESI pos. ion) m/z: 528 (MH+). Calc'd exact mass for $C_{29}H_{26}FN_5O_4$: 527.

EXAMPLE 102

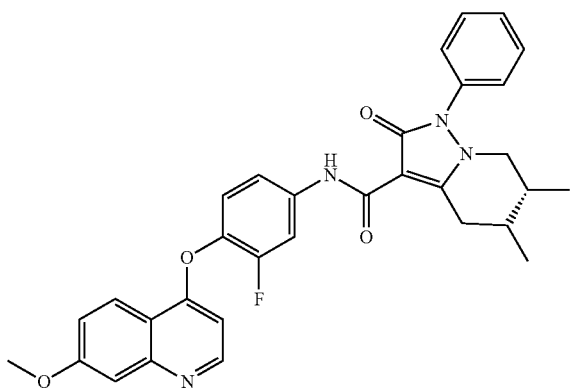

(S)-1-(2-(dimethylamino)propyl)-N-(3-fluoro-4-(7-methoxyquinolin-4-yloxy)phenyl)-5-methyl-3-oxo-2-phenyl-2,3-dihydro-1H-pyrazole-4-carboxamide: MS (ESI pos. ion) m/z: 570 (MH+). Calc'd exact mass for $C_{32}H_{32}FN_5O_4$: 569. $^1$H NMR (300 MHz, MeOH) 8.82 (1 H, d, J=6.6 Hz), 8.53 (1 H, d, J=9.2 Hz), 8.01 (1 H, dd, J=12.8, 2.3 Hz), 7.35-7.68 (9 H, m), 6.99 (1 H, dd, J=6.8, 0.9 Hz), 4.27-4.45 (2 H, m), 4.08 (3 H, s), 3.42-3.54 (1 H, m), 2.87 (3 H, s), 2.67 (6 H, s), 1.23 (3 H, d, J=6.8 Hz).

EXAMPLE 103

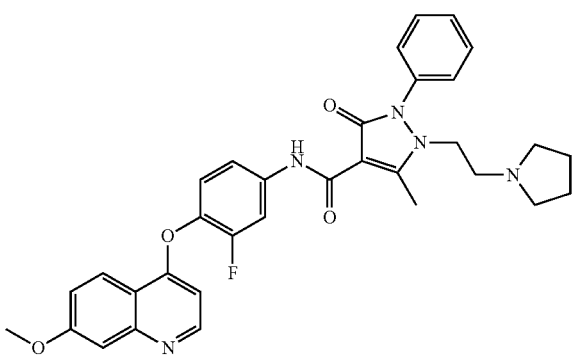

N-(3-fluoro-4-((7-(methyloxy)-4-quinolinyl)oxy)phenyl)-5-methyl-3-oxo-2-phenyl-1-(2-(1-pyrrolidinyl)ethyl)-2,3-dihydro-1H-pyrazole-4-carboxamide: MS (ESI pos. ion) m/z: 582 (MH+). Calc'd exact mass for $C_{33}H_{32}FN_5O_4$: 581. $^1$H NMR (300 MHz, MeOH) 8.82 (1 H, d, J=6.8 Hz), 8.55 (1 H, d, J=9.2 Hz), 8.02 (1 H, dd, J=12.7, 1.8 Hz), 7.37-7.68 (9 H, m), 7.00 (1 H, d, J=6.6 Hz), 4.27-4.38 (2 H, m), 4.09 (3 H, s), 3.21-3.34 (6 H, m), 2.87 (3 H, s), 2.01 (4H, m).

EXAMPLE 104

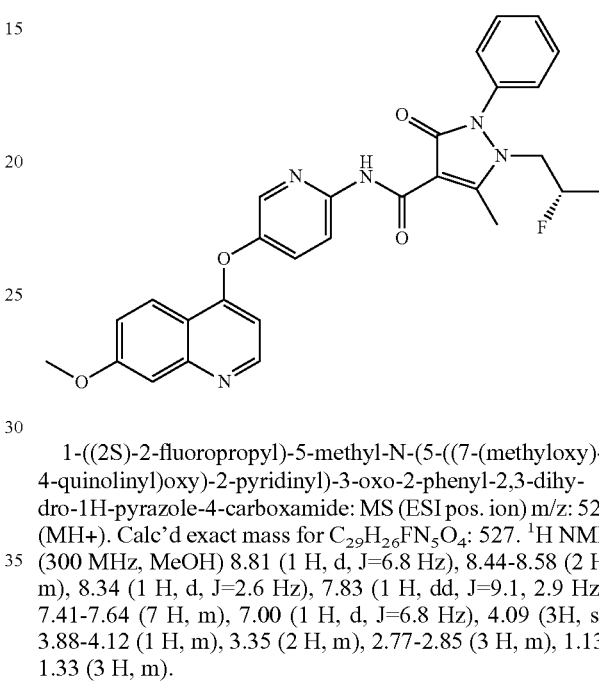

1-((2S)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide: MS (ESI pos. ion) m/z: 528 (MH+). Calc'd exact mass for $C_{29}H_{26}FN_5O_4$: 527. $^1$H NMR (300 MHz, MeOH) 8.81 (1 H, d, J=6.8 Hz), 8.44-8.58 (2 H, m), 8.34 (1 H, d, J=2.6 Hz), 7.83 (1 H, dd, J=9.1, 2.9 Hz), 7.41-7.64 (7 H, m), 7.00 (1 H, d, J=6.8 Hz), 4.09 (3H, s), 3.88-4.12 (1 H, m), 3.35 (2 H, m), 2.77-2.85 (3 H, m), 1.13-1.33 (3 H, m).

EXAMPLE 105

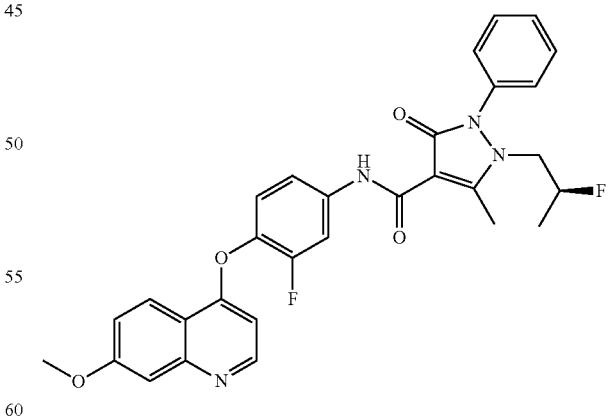

N-(3-fluoro-4-((7-(methyloxy)-4-quinolinyl)oxy)phenyl)-1-((2S)-2-fluoropropyl)-5-methyl-3-oxo-2-phenyl-2,3-dihydro-1H-pyrazole-4-carboxamide: MS (ESI pos. ion) m/z: 545 (MH+). Calc'd exact mass for $C_{30}H_{26}F_2N_4O_4$: 544.

EXAMPLE 106

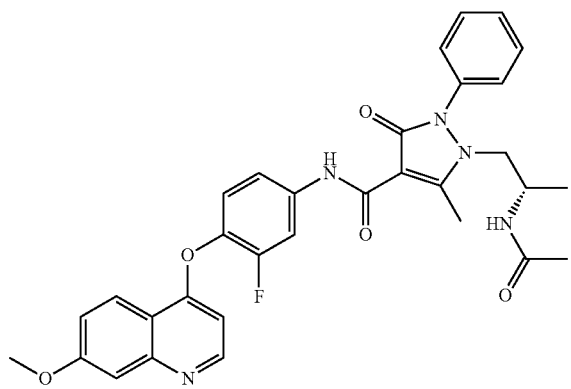

1-((2S)-2-(acetylamino)propyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide: MS (ESI pos. ion) m/z: 584 (MH+). Calc'd exact mass for $C_{32}H_{30}FN_5O_5$: 583. $^1$H NMR (300 MHz, MeOH) 8.83 (1 H, d, J=6.6 Hz), 8.57 (1H, d, J=9.4 Hz), 8.04 (1H, dd, J=12.9, 1.8 Hz), 7.39-7.66 (9H, m), 7.00 (1H, dd, J=6.8, 1.1 Hz), 4.10 (3H, s), 3.83-4.11 (3H, m), 2.80 (3H, s), 1.84 (3H, s), 0.98 (3H, d, J=6.4 Hz).

EXAMPLE 107

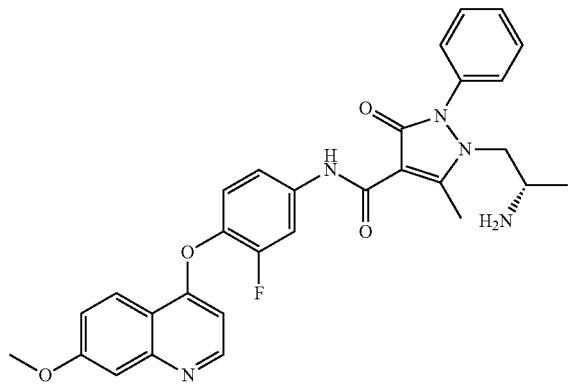

1-((2S)-2-aminopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide: MS (ESI pos. ion) m/z: 542 (MH+). Calc'd exact mass for $C_{30}H_{28}FN_5O_4$: 541. $^1$H NMR (300 MHz, MeOH) 8.83 (1 H, d, J=6.8 Hz), 8.55 (1 H, d, J=9.2 Hz), 8.04 (1 H, dd, J=12.8, 1.7 Hz), 7.39-7.69 (9 H, m), 6.99 (1 H, dd, J=6.6, 0.9 Hz), 4.06-4.31 (2 H, m), 4.09 (3 H, s), 3.28-3.41 (1 H, m), 2.86 (3 H, s), 1.14 (3 H, d, J=6.6 Hz).

EXAMPLE 108

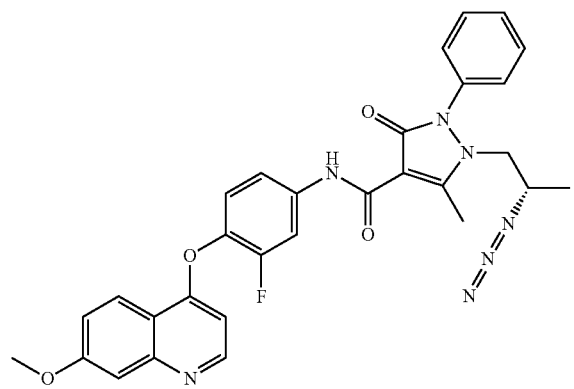

1-((2S)-2-azidopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide: MS (ESI pos. ion) m/z: 568 (MH+). Calc'd exact mass for $C_{30}H_{26}FN_7O_4$: 567. $^1$H NMR (300 MHz, CHLOROFORM-d) 10.84 (1 H, s), 8.59 (1 H, d, J=5.3 Hz), 8.27 (1 H, d, J=9.2 Hz), 7.92 (1 H, dd, J=12.6, 2.4 Hz), 7.53-7.60 (2 H, m), 7.14-7.50 (7 H, m), 6.41 (1 H, dd, J=5.3, 0.9 Hz), 3.96 (3 H, s), 3.56-3.84 (3 H, m), 2.85 (3 H, s), 1.15 (3 H, d, J=6.6 Hz).

EXAMPLE 109

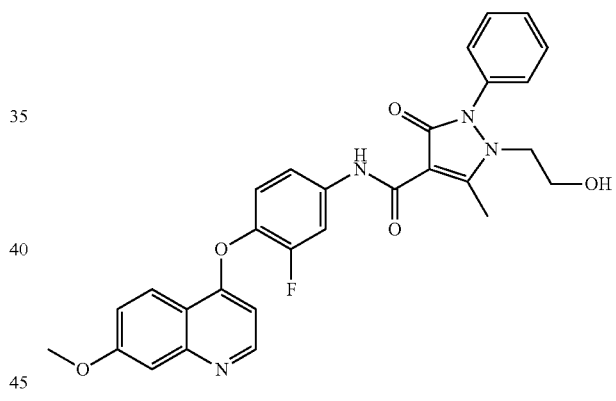

N-(3-fluoro-4-((7-(methyloxy)-4-quinolinyl)oxy)phenyl)-1-(2-hydroxyethyl)-5-methyl-3-oxo-2-phenyl-2,3-dihydro-1H-pyrazole-4-carboxamide: MS (ESI pos. ion) m/z: 529 (MH+). Calc'd exact mass for $C_{29}H_{25}FN_4O_5$: 528.

EXAMPLE 110

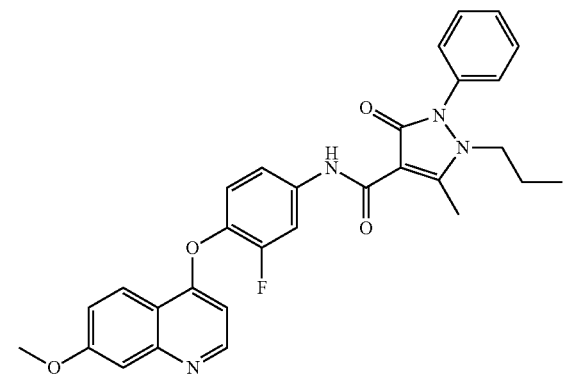

N-(3-fluoro-4-((7-(methyloxy)-4-quinolinyl)oxy)phenyl)-5-methyl-3-oxo-2-phenyl-1-propyl-2,3-dihydro-1H-pyrazole-4-carboxamide: MS (ESI pos. ion) m/z: 527 (MH+). Calc'd exact mass for $C_{30}H_{27}FN_4O_4$: 526. $^1$H NMR (400 MHz, CHLOROFORM-d) 10.91 (1 H, s), 8.59 (1 H, d, J=5.3 Hz), 8.27 (1 H, d, J=9.0 Hz), 7.91-7.93 (2 H, d, J=2.0 Hz), 7.41-7.58 (4 H, m), 7.14-7.38 (4 H, m), 6.42 (1 H, d, J=5.3 Hz), 3.96 (3 H, s), 3.76 (2 H, t, J=7.2 Hz), 2.80 (3 H, s), 1.45-1.56 (2 H, m, J=7.4, 7.4, 7.4, 7.4, 7.4 Hz), 0.80 (3 H, t, J=7.4 Hz).

EXAMPLE 111

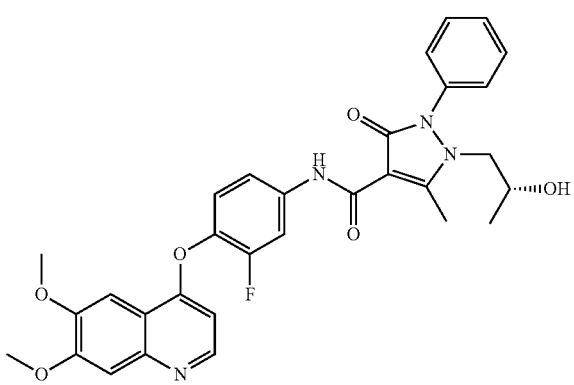

N-(4-((6,7-bis(methyloxy)-4-quinolinyl)oxy)-3-fluorophenyl)-1-((2R)-2-hydroxypropyl)-5-methyl-3-oxo-2-phenyl-2,3-dihydro-1H-pyrazole-4-carboxamide: MS (ESI pos. ion) m/z: 573 (MH+). Calc'd exact mass for $C_{31}H_{29}FN_4O_6$: 572.

EXAMPLE 112

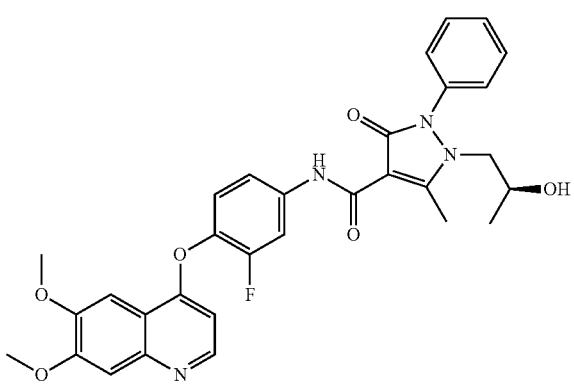

N-(4-((6,7-bis(methyloxy)-4-quinolinyl)oxy)-3-fluorophenyl)-1-((2S)-2-hydroxypropyl)-5-methyl-3-oxo-2-phenyl-2,3-dihydro-1H-pyrazole-4-carboxamide: MS (ESI pos. ion) m/z: 573 (MH+). Calc'd exact mass for $C_{31}H_{29}FN_4O_6$: 572.

EXAMPLE 113

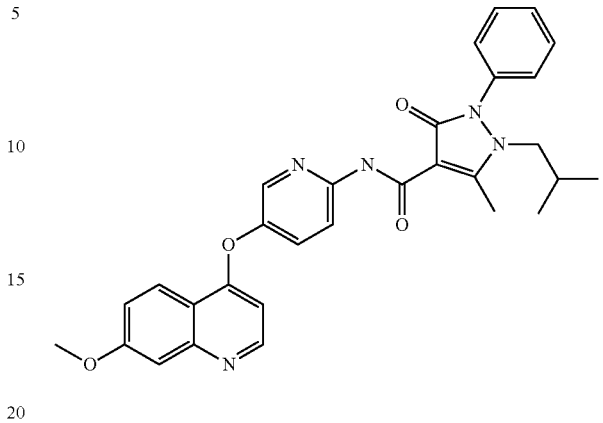

5-methyl-N-(5-((7-(methyloxy)-4-quinolinyl)oxy)-2-pyridinyl)-1-(2-methylpropyl)-3-oxo-2-phenyl-2,3-dihydro-1H-pyrazole-4-carboxamide: MS (ESI pos. ion) m/z: 524 (MH+). Calc'd exact mass for $C_{30}H_{29}N_5O_4$: 523. $^1$H NMR (400 MHz, CHLOROFORM-d) 11.28 (1 H, s), 8.60 (1 H, d, J=5.3 Hz), 8.37 (1 H, d, J=8.8 Hz), 8.24 (1 H, d, J=6.1 Hz), 8.23 (1 H, s), 7.41-7.56 (5 H, m), 7.35 (2 H, d, J=8.0 Hz), 7.23 (1 H, dd, J=9.2, 2.3 Hz), 6.43 (1 H, d, J=5.3 Hz), 3.97 (3 H, s), 3.64 (2 H, d, J=7.4 Hz), 2.81 (3 H, s), 1.84 (1 H, dt, J=13.8, 6.9 Hz), 0.77 (6 H, d, J=6.7 Hz).

EXAMPLE 114

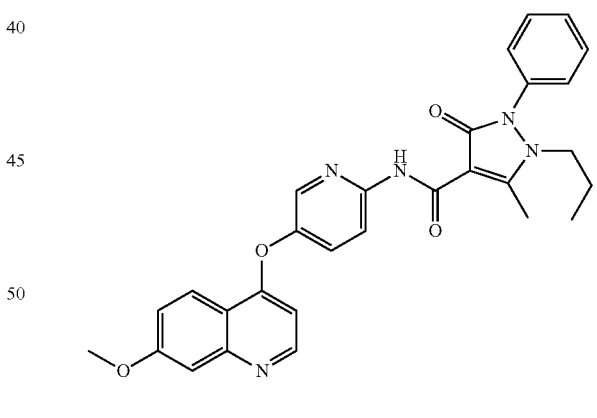

5-methyl-N-(5-((7-(methyloxy)-4-quinolinyl)oxy)-2-pyridinyl)-3-oxo-2-phenyl-1-propyl-2,3-dihydro-1H-pyrazole-4-carboxamide: MS (ESI pos. ion) m/z: 510 (MH+). Calc'd exact mass for $C_{29}H_{27}N_5O_4$: 509. $^1$H NMR (400 MHz, CHLOROFORM-d) 11.29 (1 H, s), 8.61 (1 H, d, J=5.5 Hz), 8.38 (1 H, d, J=9.0 Hz), 8.22-8.27 (2 H, m), 7.32-7.57 (7 H, m), 7.22-7.30 (1H, m), 6.46 (1 H, d, J=5.5 Hz), 3.98 (3 H, s), 3.76 (2H, t, J=7.2 Hz), 2.79-2.83 (3 H, m), 1.42-1.56 (2 H, m, J=7.4, 7.4, 7.4, 7.4 Hz), 0.70-0.86 (3 H, t, J=7.4 Hz).

EXAMPLE 115

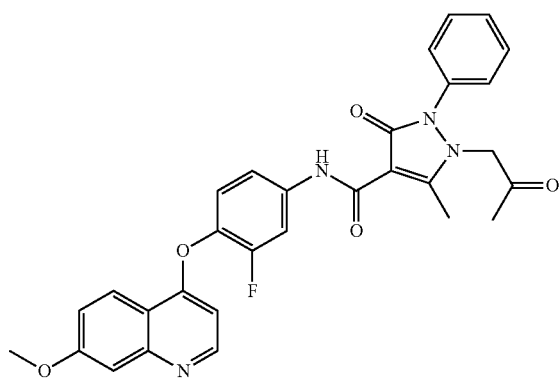

N-(3-fluoro-4-((7-(methyloxy)-4-quinolinyl)oxy)phenyl)-5-methyl-3-oxo-1-(2-oxopropyl)-2-phenyl-2,3-dihydro-1H-pyrazole-4-carboxamide: MS (ESI pos. ion) m/z: 541 (MH+). Calc'd exact mass for $C_{30}H_{25}FN_4O_5$: 540. $^1$H NMR (300 MHz, CHLOROFORM-d) 10.86 (1 H, s), 8.60 (1 H, d, J=5.3 Hz), 8.28 (1 H, d, J=9.2 Hz), 7.92 (1 H, dd, J=12.5, 2.4 Hz), 7.41-7.59 (4 H, m), 7.14-7.33 (4 H, m), 6.42 (1 H, dd, J=5.3, 0.9 Hz), 4.52 (2 H, s), 3.97 (3 H, s), 2.63-2.72 (3 H, s), 2.04-2.10 (3 H, s)

EXAMPLE 116

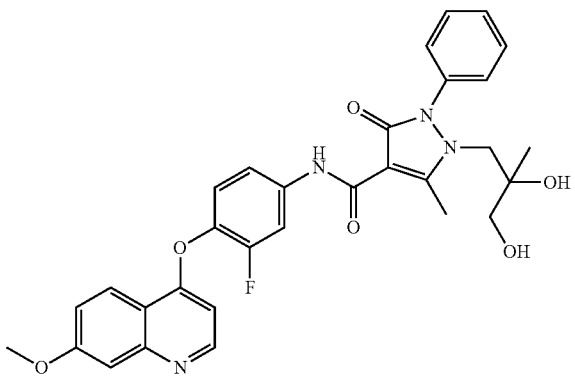

1-(2,3-dihydroxy-2-methylpropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide: MS (ESI pos. ion) m/z: 573 (MH+). Calc'd exact mass for $C_{31}H_{29}FN_4O_6$: 572. $^1$H NMR (400 MHz, CHLOROFORM-d) 10.85 (1 H, s), 8.56 (1 H, d, J=5.3 Hz), 8.27 (1 H, d, J=9.2 Hz), 7.90 (1 H, dd, J=12.5, 1.6 Hz), 7.54 (2 H, t, J=7.7 Hz), 7.38-7.47 (2 H, m), 7.14-7.32 (5 H, m), 6.42 (1 H, d, J=5.3 Hz), 4.09-4.19 (1 H, m), 3.96 (3 H, s), 3.86 (1 H, d, J=15.7 Hz), 3.34 (2 H, s), 2.89 (3 H, s), 1.07 (3 H, s).

EXAMPLE 117

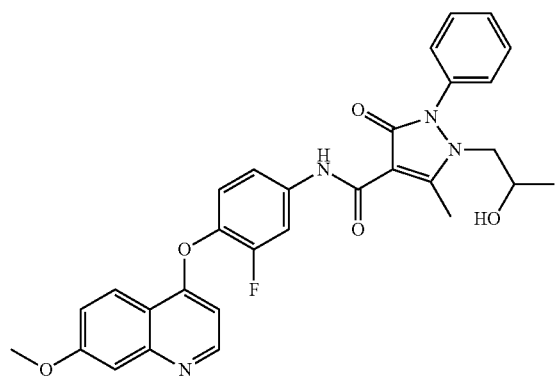

N-(3-fluoro-4-((7-(methyloxy)-4-quinolinyl)oxy)phenyl)-1-(2-hydroxypropyl)-5-methyl-3-oxo-2-phenyl-2,3-dihydro-1H-pyrazole-4-carboxamide: MS (ESI pos. ion) m/z: 543 (MH+). Calc'd exact mass for $C_{28}H_{25}FN_4O_5$: 542.

EXAMPLE 118

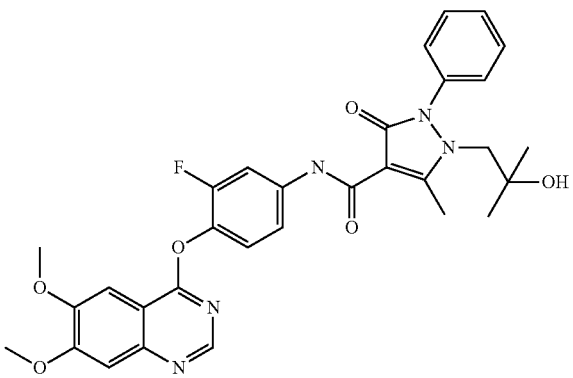

N-(4-((6,7-bis(methyloxy)-4-quinazolinyl)oxy)-3-fluorophenyl)-1-(2-hydroxy-2-methylpropyl)-5-methyl-3-oxo-2-phenyl-2,3-dihydro-1H-pyrazole-4-carboxamide: MS (ESI pos. ion) m/z: 588 (MH+). Calc'd exact mass for $C_{31}H_{30}FN_5O_6$: 587.

EXAMPLE 119

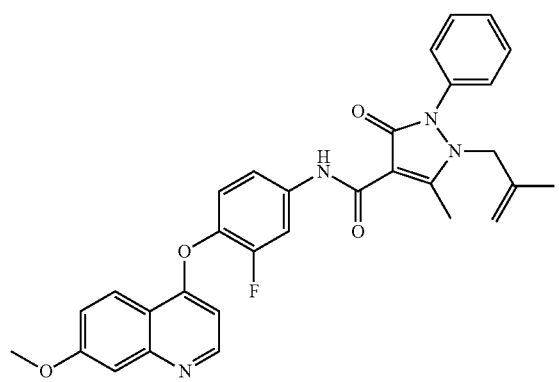

N-(3-fluoro-4-((7-(methyloxy)-4-quinolinyl)oxy)phenyl)-5-methyl-1-(2-methyl-2-propen-1-yl)-3-oxo-2-phenyl-2,3-dihydro-1H-pyrazole-4-carboxamide: MS (ESI pos. ion) m/z: 539 (MH+). Calc'd exact mass for $C_{31}H_{27}FN_4O_4$: 538.

EXAMPLE 120

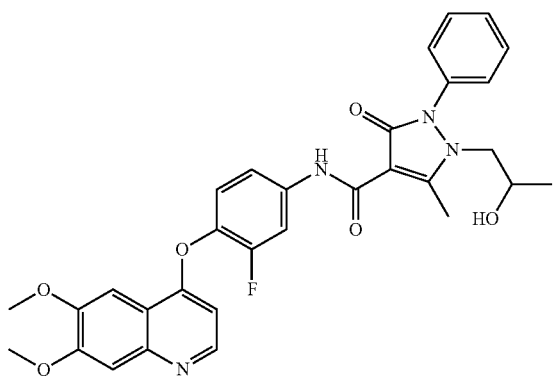

N-(4-((6,7-bis(methyloxy)-4-quinolinyl)oxy)-3-fluorophenyl)-1-((2S)-2-hydroxypropyl)-5-methyl-3-oxo-2-phenyl-2,3-dihydro-1H-pyrazole-4-carboxamide: MS (ESI pos. ion) m/z: 573 (MH+). Calc'd exact mass for $C_{31}H_{29}FN_4O_6$: 572.

EXAMPLE 121

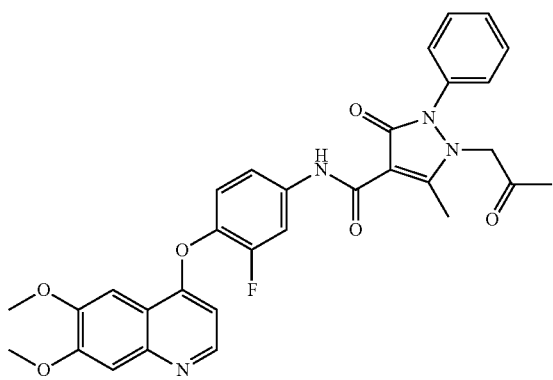

N-(4-((6,7-bis(methyloxy)-4-quinolinyl)oxy)-3-fluorophenyl)-5-methyl-3-oxo-1-(2-oxopropyl)-2-phenyl-2,3-dihydro-1H-pyrazole-4-carboxamide: MS (ESI pos. ion) m/z: 571 (MH+). Calc'd exact mass for $C_{31}H_{27}FN_4O_6$: 570.

EXAMPLE 122

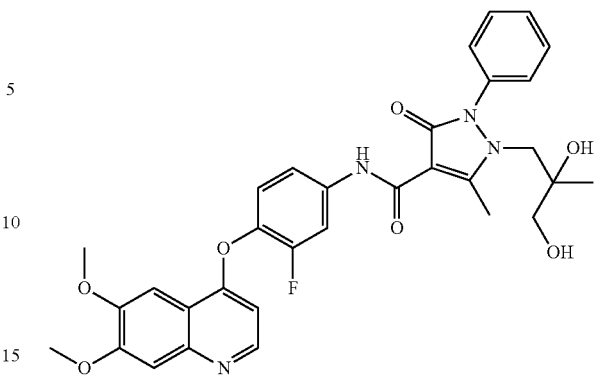

N-(4-((6,7-bis(methyloxy)-4-quinolinyl)oxy)-3-fluorophenyl)-1-(2,3-dihydroxy-2-methylpropyl)-5-methyl-3-oxo-2-phenyl-2,3-dihydro-1H-pyrazole-4-carboxamide: MS (ESI pos. ion) m/z: 603 (MH+). Calc'd exact mass for $C_{32}H_{31}FN_4O_7$: 602.

EXAMPLE 123

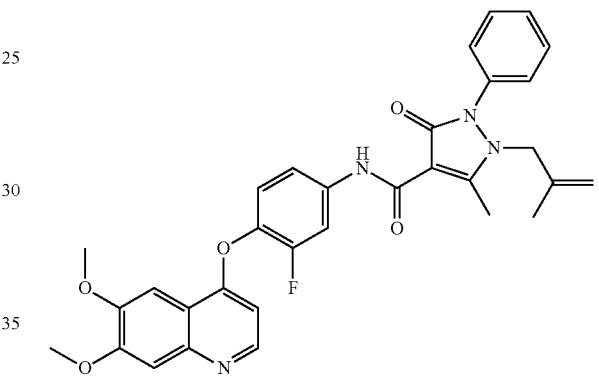

N-(4-((6,7-bis(methyloxy)-4-quinolinyl)oxy)-3-fluorophenyl)-5-methyl-1-(2-methyl-2-propen-1-yl)-3-oxo-2-phenyl-2,3-dihydro-1H-pyrazole-4-carboxamide: MS (ESI pos. ion) m/z: 569 (MH+). Calc'd exact mass for $C_{32}H_{29}FN_4O_5$: 568. $^1$H NMR (400 MHz, MeOH) 10.16 (2 H, s), 7.73 (2 H, d, J=5.7 Hz), 7.24 (2 H, s), 7.21 (1 H, d, J=1.6 Hz), 6.94 (2 H, s), 6.80-6.90 (8 H, m), 6.58-6.71 (13 H, m), 5.86 (2 H, d, J=5.5 Hz), 4.13-4.19 (17 H, m), 3.65-3.72 (8 H, m), 3.30 (15 H, d, J=1.8 Hz), 2.57-2.60 (6 H, m), 2.27 (1 H, s), 1.99-2.14 (13 H, m), 0.84 (8 H, s)

EXAMPLE 124

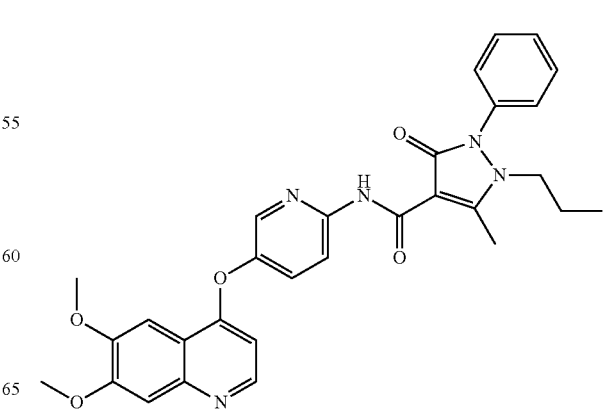

N-(5-(((6,7-bis(methyloxy)-4-quinolinyl)oxy)-2-pyridinyl)-5-methyl-3-oxo-2-phenyl-1-propyl-2,3-dihydro-1H-pyrazole-4-carboxamide: MS (ESI pos. ion) m/z: 540 (MH+). Calc'd exact mass for $C_{30}H_{29}FN_5O_5$: 539.

EXAMPLE 125

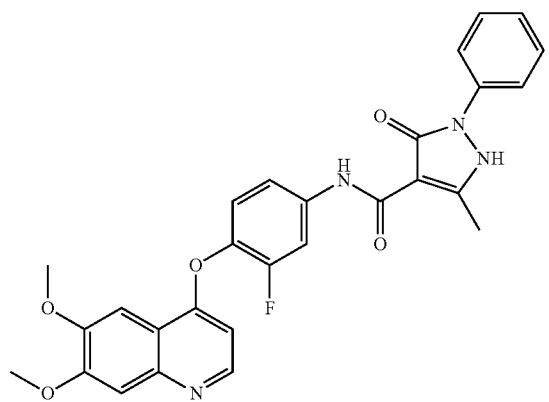

N-(4-((6,7-bis(methyloxy)-4-quinolinyl)oxy)-3-fluorophenyl)-5-methyl-3-oxo-2-phenyl-2,3-dihydro-1H-pyrazole-4-carboxamide: MS (ESI pos. ion) m/z: 515 (MH+). Calc'd exact mass for $C_{28}H_{23}FN_4O_5$: 514.

EXAMPLE 126

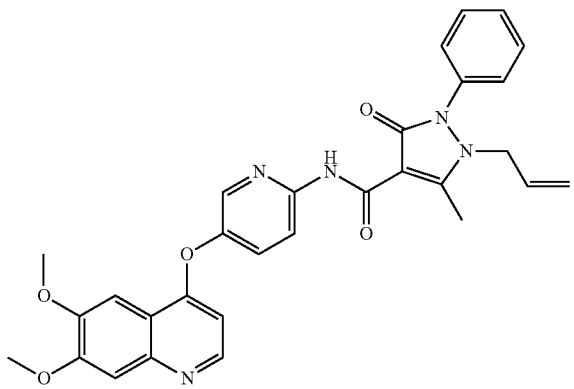

N-(5-(((6,7-bis(methyloxy)-4-quinolinyl)oxy)-2-pyridinyl)-5-methyl-3-oxo-2-phenyl-1-(2-propen-1-yl)-2,3-dihydro-1H-pyrazole-4-carboxamide: MS (ESI pos. ion) m/z: 538 (MH+). Calc'd exact mass for $C_{30}H_{27}N_5O_5$: 537.

EXAMPLE 127

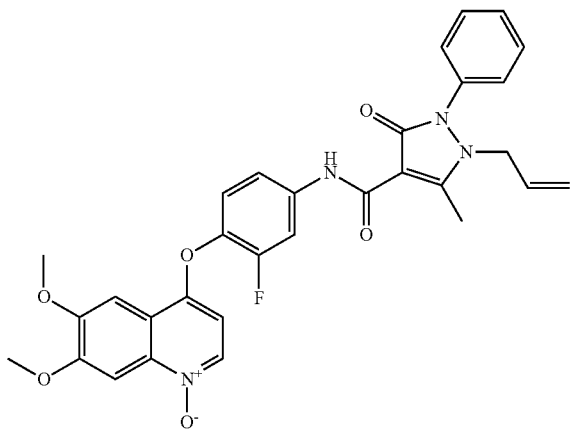

N-(4-((6,7-bis(methyloxy)-1-oxido-4-quinolinyl)oxy)-3-fluorophenyl)-5-methyl-3-oxo-2-phenyl-1-(2-propen-1-yl)-2,3-dihydro-1H-pyrazole-4-carboxamide: MS (ESI pos. ion) m/z: 571 (MH+). Calc'd exact mass for $C_{31}H_{27}FN_4O_6$: 570.
$^1$H NMR (400 MHz, MeOH) 8.36 (1 H, d, J=7.0 Hz), 7.90-7.97 (2 H, m), 7.68 (1 H, s), 7.53-7.62 (3 H, m), 7.42 (2 H, d, J=7.2 Hz), 7.30-7.37 (2 H, m), 6.59 (1 H, d, J=6.8 Hz), 5.69 (1 H, dd, J=11.2, 5.9 Hz), 5.21 (1 H, d, J=10.4 Hz), 4.93 (1 H, d, J=17.2 Hz), 4.48 (2 H, d, J=4.9 Hz), 4.01-4.11 (6 H, m), 2.77 (3 H, s).

EXAMPLE 128

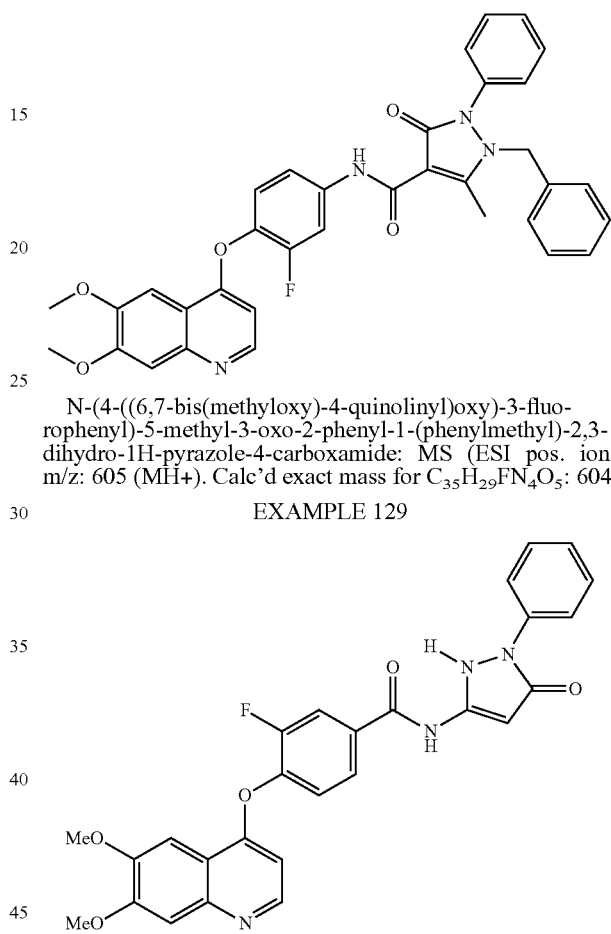

N-(4-((6,7-bis(methyloxy)-4-quinolinyl)oxy)-3-fluorophenyl)-5-methyl-3-oxo-2-phenyl-1-(phenylmethyl)-2,3-dihydro-1H-pyrazole-4-carboxamide: MS (ESI pos. ion) m/z: 605 (MH+). Calc'd exact mass for $C_{35}H_{29}FN_4O_5$: 604.

EXAMPLE 129

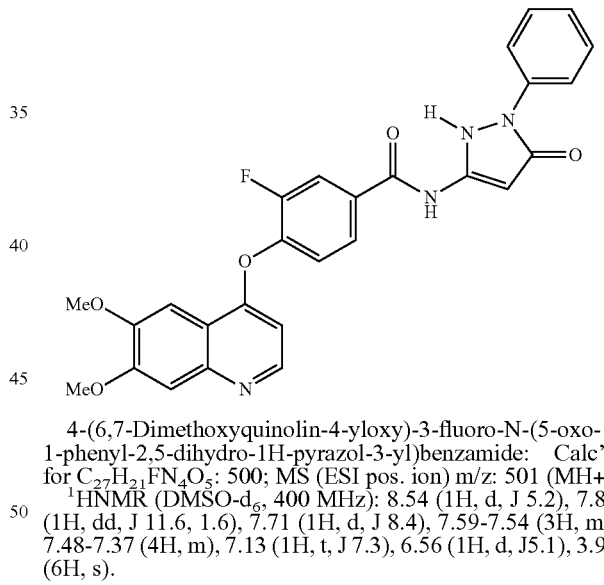

4-(6,7-Dimethoxyquinolin-4-yloxy)-3-fluoro-N-(5-oxo-1-phenyl-2,5-dihydro-1H-pyrazol-3-yl)benzamide: Calc'd for $C_{27}H_{21}FN_4O_5$: 500; MS (ESI pos. ion) m/z: 501 (MH+)
$^1$HNMR (DMSO-d$_6$, 400 MHz): 8.54 (1H, d, J 5.2), 7.88 (1H, dd, J 11.6, 1.6), 7.71 (1H, d, J 8.4), 7.59-7.54 (3H, m), 7.48-7.37 (4H, m), 7.13 (1H, t, J 7.3), 6.56 (1H, d, J 5.1), 3.96 (6H, s).

EXAMPLE 130

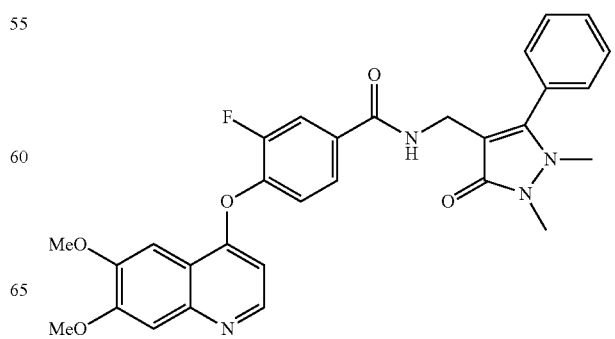

4-(6,7-Dimethoxyquinolin-4-yloxy)-N-((1,2-dimethyl-5-oxo-3-phenyl-2,5-dihydro-1H-pyrazol-4-yl)methyl)-3-fluorobenzamide: Calc'd for $C_{30}H_{27}FN_4O_5$: 542; MS (ESI pos. ion) m/z: 543 (MH+)

$^1$HNMR (CDCl$_3$, 400 MHz): 8.51 (2H, m), 7.81 (1H, dd, J1.8, 10.8), 7.71 (1H, d, J 8.3), 7.57-7.48 (5H, m), 7.44 (1H, s), 7.28 (1H, t, J 8.0), 6.42 (1H, d, J5.3), 4.46 (d, 2H, d, J 4.9), 4.06 (6H, s), 3.48 (3H, s), 3.14 (3H, s).

EXAMPLE 131

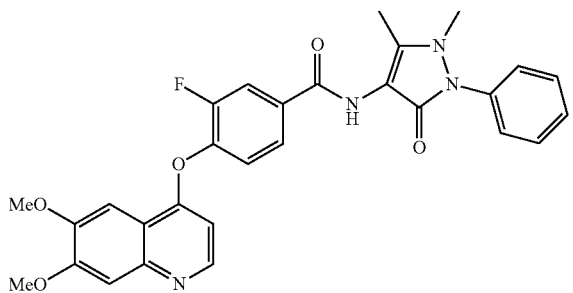

4-(6,7-Dimethoxyquinolin-4-yloxy)-N-(2,3-dimethyl-5-oxo-1-phenyl-2,5-dihydro-1H-pyrazol-4-yl)-3-fluorobenzamide: Calc'd for $C_{29}H_{25}FN_4O_5$: 528; MS (ESI pos. ion) m/z: 529 (MH+).

$^1$HNMR (CDCl$_3$, 400 MHz): 9.20 (1H, b), 8.56 (1H, d, J5.3), 7.86 (1H, J), 7.76 (1H, d, J) 7.57 (1H, s), 7.50-7.44 (3H, m), 7.40 (2H, d, J 7.4), 7.34 (1H, t, J7.2), 7.28 (1H, m), 6.56 (1H, d, J 4.9), 4.07 (3H, s), 4.06 (3H, s), 3.12 (3H, s), 2.30 (3H, s).

EXAMPLE 132

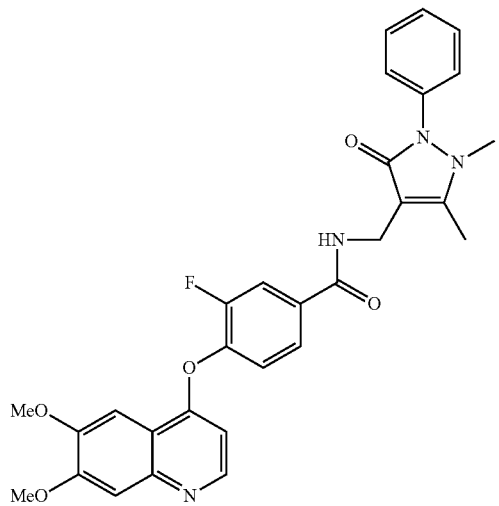

4-(6,7-Dimethoxyquinolin-4-yloxy)-N-((2,3-dimethyl-5-oxo-1-phenyl-2,5-dihydro-1H-pyrazol-4-yl)methyl)-3-fluorobenzamide: Calc'd for $C_{30}H_{27}FN_4O_5$: 542; MS (ESI pos. ion) m/z: 543 (MH+). $^1$HNMR (CDCl$_3$, 400 MHz): 8.49 (1H, d, J 5.3), 8.12 (1H, t, NH), 7.80 (1H, dd, J 1.7, 10.6), 7.67 (1H, d), 7.54 (1H, s), 7.48 (2H, t, J 8.0), 7.43 (1H, s), 7.38 (2H, d J 7.6), 7.33 (1H, t, J 7.3), 7.25 (1H, m), 6.40 (1H, d, 5.3), 4.44 (2H, d, J 5.1), 4.05 (6H, s), 3.11 (3H, s), 2.38 (3H, s).

EXAMPLE 133

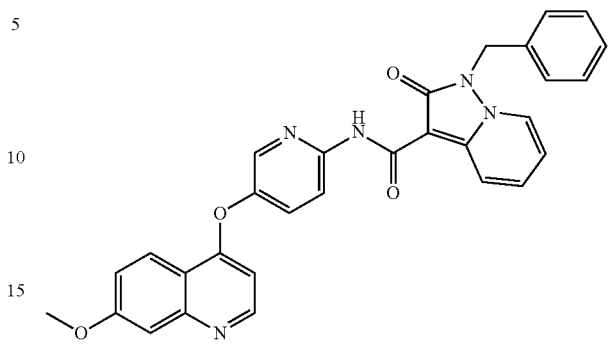

1-Benzyl-N-(5-(7-methoxyquinolin-4-yloxy)pyridin-2-yl)-2-oxo-1,2-dihydropyrazolo[1,5-a]pyridine-3-carboxamide: A mixture of HATU (760 mg, 2.0 mmol), crude 1-benzyl-2-oxo-1,2-dihydropyrazolo[1,5-a]pyridine-3-carboxylic acid (268 mg, 1.0 mmol), 5-(7-methoxyquinolin-4-yloxy)pyridin-2-amine (220 mg, 1.0 mmol), and triethylamine (2000 µl, 14 mmol) in DMF (3 mL) plus CHCL$_3$ (3 mL) was stirred at 60° C. for 4 days. Then, the mixture was diluted with EtOAc (10 mL) and H$_2$O (5 mL). The organic layer was washed with NaOH (1 N), H$_2$O, NaHCO$_3$, and dried over Na$_2$SO$_4$. The organic residue was purified on silica and further purified by trituration with EtOAc in ether (5%), resulting a light green powder. Calc'd for $C_{30}H_{23}N_5O_4$: 517; MS (ESI pos. ion) m/z: 518

$^1$HNMR (CDCl$_3$, 400 MHz): 10.96 (1H, s), 8.62 (1H, d, J 5.3), 8.48 (1H, d, J 9.0), 8.29-8.25 (2H, m), 7.73 (1H, d, J6.8), 7.55-7.53 (1H, dd, J2.7, 9.0), 7.48-7.43 (2H, m), 7.40-7.34 (3H, m), 7.29-7.23 (3H, m), 6.74 (1H, t, J 7.1), 6.46 (1H, d J 5.3), 5.48 (2H, s), 3.98 (3H, s).

EXAMPLE 134

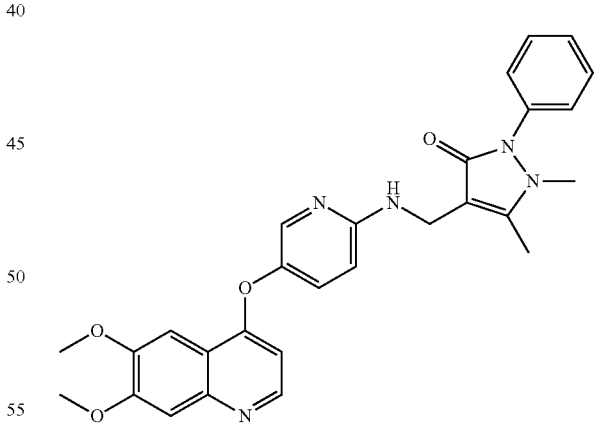

4-((5-(6,7-Dimethoxyquinolin-4-yloxy)pyridin-2-ylamino)methyl)-1,5-dimethyl-2-phenyl-1,2-dihydropyrazol-3-one Calc'd for $C_{28}H_{27}N_5O_4$: 497; MS (ESI pos. ion) m/z: 498.
$^1$HNMR (400 MHz, CDCl$_3$): 8.48 (1H, d, J 5.1), 8.06 (1H, s), 7.57 (1H, s), 7.47 (2H, t, J 7.2), 7.42 (3H, m), 7.33-7.22 (2H, m), 6.56 (1H, d, J 9.0), 6.43 (1H, d, J 5.3), 5.56 (1H, s, NH), 4.36 (2H, d, J 5.5, NCH2), 4.06 (6H, d), 3.08 (3H, s), 2.36 (3H, s).

EXAMPLE 135
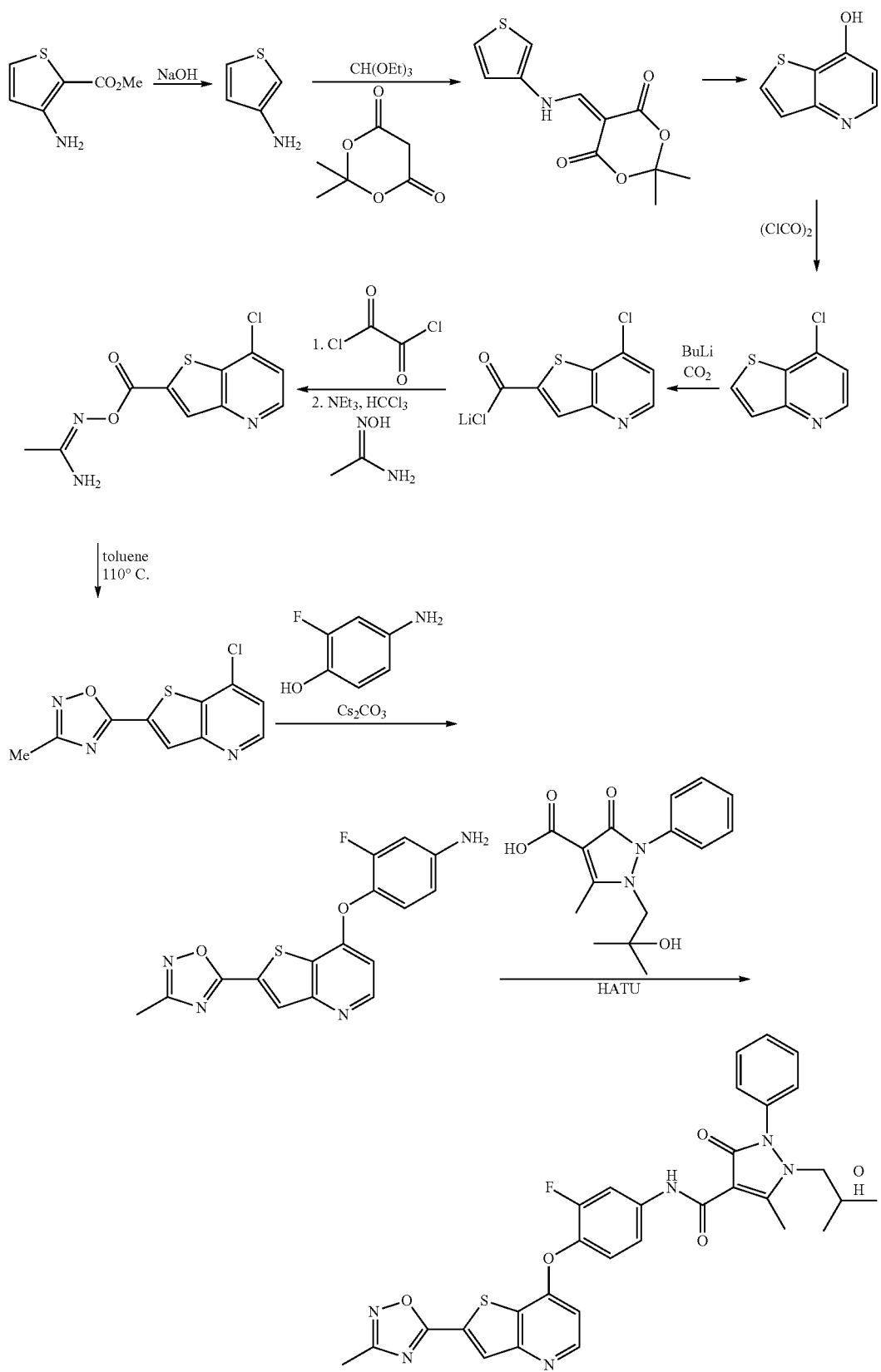

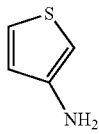

Step 1: Thiophen-3-amine. A 200-mL flask equipped with a reflux condenser and a magnetic stirbar was charged with methyl 3-aminothiophene-2-carboxylate (20.00 g, 127.2 mmol) and suspended in 2 N NaOH (140 mL, 2 equiv), then was heated to reflux for 4 h. The flask was removed from the oil bath and immersed in an ice/water bath and neutralized to pH 5 by the addition of conc. HCl (about 20 mL). The mixture was extracted with EtOAc (2×100 mL), and the combined organic extracts were washed with sat'd brine (100 mL) then dried over $Na_2SO_4$. The organic layer was dried, filtered and concentrated to a brown oil. The oil was dried under vacuum and dissolved in 1-propanol (60 mL, 5 vol), and treated with oxalic acid (11.1 g, 1.0 equiv). The resulting slurry was stirred at 40 deg C. (oil bath) for 45 min, then the precipitate was isolated by vacuum filtration and washed with cold 1-propanol. The light brown solid (6.9 g, 30% y) was dried under vacuum. The product was isolated as the likely oxalate salt (30% yield). The product was used as is in the next step.

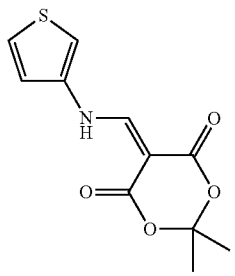

Step 2: 2,2-dimethyl-5-((thiophen-3-ylamino)methylene)-1,3-dioxane-4,6-dione. A 200-mL, rb flask equipped with a magnetic stirbar and a reflux condenser was charged with 3-aminothiophene oxalate (6.9 g, 36 mmol) and triethoxymethane (61 ml, 365 mmol) under $N_2$. After stirring for 15 min, 2,2-dimethyl-1,3-dioxane-4,6-dione (5.3 g, 36 mmol) was added in one portion to the light brown slurry, and the mixture was heated to 85 deg C. in an oil bath overnight. The next day, a dark precipitate had formed and the mixture was cooled to ambient temp. The mixture was then cooled in an ice bath and the mixture was vacuum filtered through paper. The brown-red solids were washed with MTBE, air dried, then dried under vacuum to yield 2,2-dimethyl-5-((thiophen-3-ylamino)methylene)-1,3-dioxane-4,6-dione (6.73 g, 73% yield).

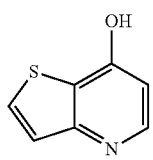

Step 3: thieno[3,2-b]pyridin-7-ol. A 200-mL rb flask was charged with 2,2-dimethyl-5-((thiophen-3-ylamino)methylene)-1,3-dioxane-4,6-dione (6.73 g, 26.6 mmol) and diphenyl ether (25 mL) and heated to about 200 deg C. for about 30-45 min and the mixture was allowed to cool to rt overnight. The mixture was scraped down with a spatula and diluted with MTBE. The mixture was filtered through paper and washed with MTBE. The brown solid was air dried to yield thieno[3,2-b]pyridin-7-ol.

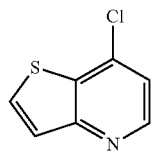

Step 4: 7-chlorothieno[3,2-b]pyridine. A 2-L, 3-neck, rb flask equipped with a mechanical overhead stirrer, a 250-mL addition funnel, and a thermocouple w/$N_2$-inlet adapter was charged with thieno[3,2-b]pyridin-7-ol (144 g, 952 mmol), chloroform (700 mL) and anhydrous N,N-dimethylformamide (100 ml, 1297 mmol). The heterogeneous mixture was cooled in an ice bath with stirring, then oxalyl dichloride (166 ml, 1905 mmol) was added dropwise via the addition funnel. Towards the end of the addition, the exotherm had diminished so the remaining reagent was added more quickly, which resulted in rapid off-gassing and the eruption of a portion of the contents out of the vessel. Upon complete addition, the mixture was allowed to stir out for 2 h, at which point LC-MS analysis indicated only about 10% conversion to the desired product (71556-13-A). The ice bath was removed, and the mixture was heated to reflux with a mantle. The heterogeneous mixture quickly turned homogeneous upon reaching temperature, and LC-MS indicated complete conversion after 1 h @ reflux (71556-13-B). After standing at ambient temp over the weekend, an orange solid had formed from the dark brown supernate. The mixture was cooled in an ice bath, then diluted with MTBE (800 mL), resulting in the exothermic precipitation of copious amounts of a dense, mustard-brown solid. The solid was isolated by vacuum filtration and washed with MTBE until the filtrate was colorless to yield the solid and a cloudy, bright orange filtrate. The solid product was then carefully partitioned between DCM (1 L) and sat'd aq. $NaHCO_3$ (1 L). The phases were mixed and the light brown aqueous layer was back extracted with DCM (500 mL). The combined organic layers were washed with sat'd brine, then dried over anhydrous $Na_2SO_4$. MTBE (500 mL) was added, then concentrated by about 200 mL, then hexane (500 mL) was added to form a dark brown precipitate. The mixture was further concentrated by 100 mL, then cooled in an ice bath. The mixture was then filtered and washed with hexane/MTBE (200 mL). The filtrate was then concentrated to dryness to yield the title compound as a light brown oil that crystallized to a dark rust colored, oily solid (97.7 g, 60.5% yield).

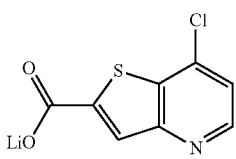

Step 5: lithium 7-chlorothieno[3,2-b]pyridine-2-carboxylate. A solution of 7-chlorothieno[3,2-b]pyridine (40 g, 0.236 mol) in THF (400 mL) was cooled to −78 deg C., dropwise added butyl lithium (1.5 M in hexanes, 103.8 mL, 0.259 mol). After stirring for 1 h, the mixture was quenched with $CO_2$ fgas with the formation of precipitate. The mixture was allowed to warm to rt, diluted with Et2O and filtered slowly. The filter cake was washed with ether and dried under vacuum. The crude mixture was dissolved in methanol and stirred with activated carbon and filtered through a pad of celite and the volume concentrated. The solution was triturated with ether and the solid collected and further triturated with isopropanol to provide the title compound: MS (ESI pos. ion) m/z: 214 (its corresponding acid form). Calc'd exact mass for $C_{31}H_{27}FN_6O_5S$: 214.

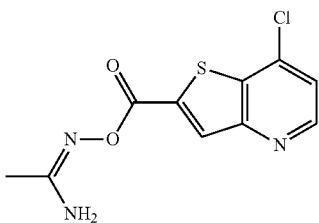

Step 6: (1Z)-N'-(((7-chlorothieno[3,2-b]pyridin-2-yl)carbonyl)oxy)ethanimidamide. A 100 mL round bottom flask was charged with lithium 7-chlorothieno[3,2-b]pyridine-2-carboxylate (0.500 g, 2.28 mmol), methylene chloride (15 ml), and 6 drops of DMF. Oxalyl chloride (0.248 ml, 2.85 mmol) was added dropwise, and the reaction mixture was stirred at room temperature for 3 hours then concentrated in vacuo to yield 7-chlorothieno[3,2-b]pyridine-2-carbonyl chloride as a brown solid. This material was suspended in chloroform (5 mL). N'-hydroxyacetamidine (0.186 g, 2.50 mmol), triethylamine (0.347 ml, 2.50 mmol), and chloroform (15 mL) were stirred together in a 50 mL flask to form a slurry, which was slowly added to the 7-chlorothieno[3,2-b]pyridine-2-carbonyl chloride suspension, then stirred for 1.5 hours at room temperature. The reaction mixture was diluted with chloroform (50 mL) and washed with water (50 mL), sat. aq. $NaHCO_3$ (50 mL) and brine (50 mL). The organic layer was dried with $MgSO_4$, filtered, and concentrated in vacuo. The resulting brown solid was triturated with toluene, and the precipitate collected to obtain the title compound (0.282 g, 46% yield) as a tan solid.

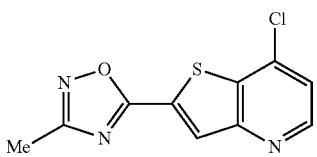

Step 7: 7-chloro-2-(3-methyl-1,2,4-oxadiazol-5-yl)thieno[3,2-b]pyridine. A 50 mL round bottom flask with a reflux condenser was charged with (1 Z)-N'-(((7-chlorothieno[3,2-b]pyridin-2-yl)carbonyl)oxy)ethanimidamide (0.282 g, 1.04 mmol) and toluene (10 ml) and heated to 110° C. and stirred for 18 hours. LC/MS analysis indicated a mixture of the product and 7-chlorothieno[3,2-b]pyridine-2-carboxylic acid. The reaction was diluted with chloroform (30 mL) and washed with water (30 mL), sat. aq. $NaHCO_3$ (30 mL), and brine (30 mL). The organic layer was dried with $MgSO_4$, filtered, and concentrated in vacuo to yield 7-chloro-2-(3-methyl-1,2,4-oxadiazol-5-yl)thieno[3,2-b]pyridine (0.1128 g, 43% yield) as a light yellow solid, which was used without further purification.

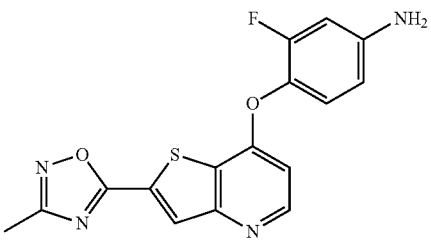

Step 8: 3-fluoro-4-(2-(3-methyl-1,2,4-oxadiazol-5-yl)thieno[3,2-b]pyridin-7-yloxy)benzenamine. A 15 mL sealed tube was charged with 7-chloro-2-(3-methyl-1,2,4-oxadiazol-5-yl)thieno[3,2-b]pyridine (0.113 g, 0.449 mmol), 4-amino-2-fluorophenol (0.071 g, 0.56 mmol), cesium carbonate (0.512 g, 1.57 mmol), and DMF (2.00 ml) and sealed. The reaction mixture was stirred at 90° C. for 18 hours, allowed to cool to room temperature, then diluted with chloroform (50 mL) and washed with water (50 mL), sat. aq. $NaHCO_3$ (50 mL), and brine (50 mL). The organic layer was dried with $MgSO_4$, filtered, and concentrated in vacuo to yield a black solid. The product was purified by silica gel chromatography eluting with 3% methanol in methylene chloride to yield 3-fluoro-4-(2-(3-methyl-1,2,4-oxadiazol-5-yl)thieno[3,2-b]pyridin-7-yloxy)benzenamine (0.074 g, 48% yield) as a yellow solid.

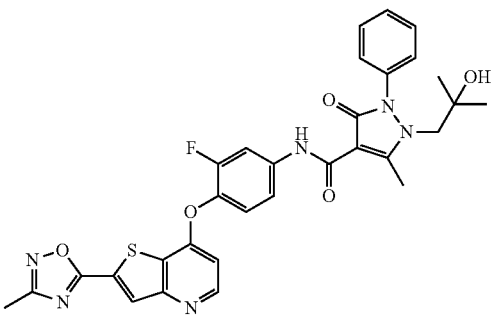

Step 9: N-(3-fluoro-4-(2-(3-methyl-1,2,4-oxadiazol-5-yl)thieno[3,2-b]pyridin-7-yloxy)phenyl)-1-(2-hydroxy-2-methylpropyl)-5-methyl-3-oxo-2-phenyl-2,3-dihydro-1H-pyrazole-4-carboxamide. A 16 mm sealed tube was charged with 3-fluoro-4-(2-(3-methyl-1,2,4-oxadiazol-5-yl)thieno[3,2-b]pyridin-7-yloxy)benzenamine (0.0740 g, 0.22 mmol), 1-(2-hydroxy-2-methylpropyl)-5-methyl-3-oxo-2-phenyl-2,3-dihydro-1H-pyrazole-4-carboxylic acid (0.094 g, 0.32 mmol), EDC (0.062 g, 0.32 mmol), HOBT (0.033 g, 0.22 mmol), Hunig's Base (0.13 ml, 0.76 mmol), and DMF (1.00 ml), sealed, and stirred at room temperature for 18 hours. LC/MS analysis indicated the presence of remaining 3-fluoro-4-(2-(3-methyl-1,2,4-oxadiazol-5-yl)thieno[3,2-b]pyridin-7-yloxy)benzenamine, so additional 1-(2-hydroxy-2-methylpropyl)-5-methyl-3-oxo-2-phenyl-2,3-dihydro-1H-pyrazole-4-carboxylic acid (0.031 g, 0.11 mmol) was added and the reaction mixture was stirred at 50° C. for 8 hours. The flask was allowed to cool to room temperature, the mixture was diluted with chloroform (25 mL), then washed with water (25 mL), sat. aq. NaHCO$_3$ (25 mL), and brine (25 mL). The organic layer was dried with MgSO$_4$, filtered, and concentrated in vacuo to yield a tan oil. The product was purified by silica gel chromatography eluting with 3% methanol in methylene chloride. The isolated yellow solid was triturated with EtOAc to yield N-(3-fluoro-4-(2-(3-methyl-1,2,4-oxadiazol-5-yl)thieno[3,2-b]pyridin-7-yloxy)phenyl)-1-(2-hydroxy-2-methylpropyl)-5-methyl-3-oxo-2-phenyl-2,3-dihydro-1H-pyrazole-4-carboxamide (0.035 g, 26% yield). MS (ESI pos. ion) m/z: 615 (MH+). Calc'd exact mass for C8H4ClNO2S: 614. $^1$H NMR (400 MHz, DMSO-d$_6$) 11.00 (s, 1 H), 8.68 (d, J=5.31 Hz, 1 H), 8.49 (s, 1 H), 7.96-8.04 (m, 1H), 7.43-7.60 (m, 4 H), 7.35 (d, J=8.21 Hz, 3 H), 6.89 (d, J=5.31 Hz, 1 H), 4.84 (s, 1 H), 3.87 (s, 2 H), 2.80 (s, 3 H), 2.46 (s, 3 H), 0.96 (s, 6 H).

EXAMPLE 136

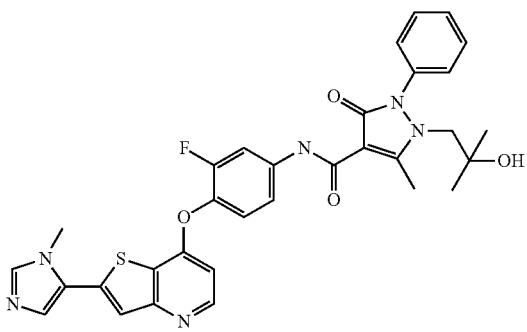

N-(3-fluoro-4-((2-(1-methyl-1H-imidazol-5-yl)thieno[3,2-b]pyridin-7-yl)oxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 613 (MH$^+$). Calc'd exact mass for C$_{32}$H$_{29}$FN$_6$O$_4$S: 612. $^1$H NMR (400 MHz, DMSO-d$_6$) 10.97 (s, 1 H), 8.52 (d, J=5.43 Hz, 1 H), 7.99 (dd, J=13.14, 2.15 Hz, 1 H), 7.87 (s, 1 H), 7.78 (s, 1 H), 7.56 (t, J=7.71 Hz, 2 H), 7.40-7.50 (m, 3 H), 7.35 (d, J=7.83 Hz, 3 H), 6.65 (d, J=5.43 Hz, 1 H), 4.85 (s, 1 H), 3.90 (s, 3H), 3.82-3.88 (m, 2 H), 2.79 (s, 3 H), 0.96 (s, 6 H).

EXAMPLE 137

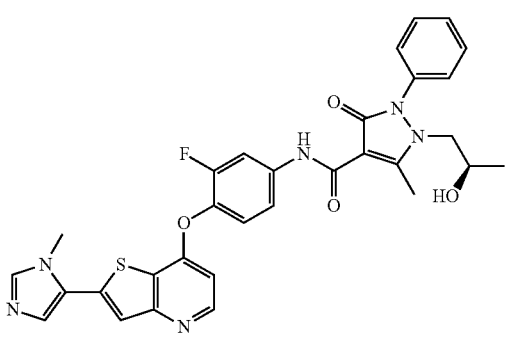

N-(3-fluoro-4-((2-(1-methyl-1H-imidazol-5-yl)thieno[3,2-b]pyridin-7-yl)oxy)phenyl)-1-((2R)-2-hydroxypropyl)-5-methyl-3-oxo-2-phenyl-2,3-dihydro-1H-pyrazole-4-carboxamide: MS (ESI pos. ion) m/z: 599 (MH$^+$). Calc'd exact mass for C$_{31}$H$_{27}$FN$_6$O$_4$S: 598.

EXAMPLE 138

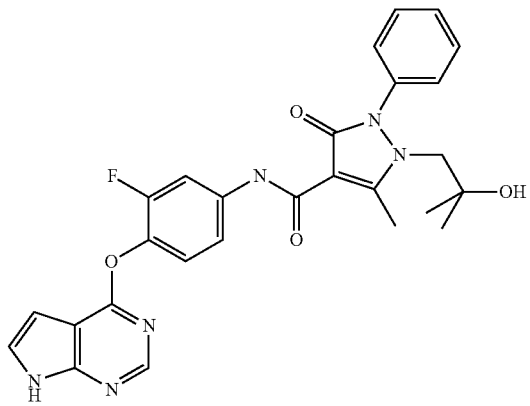

N-(3-fluoro-4-(7H-pyrrolo[2,3-d]pyrimidin-4-yloxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 517 (MH$^+$). Calc'd exact mass for C$_{27}$H$_{25}$FN$_6$O$_4$: 516. $^1$H NMR (400 MHz, DMSO-d$_6$) 12.27 (s, 1 H), 10.91 (s, 1 H), 8.30 (s, 1 H), 7.88 (dd, J=12.88, 2.27 Hz, 1 H), 7.56 (t, J=7.77 Hz, 2 H), 7.50 (d, J=3.41 Hz, 1 H), 7.46 (t, 1 H), 7.32-7.39 (m, 3 H), 7.24-7.31 (m, 1 H), 6.58 (d, J=3.41 Hz, 1 H), 4.83 (s, 1 H), 3.86 (s, 2 H), 2.80 (s, 3 H), 0.96 (s, 6 H).

EXAMPLE 139

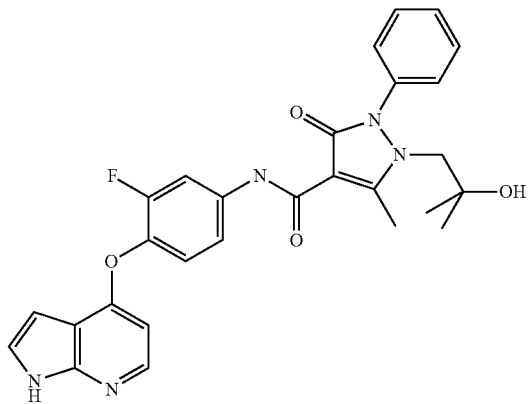

N-(3-fluoro-4-(1H-pyrrolo[2,3-b]pyridin-4-yloxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 516 (MH$^+$). Calc'd exact mass for C$_{28}$H$_{26}$FN$_5$O$_4$: 515. $^1$H NMR (400 MHz, DMSO-d$_6$) 11.77 (s, 1 H), 10.92 (s, 1 H), 8.07 (d, J=5.43 Hz, 1 H), 7.88-7.97 (m, 1 H), 7.56 (t, J=7.77 Hz, 2 H), 7.24-7.41 (m, 6 H), 6.37 (d, J=5.43 Hz, 1 H), 6.24 (s, 1 H), 4.84 (s, 1 H), 3.86 (s, 2 H), 2.79 (s, 3 H), 0.96 (s, 6 H).

EXAMPLE 140

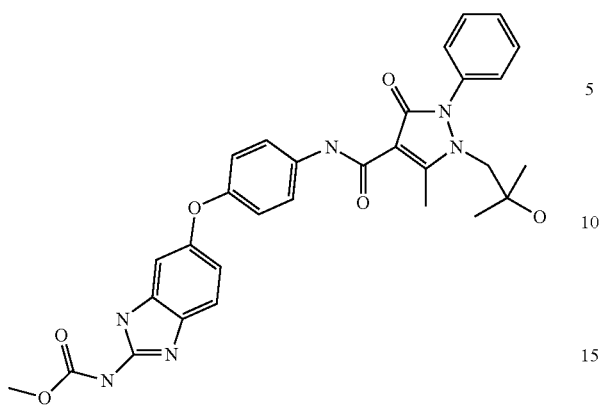

Methyl (6-((4-(((1-(2-hydroxy-2-methylpropyl)-5-methyl-3-oxo-2-phenyl-2,3-dihydro-1H-pyrazol-4-yl)carbonyl)amino)phenyl)oxy)-1H-benzimidazol-2-yl)carbamate MS (ESI pos. ion) m/z: 571 (MH+). Calc'd exact mass for $C_{30}H_{30}N_6O_6$: 570. $^1$H NMR (400 MHz, DMSO-$d_6$) 10.66 (s, 1 H), 7.51-7.61 (m, 4 H), 7.40-7.48 (m, 1 H), 7.29-7.39 (m, 3H), 7.01 (d, J=1.89 Hz, 1 H), 6.88-6.95 (m, 2 H), 6.79 (dd, J=8.53, 2.34 Hz, 1 H), 4.80 (s, 1H), 3.84 (s, 2 H), 3.74 (s, 3 H), 2.78 (s, 3 H), 0.95 (s, 6 H).

EXAMPLE 141

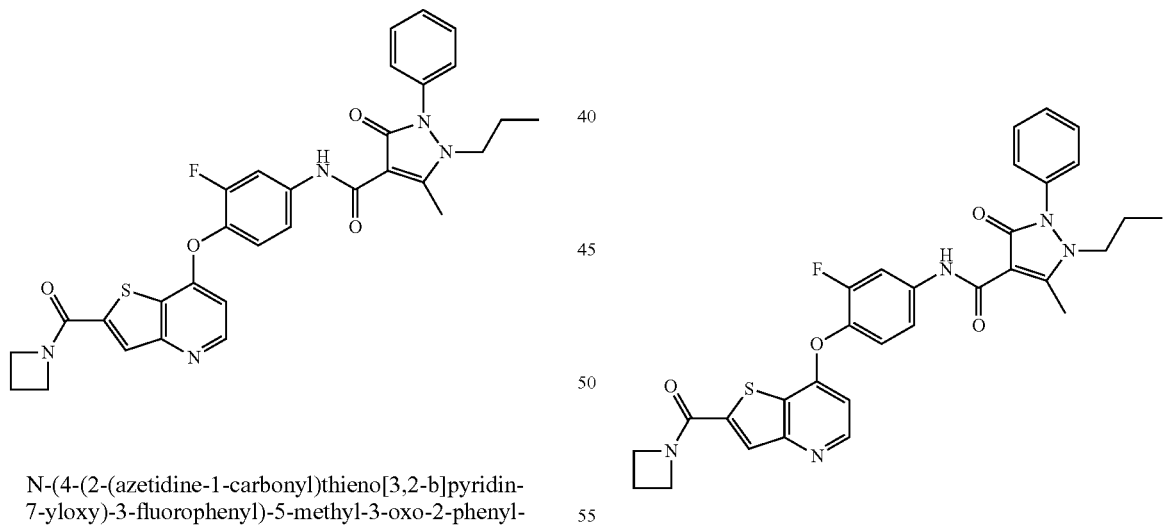

N-(4-(2-(azetidine-1-carbonyl)thieno[3,2-b]pyridin-7-yloxy)-3-fluorophenyl)-5-methyl-3-oxo-2-phenyl-1-propyl-2,3-dihydro-1H-pyrazole-4-carboxamide

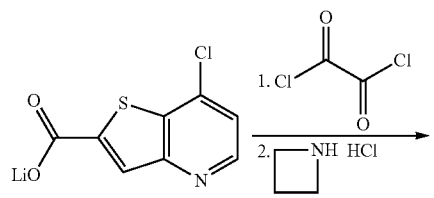

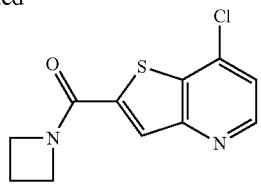

Azetidin-1-yl(7-chlorothieno[3,2-b]pyridin-2-yl)methanone

A 50 mL round bottom flask was charged with lithium 7-chlorothieno[3,2-b]pyridine-2-carboxylate (0.500 g, 2.28 mmol), methylene chloride (15 ml), and 12 drops of DMF. Oxalyl chloride (0.298 ml, 3.42 mmol) was added dropwise, and the mixture was stirred at room temperature for 3 hours and concentrated to yield a tan solid. This was redissolved in methylene chloride (15 ml). Azetidine hydrochloride (0.426 g, 4.55 mmol) was added in one portion and Hunig's Base (1.59 ml, 9.11 mmol) was added dropwise. This mixture was stirred at room temperature overnight, then diluted with methylene chloride (15 mL) and washed with water (25 mL), sat. NaHCO$_3$ (25 mL), and brine (25 mL). The organic layer was dried with MgSO$_4$, filtered, and concentrated in vacuo to yield azetidin-1-yl(7-chlorothieno[3,2-b]pyridin-2-yl)methanone (0.58 g, 100% yield) as a tan solid.

N-(4-(2-(azetidine-1-carbonyl)thieno[3,2-b]pyridin-7-yloxy)-3-fluorophenyl)-5-methyl-3-oxo-2-phenyl-1-propyl-2,3-dihydro-1H-pyrazole-4-carboxamide: MS (ESI pos. ion) m/z: 586 (MH+). Calc'd exact mass for $C_{31}H_{28}FN_5O_4S$: 585. $^1$H NMR (400 MHz, DMSO-$d_6$) 10.96 (s, 1 H), 8.60 (d, J=5.56 Hz, 1 H), 7.98 (d, J=14.53 Hz, 1 H), 7.91 (s, 1 H), 7.60 (t, J=7.52 Hz, 2 H), 7.42-7.55 (m, 4 H), 7.35 (d, J=9.22 Hz, 1 H), 6.77 (d, J=5.18 Hz, 1 H), 4.63 (t, J=7.20 Hz, 2 H), 4.12 (t, J=7.64 Hz, 2 H), 3.83 (t, J=7.33 Hz, 2 H), 2.75 (s, 3 H), 2.31-2.40 (m, 2 H), 1.35-1.45 (m, 2 H), 0.69 (t, J=7.39 Hz, 3 H)

EXAMPLE 142

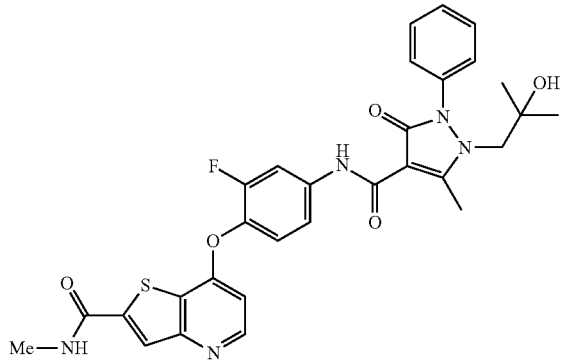

7-(2-fluoro-4-(1-(2-hydroxy-2-methylpropyl)-5-methyl-3-oxo-2-phenyl-2,3-dihydro-1H-pyrazole-4-carboxamido)phenoxy)-N-methylthieno[3,2-b]pyridine-2-carboxamide: MS (ESI pos. ion) m/z: 590 (MH+). Calc'd exact mass for $C_{30}H_{28}FN_5O_5S$: 589. $^1$H NMR (400 MHz, DMSO-$d_6$) 10.99 (s, 1 H), 8.95 (d, J=4.80 Hz, 1 H), 8.58 (d, J=5.43 Hz, 1 H), 8.21 (s, 1H), 7.99 (dd, J=13.14, 2.27 Hz, 1 H), 7.57 (t, J=7.83 Hz, 2 H), 7.44-7.51 (m, 2 H), 7.36 (d, J=7.58 Hz, 3 H), 6.76 (d, J=5.31 Hz, 1 H), 4.86 (s, 1 H), 3.87 (s, 2 H), 2.85 (d, J=4.67 Hz, 3H), 2.80 (s, 3 H), 0.97 (s, 6 H).

EXAMPLE 143

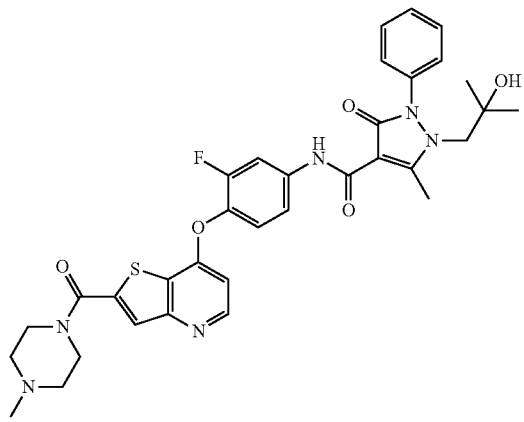

N-(3-fluoro-4-(2-(1-methylpiperazine-4-carbonyl)thieno[3,2-b]pyridin-7-yloxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 659 (MH+). Calc'd exact mass for $C_{34}H_{35}FN_6O_5S$: 658. $^1$H NMR (400 MHz, DMSO-$d_6$) 10.98 (s, 1 H), 8.59 (d, J=5.30 Hz, 1 H), 7.98 (dd, J=13.07, 2.21 Hz, 1 H), 7.84 (s, 1 H), 7.56 (t, J=7.71 Hz, 2 H), 7.42-7.51 (m, 2 H), 7.35 (d, J=7.45 Hz, 3 H), 6.76 (d, J=5.43 Hz, 1 H), 4.84 (s, 1 H), 3.86 (s, 2 H), 3.67 (bs, 4 H), 2.79 (s, 3 H), 2.37 (bs, 4 H), 2.21 (s, 3 H), 0.96 (s, 6 H)

EXAMPLE 144

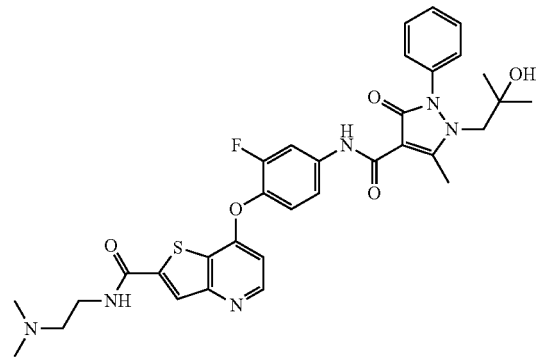

N-(2-(dimethylamino)ethyl)-7-(2-fluoro-4-(1-(2-hydroxy-2-methylpropyl)-5-methyl-3-oxo-2-phenyl-2,3-dihydro-1H-pyrazole-4-carboxamido)phenoxy)thieno[3,2-b]pyridine-2-carboxamide: MS (ESI pos. ion) m/z: 647 (MH+). Calc'd exact mass for $C_{33}H_{35}FN_6O_5S$: 646.

EXAMPLE 145

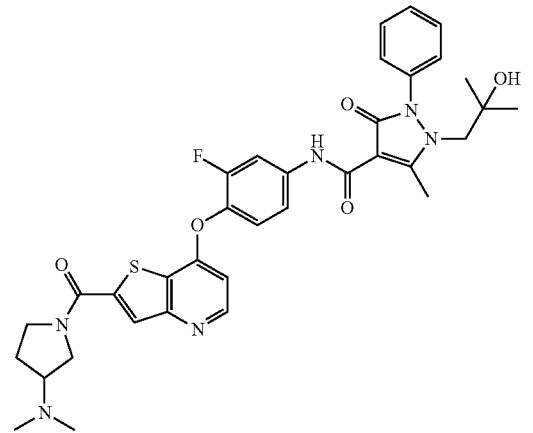

N-(4-(2-(3-(dimethylamino)pyrrolidine-1-carbonyl)thieno[3,2-b]pyridin-7-yloxy)-3-fluorophenyl)-1-(2-hydroxy-2-methylpropyl)-5-methyl-3-oxo-2-phenyl-2,3-dihydro-1H-pyrazole-4-carboxamide: MS (ESI pos. ion) m/z: 673 (MH+). Calc'd exact mass for $C_{35}H_{37}FN_6O_5S$: 672.

EXAMPLE 146

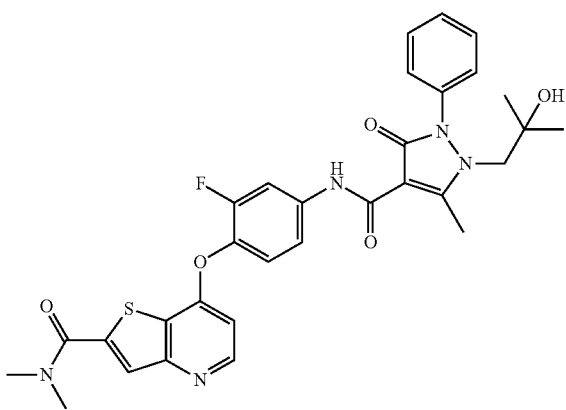

7-(2-fluoro-4-(1-(2-hydroxy-2-methylpropyl)-5-methyl-3-oxo-2-phenyl-2,3-dihydro-1H-pyrazole-4-carboxamido)phenoxy)-N,N-dimethylthieno[3,2-b]pyridine-2-carboxamide: MS (ESI pos. ion) m/z: 604 (MH+). Calc'd exact mass for $C_{31}H_{30}FN_5O_5S$: 603. $^1$H NMR (400 MHz, DMSO-$d_6$) 10.98 (s, 1 H), 8.58 (d, J=5.43 Hz, 1 H), 7.98 (dd, J=13.07, 1.96 Hz, 1H), 7.94 (s, 1 H), 7.56 (t, J=7.71 Hz, 2 H), 7.43-7.51 (m, 2 H), 7.35 (d, J=8.08 Hz, 3 H), 6.76 (d, J=5.43 Hz, 1 H), 4.85 (s, 1 H), 3.86 (s, 2 H), 3.23-3.30 (m, 3 H), 3.06 (s, 3 H), 2.79 (s, 3 H), 0.96 (s, 6 H).

EXAMPLE 147

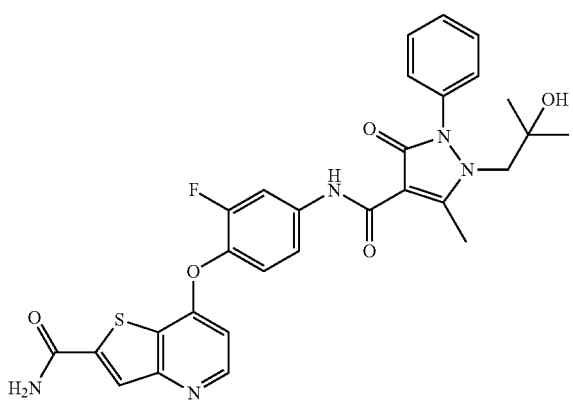

7-(2-fluoro-4-(1-(2-hydroxy-2-methylpropyl)-5-methyl-3-oxo-2-phenyl-2,3-dihydro-1H-pyrazole-4-carboxamido)phenoxy)thieno[3,2-b]pyridine-2-carboxamide: MS (ESI pos. ion) m/z: 576 (MH+). Calc'd exact mass for $C_{29}H_{26}FN_5O_5S$: 575. $^1$H NMR (400 MHz, DMSO-$d_6$) 10.98 (s, 1 H), 8.58 (d, J=5.30 Hz, 1 H), 8.42 (s, 1 H), 8.26 (s, 1 H), 7.95-8.01 (m, 1 H), 7.86 (s, 1 H), 7.56 (t, J=7.64 Hz, 2 H), 7.43-7.51 (m, 2 H), 7.35 (d, J=7.83 Hz, 3 H), 6.75 (d, J=5.43 Hz, 1 H), 5.76 (s, 1 H), 3.86 (s, 2 H), 2.79 (s, 3 H), 0.96 (s, 6 H).

EXAMPLE 148

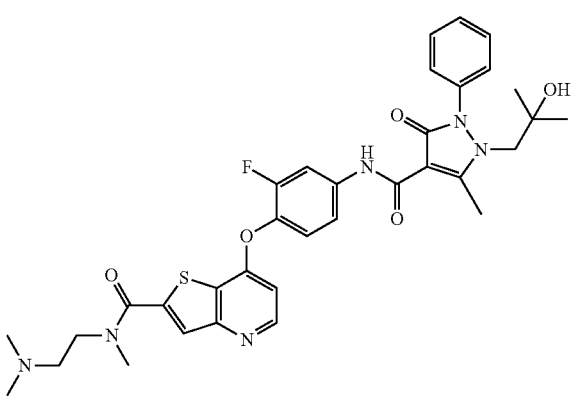

N-(2-(dimethylamino)ethyl)-7-(2-fluoro-4-(1-(2-hydroxy-2-methylpropyl)-5-methyl-3-oxo-2-phenyl-2,3-dihydro-1H-pyrazole-4-carboxamido)phenoxy)-N-methylthieno[3,2-b]pyridine-2-carboxamide: MS (ESI pos. ion) m/z: 661 (MH+). Calc'd exact mass for $C_{34}H_{37}FN_6O_5S$: 660.

EXAMPLE 149

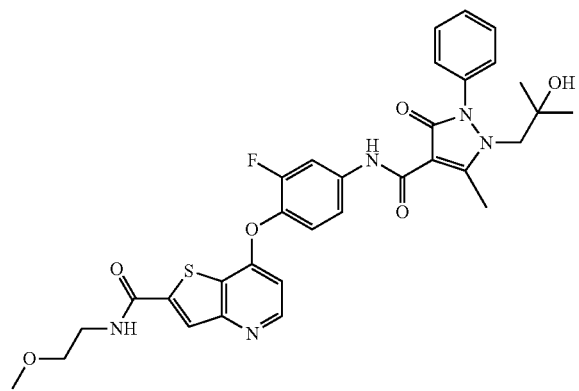

7-(2-fluoro-4-(1-(2-hydroxy-2-methylpropyl)-5-methyl-3-oxo-2-phenyl-2,3-dihydro-1H-pyrazole-4-carboxamido)phenoxy)-N-(2-methoxyethyl)thieno[3,2-b]pyridine-2-carboxamide: MS (ESI pos. ion) m/z: 634 (MH+). Calc'd exact mass for $C_{32}H_{32}FN_5O_6S$: 633.

EXAMPLE 150

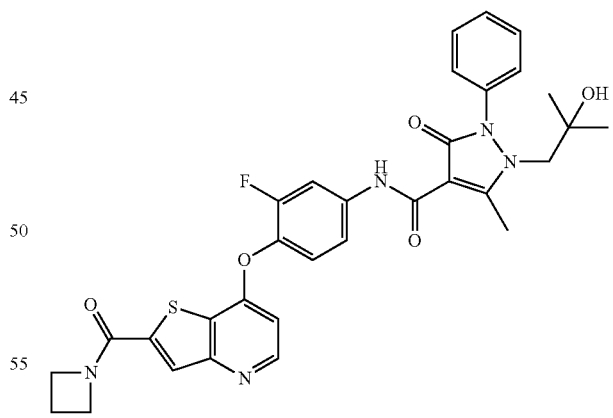

N-(4-(2-(azetidine-1-carbonyl)thieno[3,2-b]pyridin-7-yloxy)-3-fluorophenyl)-1-(2-hydroxy-2-methylpropyl)-5-methyl-3-oxo-2-phenyl-2,3-dihydro-1H-pyrazole-4-carboxamide: MS (ESI pos. ion) m/z: 616 (MH+). Calc'd exact mass for $C_{32}H_{30}FN_5O_5S$: 615.

EXAMPLE 151

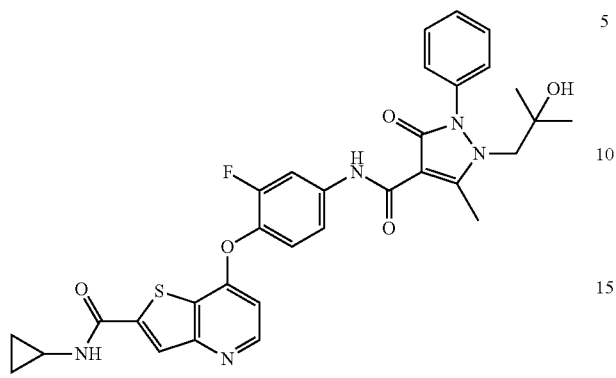

N-cyclopropyl-7-(2-fluoro-4-(1-(2-hydroxy-2-methyl-propyl)-5-methyl-3-oxo-2-phenyl-2,3-dihydro-1H-pyrazole-4-carboxamido)phenoxy)thieno[3,2-b]pyridine-2-carboxamide: MS (ESI pos. ion) m/z: 616 (MH+). Calc'd exact mass for $C_{32}H_{30}FN_5O_5S$: 615. $^1H$ NMR (400 MHz, DMSO-$d_6$) 10.98 (s, 1 H), 8.93 (d, J=4.04 Hz, 1 H), 8.57 (d, J=5.31 Hz, 1 H), 8.22 (s, 1 H), 7.94-8.01 (m, 2H), 7.56 (t, J=7.83 Hz, 2 H), 7.43-7.50 (m, 2 H), 7.35 (d, J=7.83 Hz, 3H), 6.75 (d, J=5.43 Hz, 1 H), 4.84 (s, 1 H), 3.87 (s, 2 H), 2.79 (s, 3 H), 0.96 (s, 6 H), 0.72-0.78 (m, 2 H), 0.60-0.66 (m, 2 H)

EXAMPLE 152

7-(2-fluoro-4-(5-methyl-3-oxo-2-phenyl-1-propyl-2,3-dihydro-1H-pyrazole-4-carboxamido) phenoxy)thieno[3,2-b]pyridine-2-carboxamide: MS (ESI pos. ion) m/z: 546 (MH+). Calc'd exact mass for $C_{28}H_{24}FN_5O_4S$: 545.

EXAMPLE 153

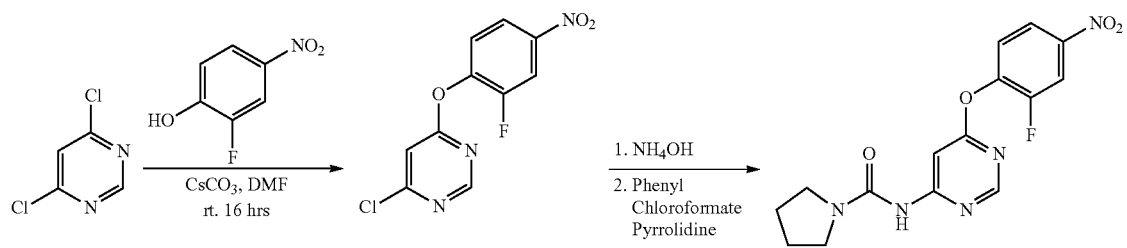

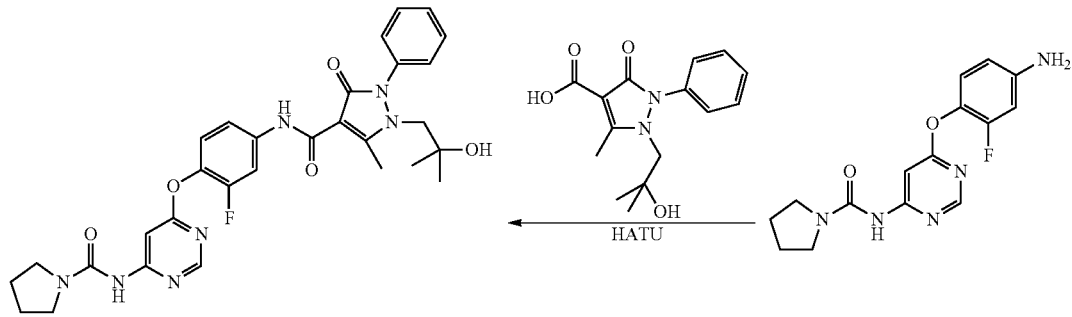

-continued

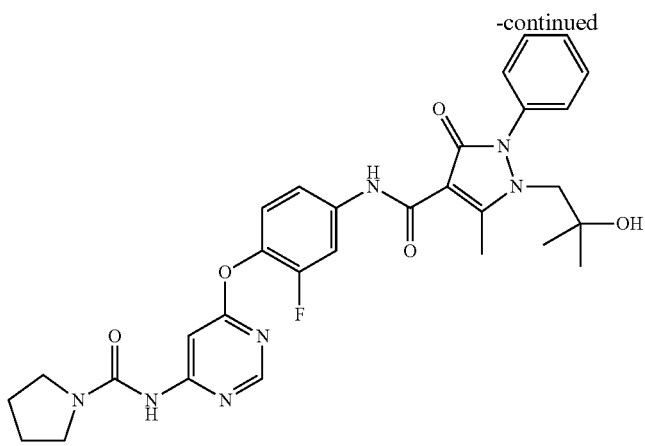

N-(3-fluoro-4-(6-(pyrrolidine-1-carboxamido)pyrimidin-4-yloxy)phenyl)-1-(2-hydroxy-2-methylpropyl)-5-methyl-3-oxo-2-phenyl-2,3-dihydro-1H-pyrazole-4-carboxamide

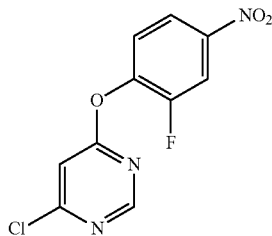

Step 1: 4-chloro-6-(2-fluoro-4-nitrophenoxy)pyrimidine. 6,6-dichloropyrimidine (1.000 g, 7 mmol) was dissolved in N,N-dimethylformamide (5 ml, 7 mmol), then 2-fluoro-4-nitrophenol (1 g, 7 mmol) was added into the mixture. Then Cesium Carbonate (2 g, 10 mmol) was added into the mixture with stirring. The mixture was stirred at ambient temperature under nitrogen overnight. The progress of the reaction was monitored by LC/MS, which had confirmed completion. Then diluted the mixture with water was stirred an additional 3 hours. The precipitate was collected by filtration and washed with hexanes. The solid was dried in a reduced-pressure oven overnight to give the desired product 4-chloro-6-(2-fluoro-4-nitrophenoxy)pyrimidine (1.500 g, 6 mmol, 83% yield) as a yellow solid. MS (ESI pos. ion) m/z: 270 (MH+). Calc'd exact mass for $C_{10}H_5ClFN_3O_3$: 269. $^1$HNMR (300 MHz, CDCl$_3$): 7.14 (s, 1H), 7.43 (s, 1H), 8.14 (s, 2H), 8.55 (s, 1H).

Step 2: N-(6-(2-fluoro-4-nitrophenoxy)pyrimidin-4-yl)pyrrolidine-1-carboxamide. 4-chloro-6-(2-fluoro-4-nitrophenoxy)pyrimidine (0.300 g, 1 mmol) was mixed with ammonium hydroxide (3 ml, 77 mmol) in a microwave vial. The resulting mixture was capped, and then placed into a CEM microwave for 10 minutes at 90° C., while 40 Watts of energy was supplied via Powermax. The mixture was diluted with water and stirred an additional 20 minutes. The precipitate was collected by filtration and washed with hexanes. The solid was dried in a reduced-pressure oven overnight to give desired product 6-(2-fluoro-4-nitrophenoxy)pyrimidin-4-amine (0.120 g, 0.5 mmol, 43% yield) as yellow solid, which was carried into the next step of the synthesis as crude material.

6-(2-fluoro-4-nitrophenoxy)pyrimidin-4-amine (0.550 g, 2.2 mmol) was dissolved in tetrahydrofuran (10 ml). Then triethylamine (0.61 ml, 4.4 mmol) was added to the mixture with stirring. Then phenyl chloroformate (0.55 ml, 4.4 mmol) was added slowly to the mixture. The mixture was stirred at ambient temperature for 1.5 hours. Then pyrrolidine (1.8 ml, 22 mmol) was added to the mixture, and the mixture was stirred an additional 30 minutes. The mixture was diluted with sat. ammonium chloride and dichloromethane and stirred an additional 10 minutes. The organic layer was collected by extracting with dichloromethane (3×10 ml). Combined organic layer was dried over sodium sulfate, filtered, and concentrated in-vacuo. The crude was purified by chromatography (Amino-Propyl silica gel column) in a gradient of 1-5% MeOH/dichloromethane to give an oil. The oil was recrystallized from dichloromethane/hexanes to give the desired product N-(6-(2-fluoro-4-nitrophenoxy)pyrimidin-4-yl)pyrrolidine-1-carboxamide (0.330 g, 0.95 mmol, 43% yield) as yellow solid. MS (ESI pos. ion) m/z: 348 (MH+). Calc'd exact mass for $C_{15}H_{14}FN_5O_4$: 347. 1NMR (300 MHz, CDCl$_3$): 1.94 (s, 4H), 3.37-3.49 (m, 4H), 5.23 (s, 1H), 7.09-7.21 (m, 1H), 7.29-7.38 (m, 1H), 7.99-8.09 (m, 2H), 8.25 (d, J=0.73 Hz, 1H).

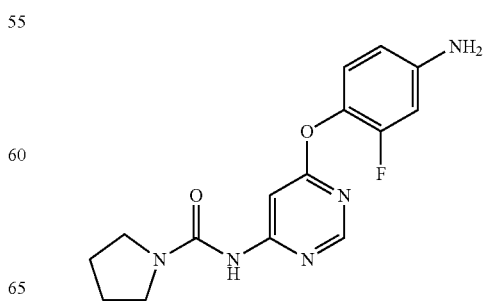

Step 3: N-(6-(4-amino-2-fluorophenoxy)pyrimidin-4-yl)pyrrolidine-1-carboxamide. N-(6-(2-fluoro-4-nitrophenoxy)pyrimidin-4-yl)pyrrolidine-1-carboxamide (0.320 g, 0.921 mmol) was dissolved in a mixture of 3:1 ethanol/water (8 ml). Then iron (0.276 g, 4.95 mmol) and ammonium chloride (0.0281 g, 0.525 mmol) was added to the mixture with stirring. The mixture was placed in a pre-heated oil bath (80° C.) for 1 hour. The oil bath was removed to allow the mixture to cool to ambient temperature. The mixture was filtered through a filter diskette. The flask was rinsed with methanol (3×10 ml) and filtered through diskette. Combined organic solution was concentrated in-vacuo. Then water was added to the mixture with stirring. The precipitate was collected by filtration and washed with hexanes. The solid was dried in a reduced-pressure oven to give the desired product N-(6-(4-amino-2-fluorophenoxy)pyrimidin-4-yl)pyrrolidine-1-carboxamide (0.240 g, 0.756 mmol, 82% yield) as a yellow solid. MS (ESI pos. ion) m/z: 318 (MH+). Calc'd exact mass for $C_{15}H_{16}FN_5O_2$: 317. $^1$HNMR (300 MHz, CDCl$_3$): 1.91-2.05 (s, 4H), 3.41-3.54 (t, 4H), 6.41-6.52 (m, 2H), 6.92-7.01 (t, 1H), 7.21 (s, 1H), 7.63 (s, 1H), 8.36 (s, 1H).

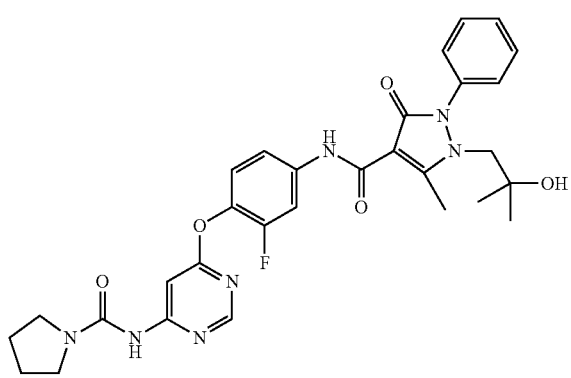

Step 4: N-(3-flouro-4-(6-(pyrrolidine-1-carboxamido)pyrimidin-4-yloxy)phenyl)-1-(2-hydroxy-2-methylpropyl)-5-methyl-3-oxo-2-phenyl-2,3-dihydro-1H-pyrazole-4-carboxamide. 1-(2-hydroxy-2-methylpropyl)5-methyl-3-oxo-2-phenyl-2,3-dihydro-1H-pyrazole-4-carboxylic acid (0.230 g, 0.792 mmol) was dissolved in dichloromethane (10 ml). Then DMF (0.5 ml) was added to the mixture while stirring. Then N-(6-(4-amino-2-fluorophenoxy)pyrimidin-4-yl)pyrrolidine-1-carboxamide (0.277 g, 0.871 mmol), along with TEA (0.33 ml, 2.38 mmol) was added to the mixture and stirred 5 minutes at ambient temperature. Then HATU (0.301 g, 0.792 mmol) was added into the mixture in one portion. The resulting mixture was allowed to stir under inert atmosphere for 3 hours. The reaction was monitored by LC/MS, which confirmed completion. The mixture was diluted with dichloromethane and water and with 4:1 dichloromethane/methanol (3×20 ml). Combined organic layer was dried over sodium sulfate, filtered, and concentrated in-vacuo. The crude was purified by chromatography (Amino-Propyl silica gel column, in a gradient of 1-5% MeOH/dichloromethane to give an oil. The oil was recrystallized from dichloromethane/hexanes to give the desired product N-(3-fluoro-4-(6-(pyrrolidine-1-carboxamido)pyrimidin-4-yloxy)phenyl)-1-(2-hydroxy-2-methylpropyl)-5-methyl-3-oxo-2-phenyl-2,3-dihydro-1H-pyrazole-4-carboxamide (0.330 g, 0.56 mmol, 70% yield) as a white solid. MS (ESI pos. ion) m/z: 590 (MH+). Calc'd exact mass for $C_{30}H_{32}FN_7O_5$: 589. $^1$HNMR (300 MHz, CDCl$_3$): 1.05 (s, 6H), 1.91 (s, 4H), 2.21 (s, 1H), 2.78 (s, 3H), 3.40 (s, 4H), 3.78 (s, 2H), 7.01-7.22 (m, 4H), 7.31-7.48 (m, 2H), 7.59 (s, 1H), 7.79 (dd, J=12.42, 2.19 Hz, 1H), 8.26 (s, 1H), 10.75 (s, 1H).

EXAMPLE 154

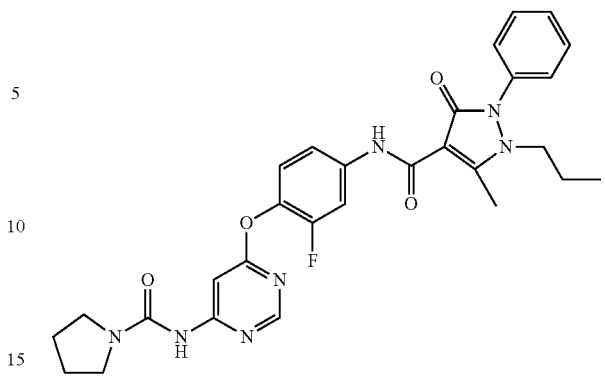

N-(3-fluoro-4-(6-(pyrrolidine-1-carboxamido)pyrimidin-4-yloxy)phenyl)-5-methyl-3-oxo-2-phenyl-1-propyl-2,3-dihydro-1H-pyrazole-4-carboxamide: MS (ESI pos. ion) m/z: 560 (MH+). Calc'd exact mass for $C_{29}H_{30}FN_7O_4$: 559. $^1$HNMR (300 MHz, CDCl$_3$): 0.80 (t, J=7.38 Hz, 3H), 1.61 (s, 4H), 1.99 (s, 4H), 2.80 (s, 3H), 3.49 (s, 4H), 3.74 (t, J=7.16 Hz, 2H), 7.11 (t, J=8.55 Hz, 1H), 7.34 (s, 1H), 7.37 (d, J=1.32 Hz, 1H), 7.47 (d, J=7.31 Hz, 1H), 7.55 (t, J=7.38 Hz, 2H), 7.69 (s, 1H), 7.86 (dd, J=12.42, 2.34 Hz, 1H), 8.35 (s, 1H), 10.81 (s, 1H).

EXAMPLE 155

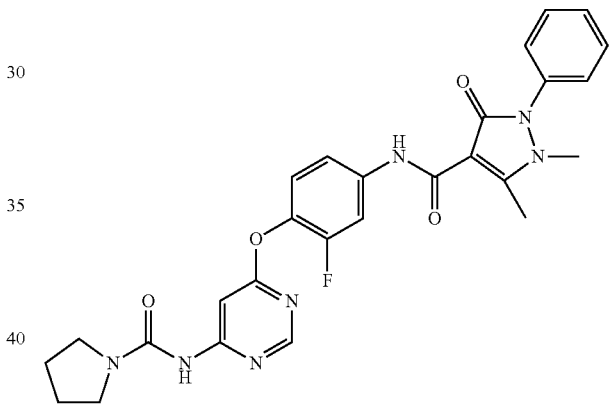

N-(6-(4-(1,5-dimethyl-3-oxo-2-phenyl-2,3-dihydro-1H-pyrazole-4-carboxamido)-2-fluorophenoxy)pyrimidin-4-yl)morpholine-4-carboxamide: MS (ESI pos. ion) m/z: 532 (MH+). Calc'd exact mass for $C_{27}H_{26}FN_7O_4$: 531. $^1$HNMR (300 MHz, CDCl$_3$): 2.71 (s, 2H), 3.28 (s, 2H), 3.37-3.46 (m, 3H), 4.05 (q, J=7.06 Hz, 4H), 7.05 (d, J=8.48 Hz, 2H), 7.16-7.21 (m, 2H), 7.26-7.31 (m, 2H), 7.36-7.51 (m, 2H), 8.35 (s, 1H), 10.81 (s, 1H).

EXAMPLE 156

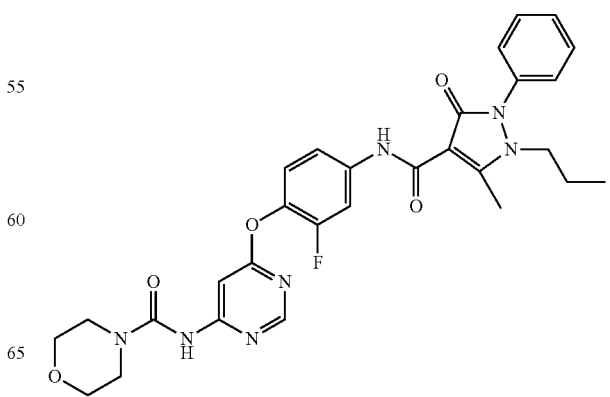

N-(6-(2-fluoro-4-(5-methyl-3-oxo-2-phenyl-1-propyl-2,3-dihydro-1H-pyrazole-4-carboxamido)phenoxy)pyrimidin-4-yl)morpholine-4-carboxamide: MS (ESI pos. ion) m/z: 576 (MH+). Calc'd exact mass for $C_{29}H_{30}FN_7O_5$: 575. $^1$NMR (300 MHz, CDCl$_3$): 0.80 (s, 3H), 1.26 (s, 1H), 1.62 (s, 4H), 2.80 (s, 4H), 3.53 (s, 5H), 3.75 (s, 3H), 7.11 (s, 1H), 7.26 (s, 2H), 7.55 (s, 5H), 7.84 (s, 1H), 8.36 (s, 1H), 10.83 (s, 1H).

EXAMPLE 157

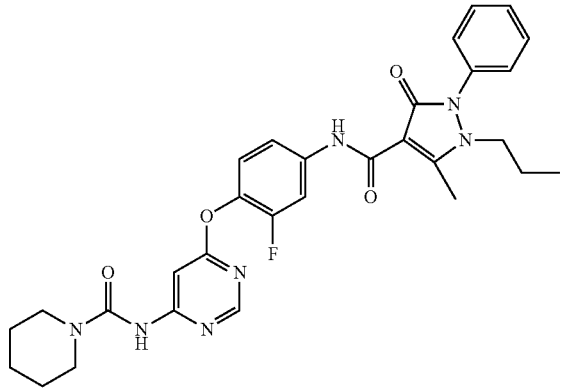

N-(6-(2-fluoro-4-(5-methyl-3-oxo-2-phenyl-1-propyl-2,3-dihydro-1H-pyrazole-4-carboxamido)phenoxy)pyrimidin-4-yl)piperidine-1-carboxamide: MS (ESI pos. ion) m/z: 574 (MH+). Calc'd exact mass for $C_{30}H_{32}FN_7O_4$: 573. $^1$NMR (300 MHz, CDCl$_3$): 0.80 (t, J=7.45 Hz, 3H), 1.38-1.59 (m, 2H), 1.65 (s, 8H), 2.80 (s, 3H), 3.49 (d, J=5.26 Hz, 4H), 3.74 (t, J=7.31 Hz, 2H), 7.11 (t, J=8.55 Hz, 1H), 7.23-7.29 (m, 1H), 7.41-7.62 (m, 4H), 7.86 (dd, J=12.50, 2.27 Hz, 1H), 8.35 (s, 1H), 10.81 (s, 1H).

EXAMPLE 158

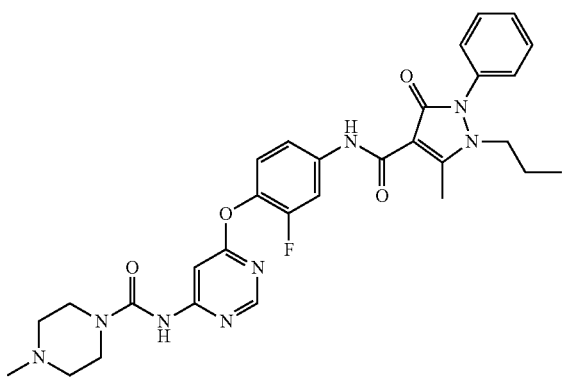

N-(6-(2-fluoro-4-(5-methyl-3-oxo-2-phenyl-1-propyl-2,3-dihydro-1H-pyrazole-4-carboxamido)phenoxy)pyrimidin-4-yl)-4-methylpiperazine-1-carboxamide: MS (ESI pos. ion) m/z: 589 (MH+). Calc'd exact mass for $C_{30}H_{33}FN_8O_4$: 588. $^1$NMR (300 MHz, CDCl$_3$): 0.79 (t, J=7.38 Hz, 3H), 1.43-1.56 (m, J=7.31 Hz, 2H), 2.35 (s, 3H), 2.48 (s, 4H), 2.80 (s, 3H), 3.57 (s, 4H), 3.75 (t, J=7.31 Hz, 2H), 5.28-5.34 (m, 1H), 7.11 (t, J=8.55 Hz, 1H), 7.22-7.30 (m, 2H), 7.32-7.62 (m, 3H), 7.86 (dd, J=12.42, 2.34 Hz, 1H), 8.35 (s, 1H), 10.83 (s, 1H).

EXAMPLE 159

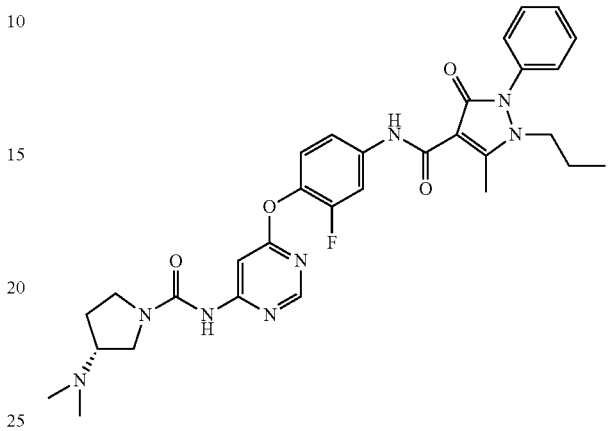

(R)-N-(4-(6-(3-(dimethylamino)pyrrolidine-1-carboxamido)pyrimidin-4-yloxy)-3-fluorophenyl)-5-methyl-3-oxo-2-phenyl-1-propyl-2,3-dihydro-1H-pyrazole-4-carboxamide: MS (ESI pos. ion) m/z: 603 (MH+). Calc'd exact mass for $C_{31}H_{35}FN_8O_4$: 602. $^1$NMR (300 MHz, CDCl$_3$): 0.79 (t, J=7.45 Hz, 3H), 1.43-1.56 (m, 2H), 2.25-2.32 (m, 6H), 2.79 (s, 4H), 3.24 (s, 1H), 3.47 (s, 3H), 3.62-3.80 (m, 4H), 5.30 (s, 1H), 7.11 (t, J=8.55 Hz, 1H), 7.32-7.38 (m, 2H), 7.43-7.56 (m, 3H), 7.58 (s, 1H), 7.83 (s, 1H), 8.34 (s, 1H), 10.83 (s, 1H).

EXAMPLE 160

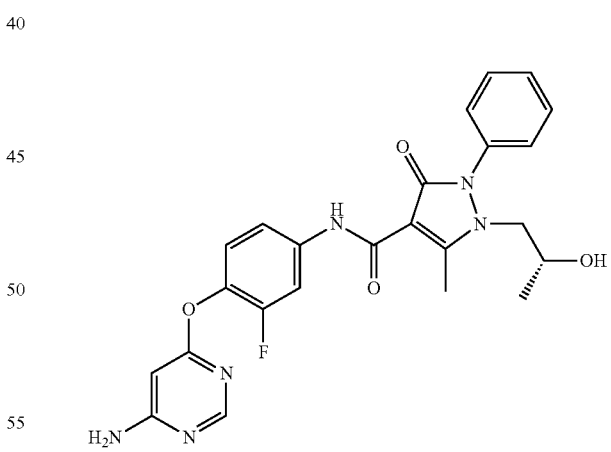

(R)-N-(4-(6-aminopyrimidin-4-yloxy)-3-fluorophenyl)-1-(2-hydroxypropyl)-5-methyl-3-oxo-2-phenyl-2,3-dihydro-1H-pyrazole-4-carboxamide: MS (ESI pos. ion) m/z: 479 (MH+). Calc'd exact mass for $C_{24}H_{23}FN_6O_4$: 478. $^1$NMR (300 MHz, CDCl$_3$): 0.98 (d, J=5.99 Hz, 3H), 2.72 (s, 3H), 3.45-3.58 (m, 1H), 3.67-3.85 (m, 2H), 4.96 (s, 2H), 5.23 (s, 1H), 5.78 (s, 1H), 7.00-7.20 (m, 3H), 7.31-7.49 (m, 3H), 7.76 (dd, J=12.50, 2.12 Hz, 1H), 8.14 (s, 1H), 10.75 (s, 1H).

EXAMPLE 161
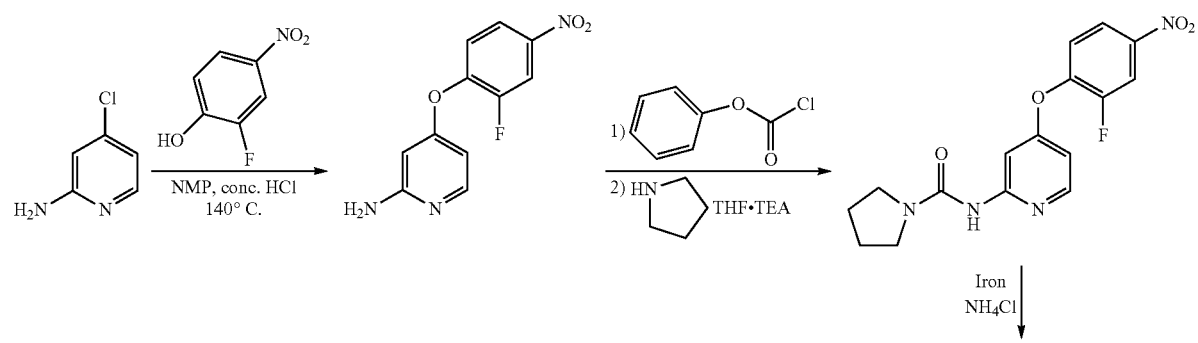
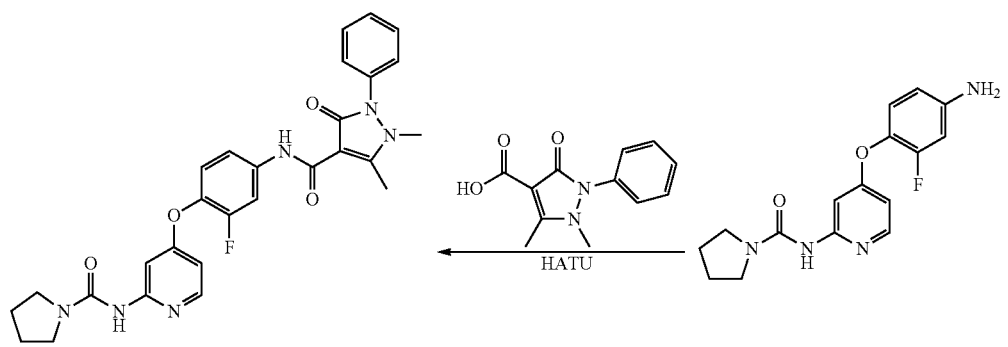
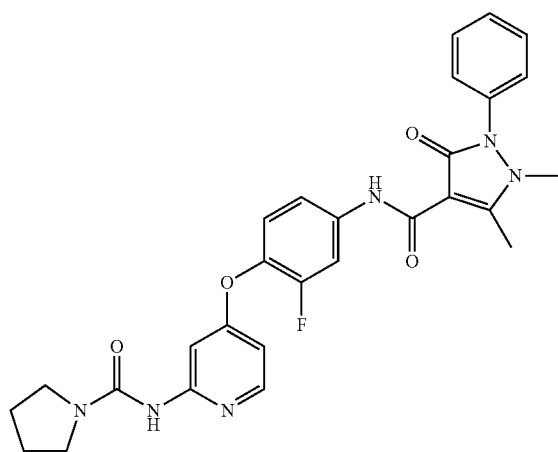

N-(3-fluoro-4-(2-(pyrrolidine-1-carboxamido)pyridin-4-yloxy)phenyl)-1,5-dimethyl-3-oxo-2-phenyl-2,3-dihydro-1H-pyrazole-4-carboxamide

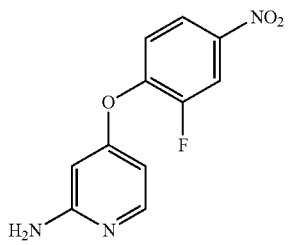

Step 1: 4-(2-fluoro-4-nitrophenoxy)pyridin-2-amine. 4-chloropyridin-2-amine (0.500 g, 3.9 mmol) was added to a microwave vial, along with 1-methyl-2-pyrrolidinone (1 ml, 10 mmol). The mixture was stirred into a homogeneous mixture, then 2-fluoro-4-nitrophenol (1.2 g, 7.8 mmol) was added to the mixture. After 2 minutes of stirring, conc. HCl (4 drops) was added to the mixture. The capped vial was placed into a CEM microwave for 25 minutes at 140° C., while 60 Watts of power was supplied via Powermax. The mixture was transferred to a round bottomed flask, and warm ethyl acetate was added with stirring. Then conc. HCl was added dropwise into the mixture to form HCl salt. The precipitate was collected by filtration and washed with hexanes to give desired product 4-(2-fluoro-4-nitrophenoxy)pyridin-2-amine (0.480 g, 1.9 mmol, 50% yield) as a beige solid. MS (ESI pos. ion) m/z: 250 (MH+). Calc'd exact mass for $C_{11}H_8ClFN_3O_3$: 249. $^1$HNMR (300 MHz, $CD_3OD$): 1.17 (t, J=7.31 Hz, 1H), 3.02 (m, 1H), 6.19 (d, J=2.19 Hz, 1H), 6.59 (dd, J=7.23, 2.41 Hz, 1H), 7.48-7.57 (m, 1H), 7.71-7.79 (m, 1H), 8.08-8.23 (m, 2H).

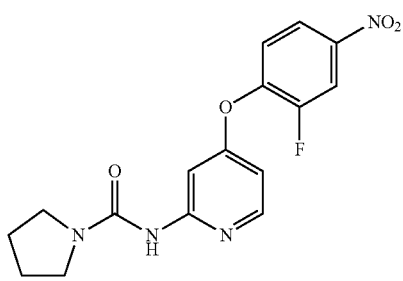

Step 2: N-(4-(2-fluoro-4-nitrophenoxy)pyridin-2-yl)pyrrolidine-1-carboxamide. 4-(2-fluoro-4-nitrophenoxy)pyridin-2-amine (0.150 g, 0.60 mmol) was dissolved in THF (10 ml). Then triethylamine (0.17 ml, 1.2 mmol) was added to the mixture while stirring. Then phenyl chloroformate (0.15 ml, 1.2 mmol) was added to the mixture dropwise. The mixture was stirred at ambient temperature for 1.5 hours. Then pyrrolidine (0.50 ml, 6.0 mmol) was added to the mixture and stirred an additional 30 minutes. The mixture was diluted with sat. ammonium chloride (10 ml) and dichloromethane (10 ml) and stirred 10 minutes and was collected by extracted with dichloromethane (3×10 ml). The organic layer was dried over sodium sulfate, filtered, and concentrated in-vacuo. The crude was purified by chromatography (Amino-Propyl silica gel column) in a gradient of 1-5% MeOH/dichloromethane to give the desired product N-(4-(2-fluoro-4-nitrophenoxy)pyridin-2-yl)pyrrolidine-1-carboxamide (0.184 g, 0.53 mmol, 88% yield) as tan oil. MS (ESI pos. ion) m/z: 347 (MH+). Calc'd exact mass for $C_{16}H_{15}FN_4O_4$: 346. $^1$HNMR (300 MHz, $CDCl_3$): 1.96 (s, 4H), 3.44 (t, J=6.65 Hz, 4H), 6.81-6.96 (m, 2H), 8.06-8.18 (m, 4H).

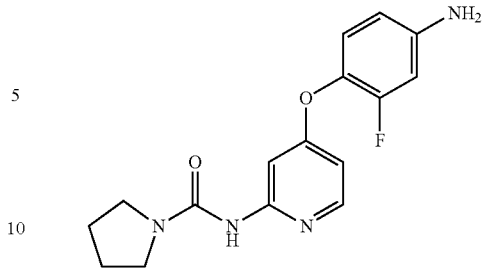

Step 3: N-(4-(4-amino-2-fluorophenoxy)pyridin-2-yl)pyrrolidine-1-carboxamide. N-(4-(2-fluoro-4-nitrophenoxy)pyridin-2-yl)pyrrolidine-1-carboxamide (0.180 g, 0.52 mmol) was dissolved in a mixture of 3:1 ethanol/water (4 ml) with stirring. Then iron (0.160 g, 2.8 mmol) and ammonium chloride (0.016 g, 0.30 mmol) was added to the mixture. The mixture was placed in a pre-heated oil-bath (80° C.) for 1 hour. The oil bath was removed, and the mixture was allowed to cool to ambient temperature. The mixture was filtered through filter diskette. The flask was rinsed with methanol (3×10 ml), and the combined filtrate was evaporated in-vacuo. The residue was diluted with dichloromethane and 1N NaOH (2 ml). The organic were extracted with dichloromethane (3×10 ml), dried over sodium sulfate, filtered and concentrated in vacuo. to give the desired product N-(4-(4-amino-2-fluorophenoxy)pyridin-2-yl)pyrrolidine-1-carboxamide (0.125 g, 0.4 mmol, 76% yield) as a tan oil. MS (ESI pos. ion) m/z: 317 (MH+). Calc'd exact mass for $C_{16}H_{17}FN_4O_2$: 316. $^1$HNMR (300 MHz, $CDCl_3$): 1.96 (s, 4H), 3.44 (s, 4H), 6.52 (d, J=3.07 Hz, 2H), 6.96 (s, 1H), 7.26 (s, 1H), 7.67 (s, 1H), 8.01 (d, J=5.70 Hz, 1H).

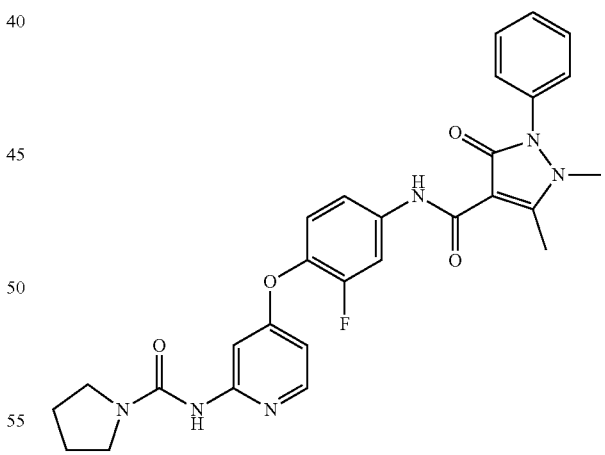

Step 4: N-(3-fluoro-4-(2-(pyrrolidine-1-carboxamido)pyridin-4-yloxy)phenyl)-1,5-dimethyl-3-oxo-2-phenyl-2,3-dihydro-1H-pyrazole-4-carboxamide. The title compound was prepared following the previously described procedure. MS (ESI pos. ion) m/z: 531 (MH+). Calc'd exact mass for $C_{28}H_{27}FN_6O_4$: 530. $^1$HNMR (300 MHz, $CDCl_3$): 1.70 (s, 1H), 1.88 (s, 4H), 2.69-2.75 (m, 3H), 3.29 (s, 3H), 3.37 (t, J=6.58 Hz, 4H), 6.41 (dd, J=5.70, 2.34, 1H), 6.92 (s, 1H), 7.02 (t, J=8.70, 1H), 7.17 (ddd, J=8.84, 2.34, 1.24 Hz, 1H), 7.26-

7.32 (m, 2H), 7.37-7.52 (m, 2H), 7.67 (d, J=2.34, 1H), 7.80 (dd, J=12.57, 2.34, 1H), 7.94 (d, J=5.85, 1H), 10.75 (s, 1H).

EXAMPLE 162

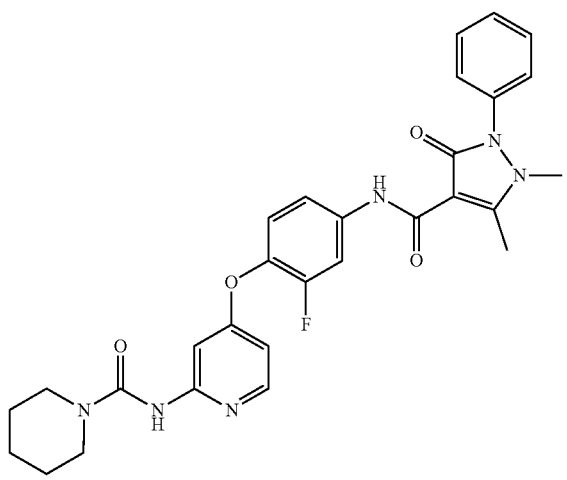

N-(4-(4-(1,5-dimethyl-3-oxo-2-phenyl-2,3-dihydro-1H-pyrazole-4-carboxamido)-2-fluorophenoxy)pyridin-2-yl)piperidine-1-carboxamide: MS (ESI pos. ion) m/z: 545 (MH+). Calc'd exact mass for $C_{29}H_{29}FN_6O_4$: 544. $^1$HNMR (300 MHz, CDCl$_3$): 1.61 (s, 5H), 1.74 (s, 1H), 2.79 (s, 3H), 3.37 (s, 3H), 3.45 (d, J=5.46 Hz, 4H), 6.49 (td, J=6.36, 1.79 Hz, 1H), 7.09 (t, J=8.76 Hz, 1H), 7.34-7.39 (m, 2H), 7.44-7.66 (m, 4H), 7.86 (dd, J=12.43, 2.26 Hz, 1H), 7.95-8.04 (m, 1H), 10.81 (s, 1H).

EXAMPLE 163

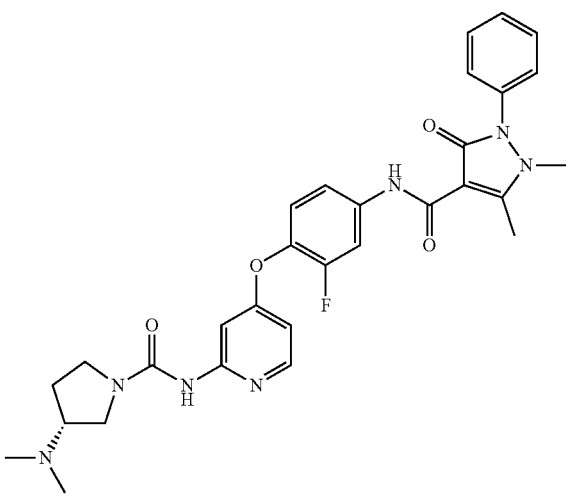

(R)-N-(4-(2 (3-(dimethylamino)pyrrolidine-1-carboxamido)pyridin-4-yloxy)-3-fluorophenyl)-1,5-dimethyl-3-oxo-2-phenyl-2,3-dihydro-1H-pyrazole-4-carboxamide: MS (ESI pos. ion) m/z: 574 (MH+). Calc'd exact mass for $C_{30}H_{32}FN_7O_4$: 573. $^1$HNMR (300 MHz, CDCl$_3$): 1.62 (s, 5H), 2.27 (s, 5H), 2.79 (s, 3H), 3.20 (t, J=9.14 Hz, 1H), 3.37 (s, 2H), 3.41 (dd, J=10.17, 3.20 Hz, 1H), 3.65 (s, 1H), 6.49 (dd, J=5.84, 2.26 Hz, 1H), 6.97 (s, 1H), 7.09 (t, J=8.76 Hz, 1H), 7.21-7.25 (m, 1H), 7.34-7.39 (m, 2H), 7.44-7.59 (m, 1H), 7.72 (d, J=2.07 Hz, 1H), 7.87 (dd, J=12.62, 2.26, Hz, 1H), 8.02 (d, J=5.84 Hz, 1H), 10.81 (s, 1H).

EXAMPLE 164

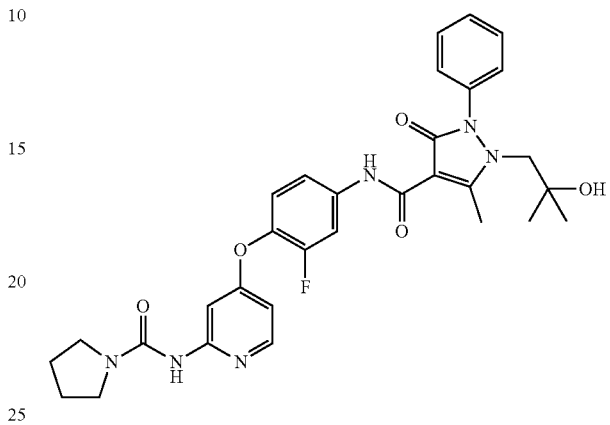

N-(3-fluoro-4-(2-(pyrrolidine-1-carboxamido)pyridin-4-yloxy)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 589 (MH+). Calc'd exact mass for $C_{31}H_{33}FN_6O_5$: 588. $^1$HNMR (300 MHz, CDCl$_3$): 1.12 (s, 6H), 1.95 (s, 4H), 2.20 (s, 1H), 2.86 (s, 3H), 3.38-3.53 (m, 4H), 3.86 (s, 2H), 5.30 (s, 2H), 6.48 (dd, J=5.55, 2.05 Hz, 1H), 7.01-7.13 (m, 2H), 7.19-7.32 (m, 1H), 7.39-7.57 (m, 3H), 7.73 (d, J=2.05 Hz, 1H), 7.87 (dd, J=12.50, 2.12 Hz, 1H), 8.00 (d, J=5.70 Hz, 1H), 10.82 (s, 1H).

EXAMPLE 165

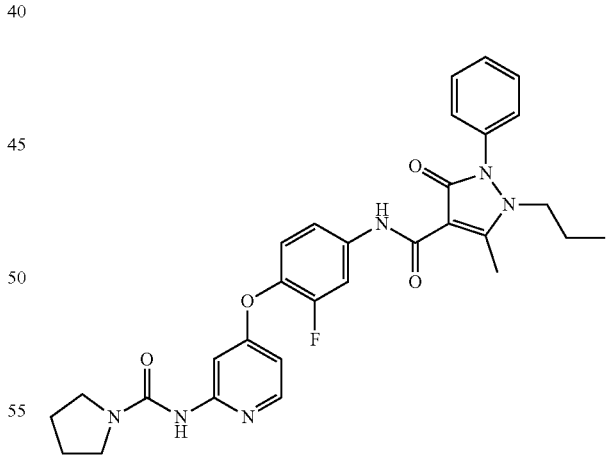

N-(3-fluoro-4-(2-(pyrrolidine-1-carboxamido)pyridin-4-yloxy)phenyl)-5-methyl-3-oxo-2-phenyl-1-propyl-2,3-dihydro-1H-pyrazole-4-carboxamide: MS (ESI pos. ion) m/z: 559 (MH+). Calc'd exact mass for $C_{30}H_{31}FN_6O_4$: 558. $^1$HNMR (300 MHz, CDCl$_3$): 0.80 (t, J=7.45 Hz, 3H), 1.58 (s, 2H), 1.95 (s, 4H), 2.80 (s, 3H), 3.41-3.48 (m, 4H), 3.72-3.78 (m, 2H), 6.96 (s, 1H), 7.09 (s, 1H), 7.33-7.38 (m, 2H), 7.46 (s, 1H), 7.52-7.59 (m, 1H), 7.74 (d, J=2.19 Hz, 1H), 8.02 (d, J=5.85 Hz, 1H), 10.82 (s, 1H).

EXAMPLE 166

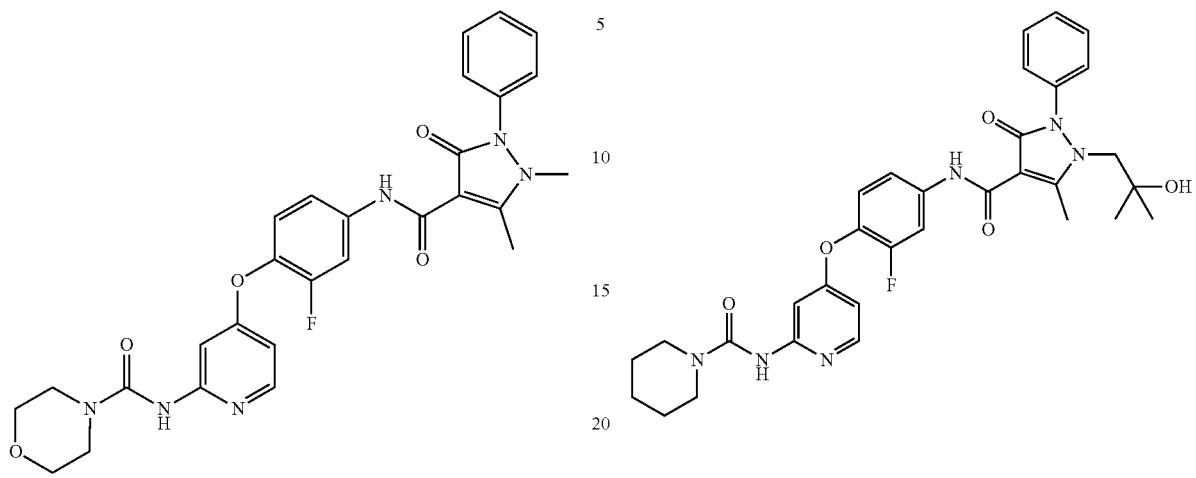

N-(4-(4-(1,5-dimethyl-3-oxo-2-phenyl-2,3-dihydro-1H-pyrazole-4-carboxamido)-2-fluorophenoxy)pyridin-2-yl) morpholine-4-carboxamide: MS (ESI pos. ion) m/z: 547 (MH+). Calc'd exact mass for $C_{28}H_{27}FN_6O_5$: 546. $^1$HNMR (300 MHz, CDCl$_3$): 2.79 (s, 3H), 3.37 (s, 3H), 3.43-3.52 (m, 4H), 3.66-3.76 (m, 4H), 6.51 (dd, J=5.85, 2.19 Hz, 1H), 7.09 (t, J=8.70 Hz, 1H), 7.20-7.25 (m, 1H), 7.33-7.40 (m, 2H), 7.44-7.64 (m, 4H), 7.88 (dd, J=12.57, 2.48 Hz, 1H), 8.02 (d, j=5.70 Hz, 1H), 10.83 (s, 1H).

EXAMPLE 167

N-(4-(2-fluoro-4-(1-(2-hydroxy-2-methylpropyl)-5-methyl-3-oxo-2-phenyl-2,3-dihydro-1H-pyrazole-4-carboxamido)phenoxy)pyridin-2-yl)piperidine-1-carboxamide: MS (ESI pos. ion) m/z: 603 (MH+). Calc'd exact mass for $C_{32}H_{35}FN_6O_5$: 602. $^1$HNMR (300 MHz, CDCl$_3$): 1.12 (s, 6H), 1.61 (s, 6H), 2.28 (s, 1H), 2.86 (s, 3H), 3.44 (d, J=4.97 Hz, 4H), 3.86 (s, 2H), 5.30 (s, 1H), 6.46 (dd, J=5.77, 2.12 Hz, 1H), 7.08 (t, J=8.70 Hz, 1H), 7.21 (d, J=1.02 Hz, 1H), 7.27 (t, J=8.18 Hz, 1H), 7.40-7.57 (m, 3H), 7.65 (d, J=1.90 Hz, 1H), 7.87 (dd, J=12.64, 2.27 Hz, 1H), 8.00 (d, J=5.85 Hz, 1H), 10.82 (s, 1H).

EXAMPLE 168

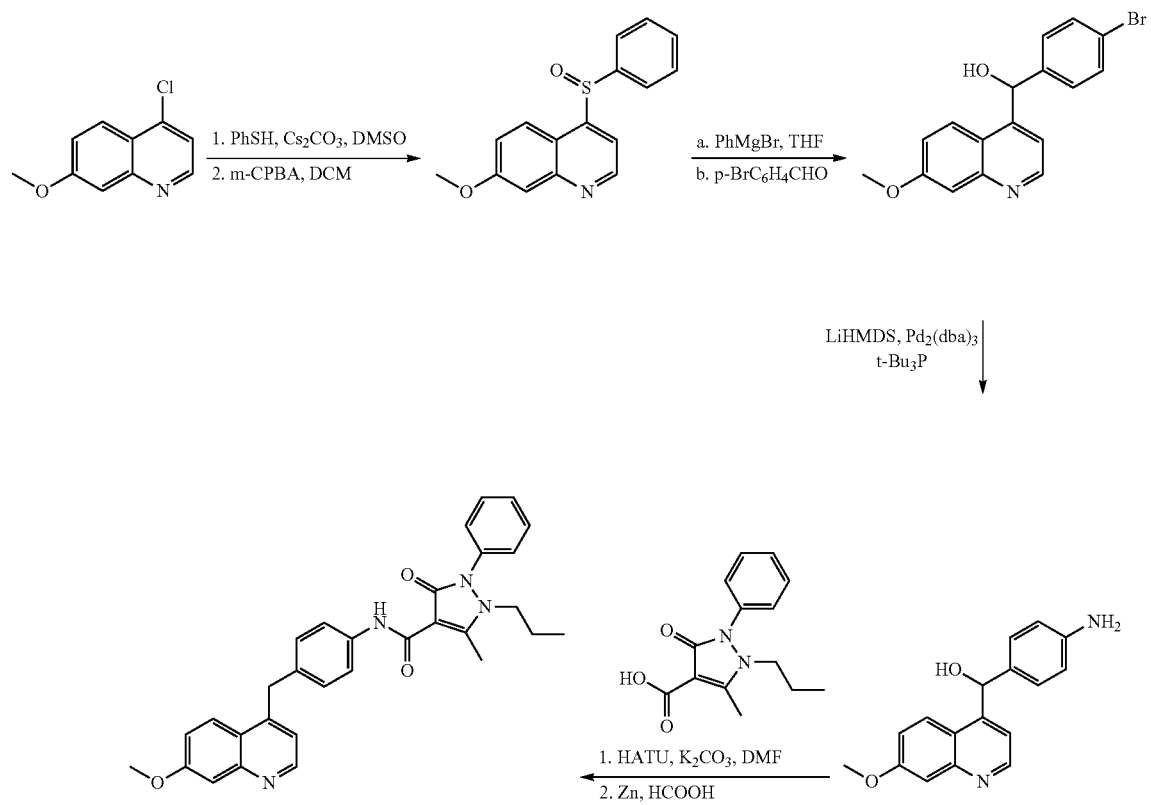

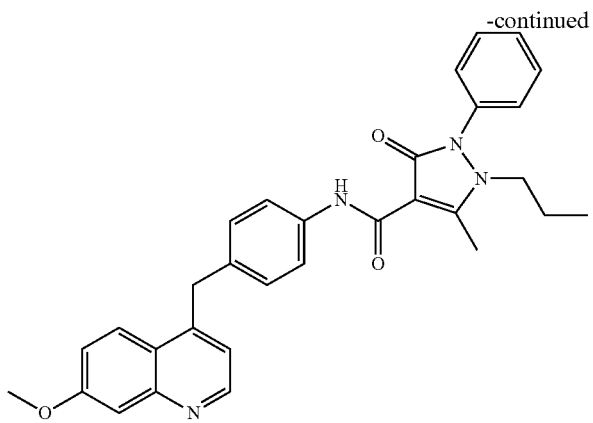

5-methyl-N-(4-((7-(methyloxy)-4-quinolinyl)methyl)phenyl)-3-oxo-2-phenyl-1-propyl-2,3-dihydro-1H-pyrazole-4-carboxamide

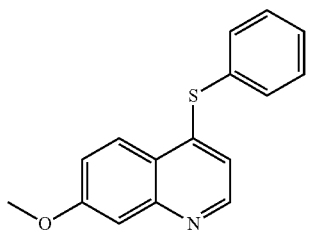

Step 1: 7-methoxy-4-(phenylthio)quinoline. In a 25 mL sealed tube under $N_2$, were dissolved 4-chloro-7-methoxyquinoline (1.00 g, 5.16 mmol), thiophenol (0.528 ml, 5.16 mmol) and cesium carbonate (2.52 g, 7.75 mmol) in 5 mL of DMSO then heated at 100° C. After 2 h, the crude reaction mixture was directly purified by MPLC (ISCO, dichloromethane:MeOH 100:0 to 90:10) to afford 7-methoxy-4-(phenylthio)quinoline (1.32 g, 95.6% yield) as an off-white solid. MS (ESI pos. ion) m/z: 268 (MH+). Calc'd exact mass for $C_{16}H_{13}NOS$: 267. $^1$H NMR (400 MHz, CDCl$_3$): 8.49 (d, J=4.93 Hz, 1 H), 8.13 (d, J=9.22 Hz, 1 H), 7.56-7.62 (m, 2 H), 7.45-7.53 (m, 4 H), 7.23-7.29 (m, 1 H), 6.68 (d, J=4.93 Hz, 1 H), 3.98 (s, 3 H).

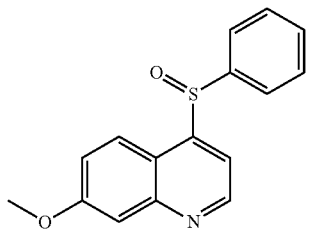

Step 2. 7-methoxy-4-(phenylsulfinyl)quinoline. In a 50 mL round bottom flask under $N_2$, was dissolved 7-methoxy-4-(phenylthio)quinoline (1.38 g, 5.16 mmol) in 50 mL of dichloromethane then cooled to −78° C. Solid m-CPBA (77%) (1.25 g, 7.23 mmol) was added potionwise to the reaction, and the mixture was warmed slowly over 3 h to rt. After 3 h, the reaction mixture was diluted with dichloromethane and then neutralized with aqueous NaHCO$_3$ (sat.). The aqueous phase was extracted three times with dichloromethane, and then the organic layer was dried over Na$_2$SO$_4$, filtered and concentrated under reduced pressure. The crude mixture was purified by MPLC (ISCO. DCM:MeOH 100:0 to 90:10) to afford 7-methoxy-4-(phenylsulfinyl)quinoline (1.37 g, 93.7% yield) as an off-white foam. MS (ESI pos. ion) m/z: 284 (MH+). Calc'd exact mass for $C_{16}H_{13}NO_2S$: 283.

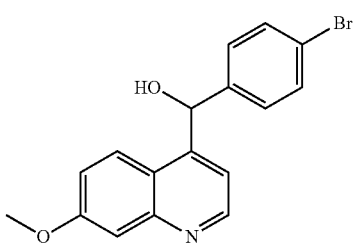

Step 3. (4-bromophenyl)(7-methoxyquinolin-4-yl)methanol. In a 100 mL round bottom flask under $N_2$, was dissolved 7-methoxy-4-(phenylsulfinyl)quinoline (650 mg, 2.29 mmol) in 10 mL of THF and then the solution was cooled to −78° C. and treated with PhMgBr (3M in Et$_2$O) (1.50 mL, 4.59 mmol). The reaction mixture was then warmed to rt. After 30 min, the mixture was cooled again to −78° C., and solid 4-bromobenzaldehyde (1.27 g, 6.88 mmol) was added. Then, the reaction mixture was warmed to rt. After 2 h the reaction mixture was neutralized with aqueous NH$_4$Cl (sat.). The aqueous phase was extracted three times with dichloromethane, and then the organic layer was dried over Na$_2$SO$_4$, filtered and concentrated under reduced pressure. The crude mixture was purified by MPLC (ISCO dichloromethane: MeOH 100:0 to 90:10) to afford (4-bromophenyl)(7-methoxyquinolin-4-yl)methanol (540 mg, 68.4% yield) as a yellow solid. MS (ESI pos. ion) m/z: 345 (M2H+). Calc'd exact mass for $C_{17}H_{14}BrNO_2$: 343. $^1$H NMR (400 MHz, CDCl$_3$) 8.83 (d, J=4.42 Hz, 1 H), 7.81 (d, J=9.35 Hz, 1 H), 7.53 (d, J=4.42 Hz, 1 H), 7.44-7.49 (m, 3 H), 7.25 (d, J=8.34 Hz, 2 H), 7.14 (dd, J=9.28, 2.59 Hz, 1 H), 6.43 (s, 1 H), 3.93 (s, 3 H).

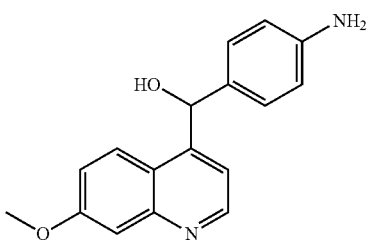

Step 4: (4-aminophenyl)(7-methoxyquinolin-4-yl)methanol. In a 25 mL sealed tube under $N_2$, were dissolved $Pd_2(dba)_3$ (84 mg, 92 µmol), t-$Bu_3P$ (1M in PhMe) (92 µl, 92 µmol), (4-bromophenyl)(7-methoxyquinolin-4-yl)methanol (316 mg, 918 µmol) and LiHMDS (1M in THF) (2.75 mL, 2.75 mmol) in 3.5 mL of toluene and the solution was then heated at 80° C. After 3 h, the crude reaction mixture was neutralized by adding 5 drops of MeOH and then directly purified by MPLC (ISCO, dichloromethane:MeOH 100:0 to 90:10) to afford (4-aminophenyl)(7-methoxyquinolin-4-yl)methanol (140 mg, 54% yield). MS (ESI pos. ion) m/z: 281 (MH+). Calc'd exact mass for $C_{17}H_{16}N_2O_2$: 280.

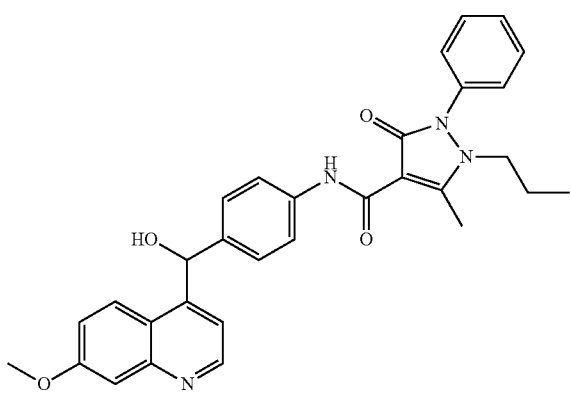

Step 5: N-(4-((S)-hydroxy(7-(methyloxy)-4-quinolinyl)methyl)phenyl)-5-methyl-3-oxo-2-phenyl-1-propyl-2,3-dihydro-1H-pyrazole-4-carboxamide. In a 10 mL sealed tube under $N_2$, were dissolved HATU (250 mg, 658 µmol), (4-aminophenyl)(7-methoxyquinolin-4-yl)methanol (123 mg, 439 µmol), 5-methyl-3-oxo-2-phenyl-1-propyl-2,3-dihydro-1H-pyrazole-4-carboxylic acid (143 mg, 548 mmol) and $K_2CO_3$ (182 mg, 1316 mmol) in 2 mL of DMF at rt. After 10 h, the reaction mixture was heated at 60° C. for 3 h and then diluted with dichloromethane, and treated with aqueous NaOH (1N). The aqueous phase was extracted with dichloromethane, and then the organic layer was dried over $Na_2SO_4$, filtered and concentrated under reduced pressure. The crude mixture was purified by MPLC (ISCO, dichloromethane:MeOH 100:0 to 90:10) to afford N-(4-(hydroxy(7-methoxyquinolin-4-yl)methyl)phenyl)-5-methyl-3-oxo-2-phenyl-1-propyl-2,3-dihydro-1H-pyrazole-4-carboxamide (208 mg, 90.7% yield) as an off-white solid. MS (ESI pos. ion) m/z: 523 (MH+). Calc'd exact mass for $C_{31}H_{30}N_4O_4$: 522. $^1$H NMR (400 MHz, DMSO-$d_6$) 10.67 (s, 1 H), 8.83 (d, J=4.55 Hz, 1 H), 8.05 (d, J=9.35 Hz, 1 H), 7.53-7.61 (m, 3 H), 7.46-7.52 (m, 3 H), 7.36-7.44 (m, 3 H), 7.31 (d, J=8.59 Hz, 2 H), 7.16 (dd, J=9.16, 2.72 Hz, 1 H), 6.32 (d, J=4.42 Hz, 1 H), 6.15 (d, J=4.29 Hz, 1 H), 3.88 (s, 3 H), 3.79 (t, J=7.20 Hz, 2 H), 2.71 (s, 3 H), 1.33-1.41 (m, 2 H), 0.66 (t, J=7.39 Hz, 3 H).

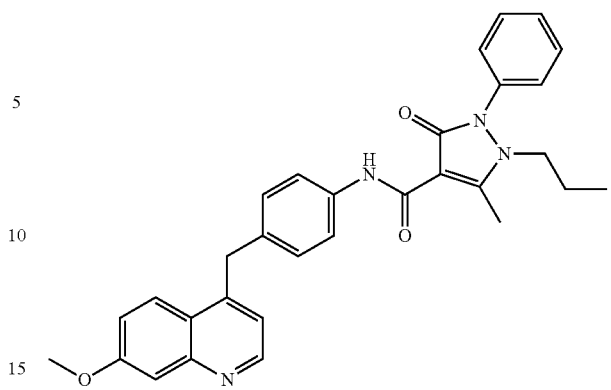

Step 6: 5-methyl-N-(4-((7-(methyloxy)-4-quinolinyl)methyl)phenyl)-3-oxo-2-phenyl-1-propyl-2,3-dihydro-1H-pyrazole-4-carboxamide. In a 25 mL round bottom flask was dissolved N-(4-(hydroxy(7-methoxyquinolin-4-yl)methyl)phenyl)-5-methyl-3-oxo-2-phenyl-1-propyl-2,3-dihydro-1H-pyrazole-4-carboxamide (104 mg, 199 µmol) in 4 mL of formic acid and the resultant was then treated with zinc dust (325 mg, 4975 µmol) and heated at 60° C. After 6 h the reaction mixture was diluted with ethyl acetate, filtered over Celite and neutralized with aqueous $NaHCO_3$ (sat.). The aqueous phase was extracted with ethyl acetate, and then the organic layer was dried over $Na_2SO_4$, filtered and concentrated under reduced pressure. The crude mixture was purified by MPLC (ISCO, dichloromethane: 1% $NH_4OH$ in MeOH, 100:0 to 90:10) to afford N-(4-((7-methoxyquinolin-4-yl)methyl)phenyl)-5-methyl-3-oxo-2-phenyl-1-propyl-2,3-dihydro-1H-pyrazole-4-carboxamide (25 mg, 25% yield) as an off-white solid. MS (ESI pos. ion) m/z: 507 (MH+). Calc'd exact mass for $C_{31}H_{30}N_4O_3$: 506. $^1$H NMR (400 MHz, DMSO-$d_6$) 10.65 (s, 1 H), 8.74 (d, J=4.42 Hz, 1 H), 8.10 (d, J=9.22 Hz, 1 H), 7.57 (t, J=7.52 Hz, 2 H), 7.46-7.52 (m, 3 H), 7.35-7.44 (m, 3 H), 7.14-7.28 (m, 4 H), 4.38 (s, 2 H), 3.90 (s, 3 H), 3.79 (t, J=7.14 Hz, 2 H), 2.72 (s, 3 H), 1.32-1.41 (m, 2 H), 0.66 (t, J=7.39 Hz, 3 H).

EXAMPLE 169

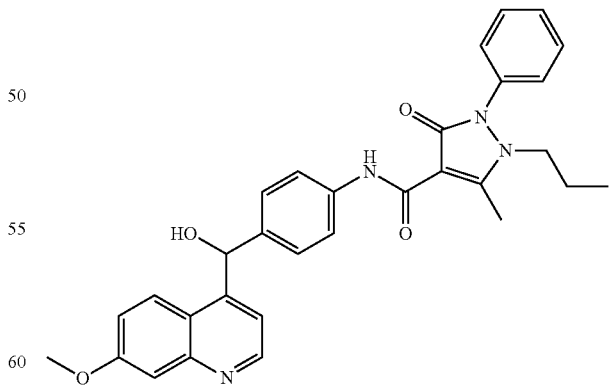

N-(4-(hydroxy(7-methoxyquinolin-4-yl)methyl)phenyl)-5-methyl-3-oxo-2-phenyl-1-propyl-2,3-dihydro-1H-pyrazole-4-carboxamide: MS (ESI pos. ion) m/z: 523 (MH+). Calc'd exact mass for $C_{31}H_{30}N_4O_4$: 522. $^1$H NMR (400 MHz, DMSO-$d_6$) 10.67 (s, 1 H), 8.83 (d, J=4.55 Hz, 1 H), 8.05 (d, J=9.35 Hz, 1 H), 7.53-7.61 (m, 3 H), 7.46-7.52 (m, 3 H), 7.36-7.44 (m, 3 H), 7.31 (d, J=8.59 Hz, 2 H), 7.16 (dd, J=9.16, 2.72 Hz, 1 H), 6.32 (d, J=4.42 Hz, 1H), 6.15 (d, J=4.29 Hz, 1 H), 3.88 (s, 3 H), 3.79 (t, J=7.20 Hz, 2 H), 2.71 (s, 3 H), 1.33-1.41 (m, 2 H), 0.66 (t, J=7.39 Hz, 3 H).

EXAMPLE 170

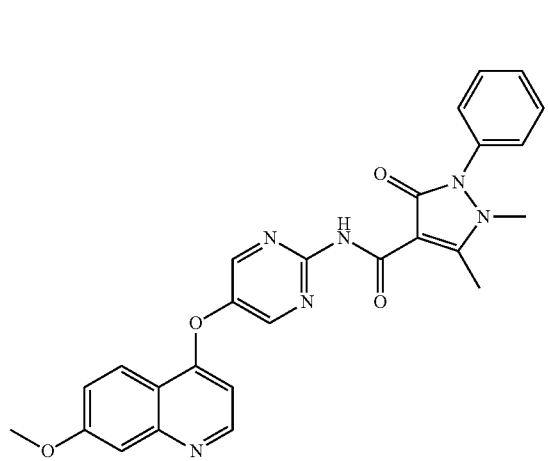

1,5-dimethyl-N-(5-((7-(methyloxy)-4-quinolinyl)oxy)-2-pyrimidinyl)-3-oxo-2-phenyl-2,3-dihydro-1H-pyrazole-4-carboxamide: MS (ESI pos. ion) m/z: 483 (MH+). Calc'd exact mass for $C_{26}H_{22}N_6O_4$: 482.

EXAMPLE 171

5-methyl-N-(4-((7-(methyloxy)-4-quinolinyl)sulfinyl)phenyl)-3-oxo-2-phenyl-1-propyl-2,3-dihydro-1H-pyrazole-4-carboxamide: MS (ESI pos. ion) m/z: 541 (MH+). Calc'd exact mass for $C_{30}H_{28}N_4O_4S$: 540. $^1$H NMR (400 MHz, DMSO-$d_6$+CDCl$_3$) 10.90 (s, 1 H), 9.06 (d, J=4.55 Hz, 1 H), 8.02 (d, J=9.09 Hz, 1 H), 7.97 (d, J=4.42 Hz, 1 H), 7.65-7.74 (m, 4 H), 7.55 (t, J=7.58 Hz, 2 H), 7.44-7.51 (m, 2 H), 7.37 (d, J=7.45 Hz, 2 H), 7.28 (dd, J=9.16, 2.46 Hz, 1 H), 3.90 (s, 3 H), 3.79 (t, J=7.26 Hz, 2 H), 2.70 (s, 3H), 1.32-1.44 (m, 2 H), 0.67 (t, J=7.39 Hz, 3 H).

EXAMPLE 172

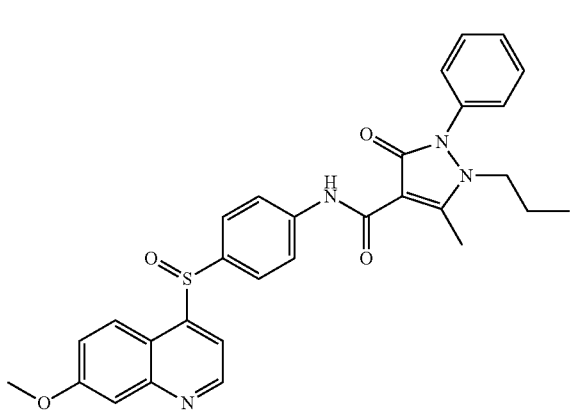

1-(2-hydroxy-2-methylpropyl)-5-methyl-N-(4-((7-(methyloxy)-4-quinolinyl)thio)phenyl)-3-oxo-2-phenyl-2,3-dihydro-1H-pyrazole-4-carboxamide: MS (ESI pos. ion) m/z: 555 (MH+). Calc'd exact mass for $C_{31}H_{30}N_4O_4S$: 554.

EXAMPLE 173

5-methyl-N-(4-((7-(methyloxy)-4-quinolinyl)thio)phenyl)-3-oxo-2-phenyl-1-propyl-2,3-dihydro-1H-pyrazole-4-carboxamide: MS (ESI pos. ion) m/z: 525 (MH+). Calc'd exact mass for $C_{30}H_{28}N_4O_3S$: 524. $^1$H NMR (400 MHz, DMSO-$d_6$): 10.96 (s, 1 H), 8.53 (d, J=4.80 Hz, 1 H), 8.07 (d, J=9.22 Hz, 1 H), 7.79 (d, J=8.46 Hz, 2 H), 7.55-7.63 (m, 4 H), 7.52 (t, J=7.20 Hz, 1 H), 7.37-7.47 (m, 3 H), 7.32 (dd, J=9.09, 2.27 Hz, 1 H), 6.61 (d, J=4.80 Hz, 1 H), 3.93 (s, 3 H), 3.83 (t, J=7.07 Hz, 2 H), 2.75 (s, 3 H), 1.31-1.47 (m, 2 H), 0.69 (t, J=7.39 Hz, 3 H).

EXAMPLE 174

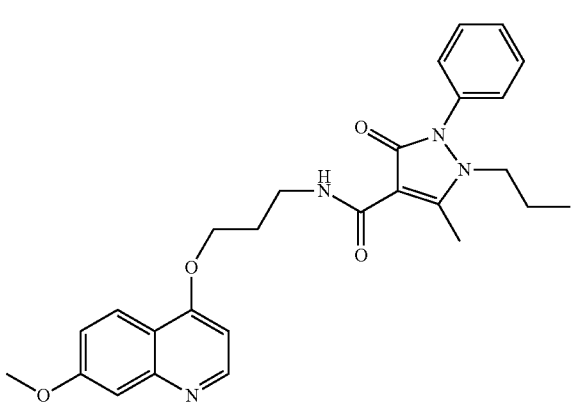

5-methyl-N-(3-((7-(methyloxy)-4-quinolinyl)oxy)propyl)-3-oxo-2-phenyl-1-propyl-2,3-dihydro-1H-pyrazole-4-carboxamide: MS (ESI pos. ion) m/z: 475 (MH+). Calc'd exact mass for $C_{27}H_{30}N_4O_4$: 474.

EXAMPLE 175

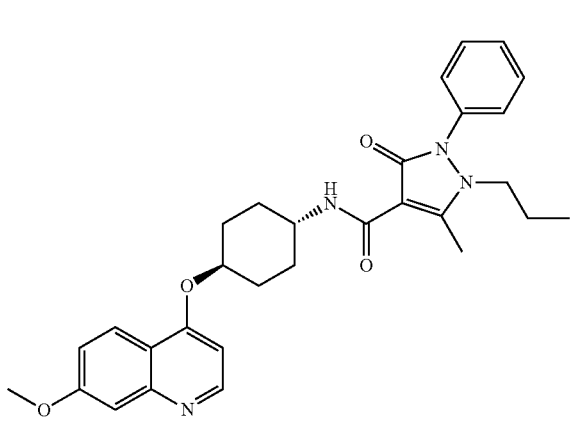

5-methyl-N-(trans-4-((7-(methyloxy)-4-quinolinyl)oxy)cyclohexyl)-3-oxo-2-phenyl-1-propyl-2,3-dihydro-1H-pyrazole-4-carboxamide: MS (ESI pos. ion) m/z: 515 (MH+). Calc'd exact mass for $C_{30}H_{34}N_4O_4$: 514. $^1$H NMR (400 MHz, DMSO-$d_6$) 8.61 (d, J=5.31 Hz, 1H), 8.56 (d, J=7.83 Hz, 1 H), 8.03 (d, J=9.09 Hz, 1 H), 7.56 (t, J=7.64 Hz, 2 H), 7.47 (t, J=7.20 Hz, 1 H), 7.38 (d, J=7.58 Hz, 2 H), 7.30 (d, J=2.40 Hz, 1 H), 7.11-7.21 (m, 1 H), 6.96 (d, J=5.31 Hz, 1 H), 4.66-4.78 (m, 1 H), 3.89 (s, 3 H), 3.81-3.95 (m, 1 H), 3.74 (t, J=7.20 Hz, 2 H), 2.68 (s, 3 H), 2.11 (d, J=10.11 Hz, 2 H), 1.99 (d, J=12.25 Hz, 2H), 1.60-1.75 (m, 2 H), 1.40-1.52 (m, 2 H), 1.29-1.39 (m, 2 H), 0.66 (t, J=7.45 Hz, 3 H).

EXAMPLE 176

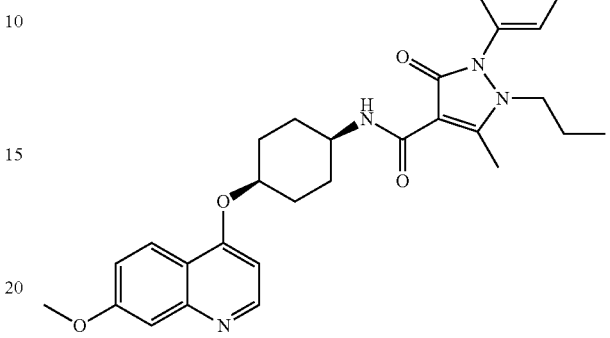

5-methyl-N-(cis-4-((7-(methyloxy)-4-quinolinyl)oxy)cyclohexyl)-3-oxo-2-phenyl-1-propyl-2,3-dihydro-1H-pyrazole-4-carboxamide: MS (ESI pos. ion) m/z: 515 (MH+). Calc'd exact mass for $C_{30}H_{34}N_4O_4$: 514.

EXAMPLE 177

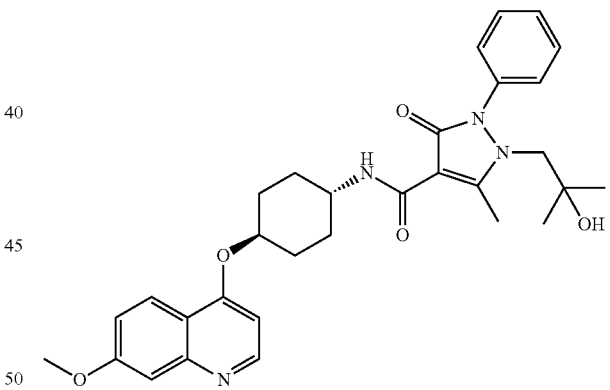

1-(2-hydroxy-2-methylpropyl)-5-methyl-N-(trans-4-((7-(methyloxy)-4-quinolinyl)oxy)cyclohexyl)-3-oxo-2-phenyl-2,3-dihydro-1H-pyrazole-4-carboxamide: MS (ESI pos. ion) m/z: 545 (MH+). Calc'd exact mass for $C_{31}H_{36}N_4O_5$: 544. $^1$H NMR (400 MHz, DMSO-$d_6$): 8.61 (d, J=5.18 Hz, 1 H), 8.58 (d, J=7.83 Hz, 1 H), 8.03 (d, J=8.97 Hz, 1 H), 7.53 (t, J=7.71 Hz, 2 H), 7.41 (t, J=7.26 Hz, 1 H), 7.26-7.31 (m, 3 H), 7.17 (dd, J=9.16, 2.46 Hz, 1 H), 6.96 (d, J=5.56 Hz, 1 H), 4.77 (s, 1 H), 4.68-4.78 (m, 1 H), 3.89 (s, 3 H), 3.85-3.92 (m, 1 H), 3.78 (s, 2 H), 2.73 (s, 3 H), 2.12 (d, J=13.64 Hz, 2 H), 1.99 (d, J=13.52 Hz, 2H), 1.61-1.75 (m, 2 H), 1.37-1.52 (m, 2 H), 0.93 (s, 6 H).

EXAMPLE 178

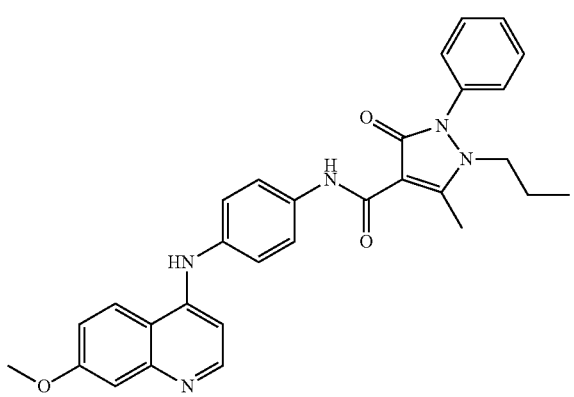

5-methyl-N-(4-((7-(methyloxy)-4-quinolinyl)amino)phenyl)-3-oxo-2-phenyl-1-propyl-2,3-dihydro-1H-pyrazole-4-carboxamide: MS (ESI pos. ion) m/z: 508 (MH+). Calc'd exact mass for $C_{30}H_{29}N_5O_3$: 507.

EXAMPLE 179

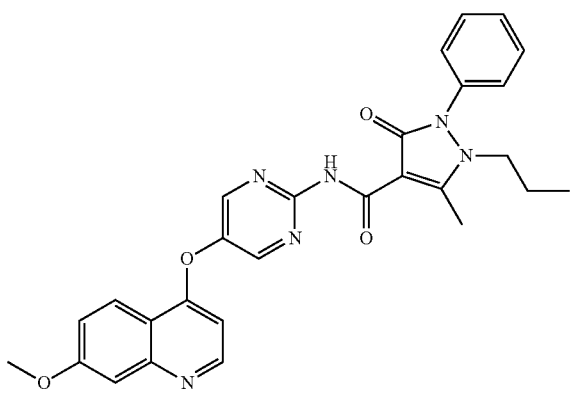

5-methyl-N-(5-((7-(methyloxy)-4-quinolinyl)oxy)-2-pyrimidinyl)-3-oxo-2-phenyl-1-propyl-2,3-dihydro-1H-pyrazole-4-carboxamide: MS (ESI pos. ion) m/z: 511 (MH+). Calc'd exact mass for $C_{28}H_{26}N_6O_4$: 510. $^1$H NMR (400 MHz, DMSO-$d_6$+CDCl$_3$) 11.45 (s, 1 H), 8.74 (s, 2H), 8.63 (d, J=4.93 Hz, 1 H), 8.23 (d, J=9.22 Hz, 1 H), 7.60 (t, J=7.20 Hz, 2 H), 7.48-7.55 (m, 1 H), 7.40-7.47 (m, 3 H), 7.31 (d, J=8.46 Hz, 1 H), 6.65 (d, J=5.05 Hz, 1 H), 3.94 (s, 3 H), 3.83 (t, J=6.51 Hz, 2 H), 2.75 (s, 3 H), 1.34-1.48 (m, 2 H), 0.70 (t, J=7.14 Hz, 3 H).

EXAMPLE 180

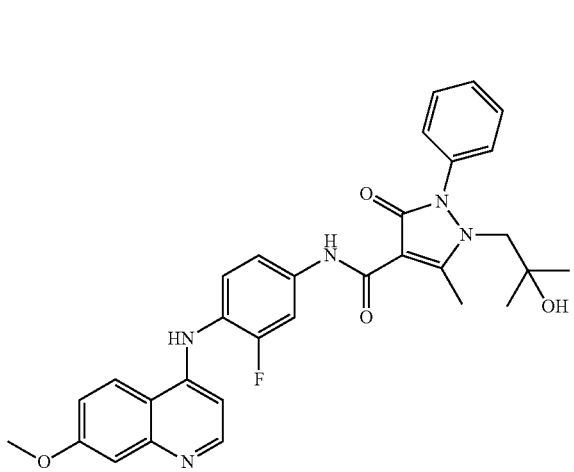

N-(3-fluoro-4-((7-(methyloxy)-4-quinolinyl)amino)phenyl)-1-(2-hydroxy-2-methylpropyl)-5-methyl-3-oxo-2-phenyl-2,3-dihydro-1H-pyrazole-4-carboxamide: MS (ESI pos. ion) m/z: 556 (MH+). Calc'd exact mass for $C_{31}H_{30}FN_5O_4$: 555.

EXAMPLE 181

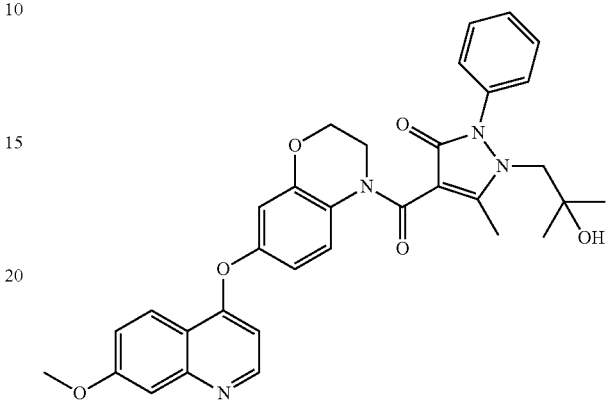

1-(2-hydroxy-2-methylpropyl)-5-methyl-4-((7-((7-(methyloxy)-4-quinolinyl)oxy)-2,3-dihydro-4H-1,4-benzoxazin-4-yl)carbonyl)-2-phenyl-1,2-dihydro-3H-pyrazol-3-one MS (ESI pos. ion) m/z: 581 (MH+). Calc'd exact mass for $C_{33}H_{32}N_4O_6$: 580. $^1$H NMR (400 MHz, DMSO-$d_6$) 8.58 (d, J=5.18 Hz, 1 H), 8.17 (d, J=9.09 Hz, 1 H), 7.76 (d, J=10.86 Hz, 1 H), 7.51 (t, J=7.77 Hz, 2 H), 7.40 (d, J=2.53 Hz, 1 H), 7.37 (t, J=7.45 Hz, 1 H), 7.28 (dd, J=9.22, 2.53 Hz, 1 H), 7.23 (d, J=7.33 Hz, 2 H), 6.82 (d, J=2.78 Hz, 1 H), 6.70 (dd, J=9.03, 2.59 Hz, 1 H), 6.47 (d, J=5.31 Hz, 1 H), 4.80 (s, 1 H), 4.31 (t, J=4.36 Hz, 2 H), 3.93 (s, 3 H), 3.89-3.96 (m, 2 H), 3.75 (s, 2 H), 2.54 (s, 3 H), 0.95 (s, 6 H).

EXAMPLE 182

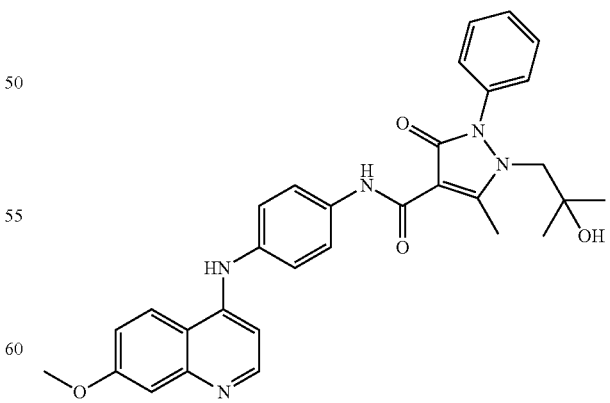

1-(2-hydroxy-2-methylpropyl)-5-methyl-N-(4-((7-(methyloxy)-4-quinolinyl)amino) phenyl)-3-oxo-2-phenyl-2,3-dihydro-1H-pyrazole-4-carboxamide: MS (ESI pos. ion) m/z: 538 (MH+). Calc'd exact mass for $C_{31}H_{31}N_5O_4$: 537.

EXAMPLE 183

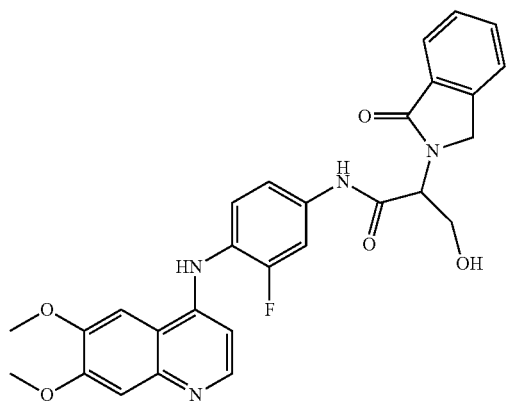

N-(4-(6,7-dimethoxyquinolin-4-yloxy)-3-fluorophenyl)-3-hydroxy-2-(1-oxoisoindolin-2-yl)propanamide: MS (ESI pos. ion) m/z: 518 (MH+). Calc'd exact mass for $C_{28}H_{24}FN_3O_6$: 517. $^1$H NMR (400 MHz, CHLOROFORM-d) 9.74 (1 H, s), 8.44 (1 H, d, J=5.3 Hz), 7.75-7.84 (2 H, m), 7.53-7.61 (2 H, m), 7.42-7.51 (2 H, m), 7.40 (1 H, s), 7.18 (1 H, t, J=8.6 Hz), 6.35 (1 H, d, J=5.3 Hz), 5.30 (3 H, s), 5.21 (1 H, t, J=5.4 Hz), 4.76 (2 H, s), 4.27-4.36 (1 H, m), 4.19-4.27 (1 H, m), 4.04 (6 H, s).

EXAMPLE 184

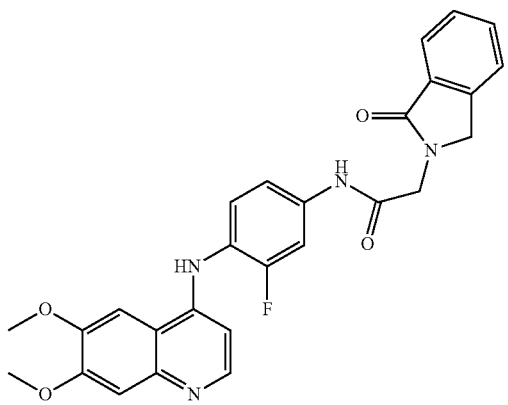

N-(4-(6,7-dimethoxyquinolin-4-yloxy)-3-fluorophenyl)-2-(1-oxoisoindolin-2-yl)acetamide: MS (ESI pos. ion) m/z: 488 (MH+). Calc'd exact mass for $C_{27}H_{22}FN_3O_5$: 487. $^1$H NMR (400 MHz, CHLOROFORM-d) 9.26 (1 H, s), 8.46 (1 H, dd, J=5.3, 0.8 Hz), 7.90 (1 H, d, J=8.0 Hz), 7.76 (1 H, d, J=12.1 Hz), 7.62 (1 H, t, J=7.5 Hz), 7.47-7.58 (3 H, m), 7.41 (1 H, s), 7.24 (1 H, s), 7.17 (1 H, t, J=8.4 Hz), 6.36 (1 H, d, J=5.1 Hz), 4.67 (2 H, s), 4.46 (2 H, s), 4.04 (6 H, s).

EXAMPLE 185

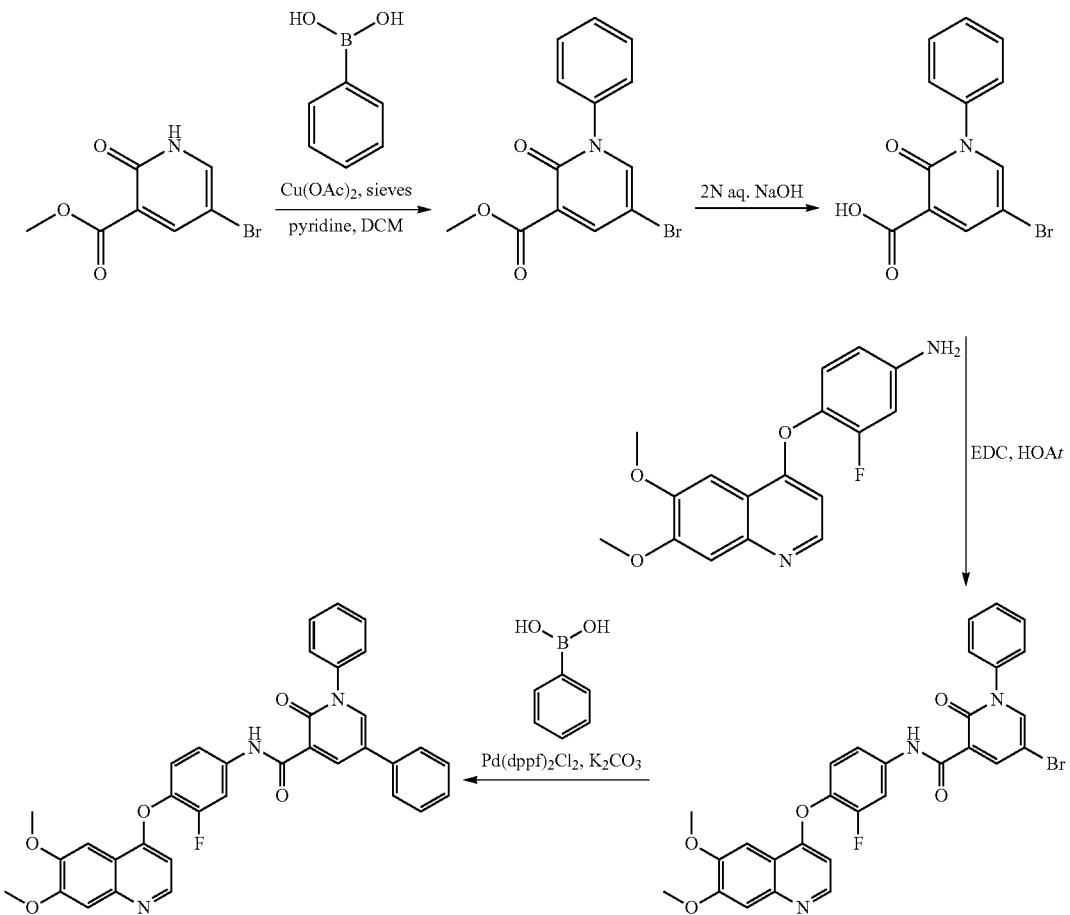

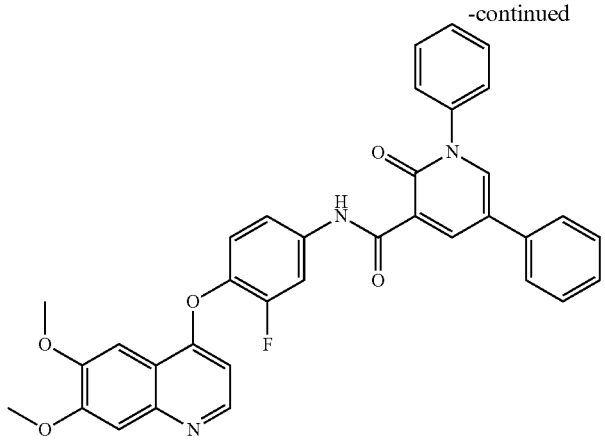

N-(4-(6,7-dimethoxyquinolin-4-yloxy)-3-fluorophenyl)-2-oxo-1,5-diphenyl-1,2-dihydropyridine-3-carboxamide

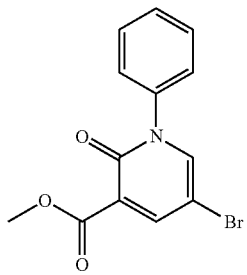

Step 1: methyl 5-bromo-2-oxo-1-phenyl-1,2-dihydropyridine-3-carboxylate: A round bottom flask was charged with methyl 5-bromo-2-oxo-1,2-dihydropyridine-3-carboxylate (0.500 g, 2.2 mmol), phenylboronic acid (0.66 g, 5.4 mmol), and copper(II) acetate (0.78 g, 4.3 mmol). Dichloromethane (25 mL) was added, followed by 4 A molecular sieves (500 mg, activated) and pyridine (0.70 mL, 8.6 mmol). The reaction mixture was stirred overnight at room temperature in the presence of air. The reaction mixture was diluted with dichloromethane and filtered through a small pad of Celite, washing well with dichloromethane. The filtrate was concentrated under vacuum. The remaining residue was purified by silica gel chromatography (1% methanol/dichloromethane) to give methyl 5-bromo-2-oxo-1-phenyl-1,2-dihydropyridine-3-carboxylate as a yellow foam/oil (0.655 g, 1.9 mmol, 89% yield). MS (ESI pos. ion) m/z: 309 (MH$^+$). Calc'd exact mass for $C_{13}H_{10}BrNO_3$: 308.

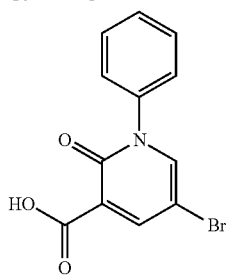

Step 2: 5-bromo-2-oxo-1-phenyl-1,2-dihydropyridine-3-carboxylic acid. Methyl 5-bromo-2-oxo-1-phenyl-1,2-dihydropyridine-3-carboxylate (0.554 g, 1.80 mmol) was dissolved in dioxane (10.5 mL) then diluted with water (3.5 mL). 2N aqueous sodium hydroxide solution (0.944 ml, 1.89 mmol) was slowly added to the mixture. The reaction mixture was stirred at room temperature overnight, then concentrated under vacuum to remove the dioxane followed by dilution with water. This aqueous layer was acidified with 1N aqueous hydrochloric acid (1.89 mL, 1.89 mmol). A precipitate formed was collected on a glass frit, and washed with minimal water. The solid was dissolved in dichloromethane and then dried over sodium sulfate. This mixture was filtered, and the filtrate was concentrated under vacuum. The remaining residue was dried under high vacuum to afford 5-bromo-2-oxo-1-phenyl-1,2-dihydropyridine-3-carboxylic acid as a yellow solid (0.458 g, 1.56 mmol, 86.6% yield). MS (ESI pos. ion) m/z: 295 (MH$^+$). Calc'd exact mass for $C_{12}H_8BrNO_3$: 294.

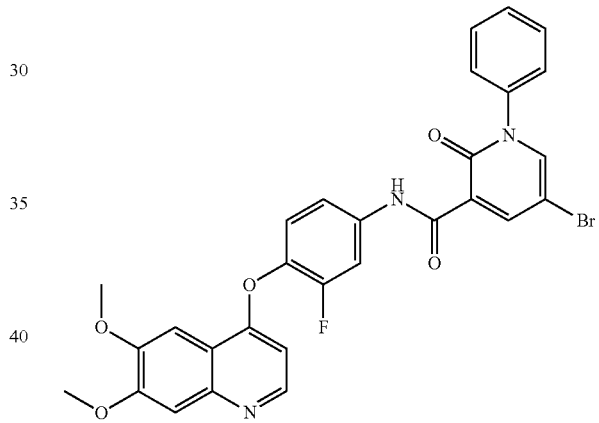

Step 3: 5-bromo-N-(4-(6,7-dimethoxyquinolin-4-yloxy)-3-fluorophenyl)-2-oxo-1-phenyl-1,2-dihydropyridine-3-carboxamide. 5-Bromo-2-oxo-1-phenyl-1,2-dihydropyridine-3-carboxylic acid (0.458 g, 1.6 mmol), 4-(6,7-dimethoxyquinolin-4-yloxy)-3-fluorobenzenamine (0.49 g, 1.6 mmol), EDC (0.45 g, 2.3 mmol), and HOAt (0.21 g, 1.6 mmol) were added to a reaction flask then suspended in N,N-dimethylformamide (7.0 mL). N,N-diisopropylethylamine (0.95 ml, 5.5 mmol) was added to the reaction mixture and stirring was continued at room temperature overnight. The reaction mixture was diluted with ethyl acetate and water and then extracted with ethyl acetate. A precipitate formed between the layers. The aqueous layer was filtered and the precipitate collected. The filtered aqueous layer was extracted with ethyl acetate (1×). The combined ethyl acetate layers were washed with brine and then dried over sodium sulfate. The precipitate was dissolved in dichloromethane and also dried over sodium sulfate. All of the organic layers were combined and concentrated under vacuum. The remaining residue was purified by silica gel chromatography (1% methanol/dichloromethane to 2% methanol/dichloromethane) to give 5-bromo-N-(4-(6,7-dimethoxyquinolin-4-yloxy)-3-fluorophenyl)-2-oxo-1-phenyl-1,2-dihydropyridine-3-carboxamide as a yellow solid (0.846 g, 1.4 mmol, 92% yield). MS (ESI pos. ion) m/z: 590 (MH$^+$). Calc'd exact mass for $C_{29}H_{21}BrFN_3O_5$: 589.

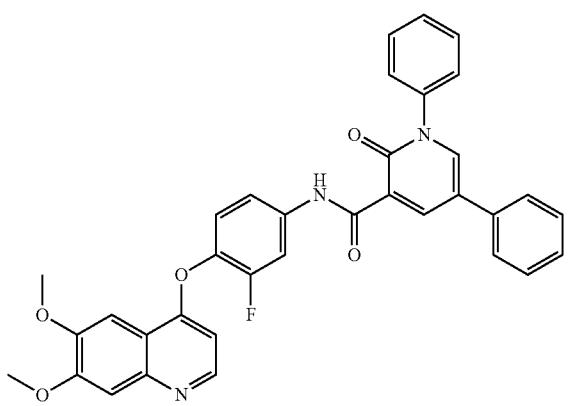

Step 4: N-(4-(6,7-dimethoxyquinolin-4-yloxy)-3-fluorophenyl)-2-oxo-1,5-diphenyl-1,2-dihydropyridine-3-carboxamide. 5-Bromo-N-(4-(6,7-dimethoxyquinolin-4-yloxy)-3-fluorophenyl)-2-oxo-1-phenyl-1,2-dihydropyridine-3-carboxamide (0.075 g, 0.13 mmol) was suspended in DMF (1.5 mL) and then was added a solution of potassium carbonate (0.053 g, 0.38 mmol) in water (0.5 mL), phenylboronic acid (0.015 g, 0.13 mmol) and PdCl$_2$(dppf)$_2$ (0.0093 g, 0.013 mmol). The reaction mixture was heated at 80° C. for 6 hours. The reaction mixture was diluted with ethyl acetate and water then extracted with ethyl acetate. The organic layer was washed with brine then dried over sodium sulfate and concentrated under vacuum. The remaining residue was purified by silica gel chromatography (1% methanol/dichloromethane to 2% methanol/dichloromethane) to give N-(4-(6,7-dimethoxyquinolin-4-yloxy)-3-fluorophenyl)-2-oxo-1,5-diphenyl-1,2-dihydropyridine-3-carboxamide as a light yellow solid (0.069 g, 0.12 mmol, 92% yield). MS (ESI pos. ion) m/z: 588 (MH$^+$). Calc'd exact mass for C$_{35}$H$_{26}$FN$_3$O$_5$: 587. $^1$H NMR (400 MHz, DMSO-d$_6$) 12.19 (s, 1 H), 8.87 (d, J=2.91 Hz, 1 H), 8.40-8.55 (m, 2 H), 8.09 (dd, J=12.82, 2.34 Hz, 1 H), 7.75 (d, J=7.33 Hz, 2 H), 7.16-7.67 (m, 12 H), 6.49 (d, J=5.05 Hz, 1 H), 3.95 (s, 6 H).

EXAMPLE 186

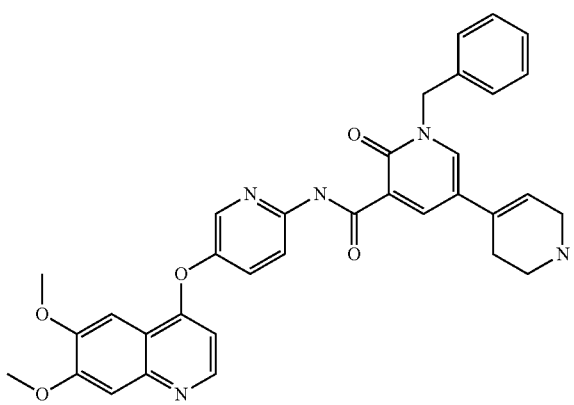

N-(5-((6,7-bis(methyloxy)-4-quinolinyl)oxy)-2-pyridinyl)-6-oxo-1-(phenylmethyl)-1,1',2',3',6,6'-hexahydro-3,4'-bipyridine-5-carboxamide: MS (ESI pos. ion) m/z: 590 (MH$^+$). Calc'd exact mass for C$_{34}$H$_{31}$N$_5$O$_5$: 589. $^1$H NMR (400 MHz, DMSO-d$_6$) 12.63 (s, 1 H), 8.64 (s, 1 H), 8.49 (d, J=5.05 Hz, 1 H), 8.32-8.45 (m, 3 H), 7.86 (d, J=8.34 Hz, 1 H), 7.54 (s, 1 H), 7.26-7.45 (m, 6 H), 6.55 (d, J=5.05 Hz, 1 H), 6.23 (s, 1 H), 5.34 (s, 2 H), 3.94 (d, J=4.29 Hz, 6 H), 3.37 (s, 3 H), 2.91 (t, J=4.42 Hz, 2 H), 2.29 (s, 2 H).

EXAMPLE 187

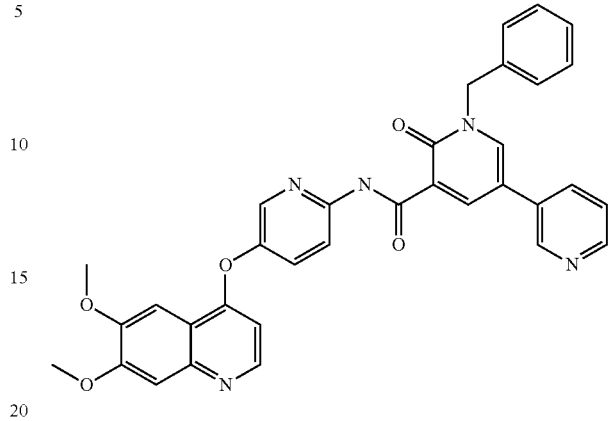

N-(5-((6,7-bis(methyloxy)-4-quinolinyl)oxy)-2-pyridinyl)-6-oxo-1-(phenylmethyl)-1,6-dihydro-3,3'-bipyridine-5-carboxamide: MS (ESI pos. ion) m/z: 586 (MH$^+$). Calc'd exact mass for C$_{34}$H$_{27}$N$_5$O$_5$: 585. $^1$H NMR (400 MHz, DMSO-d$_6$) 12.57 (s, 1 H), 8.96 (d, J=2.53 Hz, 1 H), 8.94 (d, J=1.89 Hz, 1 H), 8.84 (d, J=2.65 Hz, 1 H), 8.58-8.62 (m, 1 H), 8.50 (d, J=5.18 Hz, 1 H), 8.43 (d, J=8.97 Hz, 1 H), 8.40 (d, J=2.78 Hz, 1 H), 8.10-8.16 (m, 1 H), 7.87 (dd, J=9.09, 2.78 Hz, 1 H), 7.46-7.56 (m, 4 H), 7.36-7.44 (m, 3 H), 7.29-7.35 (m, 1 H), 6.56 (d, J=5.31 Hz, 1 H), 5.40 (s, 2 H), 3.95 (d, J=4.04 Hz, 6 H).

EXAMPLE 188

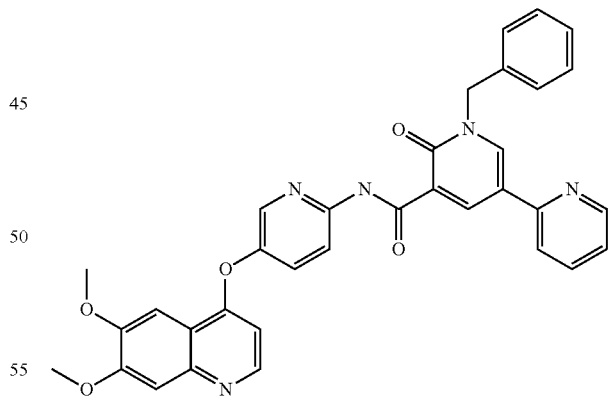

N-(5-((6,7-bis(methyloxy)-4-quinolinyl)oxy)-2-pyridinyl)-6-oxo-1'-(phenylmethyl)-1',6'-dihydro-2,3'-bipyridine-5'-carboxamide: MS (ESI pos. ion) m/z: 586 (MH$^+$). Calc'd exact mass for C$_{34}$H$_{27}$N$_5$O$_5$: 585. $^1$H NMR (400 MHz, DMSO-d$_6$) 12.54 (s, 1 H), 9.27 (d, J=2.78 Hz, 1 H), 9.19 (d, J=2.78 Hz, 1 H), 8.68 (d, J=4.17 Hz, 1 H), 8.50 (d, J=5.18 Hz, 1 H), 8.44 (d, J=8.97 Hz, 1 H), 8.40 (d, J=2.91 Hz, 1 H), 7.97-8.02 (m, 1 H), 7.90-7.96 (m, 1 H), 7.88 (dd, J=8.97, 2.91

Hz, 1 H), 7.54 (s, 1 H), 7.45-7.49 (m, 2 H), 7.36-7.43 (m, 4 H), 7.29-7.35 (m, 1 H), 6.56 (d, J=5.18 Hz, 1 H), 5.45 (s, 2 H), 3.95 (d, J=3.66 Hz, 6 H).

EXAMPLE 189

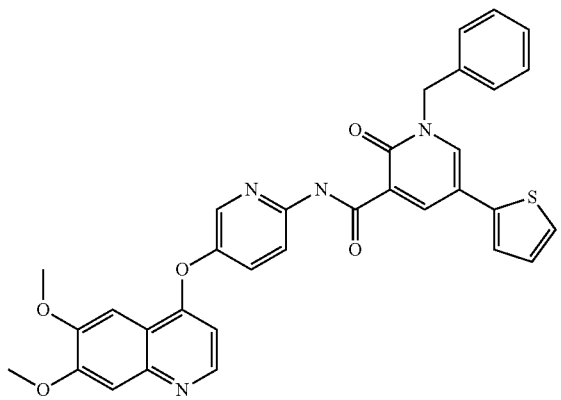

N-(5-((6,7-bis(methyloxy)-4-quinolinyl)oxy)-2-pyridinyl)-2-oxo-1-(phenylmethyl)-5-(2-thienyl)-1,2-dihydro-3-pyridinecarboxamide: MS (ESI pos. ion) m/z: 591 (MH$^+$). Calc'd exact mass for $C_{33}H_{26}N_4O_5S$: 590. $^1$H NMR (400 MHz, DMSO-d$_6$) 12.54 (s, 1 H), 8.82 (s, 1H), 8.71 (s, 1 H), 8.50 (d, J=4.80 Hz, 1 H), 8.36-8.45 (m, 2 H), 7.87 (d, J=9.85 Hz, 1 H), 7.59 (d, J=4.80 Hz, 1 H), 7.54 (s, 1 H), 7.48-7.52 (m, 1 H), 7.43-7.48 (m, 2 H), 7.35-7.43 (m, 3H), 7.28-7.36 (m, 1 H), 7.14-7.20 (m, 1 H), 6.56 (d, J=5.43 Hz, 1 H), 5.39 (s, 2 H), 3.95 (d, J=4.67 Hz, 6 H).

EXAMPLE 190

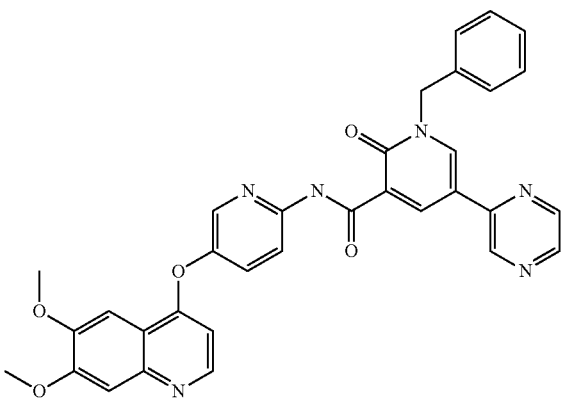

N-(5-((6,7-bis(methyloxy)-4-quinolinyl)oxy)-2-pyridinyl)-2-oxo-1-(phenylmethyl)-5-(2-pyrazinyl)-1,2-dihydro-3-pyridinecarboxamide: MS (ESI pos. ion) m/z: 587 (MH$^+$). Calc'd exact mass for $C_{33}H_{26}N_6O_5$: 586. $^1$H NMR (400 MHz, DMSO-d$_6$) 12.46 (s, 1 H), 9.32 (d, J=2.65 Hz, 1 H), 9.30 (d, J=1.39 Hz, 1 H), 9.26 (d, J=2.65 Hz, 1 H), 8.73 (dd, J=2.40, 1.64 Hz, 1 H), 8.63 (d, J=2.40 Hz, 1 H), 8.49 (d, J=5.18 Hz, 1 H), 8.43 (d, J=9.09 Hz, 1 H), 8.40 (d, J=2.78 Hz, 1 H), 7.88 (dd, J=8.97, 2.91 Hz, 1 H), 7.54 (s, 1 H), 7.46-7.52 (m, 2 H), 7.36-7.43 (m, 3 H), 7.29-7.36 (m, 1 H), 6.55 (d, J=5.18 Hz, 1 H), 5.44 (s, 2 H), 3.95 (d, J=3.92 Hz, 6 H).

EXAMPLE 191

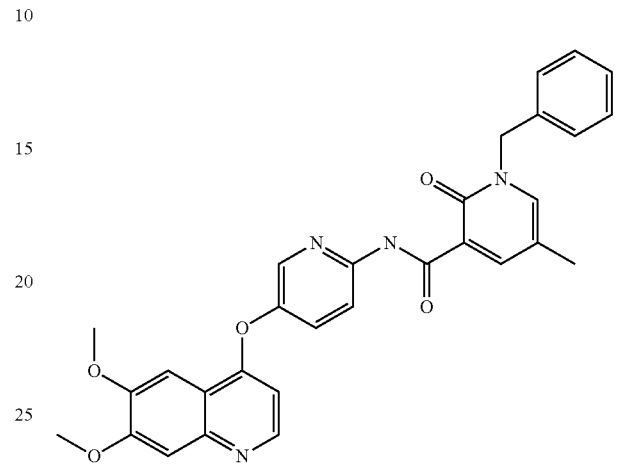

N-(5-((6,7-bis(methyloxy)-4-quinolinyl)oxy)-2-pyridinyl)-5-methyl-2-oxo-1-(phenylmethyl)-1,2-dihydro-3-pyridinecarboxamide: MS (ESI pos. ion) m/z: 523.2 (MH$^+$). Calc'd exact mass for $C_{33}H_{26}N_6O_5$: 586. $^1$H NMR (400 MHz, DMSO-d$_6$) 12.74 (s, 1 H), 8.49 (d, J=5.18 Hz, 1 H), 8.36-8.44 (m, 3 H), 8.22 (s, 1 H), 7.85 (dd, J=8.97, 2.78 Hz, 1 H), 7.54 (s, 1 H), 7.27-7.43 (m, 6 H), 6.54 (d, J=5.18 Hz, 1 H), 5.27 (s, 2 H), 3.95 (d, J=4.29 Hz, 6 H), 2.20 (s, 3 H).

EXAMPLE 192

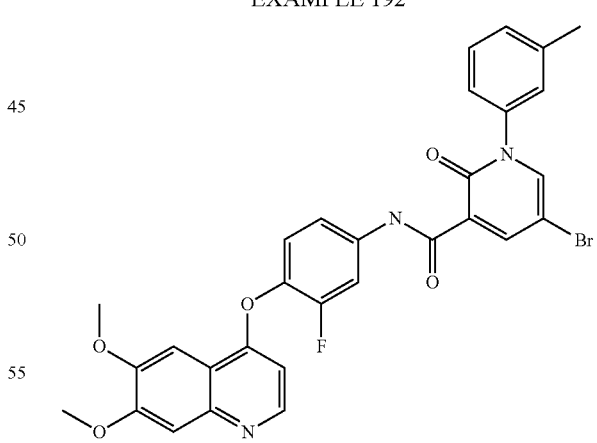

N-(4-((6,7-bis(methyloxy)-4-quinolinyl)oxy)-3-fluorophenyl)-5-bromo-1-(3-methylphenyl)-2-oxo-1,2-dihydro-3-pyridinecarboxamide: MS (ESI pos. ion) m/z: 605 (MH$^+$). Calc'd exact mass for $C_{30}H_{23}BrFN_3O_5$: 604. $^1$H NMR (400 MHz, DMSO-d$_6$) 12.00 (s, 1 H), 8.53 (d, J=2.78 Hz, 1 H), 8.46-8.51 (m, 2 H), 8.04 (dd, J=12.88, 2.40 Hz, 1 H), 7.53-7.58 (m, 1 H), 7.53 (s, 1 H), 7.42-7.50 (m, 2 H), 7.41 (s, 1 H), 7.31-7.39 (m, 3 H), 6.48 (d, J=4.93 Hz, 1 H), 3.95 (d, J=2.02 Hz, 6 H), 2.39 (s, 3 H).

EXAMPLE 193

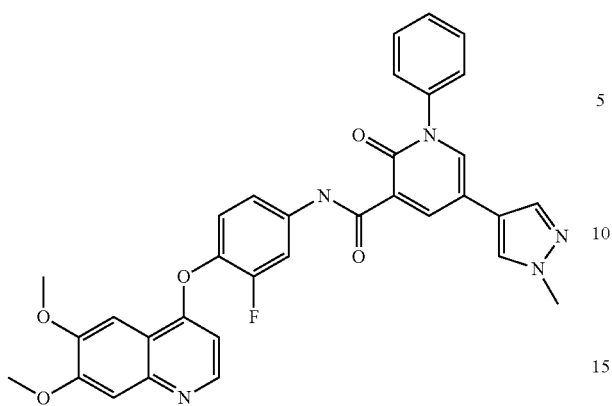

N-(4-((6,7-bis(methyloxy)-4-quinolinyl)oxy)-3-fluorophenyl)-5-(1-methyl-1H-pyrazol-4-yl)-2-oxo-1-phenyl-1,2-dihydro-3-pyridinecarboxamide: MS (ESI pos. ion) m/z: 592 (MH+). Calc'd exact mass for $C_{33}H_{26}FN_5O_5$: 591. $^1$H NMR (400 MHz, DMSO-$d_6$) 12.28 (s, 1 H), 8.76 (d, J=2.53 Hz, 1 H), 8.49 (d, J=5.31 Hz, 1 H), 8.42 (d, J=2.53 Hz, 1 H), 8.26 (s, 1 H), 8.08 (d, J=12.76 Hz, 1 H), 7.93 (s, 1 H), 7.52-7.64 (m, 7 H), 7.46 (t, J=8.65 Hz, 1 H), 7.41 (s, 1 H), 6.51 (d, J=4.93 Hz, 1 H), 3.95 (s, 6 H), 3.86 (s, 3 H).

EXAMPLE 194

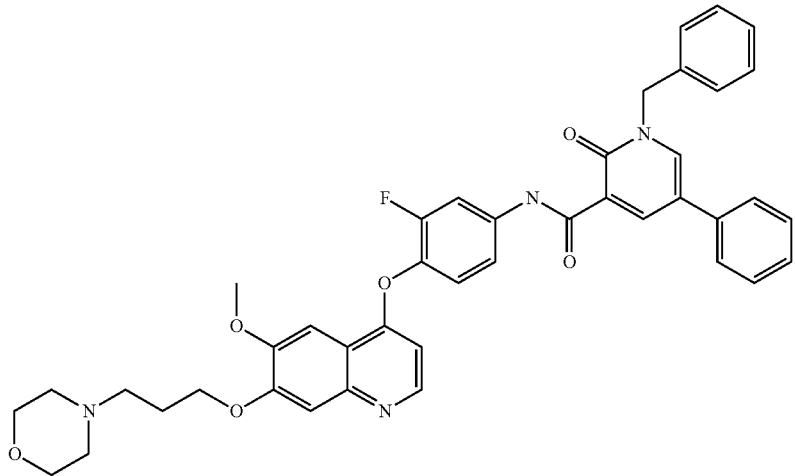

N-(3-fluoro-4-((6-(methyloxy)-7-((3-(4-morpholinyl)propyl)oxy)-4-quinolinyl) oxy)phenyl)-2-oxo-5-phenyl-1-(phenylmethyl)-1,2-dihydro-3-pyridinecarboxamide: MS (ESI pos. ion) m/z: 715 (MH+). Calc'd exact mass for $C_{42}H_{39}FN_4O_6$: 714.

EXAMPLE 195

1,1-dimethylethyl 5-(((5-(((6,7-bis(methyloxy)-4-quinolinyl)oxy)-2-pyridinyl)amino)carbonyl)-6-oxo-1-(phenylmethyl)-1,3',6,6'-tetrahydro-3,4'-bipyridine-1'(2'H)-carboxylate: MS (ESI pos. ion) m/z: 690 (MH+). Calc'd exact mass for $C_{39}H_{39}N_5O_7$: 689.

EXAMPLE 196

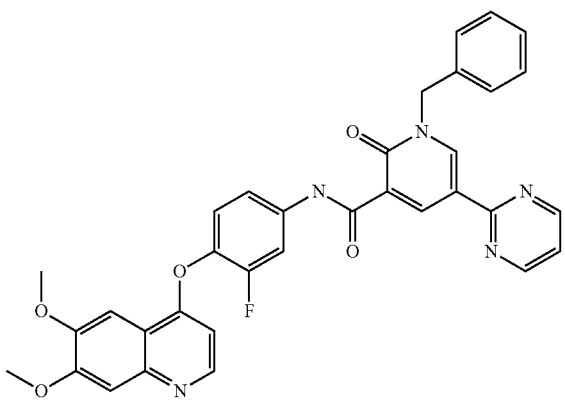

N-(4-((6,7-bis(methyloxy)-4-quinolinyl)oxy)-3-fluorophenyl)-2-oxo-1-(phenylmethyl)-5-(2-pyrimidinyl)-1,2-dihydro-3-pyridinecarboxamide: MS (ESI pos. ion) m/z: 604 (MH+). Calc'd exact mass for $C_{34}H_{26}FN_5O_5$: 603.

EXAMPLE 197

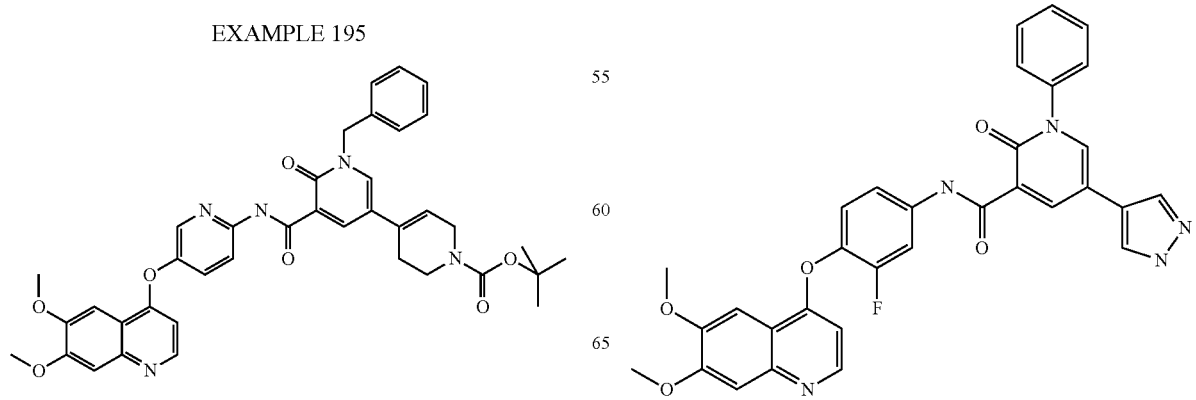

N-(4-((6,7-bis(methyloxy)-4-quinolinyl)oxy)-3-fluorophenyl)-2-oxo-1-phenyl-5-(1H-pyrazol-4-yl)-1,2-dihydro-3-pyridinecarboxamide: MS (ESI pos. ion) m/z: 578 (MH⁺). Calc'd exact mass for $C_{32}H_{24}FN_5O_5$: 577.

EXAMPLE 198

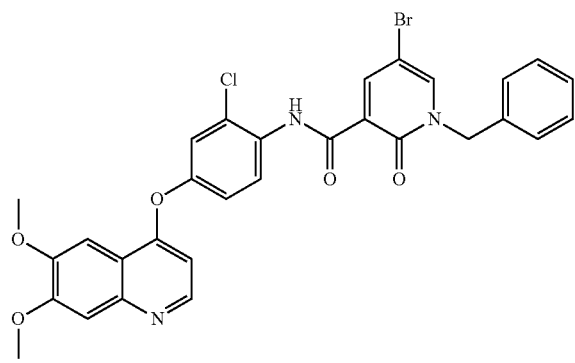

1-benzyl-5-bromo-N-(2-chloro-4-(6,7-dimethoxyquinolin-4-yloxy)phenyl)-2-oxo-1,2-dihydropyridine-3-carboxamide: MS (ESI pos. ion) m/z: 622 (MH+). Calc'd exact mass for $C_{30}H_{23}BrClN_3O_5$: 621. ¹H NMR (400 MHz, CDCl₃) 12.34 (s, 1 H), 8.66-8.72 (m, 2 H,), 8.53 (d, J=5.37 Hz, 1 H), 7.66 (d, J=2.93 Hz, 1 H), 7.52 (s, 1 H), 7.49-7.29 (m, 7 H), 7.12-7.18 (m, 1 H), 6.55 (d, J=5.37 Hz, 1 H), 5.29 (d, J=4.88 Hz, 2 H), 4.06 (s, 6 H)

EXAMPLE 199

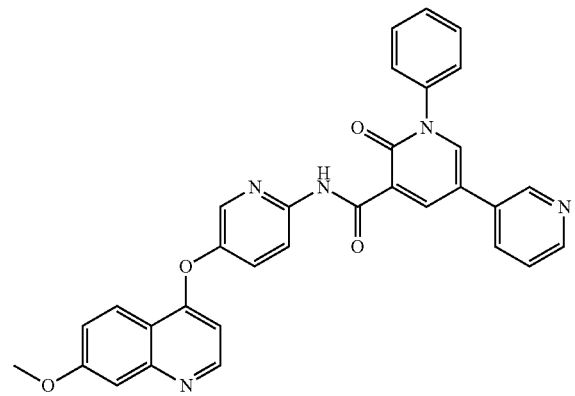

N-(5-(7-methoxyquinolin-4-yloxy)pyridin-2-yl)-2-oxo-1-phenyl-5-(pyridin-3-yl)-1,2-dihydropyridine-3-carboxamide: MS (ESI pos. ion) m/z: 542 (MH+). Calc'd exact mass for $C_{32}H_{23}N_5O_4$ 541. ¹H NMR (400 MHz, CDCl₃) 12.44 (s, 1 H), 9.03 (d, J=2.78 Hz, 1 H), 8.83 (d, J=0.51 Hz, 1H), 8.70-8.64 (m, 1 H), 8.63 (d, J=5.43 Hz, 1 H), 8.51 (d, J=9.09 Hz, 1 H), 8.28-8.23 (m, 2H), 7.93 (d, J=2.91 Hz, 1 H), 7.91-7.88 (m, 1 H), 7.65-7.39 (3m, 8 H), 7.25 (d, J=2.53 Hz, 1 H), 6.47 (d, J=5.43 Hz, 1 H), 3.99 (s, 3 H)

EXAMPLE 200

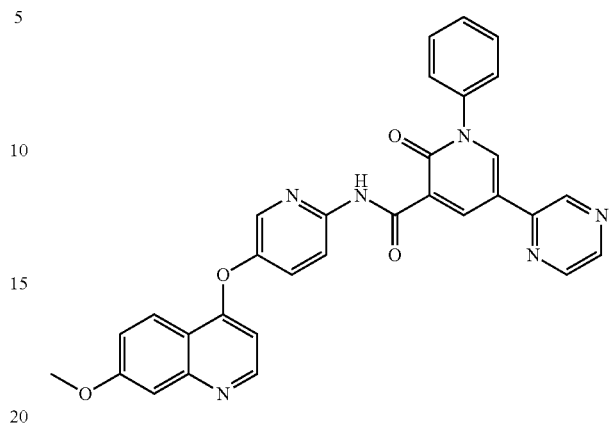

N-(5-(7-methoxyquinolin-4-yloxy)pyridin-2-yl)-2-oxo-1-phenyl-5-(pyrazin-2-yl)-1,2-dihydropyridine-3-carboxamide: MS (ESI pos. ion) m/z: 543 (MH+). Calc'd exact mass for $C_{31}H_{22}N_6O_4$ 542 1H NMR (400 MHz, CDCl₃) 12.36 (s, 1 H), 9.37 (d, J=2.78 Hz, 1 H), 9.08 (s, 1 H), 8.69-8.60 (m, 2 H), 8.59-8.50 (m, 2 H), 8.52 (d, J=8.97 Hz, 1 H), 8.28-8.23 (m, 2 H), 7.66-7.42 (3 m, 7 H), 7.24 (d, J=2.27 Hz, 1 H), 6.46 (d, J=5.31 Hz, 1 H), 3.99 (s, 3 H).

EXAMPLE 201

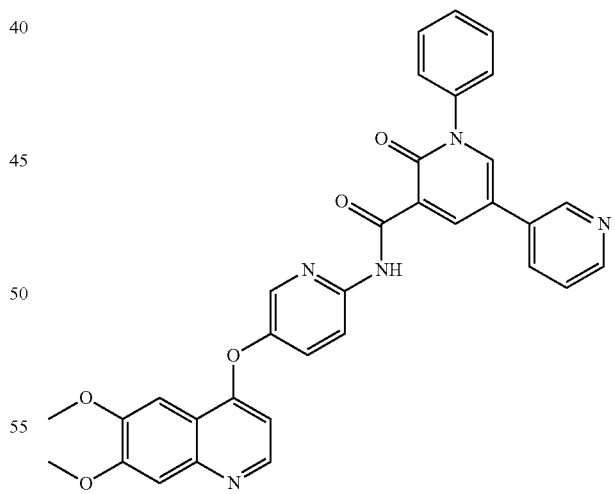

N-(5-(6,7-dimethoxyquinolin-4-yloxy)pyridin-2-yl)-2-oxo-1-phenyl-5-(pyridin-3-yl)-1,2-dihydropyridine-3-carboxamide: MS (ESI pos. ion) m/z 572 (MH+). Calc'd exact mass for $C_{33}H_{25}N_5O_5$ 571

EXAMPLE 202

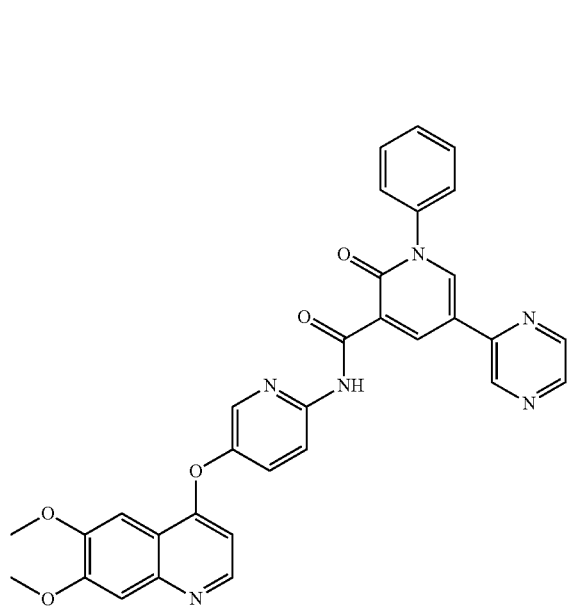

N-(5-(6,7-dimethoxyquinolin-4-yloxy)pyridin-2-yl)-2-oxo-1-phenyl-5-(pyrazin-2-yl)-1,2-dihydropyridine-3-carboxamide: MS (ESI pos. ion) m/z 573 (MH+). Calc'd exact mass for $C_{32}H_{24}N_6O_5$ 572.

EXAMPLE 203

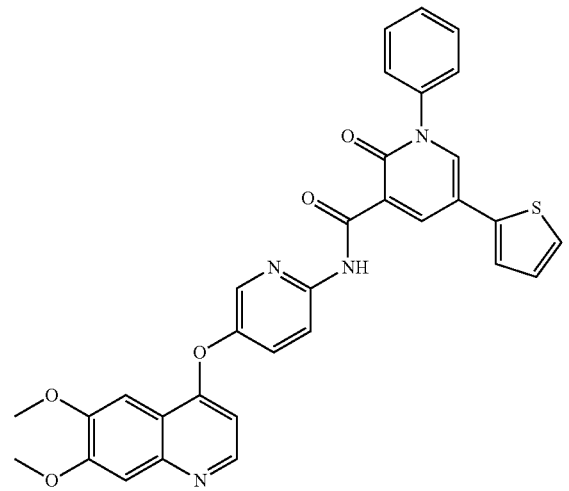

N-(5-(6,7-dimethoxyquinolin-4-yloxy)pyridin-2-yl)-2-oxo-1-phenyl-5-(thiophen-2-yl)-1,2-dihydropyridine-3-carboxamide: MS (ESI pos. ion) m/z 577 (MH+). Calc'd exact mass for $C_{32}H_{24}N_4O_5S$ 576.

EXAMPLE 204

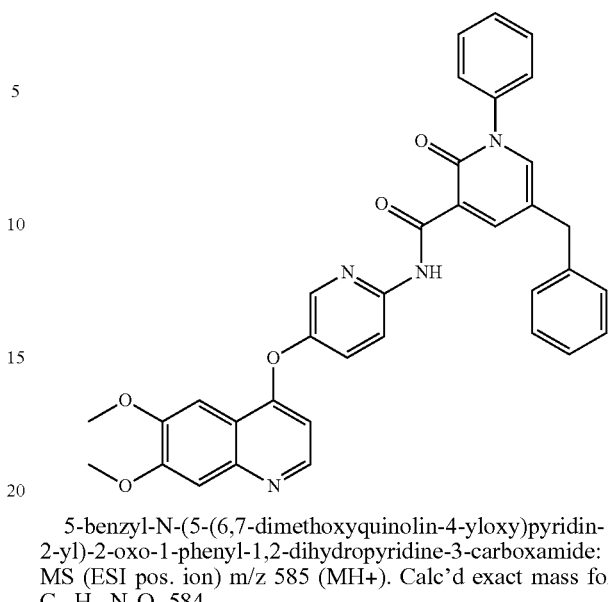

5-benzyl-N-(5-(6,7-dimethoxyquinolin-4-yloxy)pyridin-2-yl)-2-oxo-1-phenyl-1,2-dihydropyridine-3-carboxamide: MS (ESI pos. ion) m/z 585 (MH+). Calc'd exact mass for $C_{35}H_{28}N_4O_5$ 584

EXAMPLE 205

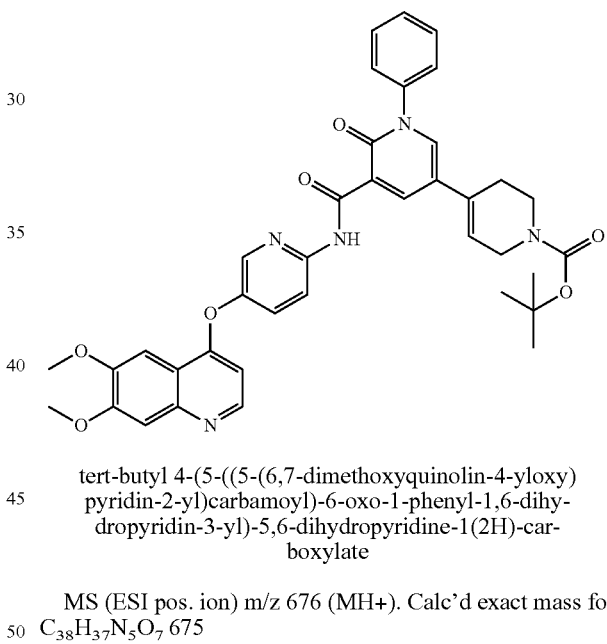

tert-butyl 4-(5-((5-(6,7-dimethoxyquinolin-4-yloxy)pyridin-2-yl)carbamoyl)-6-oxo-1-phenyl-1,6-dihydropyridin-3-yl)-5,6-dihydropyridine-1(2H)-carboxylate MS (ESI pos. ion) m/z 676 (MH+). Calc'd exact mass for $C_{38}H_{37}N_5O_7$ 675

EXAMPLE 206

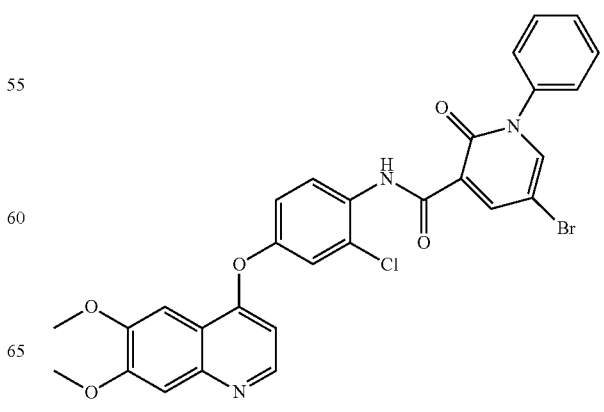

205
5-bromo-N-(2-chloro-4-(6,7-dimethoxyquinolin-4-yloxy)phenyl)-2-oxo-1-phenyl-1,2-dihydropyridine-3-carboxamide: MS (ESI pos. ion) m/z: 607 (MH+). Calc'd exact mass for $C_{29}H_{21}BrClN_3O_5$: 606 1H NMR (400 MHz, CDCl$_3$) 12.12 (s, 1 H), 8.79 (d, J=2.44 Hz, 1 H), 8.66 (d, J=8.79 Hz,
206
1H), 8.52 (d, J=4.88 Hz, 1 H), 7.78 (d, J=2.93 Hz, 1 H), 7.67-7.31 (m, 8 H), 7.07-7.21 (m, 1 H), 6.54 (d, J=4.88 Hz, 1 H), 4.05 (s, 3 H), 4.04 (s, 3 H)
EXAMPLE 207
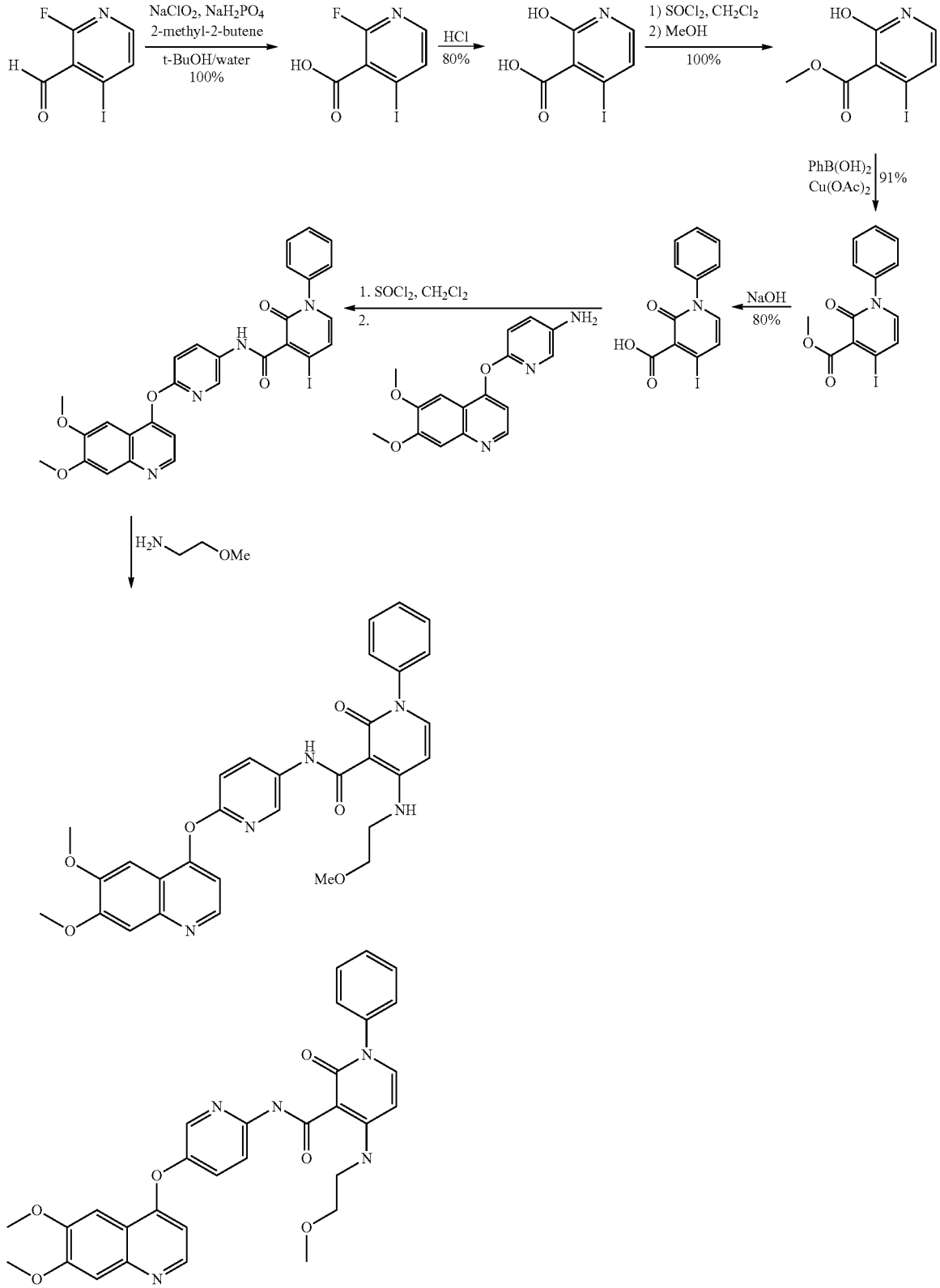

N-(5-(6,7-dimethoxyquinolin-4-yloxy)pyridin-2-yl)-4-(2-methoxyethylamino)-2-oxo-1-phenyl-1,2-dihydropyridine-3-carboxamide

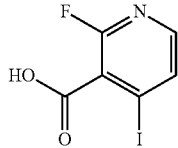

Step 1: 2-fluoro-4-iodonicotinic acid. To a stirred solution of 2-fluoro-4-iodopyridine-3-carboxaldehyde (10.0 g, 39.8 mmol) in tert-butanol (350 mL) and water (100 mL) at room temperature were added 2-methyl-2-butene (42.1 ml, 398 mmol), sodium phosphate, monobasic, monohydrate (60.5 g, 438 mmol) and sodium chlorite (18.0 g, 199 mmol). The reaction mixture was stirred at room temperature for 75 min. The reaction mixture was diluted with dichloromethane and a 6M aqueous solution of hydrochloric acid was added until pH ~2. The water layer was extracted with dichloromethane. The organic phase was dried over MgSO$_4$, filtered and concentrated in vacuo. Purification by MPLC (CH$_2$Cl$_2$/MeOH+1% AcOH: 100/0 to 80/20) afforded 2-fluoro-4-iodonicotinic acid (10.63 g, 39.8 mmol, 100% yield). MS (ESI pos. ion) m/z: 268 (MH+). Calc'd exact mass for C$_6$H$_3$FINO$_2$: 267.

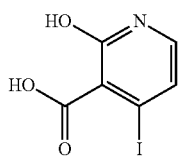

Step 2: 2-hydroxy-4-iodonicotinic acid. A suspension of 2-fluoro-4-iodonicotinic acid (896 mg, 3356 μmol) in 6M hydrochloric acid (13423 μl, 80540 μmol) was heated at 100° C. After 5 min, the reaction became a solution, and then a precipitate appeared. The reaction mixture was stirred 60 min at 100° C. and then cooled to room temperature. Filtration afforded 2-hydroxy-4-iodonicotinic acid (710 mg, 2679 μmol, 80% yield). MS (ESI pos. ion) m/z: 248 (M+H—H$_2$O). Calc'd exact mass for C$_6$H$_{4}$INO$_3$: 265.

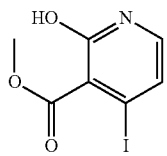

Step 3: methyl 2-hydroxy-4-iodonicotinate. Thionyl chloride (3.81 ml, 52.2 mmol) was added to a suspension of 2-hydroxy-4-iodonicotinic acid (3.46 g, 13.1 mmol) in dichloromethane (12 mL) in a pressure vessel at room temperature. The reaction mixture was then heated at 75° C. for 3 h. An aliquot was taken and hydrolyzed with methanol. LCMS analysis showed the derived methyl ester seen as major compound. The reaction mixture was cooled to room temperature and was concentrated in vacuo to give 2-hydroxy-4-iodonicotinoyl chloride. 2-hydroxy-4-iodonicotinoyl chloride in MeOH (100 mL) was stirred at room temperature for 2 h. Concentration in vacuo of the reaction mixture afforded methyl 2-hydroxy-4-iodonicotinate (3.64 g, 13.1 mmol, quantitative yield). MS (ESI pos. ion) m/z: 280 (MH+). Calc'd exact mass for C$_7$H$_{6}$INO$_3$: 279.

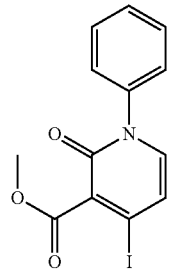

Step 4: methyl 4-iodo-2-oxo-1-phenyl-1,2-dihydropyridine-3-carboxylate. Methyl 2-hydroxy-4-iodonicotinate (123 mg, 441 μmol), phenylboronic acid (161 mg, 1322 μmol), copper acetate (160 mg, 882 μmol) were combined. Dichloroethane (6 mL) was added followed by molecular sieves 4 Å activated (490 mg) and pyridine (143 μl, 1763 μmol). The reaction mixture was stirred at 55° C. for 3 h. LCMS analysis of an aliquot showed the reaction was complete. The reaction mixture was diluted with dichloromethane and filtered through a pad of celite (rinsing with dichloromethane). The filtrate was concentrated in vacuo and purification by MPLC (ISCO, CH$_2$Cl$_2$/MeOH: 100/0 to 97.5/2.5) afforded methyl 4-iodo-2-oxo-1-phenyl-1,2-dihydropyridine-3-carboxylate (142 mg, 400 μmol, 91% yield). MS (ESI pos. ion) m/z: 356 (MH+). Calc'd exact mass for C$_{13}$H$_{10}$INO$_3$: 355.

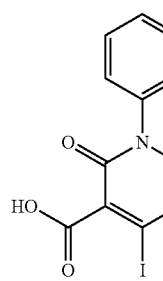

Step 5: 4-iodo-2-oxo-1-phenyl-1,2-dihydropyridine-3-carboxylic acid. To a stirred solution of methyl 4-iodo-2-oxo-1-phenyl-1,2-dihydropyridine-3-carboxylate (2.34 g, 6.59 mmol) in dioxane (39 mL) was added water (12 mL) followed by sodium hydroxide 6M solution (4.39 ml, 26.4 mmol). The reaction mixture was heated at 50° C. for 4 h. LCMS analysis of an aliquot showed the reaction was complete. The reaction mixture was cooled to room temperature and concentrated in vacuo. Water was added, and the pH was adjusted to ~3 with 6M aqueous hydrochloric acid solution. The solid formed was isolated by filtration and was dried under high vacuum overnight to give 4-iodo-2-oxo-1-phenyl-1,2-dihydropyridine-3-carboxylic acid (1.79 g, 5.25 mmol, 80% yield), which was used without further purification. MS (ESI pos. ion) m/z: 364 (M+Na). Calc'd exact mass for C$_{12}$H$_{8}$INO$_3$: 341.

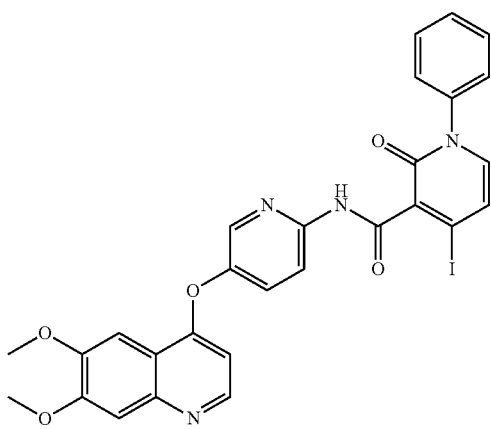

Step 6: N-(5-(6,7-dimethoxyquinolin-4-yloxy)pyridin-2-yl)-4-iodo-2-oxo-1-phenyl-1,2-dihydropyridine-3-carboxamide. To a stirred solution of 4-iodo-2-oxo-1-phenyl-1,2-dihydropyridine-3-carboxylic acid (132 mg, 387 µmol) in CH$_2$Cl$_2$ (3.9 mL) in a pressure vessel at room temperature was added thionyl chloride (113 µl, 1548 µmol). The reaction mixture was heated at 75° C. and stirred for 1 h. An aliquot was taken, hydrolized with methanol and analyzed by LCMS: the reaction was done. The reaction mixture was concentrated in vacuo. 4-iodo-2-oxo-1-phenyl-1,2-dihydropyridine-3-carbonyl chloride was used in the next step without further purification.

To a solution of 4-iodo-2-oxo-1-phenyl-1,2-dihydropyridine-3-carbonyl chloride (139 mg, 387 µmol) in dichloromethane (4 mL) at room temperature was added diisopropylethylamine (202 µl, 1160 µmol) followed by 5-(6,7-dimethoxyquinolin-4-yloxy)pyridin-2-amine (115 mg, 387 µmol). The reaction mixture was stirred at room temperature for 2 h. An aliquot was taken and analyzed by LCMS: reaction was done. The reaction mixture was diluted with methanol and directly adsorbed on silica. Purification by MPLC (CH$_2$Cl$_2$/MeOH: 100/0 to 96/4) afforded N-(5-(6,7-dimethoxyquinolin-4-yloxy)pyridin-2-yl)-4-iodo-2-oxo-1-phenyl-1,2-dihydropyridine-3-carboxamide (162 mg, 261 µmol, 68% yield for two steps). MS (ESI pos. ion) m/z: 621 (MH+). Calc'd exact mass for C$_{28}$H$_{20}$IN$_4$O$_5$: 620.

Step 7: N-(5-(6,7-dimethoxyquinolin-4-yloxy)pyridin-2-yl)-4-(2-methoxyethylamino)-2-oxo-1-phenyl-1,2-dihydropyridine-3-carboxamide. 2-methoxyethylamine (137 µl, 1573 µmol) was added to a suspension of N-(5-(6,7-dimethoxyquinolin-4-yloxy)pyridin-2-yl)-4-iodo-2-oxo-1-phenyl-1,2-dihydropyridine-3-carboxamide (122 mg, 197 µmol) in iso-propanol (1 mL). The reaction mixture was heated at 100° C. for 80 min. An aliquot was taken and analyzed by LCMS: The reaction was done. The reaction mixture was diluted with dichloromethane. The crude was adsorbed on silica and purified by MPLC (CH$_2$Cl$_2$/MeOH: 100/0 to 95/5) to afford the title compound N-(5-(6,7-dimethoxyquinolin-4-yloxy)pyridin-2-yl)-4-(2-methoxyethylamino)-2-oxo-1-phenyl-1,2-dihydropyridine-3-carboxamide (84 mg, 148 µmol, 75% yield). MS (ESI pos. ion) m/z: 568 (MH+). Calc'd exact mass for C$_{31}$H$_{29}$N$_5$O$_6$: 567. $^1$H NMR (400 MHz, DMSO-d$_6$) 13.28 (s, 1 H), 10.80-10.71 (m, 1 H), 8.49 (d, J=5.2 Hz, 1 H), 8.34 (d, J=9.1 Hz, 1 H), 8.30 (d, J=2.8 Hz, 1 H), 7.79 (dd, J=9.2, 3.1 Hz, 1 H), 7.73 (d, J=7.8 Hz, 1 H), 7.58-7.37 (m, 7 H), 6.53 (d, J=5.2 Hz, 1 H), 6.32 (d, J=8.1 Hz, 1 H), 3.95 (s, 3 H), 3.94 (s, 3 H), 3.64-3.54 (m, 4 H), 3.34 (s, 3 H).

EXAMPLE 208

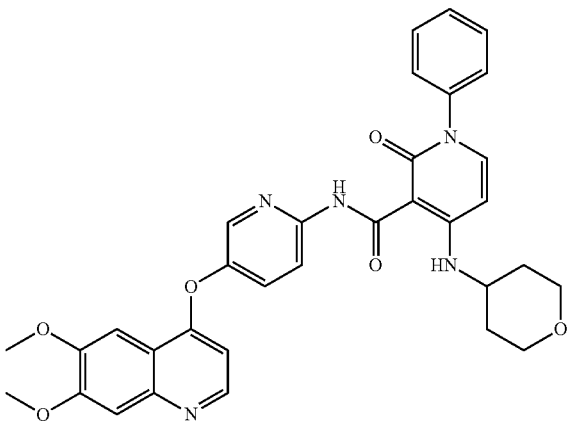

N-(5-(6,7-dimethoxyquinolin-4-yloxy)pyridin-2-yl)-2-oxo-1-phenyl-4-(tetrahydro-2H-pyran-4-ylamino)-1,2-dihydropyridine-3-carboxamide: MS (ESI pos. ion) m/z: 594 (MH+). Calc'd exact mass for C$_{33}$H$_{31}$N$_5$O$_6$: 593.

EXAMPLE 209

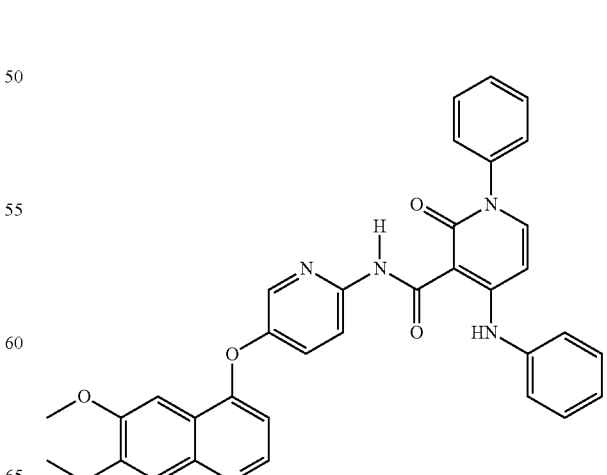

N-(5-(6,7-dimethoxyquinolin-4-yloxy)pyridin-2-yl)-2-oxo-1-phenyl-4-(phenylamino)-1,2-dihydropyridine-3-carboxamide: MS (ESI pos. ion) m/z: 586 (MH+). Calc'd exact mass for $C_{34}H_{27}N_5O_5$: 585. $^1$H NMR (400 MHz, DMSO-$d_6$) 13.33 (s, 1 H), 12.37 (s, 1 H), 8.50 (d, J=5.2 Hz, 1 H), 8.38 (d, J=9.1 Hz, 1 H), 8.35 (d, J=2.8 Hz, 1 H), 7.82 (dd, J=9.1, 3.0 Hz, 1 H), 7.72 (d, J=7.8 Hz, 1 H), 7.59-7.33 (m, 12 H), 6.56 (d, J=5.3 Hz, 1 H), 6.18 (d, J=7.8 Hz, 1 H), 3.95 (s, 3 H) 3.94 (s, 3 H).

EXAMPLE 210

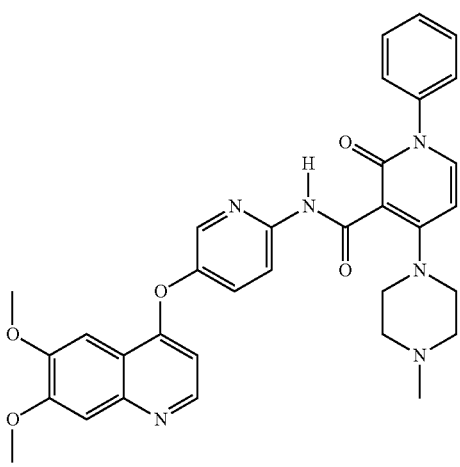

N-(5-(6,7-dimethoxyquinolin-4-yloxy)pyridin-2-yl)-4-(4-methylpiperazin-1-yl)-2-oxo-1-phenyl-1,2-dihydropyridine-3-carboxamide: MS (ESI pos. ion) m/z: 593 (MH+). Calc'd exact mass for $C_{33}H_{32}N_6O_5$: 592. $^1$H NMR (400 MHz, DMSO-$d_6$) 11.74 (s, 1 H), 8.48 (d, J=5.3 Hz, 1 H), 8.37 (d, J=9.0 Hz, 1 H), 8.30 (d, J=2.9 Hz, 1 H), 7.79 (dd, J=9.1, 2.9 Hz, 1 H), 7.61 (d, J=8.1 Hz, 1 H), 7.56-7.48 (m, 3 H), 7.47-7.37 (m, 4 H), 6.51 (d, J=5.3 Hz, 1 H), 6.45 (d, J=8.1 Hz, 1 H), 3.95 (s, 3 H), 3.94 (s, 3 H), 3.47-3.41 (m, 4 H), 2.46-2.37 (m, 4 H), 2.21 (s, 3 H).

EXAMPLE 211

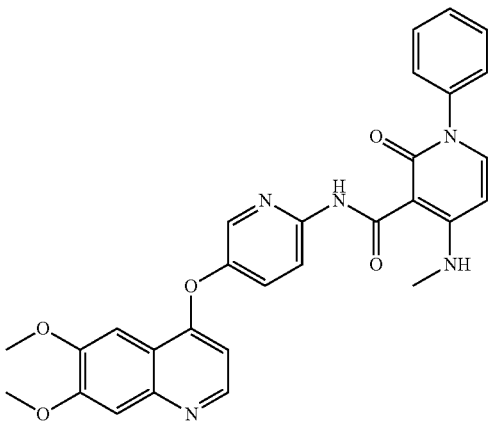

N-(5-(6,7-dimethoxyquinolin-4-yloxy)pyridin-2-yl)-4-(methylamino)-2-oxo-1-phenyl-1,2-dihydropyridine-3-carboxamide: MS (ESI pos. ion) m/z: 524 (MH+). Calc'd exact mass for $C_{29}H_{25}N_5O_5$: 523.

EXAMPLE 212

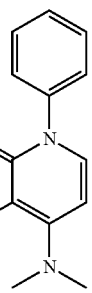

N-(5-(6,7-dimethoxyquinolin-4-yloxy)pyridin-2-yl)-4-(dimethylamino)-2-oxo-1-phenyl-1,2-dihydropyridine-3-carboxamide: MS (ESI pos. ion) m/z: 538 (MH+). Calc'd exact mass for $C_{30}H_{27}N_5O_5$: 537.

EXAMPLE 213

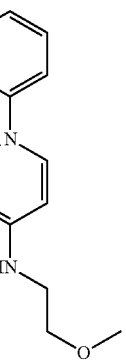

4-(2-methoxyethylamino)-N-(5-(7-methoxyquinolin-4-yloxy)pyridin-2-yl)-2-oxo-1-phenyl-1,2-dihydropyridine-3-carboxamide: MS (ESI pos. ion) m/z 538 (MH+). Calc'd exact mass for $C_{30}H_{27}N_5O_5$ 537.

EXAMPLE 214

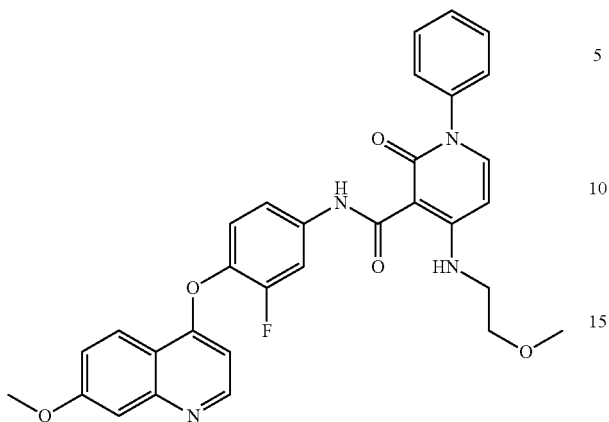

N-(3-fluoro-4-(7-methoxyquinolin-4-yloxy)phenyl)-4-(2-methoxyethylamino)-2-oxo-1-phenyl-1,2-dihydropyridine-3-carboxamide: MS (ESI pos. ion) m/z 555 (MH+). Calc'd exact mass for $C_{31}H_{27}FN_4O_5$ 554

EXAMPLE 215

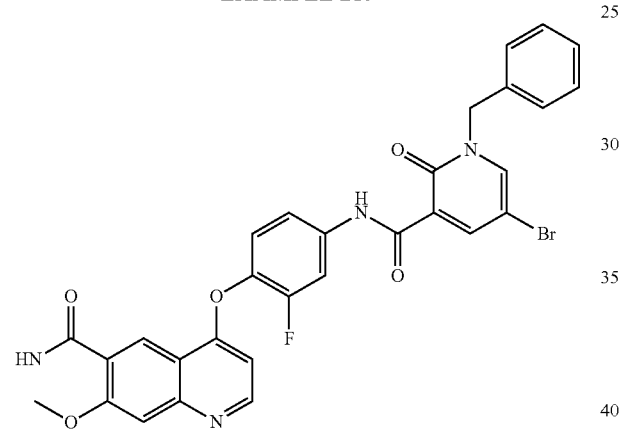

N-(4-((6,7-bis(methyloxy)-4-quinolinyl)oxy)-3-fluorophenyl)-1-cyclopentyl-6-oxo-5-(2-oxo-1-pyrrolidinyl)-1,6-dihydro-3-pyridinecarboxamide: MS (ESI pos. ion) m/z: 617 (MH+). Calc'd exact mass for $C_{30}H_{21}BrFN_4O_5$: 616

EXAMPLE 216

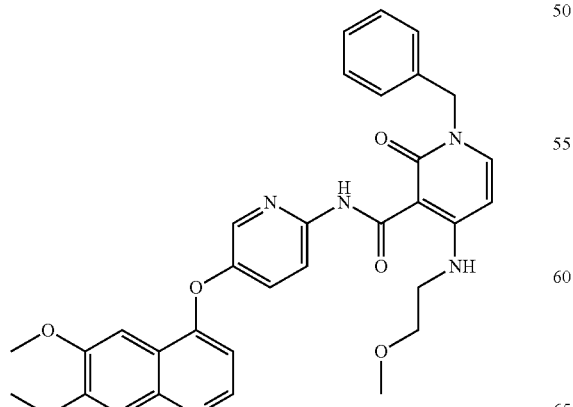

1-benzyl-N-(5-(6,7-dimethoxyquinolin-4-yloxy)pyridin-2-yl)-4-(2-methoxyethylamino)-2-oxo-1,2-dihydropyridine-3-carboxamide: MS (ESI pos. ion) m/z: 582 (MH+). Calc'd exact mass for $C_{32}H_{31}N_5O_6$: 581. 1H NMR (400 MHz, DMSO-$d_6$) 13.45 (s, 1 H) 10.58 (s, 1 H) 8.49 (d, J=5.13 Hz, 1 H) 8.33 (dd, J=5.90, 2.82 Hz, 2 H) 7.89 (d, J=7.69 Hz, 1 H) 7.79 (dd, J=9.10, 2.69 Hz, 1 H) 7.54 (s, 1 H) 7.41 (s, 1 H) 7.26-7.39 (m, 5 H) 6.52 (d, J=5.13 Hz, 1 H) 6.26 (d, J=7.69 Hz, 1 H) 5.10 (s, 2 H) 3.94 (d, J=3.33 Hz, 6 H) 3.48-3.59 (m, 4 H) 3.32 (s, 3 H)

EXAMPLE 217

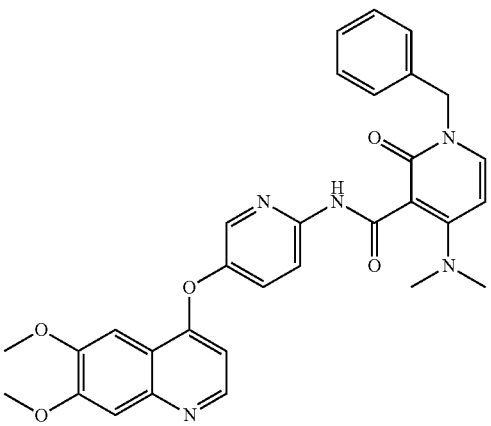

1-benzyl-N-(5-(6,7-dimethoxyquinolin-4-yloxy)pyridin-2-yl)-4-(dimethylamino)-2-oxo-1,2-dihydropyridine-3-carboxamide: MS (ESI pos. ion) m/z: 552 (MH+). Calc'd exact mass for $C_{31}H_{29}N_5O_5$: 551.

EXAMPLE 218

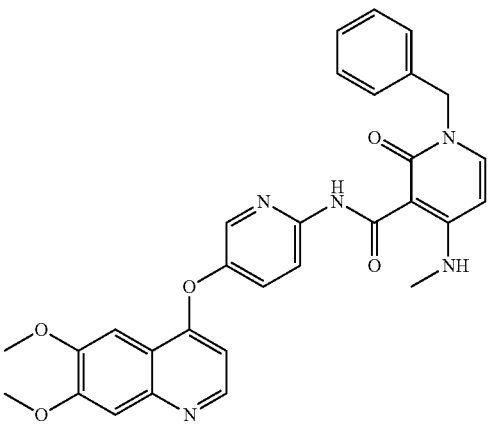

1-benzyl-N-(5-(6,7-dimethoxyquinolin-4-yloxy)pyridin-2-yl)-4-(methylamino)-2-oxo-1,2-dihydropyridine-3-carboxamide: MS (ESI pos. ion) m/z: 538 (MH+). Calc'd exact mass for $C_{30}H_{27}N_5O_5$: 537.

EXAMPLE 219

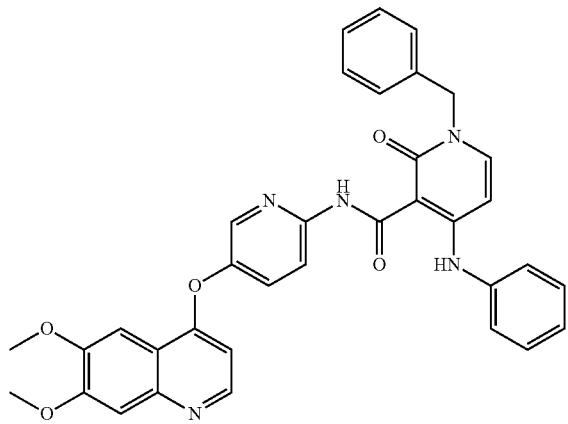

1-benzyl-N-(5-(6,7-dimethoxyquinolin-4-yloxy)pyridin-2-yl)-2-oxo-4-(phenylamino)-1,2-dihydropyridine-3-carboxamide: MS (ESI pos. ion) m/z: 600 (MH+). Calc'd exact mass for $C_{35}H_{29}N_5O_5$: 599.

EXAMPLE 220

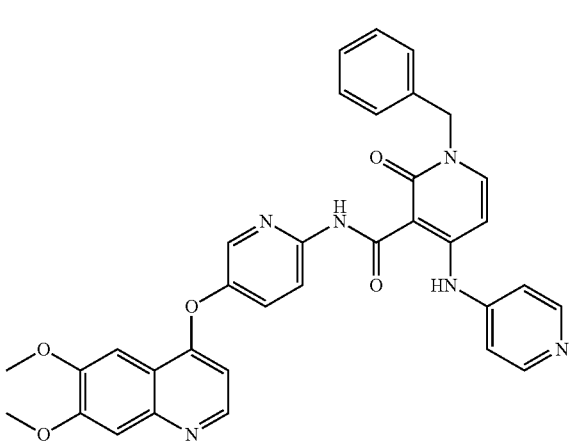

1-benzyl-N-(5-(6,7-dimethoxyquinolin-4-yloxy)pyridin-2-yl)-2-oxo-4-(pyridin-4-ylamino)-1,2-dihydropyridine-3-carboxamide: MS (ESI pos. ion) m/z: 601 (MH+). Calc'd exact mass for $C_{34}H_{28}N_6O_5$: 600. 1H NMR (400 MHz, DMSO-$d_6$) 13.48 (s, 1 H) 12.46 (s, 1 H) 8.45-8.57 (m, 3 H) 8.34 (d, J=12.05 Hz, 2 H) 8.02 (d, 1 H) 7.83 (s, 1 H) 7.52 (s, 1 H) 7.32-7.42 (m, 7 H) 6.50-6.60 (m, 2 H) 3.93 (s, 3 H) 3.92 (s, 3 H)

EXAMPLE 221

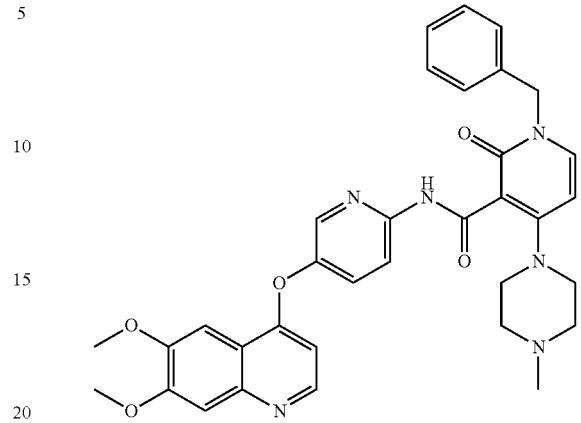

1-benzyl-N-(5-(6,7-dimethoxyquinolin-4-yloxy)pyridin-2-yl)-4-(4-methylpiperazin-1-yl)-2-oxo-1,2-dihydropyridine-3-carboxamide: MS (ESI pos. ion) m/z: 607 (MH+). Calc'd exact mass for $C_{34}H_{34}N_6O_5$: 606.

EXAMPLE 222

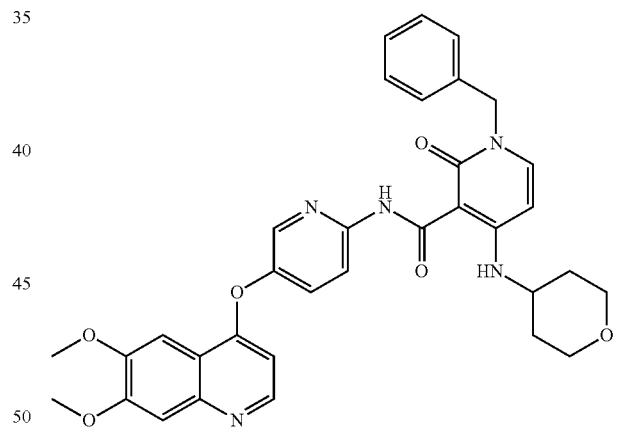

1-benzyl-N-(5-(6,7-dimethoxyquinolin-4-yloxy)pyridin-2-yl)-2-oxo-4-(tetrahydro-2H-pyran-4-ylamino)-1,2-dihydropyridine-3-carboxamide: MS (ESI pos. ion) m/z: 608 (MH+). Calc'd exact mass for $C_{34}H_{33}N_5O_6$: 607. 1 H NMR (400 MHz, DMSO-$d_6$) 13.47 (s, 1 H) 10.66 (d, J=7.58 Hz, 2 H) 8.50 (d, J=5.18 Hz, 1 H) 8.31-8.36 (m, 1 H) 7.89 (d, J=7.83 Hz, 1 H) 7.78 (dd, J=8.97, 3.03 Hz, 1H) 7.55 (s, 1 H) 7.42 (s, 1 H) 7.26-7.40 (m, 5 H) 6.53 (d, J=5.18 Hz, 1 H) 6.36 (d, J=7.83 Hz, 1 H) 5.11 (s, 2 H) 3.95 (d, J=4.04 Hz, 6 H) 3.86 (d, J=11.49 Hz, 3 H) 3.45-3.55 (m, 3 H) 1.89-1.99 (m, 2 H) 1.44-1.57 (m, 2 H)

EXAMPLE 223

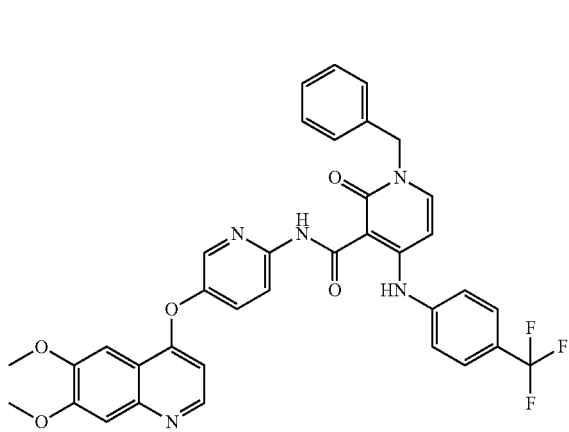

1-benzyl-N-(5-(6,7-dimethoxyquinolin-4-yloxy)pyridin-2-yl)-2-oxo-4-(4-(trifluoromethyl)phenylamino)-1,2-dihydropyridine-3-carboxamide: MS (ESI pos. ion) m/z: 668 (MH+). Calc'd exact mass for $C_{36}H_{28}F_3N_5O_5$: 667. 1 H NMR (400 MHz, DMSO-d$_6$) ☐1 ppm 13.59 (s, 2 H) 12.42 (s, 1 H) 8.82 (d, J=6.44 Hz, 1 H) 8.49 (d, J=2.91 Hz, 1 H) 8.44 (d, J=9.09 Hz, 1 H) 7.77 (s, 1 H) 7.29-7.42 (m, 5 H) 7.00 (d, J=6.44 Hz, 1 H) 5.18 (s, 2 H) 4.05 (s, 3 H) 4.03 (s, 3 H)

EXAMPLE 224

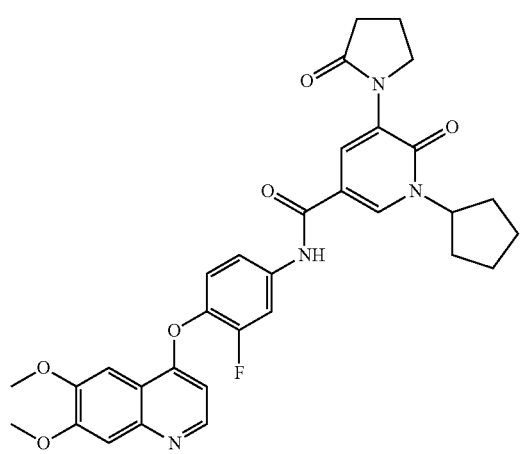

1-cyclopentyl-N-(4-(6,7-dimethoxyquinolin-4-yloxy)-3-fluorophenyl)-6-oxo-5-(2-oxopyrrolidin-1-yl)-1,6-dihydropyridine-3-carboxamide: MS (ESI pos. ion) m/z: 587 (MH+). Calc'd exact mass for $C_{32}H_{31}FN_4O_6$: 586.

EXAMPLE 225

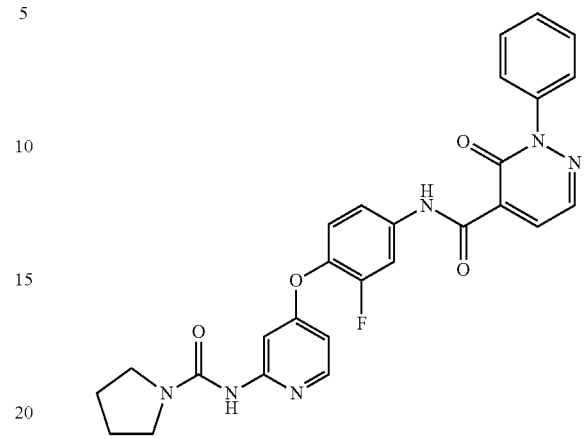

N-(3-fluoro-4-(2-(pyrrolidine-1-carboxamido)pyridin-4-yloxy)phenyl)-3-oxo-2-phenyl-2,3-dihydropyridazine-4-carboxamide: MS (ESI pos. ion) m/z: 515 (MH+). Calc'd exact mass for $C_{27}H_{23}FN_6O_4$: 514. $^1$HNMR (300 MHz, CDCl$_3$): 1.23 (s, 1H), 1.52 (s, 4H), 2.98-3.08 (m, 5H), 6.10 (s, 1H), 6.11 (d, J=4.11 Hz, 1H), 6.61 (s, 1H), 6.73 (t, J=8.61 Hz, 1H), 6.84 (s, 1H), 6.91 (s, 1H), 7.09 (d, J=6.65 Hz, 1H), 7.15 (q, J=7.96 Hz, 2H), 7.29 (s, 1H), 7.49 (d, J=12.13 Hz, 1H), 7.61 (d, J=5.67 Hz, 1H), 7.80 (d, J=3.91 Hz, 1H), 7.97 (d, J=4.11 Hz, 1H), 11.39 (s, 1H).

EXAMPLE 226

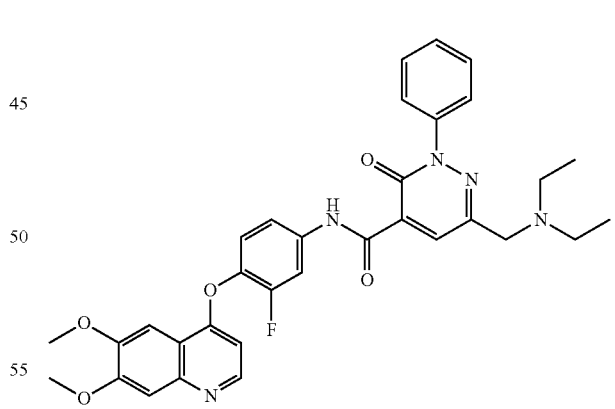

6-((diethylamino)methyl)-N-(4-(6,7-dimethoxyquinolin-4-yloxy)-3-fluorophenyl)-3-oxo-2-phenyl-2,3-dihydropyridazine-4-carboxamide: MS (ESI pos. ion) m/z: 598 (MH+). Calc'd exact mass for $C_{33}H_{32}FN_5O_5$: 597. $^1$HNMR (300 MHz, CDCl$_3$): 11.99 (s, 1H), 8.61 (s, 2H), 8.04 (s, 1H), 7.82

(s, 1H), 7.57 (m, 4H), 7.26 (s, 3H), 6.61 (s, 1H), 4.10 (d, J=6.1 Hz, 9H), 3.82 (s, 2H), 3.16 (s, 1H), 2.79 (s, 4H), 1.81 (s, 1H), 1.27 (s, 1H).

3H), 3.96 (s, 4H), 6.40 (s, 1H), 7.24 (s, 2H), 7.40 (s, 2H), 7.55 (s, 4H), 7.96 (s, 1H), 8.29 (s, 2H), 8.59 (s, 1H), 12.01 (s, 1H).

EXAMPLE 227

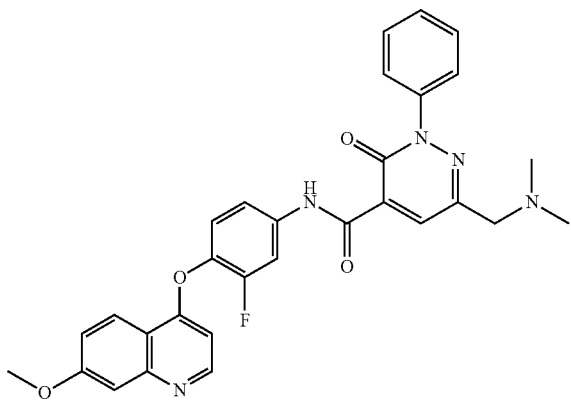

6-((dimethylamino)methyl)-N-(3-fluoro-4-(7-methoxyquinolin-4-yloxy)phenyl)-3-oxo-2-phenyl-2,3-dihydropyridazine-4-carboxamide: MS (ESI pos. ion) m/z: 540 (MH+). Calc'd exact mass for $C_{30}H_{26}FN_5O_4$: 539. $^1$HNMR (300 MHz, CDCl$_3$): 1.71 (s, 1H), 1.75 (ddd, J=6.4, 3.5, 3.3 Hz, 3H), 2.30 (s, 2H), 3.03-3.13 (m, J=6.5, 3.6, 3.3, 3.3, Hz, 3H), 3.51 (s, 1H), 3.93 (s, 2H), 6.70-6.75 (m, 2H), 7.20 (m, 2H), 7.33-7.54 (m, 6H), 7.80 (d, 1H), 8.45 (d, 1H), 8.52 (s, 1H), 11.85 (s, 1H).

EXAMPLE 228

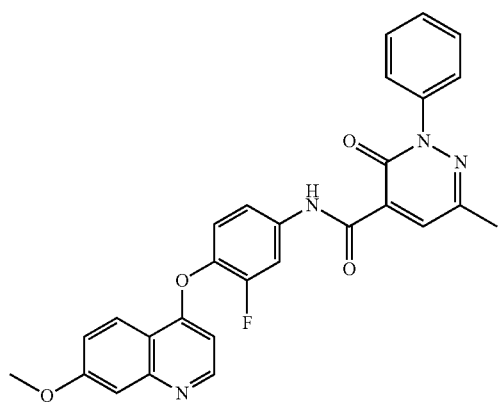

N-(3-fluoro-4-(7-methoxyquinolin-4-yloxy)phenyl)-6-methyl-3-oxo-2-phenyl-2,3-dihydropyridazine-4-carboxamide: MS (ESI pos. ion) m/z: 497 (MH+). Calc'd exact mass for $C_{28}H_{21}FN_4O_4$: 496. $^1$HNMR (300 MHz, CDCl$_3$): 2.54 (s,

EXAMPLE 229

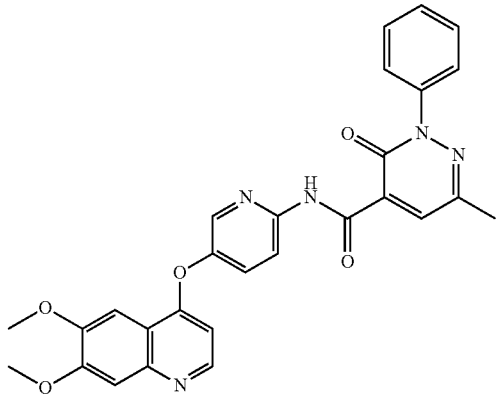

N-(5-(6,7-dimethoxyquinolin-4-yloxy)pyridin-2-yl)-6-methyl-3-oxo-2-phenyl-2,3-dihydropyridazine-4-carboxamide: MS (ESI pos. ion) m/z: 510 (MH+). Calc'd exact mass for $C_{28}H_{23}N_5O_5$: 509. $^1$HNMR (300 MHz, CDCl$_3$): 2.55 (s, 3H), 4.06 (d, J=1.2 Hz, 6H), 6.49 (d, J=5.3 Hz, 1H), 6.82 (s, 1H), 7.45-7.64 (m, 7H), 8.29-8.33 (m, 1H), 8.46 (d, J=8.9 Hz, 1H), 8.52 (d, J=5.3 Hz, 1H), 12.37 (s, 1H).

EXAMPLE 230

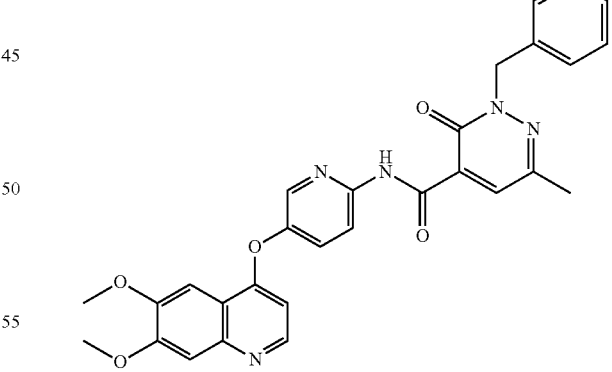

2-benzyl-N-(5-(6,7-dimethoxyquinolin-4-yloxy)pyridin-2-yl)-6-methyl-3-oxo-2,3-dihydropyridazine-4-carboxamide: MS (ESI pos. ion) m/z: 524 (MH+). Calc'd exact mass for $C_{29}H_{25}N_5O_5$: 523. $^1$HNMR (300 MHz, CDCl$_3$): 2.48 (s, 3H), 4.06 (s, 6H), 5.30 (s, 2H), 5.42 (s, 2H), 6.46 (d, J=5.3 Hz, 1H), 7.35 (d, J=6.7 Hz, 2H), 7.43-7.61 (m, 3H), 8.17 (s, 1H), 8.34 (s, 1H), 8.44 (d, J=8.9 Hz, 1H), 8.52 (d, J=5.1 Hz, 1H), 12.50 (s, 1H).

EXAMPLE 231

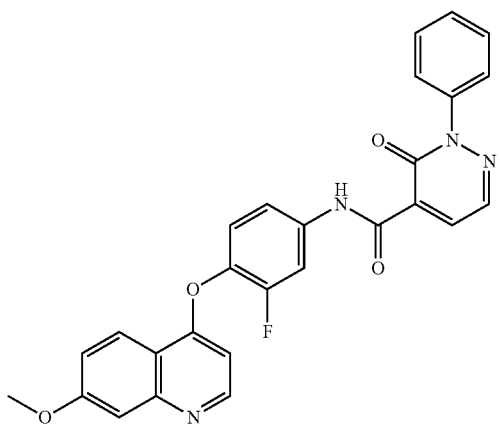

N-(3-fluoro-4-(7-methoxyquinolin-4-yloxy)phenyl)-3-oxo-2-phenyl-2,3-dihydropyridazine-4-carboxamide: MS (ESI pos. ion) m/z: 483 (MH+). Calc'd exact mass for $C_{27}H_{19}FN_4O_4$: 482. $^1$HNMR (300 MHz, CDCl$_3$): 3.97 (s, 3H), 5.30 (s, 1H), 6.41 (d, J=4.1 Hz, 1H), 7.19-7.28 (m, 3H), 7.58 (s, 3H), 7.96 (d, J=11.8 Hz, 1H), 8.24 (d, J=2.9 Hz, 2H), 8.28 (s, 1H), 8.42 (d, J=3.9 Hz, 1H), 8.60 (d, J=5.0 Hz, 1H), 11.89 (s, 1H).

EXAMPLE 232

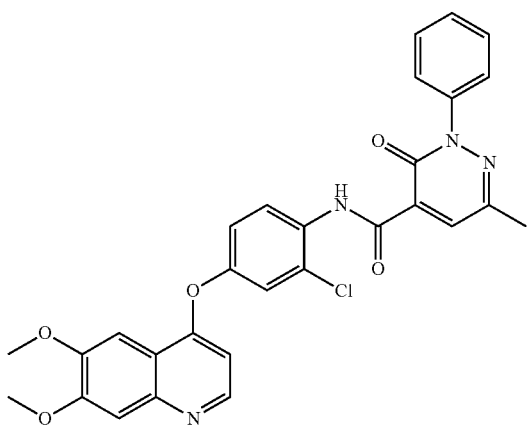

N-(2-chloro-4-(6,7-dimethoxyquinolin-4-yloxy)phenyl)-6-methyl-3-oxo-2-phenyl-2,3-dihydropyridazine-4-carboxamide: MS (ESI pos. ion) m/z: 543 (MH+). Calc'd exact mass for $C_{29}H_{23}ClN_4O_5$ 542. 1 H NMR (400 MHz, CDCl$_3$) 12.24 (s, 1 H), 8.68 (d, J=9.28 Hz, 1 H,), 8.53 (d, J=5.37 Hz, 1 H) 8.32 (s, 1 H) 7.73-7.40 (m, 7 H) 7.30 (s, 1H) 7.17 (d, J=7.81, 1H) 6.57 (d, J=4.40 Hz, 1 H,), 4.07 (s, 3 H), 4.05 (s, 3 H), 2.54 (s, 3 H,)

EXAMPLE 233

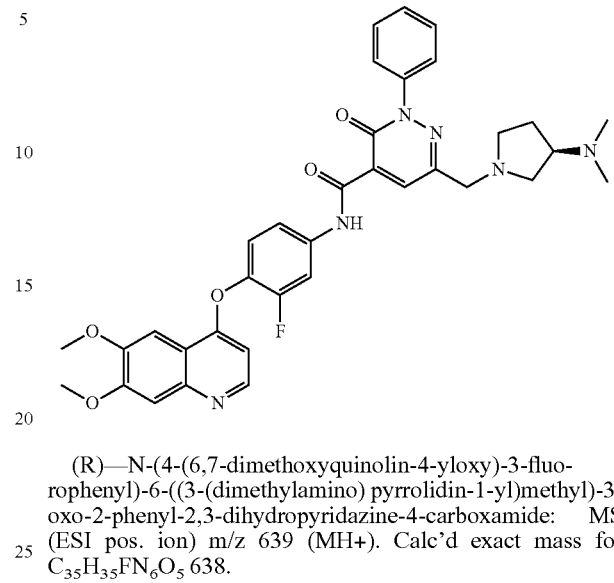

(R)—N-(4-(6,7-dimethoxyquinolin-4-yloxy)-3-fluorophenyl)-6-((3-(dimethylamino) pyrrolidin-1-yl)methyl)-3-oxo-2-phenyl-2,3-dihydropyridazine-4-carboxamide: MS (ESI pos. ion) m/z 639 (MH+). Calc'd exact mass for $C_{35}H_{35}FN_6O_5$ 638.

EXAMPLE 234

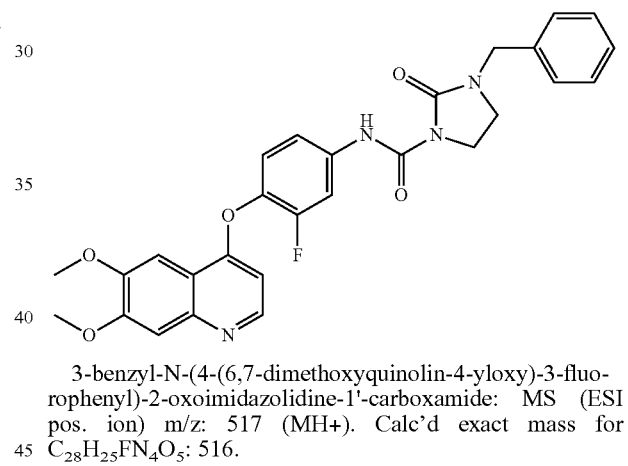

3-benzyl-N-(4-(6,7-dimethoxyquinolin-4-yloxy)-3-fluorophenyl)-2-oxoimidazolidine-1'-carboxamide: MS (ESI pos. ion) m/z: 517 (MH+). Calc'd exact mass for $C_{28}H_{25}FN_4O_5$: 516.

EXAMPLE 235

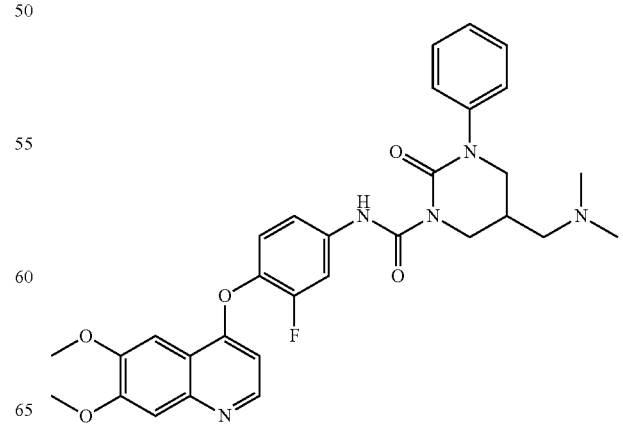

N-(4-(6,7-dimethoxyquinolin-4-yloxy)-3-fluorophenyl)-5-((dimethylamino)methyl)-2-oxo-3-phenyl-tetrahydropyrimidine-1(2H)-carboxamide: MS (ESI pos. ion) m/z: 574 (MH+). Calc'd exact mass for $C_{31}H_{32}FN_5O_5$: 573.

EXAMPLE 236

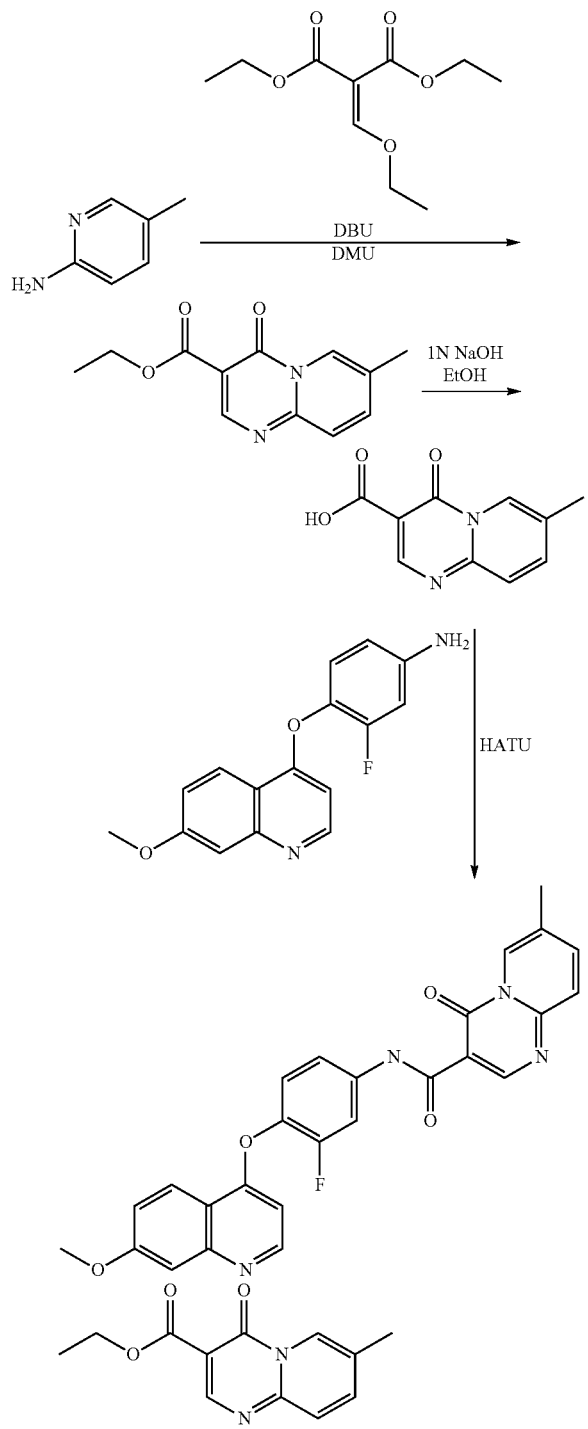

Step 1: Ethyl 7-methyl-4-oxo-4H-pyrido[1,2-a]pyrimidine-3-carboxylate. A mixture of diethyl 2-(ethoxymethylene)malonate (0.60 g, 3 mmol), 5-methylpyridin-2-amine (0.20 g, 2 mmol), DBU (0.1 ml, 0.9 mmol) in acetonitrile (2 g, 49 mmol) was heated under Microwave (CEM) at 150° C. (150 W) for 20 min. The resultant was diluted with dichloromethane and water, and the organic layer was dried over sodium sulfate. The organic solution was concentrated, and the residue was crystallized in dichloromethane and diethyl ether to give the title compound as a pale yellow solid (0.25 g, 58%): MS (ESI pos. ion) m/z: 233 (MH+). Calc'd exact mass for $C_{12}H_{12}N_2O_3$: 232.

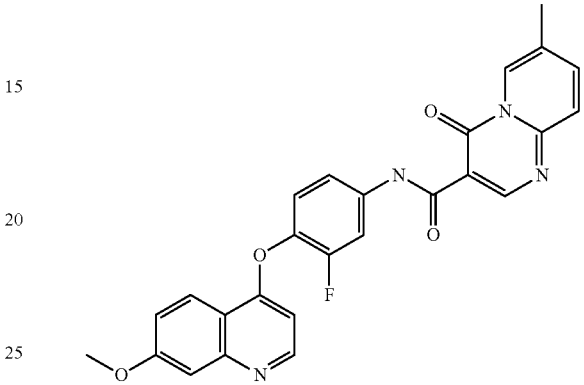

Steps 2 and 3: N-(3-fluoro-4-(7-methoxyquinolin-4-yloxy)phenyl)-7-methyl-4-oxo-4H-pyrido[1,2-a]pyrimidine-3-carboxamide. To a suspension of ethyl 7-methyl-4-oxo-4H-pyrido[1,2-a]pyrimidine-3-carboxylate (0.11 g, 0.47 mmol) in ethanol was added 1 N NaOH solution (3 mL, 3 mmol) at RT. The reaction mixture was stirred for 16 at RT. The resultant was concentrated, and the residue was diluted with water. The aqueous solution was washed with diethyl ether and then acidified with 2N HCl solution and extracted with dichloromethane. The organic solution was dried over magnesium sulfate and concentrated to give a yellow solid (0.090 g, 93%): MS (ESI pos. ion) m/z: 205 (MH+). Calc'd exact mass for $C_{10}H_8N_2O_3$: 204. A mixture of 3-fluoro-4-(7-methoxyquinolin-4-yloxy)benzenamine (0.08 g, 0.3 mmol), 7-methyl-4-oxo-4H-pyrido[1,2-a]pyrimidine-3-carboxylic acid (0.08 g, 0.4 mmol), HATU (0.4 g, 0.8 mmol) in dichloromethane was stirred for 16 h. Then, the mixture was diluted with dichloromethane and aq. NaHCO3 solution. The organic layer was separated, dried over Na2SO4 and concentrated. The residue was purified by ISCO (0-5% MeOH in EtOAc) to give the title compound as a yellow solid (0.032 g, 24%): MS (ESI pos. ion) m/z: 471 (MH+), Calc'd exact mass for $C_{26}H_{19}FN_4O_4$: 470; $^1$HNMR (400 MHz, CDCl$_3$): 11.4 (s, 1H), 9.4 (s, 1H), 9.1 (s, 1H), 8.6 (d, J=6 Hz, 1H), 8.3 (d, J=9 Hz, 1H), 8.0 (dd, J=3, 12 Hz, 1H), 7.9 (m, 2H), 7.5 (m, 1H), 7.4 (d, J=3 Hz, 1H), 7.0-7.3 (m, 2H), 6.4 (d, J=3 Hz, 1H), 3.98 (s, 3H), 2.57 (s, 3H).

EXAMPLE 237

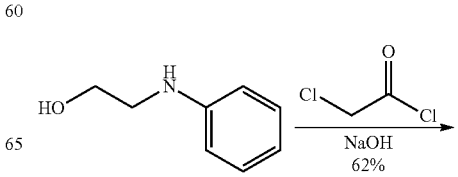

-continued

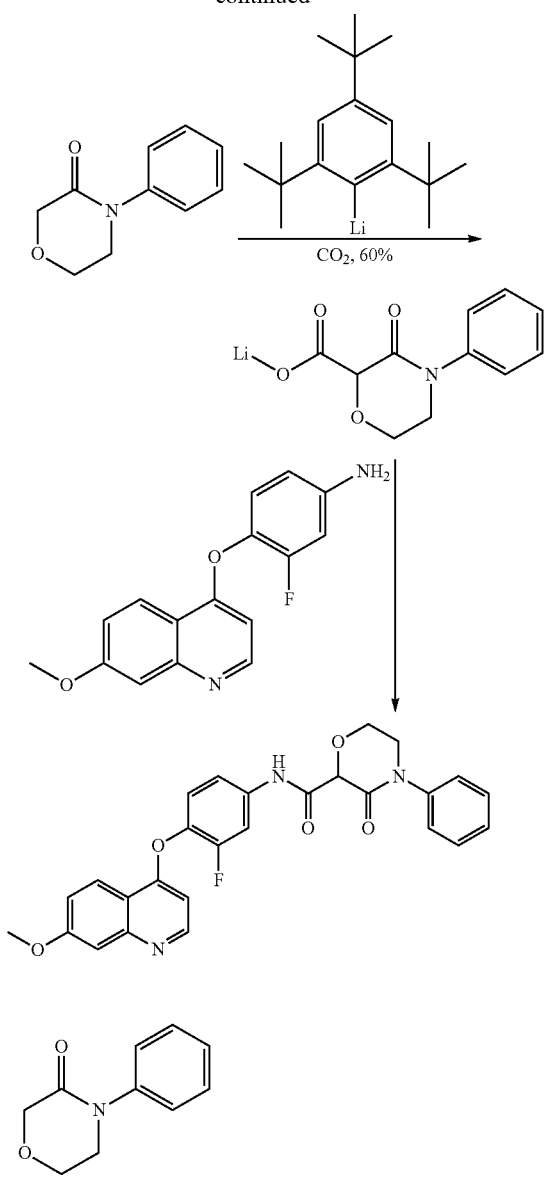

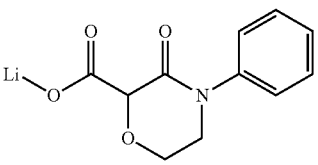

Step 2: Lithium 3-oxo-4-phenylmorpholine-2-carboxylate. A dry 100 mL Schlenk-type flask was fitted with a nitrogen/vacuum line and charged with 2-bromo-1,3,5-tri-tert-butylbenzene (0.521 g, 1.601 mmol), 20 mL dry THF, and a stirbar. The solution was cooled to −78° C. and treated with 2.5M butyllithium (0.582 ml, 1.456 mmol). The reaction was stirred for 15 min and treated with 4-phenylmorpholin-3-one (0.258 g, 1.456 mmol) dissolved in 2 mL dry THF dropwise over 5 min. The reaction was stirred for 2 h at −78° C. The side arm compartment of the Schlenk-type flask was charged with ~1 g dry ice. The system was sealed, and the dry ice was allowed to sublime into the solution. After 30 min, a nitrogen needle was fitted to the flask, and a solid was noted in the solution. The cooling bath was removed, which caused the solids to bubble (presumably dry ice). The solution was allowed to warm to RT overnight. The solution was diluted with 40 mL water and extracted with dichloromethane (2×10 mL). The water was concentrated in vacuo and dried at 60° C. and 0.15 mmHg to afford lithium 3-oxo-4-phenylmorpholine-2-carboxylate (0.200 g, 60.5% yield). $^1$H NMR (400 MHz, D$_2$O) 3.72 (t, J=5.23 Hz, 2 H), 3.99 (dt, J=12.10, 5.29 Hz, 1 H), 4.08 (dt, J=12.15, 5.22 Hz, 1 H), 4.61 (s, 1 H), 7.24-7.28 (m, 2 H), 7.32 (tt, 1 H), 7.38-7.44 (m, 2 H).

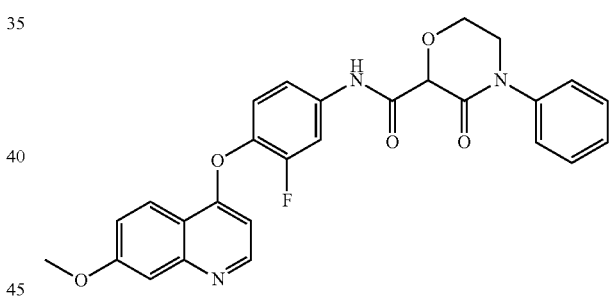

Step 1: 4-Phenylmorpholin-3-one. A 250-mL flask was charged with 2-anilinoethanol (9.17 ml, 73.2 mmol), 9 mL dry EtOH, an overhead stirrer, a calibrated pH probe, and 27 mL water. An addition funnel was charged with 10 N sodium hydroxide solution (45.4 ml, 454 mmol). The solution was heated to 41° C., and treated with chloracetyl chloride (17.5 ml, 220 mmol) via a syringe pump over 1 h. The sodium hydroxide solution was simultaneously added to the stirring solution so that the pH was maintained between 12 and 12.5. After the addition was complete, the solution was cooled to 0° C. and stirred for 1 h. The solids were collected and washed with water (2×60 mL cold water). The solids were dried at 50° C. at 0.2 mm Hg for 36 h to afford 4-phenylmorpholin-3-one (8.10 g, 62.5% yield). $^1$H NMR (400 MHz, CHLOROFORM-d) 3.75-3.80 (m, 2 H) 4.02-4.06 (m, 2 H) 4.35 (s, 2 H) 7.27-7.36 (m, 3 H) 7.39-7.46 (m, 2 H). $^{13}$C NMR (101 MHz, CHLOROFORM-d) 49.69 (s, 1 C) 64.14 (s, 1 C) 68.57 (s, 1 C) 125.48 (s, 2 C) 127.15 (s, 1 C) 129.30 (s, 2 C) 141.31 (s, 1 C) 166.59 (s, 1 C).

Step 3: N-(3-Fluoro-4-(7-methoxyquinolin-4-yloxy)phenyl)-3-oxo-4-phenylmorpholine-2-carboxamide. A dry, 10 mL schlenk-type flask was charged with a stirbar, lithium 3-oxo-4-phenylmorpholine-2-carboxylate (0.096 g, 0.42 mmol), triethylammonium hydrochloride (0.058 g, 0.42 mmol), 3H-[1,2,3]triazolo[4,5-b]pyridin-3-ol (0.072 g, 0.53 mmol), and evacuated. The flask was back-filled with nitrogen and treated with 2 mL dry THF and 1 mL dry NMP. To the stirring solution was added Si-DCC (0.55 g, 0.53 mmol) followed by 3-fluoro-4-(7-methoxyquinolin-4-yloxy)benzenamine (0.100 g, 0.35 mmol). The reaction was stirred for 3 d at RT, and then 60° C. for 24 h. The slurry was filtered through a 0.22 μm frit, and the THF removed. The crude was purified by HPLC (Waters Spherisorb S5 column (PN PSS830195, 20×250 mm, 60 Å pore, 5 μm particle size)) to afford the title compound (0.026 g, 15.2% yield) $^1$H NMR (400 MHz, Chloroform-d) 3.74 (ddd, J=12.32, 3.72, 3.52 Hz, 1 H), 3.95-4.03 (m, 4 H), 4.23 (dt, J=12.42, 3.91 Hz, 1 H), 4.27-4.38 (m, 1 H), 5.06 (s, 1 H), 6.37 (dd, J=5.23, 1.12 Hz, 1 H), 7.20 (t, J=8.56 Hz, 1 H), 7.24 (dd, J=9.15, 2.49 Hz, 1 H), 7.27 (ddd, J=8.83, 2.47, 1.12 Hz, 1 H), 7.32-7.41 (m, 3 H), 7.43 (d, J=2.45 Hz, 1

H), 7.46-7.51 (m, 2 H), 7.81 (dd, J=12.03, 2.35 Hz, 1 H), 8.26 (d, J=9.19 Hz, 1 H), 8.59 (d, J=5.18 Hz, 1 H), 9.66 (br. s., 1 H). MS (ESI pos. ion) m/z=488, calc'd for $C_{27}H_{22}FN_3O_5$ 487.

EXAMPLE 238

N-(5-(7-methoxyquinolin-4-yloxy)pyridin-2-yl)-1-methyl-3-oxo-2-phenyl-2,3-dihydro-1H-pyrazole-4-carboxamide

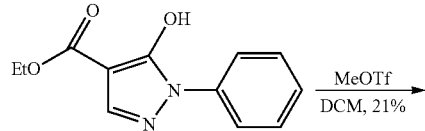

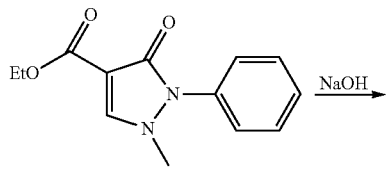

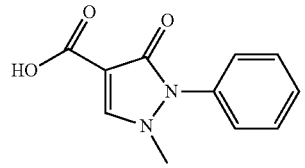

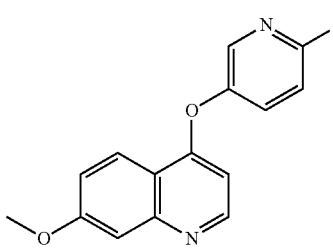

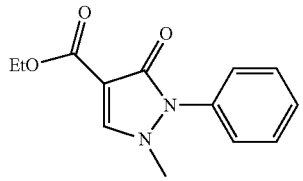

Step 1: Ethyl 1-methyl-3-oxo-2-phenyl-2,3-dihydro-1H-pyrazole-4-carboxylate. To a solution of ethyl 3-oxo-2-phenyl-2,3-dihydro-1H-pyrazole-4-carboxylate (1000 mg, 5.0 mmol) in dichloromethane (10 mL) was added methyl trifluoromethanesulfonate (1200 mg, 7.3 mmol). The red solution was stirred at room temperature. After 14 h, the mixture was partitioned between dichloromethane and $NaHCO_3$ (sat). The aqueous was extracted with dichloromethane (2×). The combined organic was dried over $Na_2SO_4$, concentrated and purified on silica. The product was triturated with EtOAc-hexane-$CHCl_3$ to give the pure product as crystals (260 mg, 21%). Calc'd for $C_{12}H_{12}N_2O_3$, 232.08; MS (ESI pos. ion) m/z: 233 (MH+). $^1$H NMR (400 MHz, CHLOROFORM-d): 1.36 (t, J=7.04 Hz, 3 H), 3.39 (s, 3 H), 4.32 (q, J=7.17 Hz, 2 H), 7.32 (d, J=7.43 Hz, 2 H), 7.42 (t, J=7.34 Hz, 1 H), 7.50 (t, J=7.73 Hz, 2 H), 7.99 (s, 1 H).

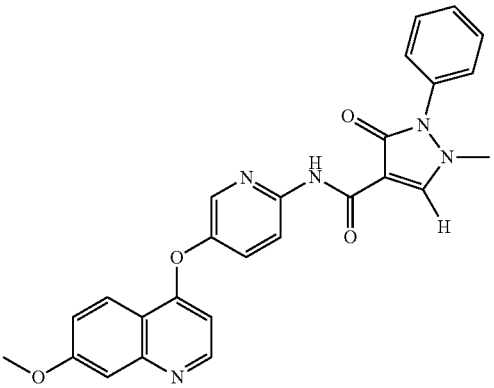

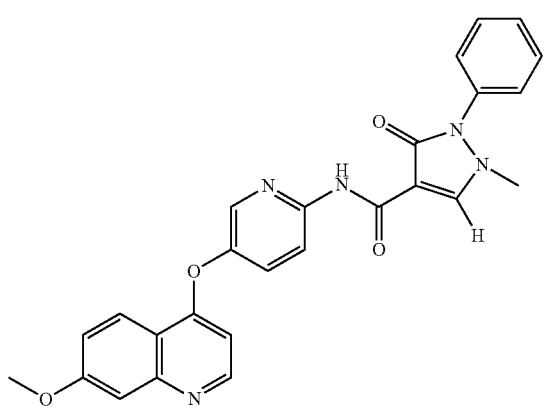

Step 2: N-(5-(7-methoxyquinolin-4-yloxy)pyridin-2-yl)-1-methyl-3-oxo-2-phenyl-2,3-dihydro-1H-pyrazole-4-carboxamide. A solution of ethyl 1-methyl-3-oxo-2-phenyl-2,3-dihydro-1H-pyrazole-4-carboxylate (260 mg, 1056 µmol) in MeOH was treated with NaOH (1000 µl, 5000 µmol) in $H_2O$ (3 mL). The mixture was heated to 60° C. for 30 min and then cooled to room temperature. Then, the mixture was neutralized with aq. HCl (5 N, 1.1 mL) and concentrated to dryness. The residue was further dried with (azeotrope distillation with toluene, 3×5 mL). The resulting carboxylic acid was mixed with 5-(7-methoxyquinolin-4-yloxy)pyridin-2-amine (282 mg, 1054 µmol), $Et_3N$ (500 µl, 3587 µmol), and HATU (401 mg, 1054 µmol) in DMF (4 mL)-dichloromethane (5 mL) and was stirred at 60° C. for 2 h. Upon cooling to room temperature, the mixture was diluted with EtOAc containing 10% MeOH (30 mL) and washed with $H_2O$. The organic layer was dried over $Na_2SO_4$, concentrated, and eluded on silica (1-10% 2N $NH_3$-MeOH in $CHCl_3$). The product was further purified on preparative HPLC to afford a white powder (100 mg, 20%).

Calc'd for $C_{26}H_{21}N_5O_4$: 467.16; MS (ESI pos. ion) m/z: 468 (MH+). $^1$H NMR (400 MHz, DMSO-$d_6$) 3.49 (s, 3 H) 3.95 (s, 3 H) 6.55 (d, J 5.1, 1 H) 7.30 (dd, J 2.0, 9.0, 1 H) 7.42 (s, 1 H) 7.59 (s, 17 H) 7.50-7.60 (m, 5 H), 7.84 (dd, J 2.8, 9.2, 1H), 8.22 (d, J 9.2, 1H), 8.34-8.38 (m, 2 H) 8.62 (d, J 5.3, 1 H) 8.69 (s, 1 H) 10.86 (s, 1 H).

EXAMPLE 239

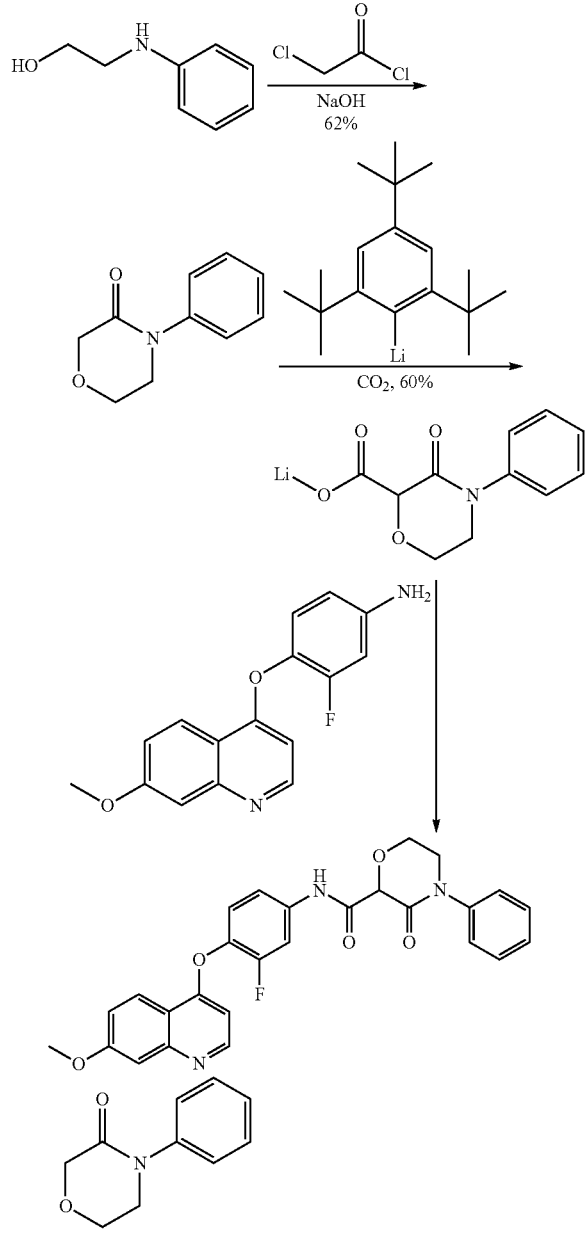

Step 1: 4-Phenylmorpholin-3-one. A 250-mL flask was charged with 2-anilinoethanol (9.17 ml, 73.2 mmol), 9 mL dry EtOH, an overhead stirrer, a calibrated pH probe, and 27 mL water. An addition funnel was charged with 10 N sodium hydroxide solution (45.4 ml, 454 mmol). The solution was heated to 41° C., and treated with chloracetyl chloride (17.5 ml, 220 mmol) via a syringe pump over 1 h. The sodium hydroxide solution was simultaneously added to the stirring solution so that the pH was maintained between 12 and 12.5. After the addition was complete, the solution was cooled to 0° C. and stirred for 1 h. The solids were collected and washed with water (2×60 mL cold water). The solids were dried at 50° C. at 0.2 mm Hg for 36 h to afford 4-phenylmorpholin-3-one (8.10 g, 62.5% yield). $^1$H NMR (400 MHz, CHLOROFORM-d) 3.75-3.80 (m, 2 H) 4.02-4.06 (m, 2 H) 4.35 (s, 2 H) 7.27-7.36 (m, 3 H) 7.39-7.46 (m, 2 H). $^{13}$C NMR (101 MHz, CHLOROFORM-d) 49.69 (s, 1 C) 64.14 (s, 1 C) 68.57 (s, 1 C) 125.48 (s, 2 C) 127.15 (s, 1 C) 129.30 (s, 2 C) 141.31 (s, 1 C) 166.59 (s, 1 C).

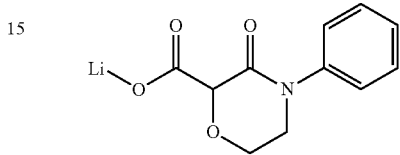

Step 2: Lithium 3-oxo-4-phenylmorpholine-2-carboxylate. A dry 100 mL Schlenk-type flask was fitted with a nitrogen/vacuum line and charged with 2-bromo-1,3,5-tri-tert-butylbenzene (0.521 g, 1.601 mmol), 20 mL dry THF, and a stirbar. The solution was cooled to −78° C. and treated with 2.5M butyllithium (0.582 ml, 1.456 mmol). The reaction was stirred for 15 min and treated with 4-phenylmorpholin-3-one (0.258 g, 1.456 mmol) dissolved in 2 mL dry THF dropwise over 5 min. The reaction was stirred for 2 h at −78° C. The side arm compartment of the Schlenk-type flask was charged with ~1 g dry ice. The system was sealed, and the dry ice was allowed to sublime into the solution. After 30 min, a nitrogen needle was fitted to the flask, and a solid was noted in the solution. The cooling bath was removed, which caused the solids to bubble (presumably dry ice). The solution was allowed to warm to RT overnight. The solution was diluted with 40 mL water and extracted with dichloromethane (2×10 mL). The water was concentrated in vacuo and dried at 60° C. and 0.15 mmHg to afford lithium 3-oxo-4-phenylmorpholine-2-carboxylate (0.200 g, 60.5% yield). $^1$H NMR (400 MHz, $D_2O$) 3.72 (t, J=5.23 Hz, 2 H), 3.99 (dt, J=12.10, 5.29 Hz, 1 H), 4.08 (dt, J=12.15, 5.22 Hz, 1 H), 4.61 (s, 1 H), 7.24-7.28 (m, 2 H), 7.32 (tt, 1 H), 7.38-7.44 (m, 2 H).

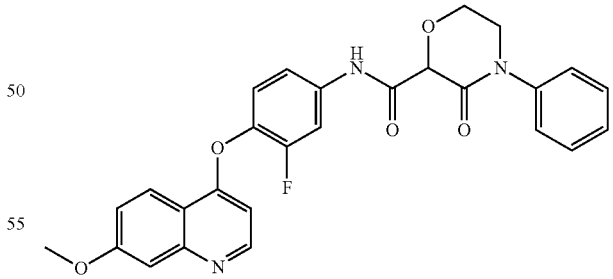

Step 3: N-(3-Fluoro-4-(7-methoxyquinolin-4-yloxy)phenyl)-3-oxo-4-phenylmorpholine-2-carboxamide. A dry, 10 mL schlenk-type flask was charged with a stirbar, lithium 3-oxo-4-phenylmorpholine-2-carboxylate (0.096 g, 0.42 mmol), triethylammonium hydrochloride (0.058 g, 0.42 mmol), 3H-[1,2,3]triazolo[4,5-b]pyridin-3-ol (0.072 g, 0.53 mmol), and evacuated. The flask was back-filled with nitrogen and treated with 2 mL dry THF and 1 mL dry NMP. To the stirring solution was added Si-DCC (0.55 g, 0.53 mmol)

followed by 3-fluoro-4-(7-methoxyquinolin-4-yloxy)benzenamine (0.100 g, 0.35 mmol). The reaction was stirred for 3 d at RT, and then 60° C. for 24 h. The slurry was filtered through a 0.22 μm frit, and the THF removed. The crude was purified by HPLC (Waters Spherisorb S5 column (PN PSS830195, 20×250 mm, 60 Å pore, 5 μm particle size)) to afford the title compound (0.026 g, 15.2% yield) $^1$H NMR (400 MHz, Chloroform-d) 3.74 (ddd, J=12.32, 3.72, 3.52 Hz, 1 H), 3.95-4.03 (m, 4 H), 4.23 (dt, J=12.42, 3.91 Hz, 1 H), 4.27-4.38 (m, 1 H), 5.06 (s, 1 H), 6.37 (dd, J=5.23, 1.12 Hz, 1 H), 7.20 (t, J=8.56 Hz, 1 H), 7.24 (dd, J=9.15, 2.49 Hz, 1 H), 7.27 (ddd, J=8.83, 2.47, 1.12 Hz, 1 H), 7.32-7.41 (m, 3 H), 7.43 (d, J=2.45 Hz, 1 H), 7.46-7.51 (m, 2 H), 7.81 (dd, J=12.03, 2.35 Hz, 1 H), 8.26 (d, J=9.19 Hz, 1 H), 8.59 (d, J=5.18 Hz, 1 H), 9.66 (br. s., 1 H). MS (ESI pos. ion) m/z=488, calc'd for $C_{27}H_{22}FN_3O_5$ 487.

The following additional compounds can also be made using the methodology generally set forth above:

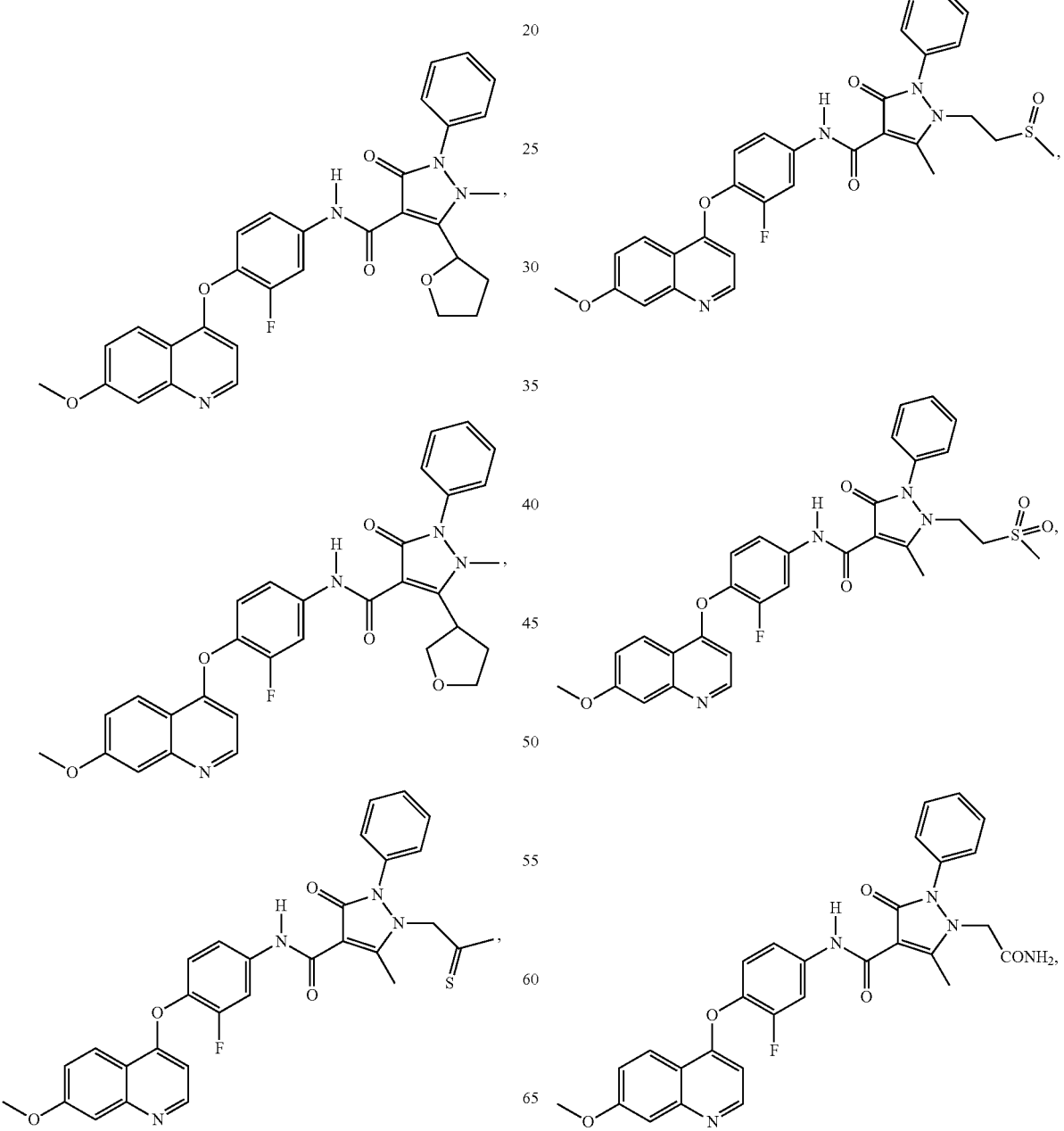

233
-continued
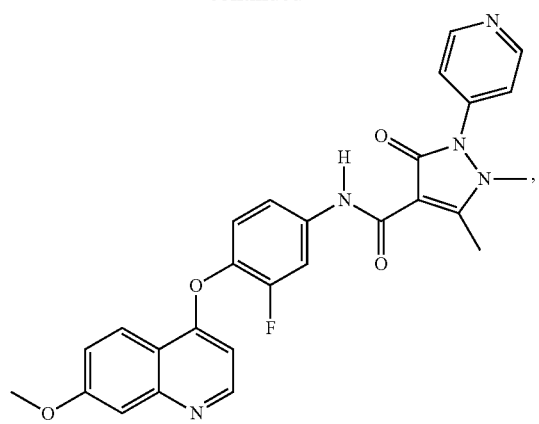
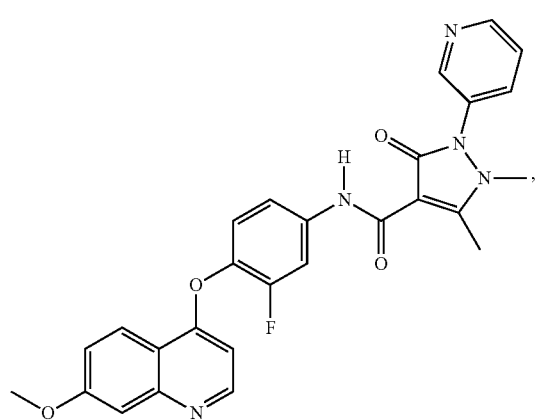
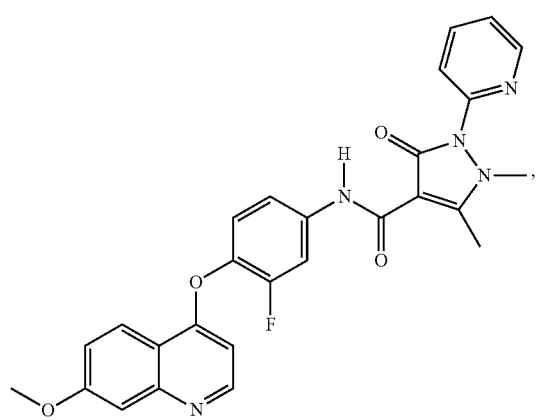
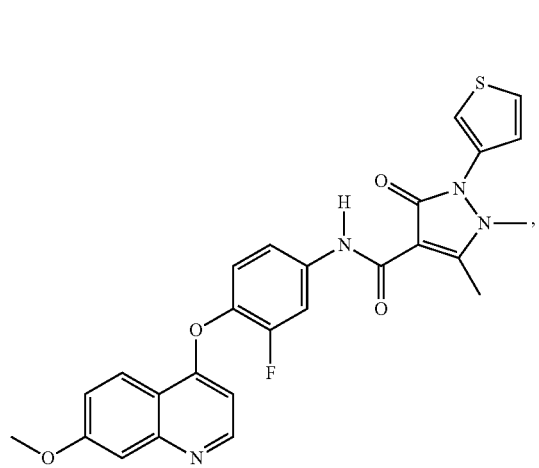
234
-continued
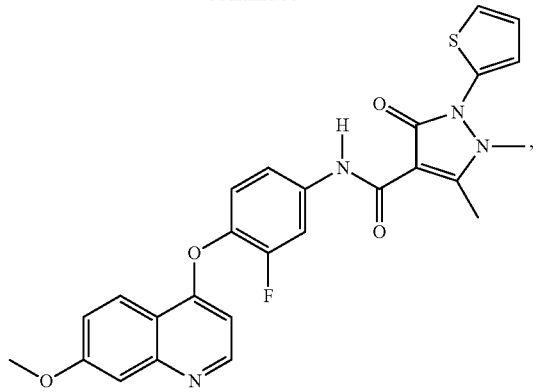
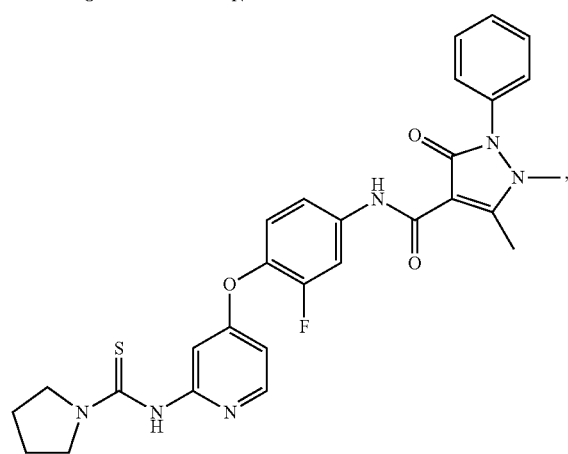
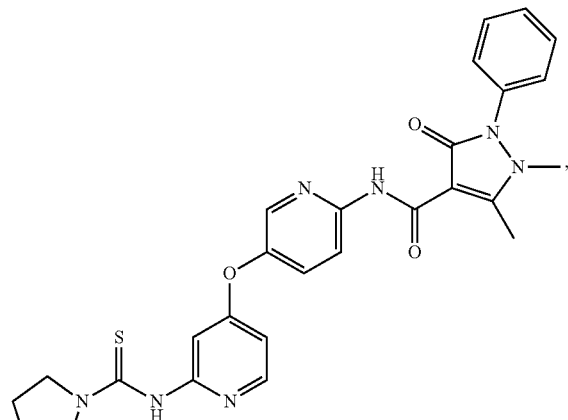
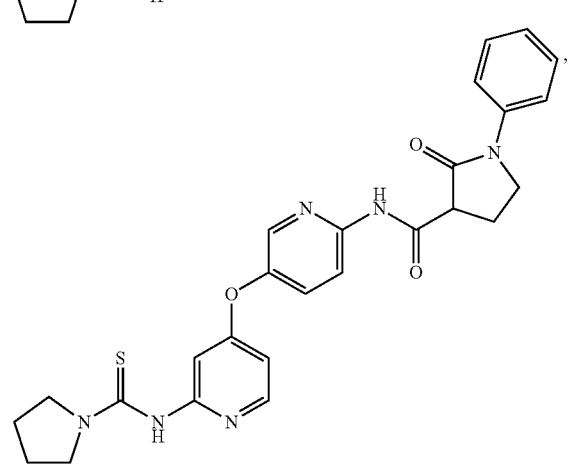

235
-continued
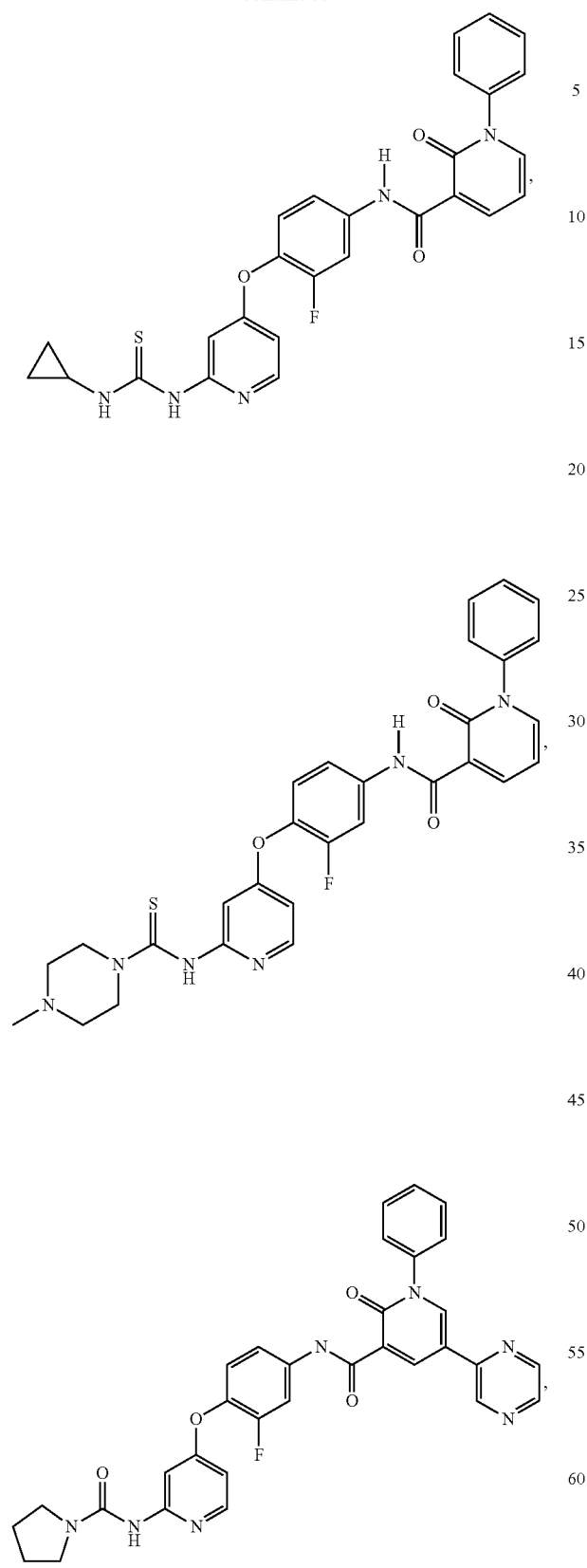
236
-continued
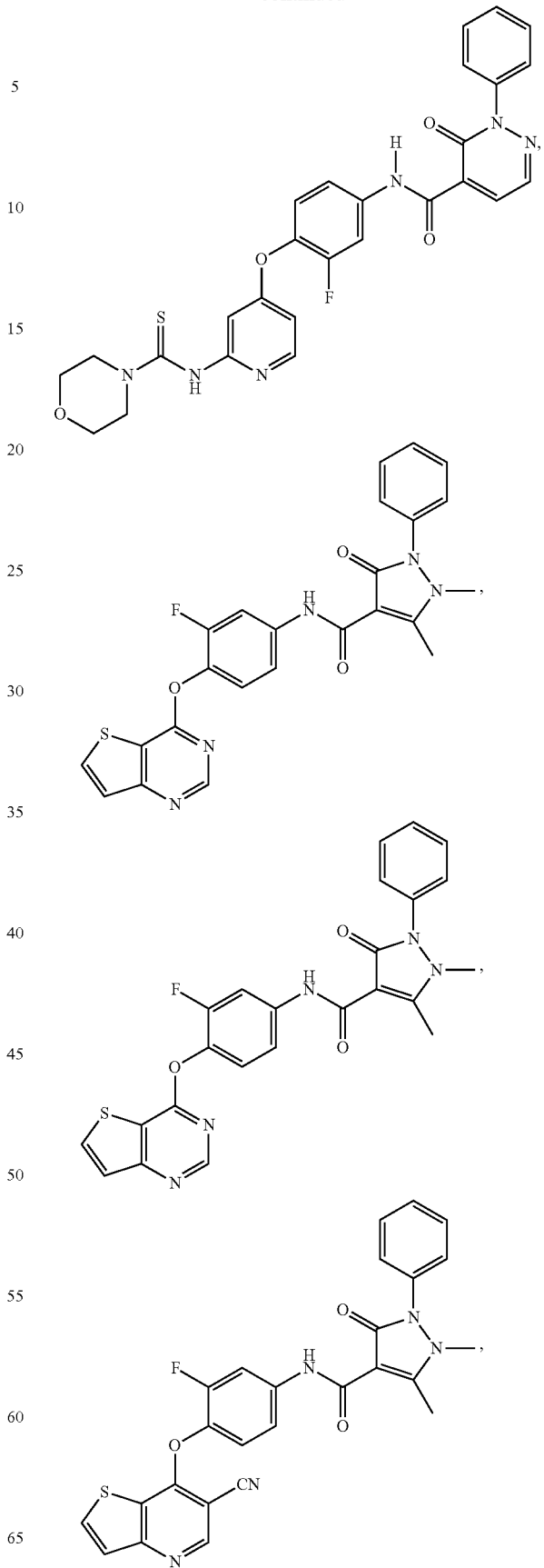

237
-continued
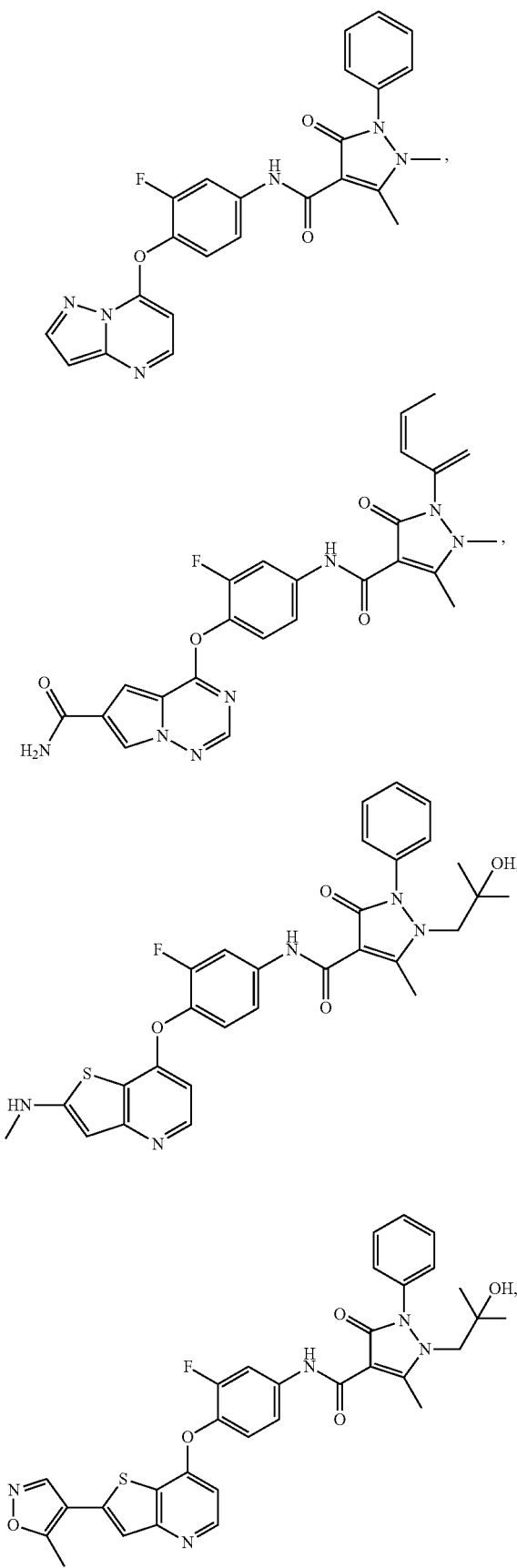
238
-continued
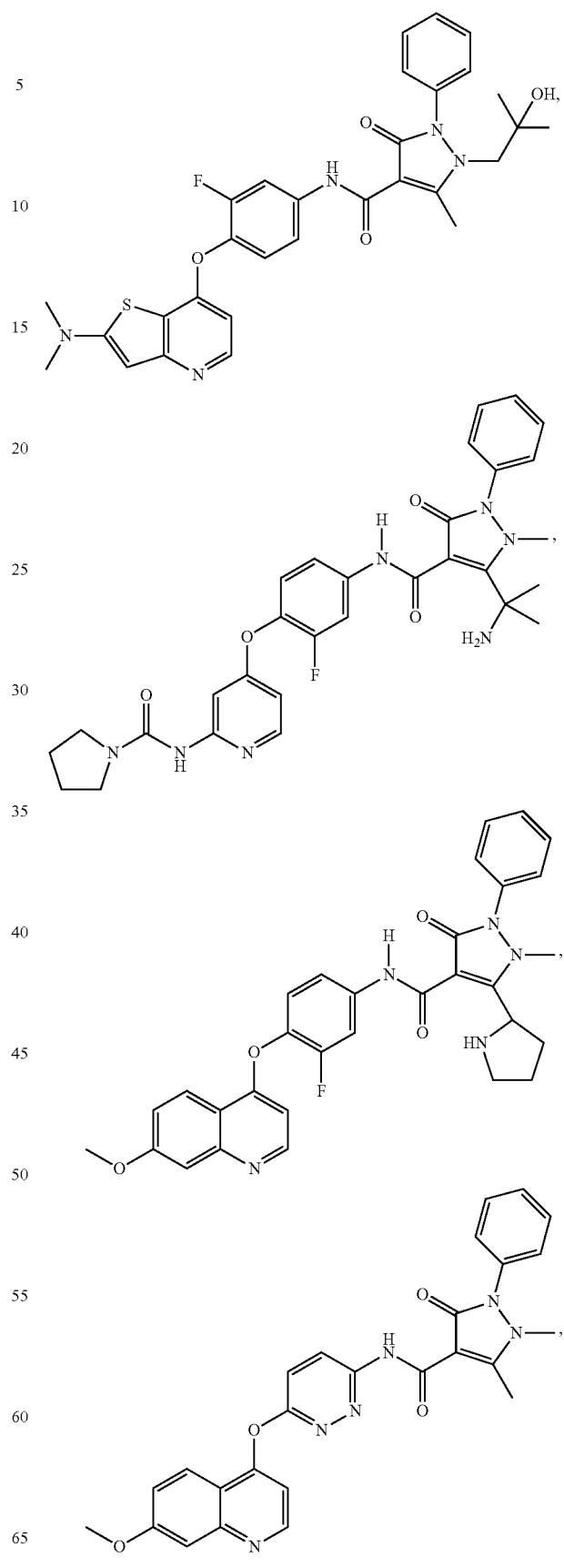

239
-continued
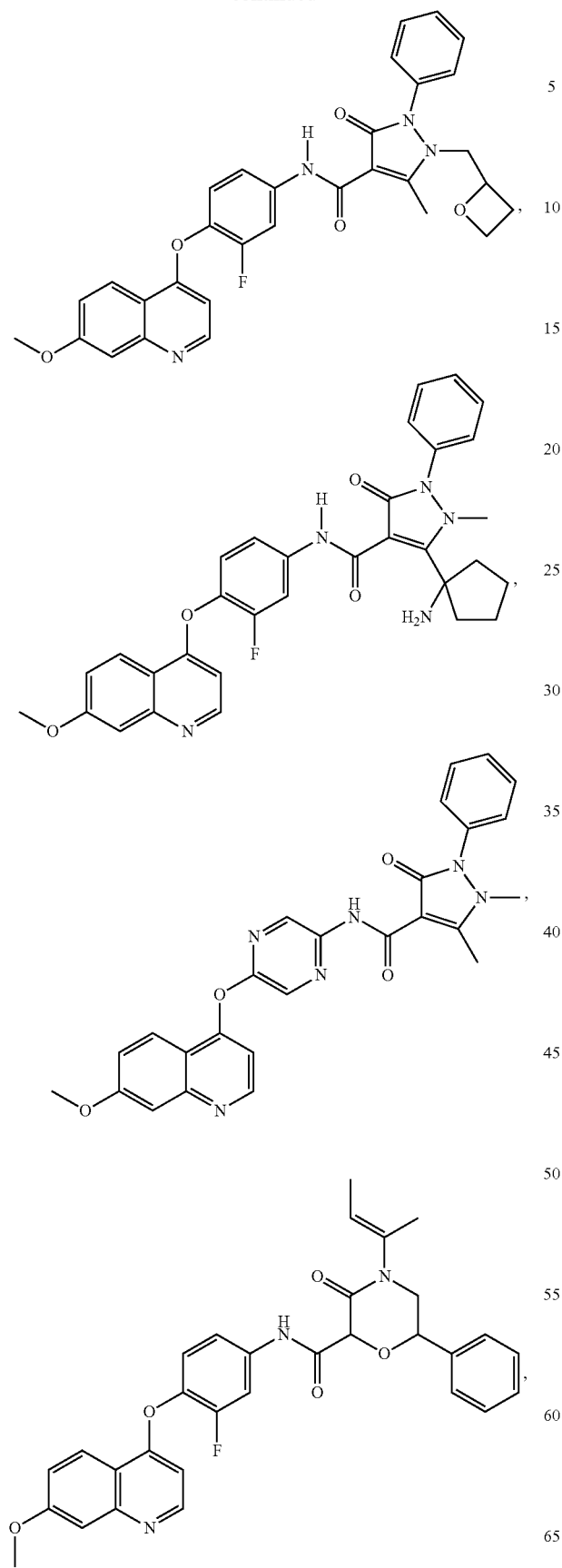
240
-continued
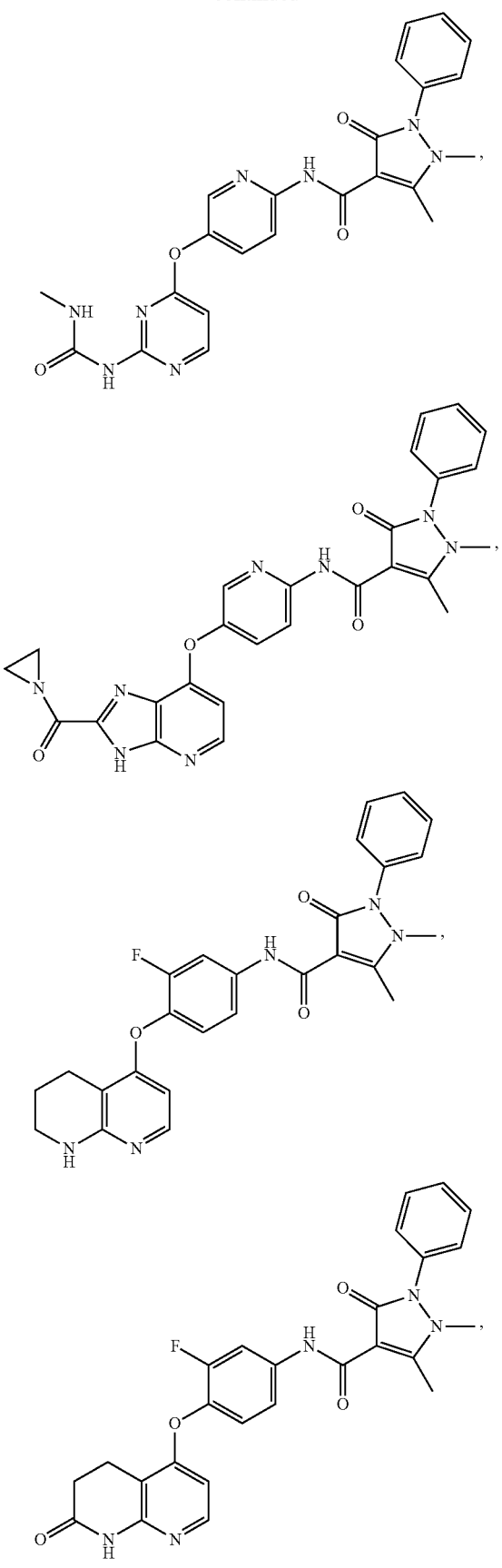

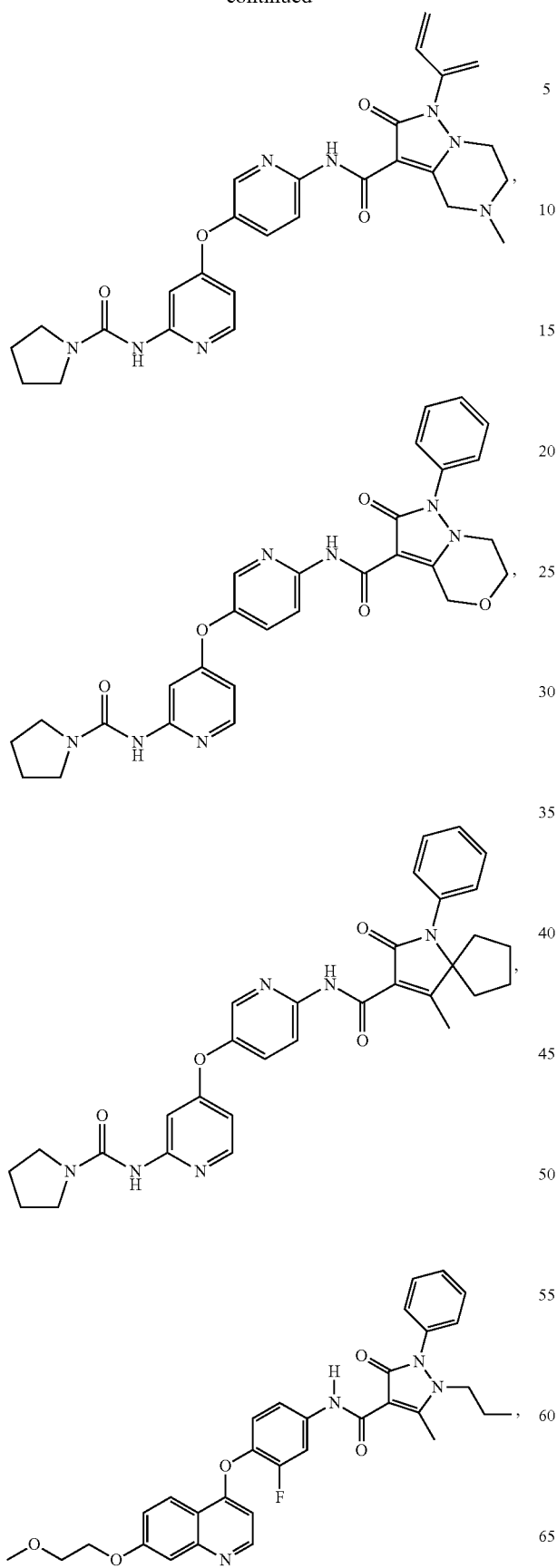
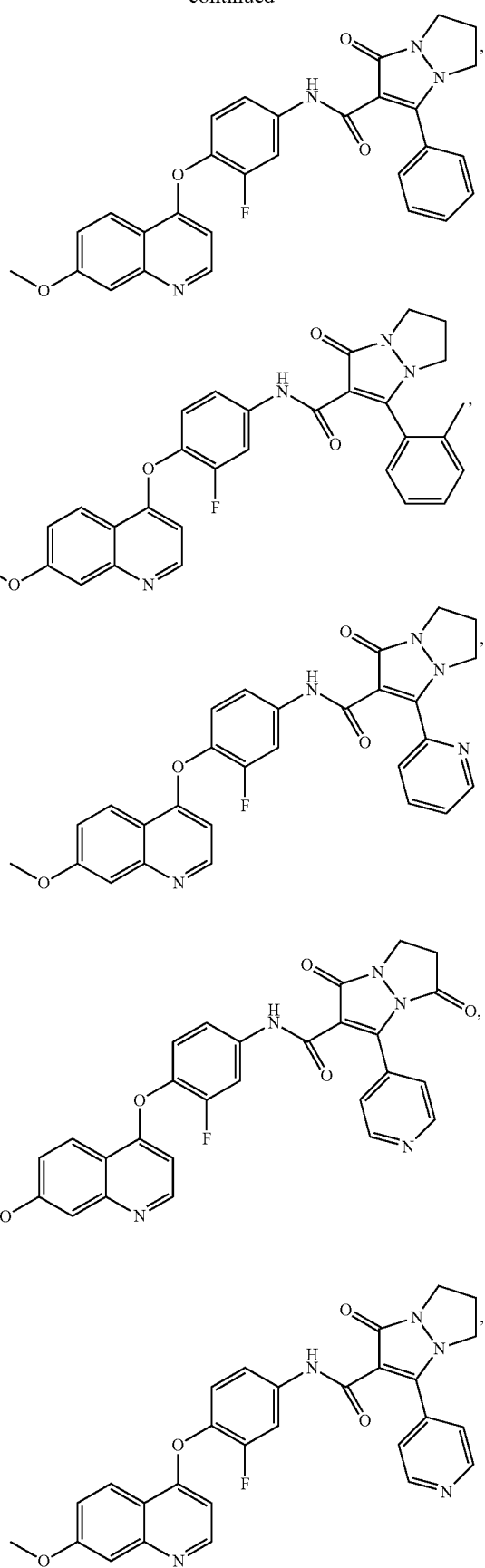

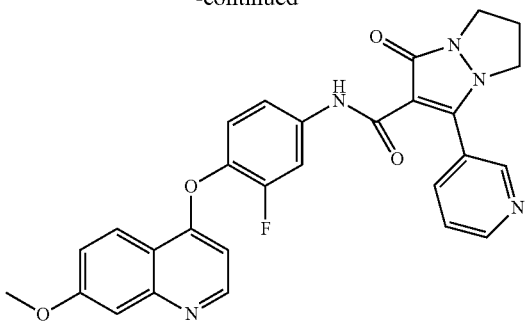

Although the pharmacological properties of the compounds of Formulas I-II vary with structural change, in general, activity possessed by compounds of Formulas I-II may be demonstrated in vivo. The pharmacological properties of the compounds of this invention may be confirmed by a number of pharmacological in vitro assays. The exemplified pharmacological assays, which follow have been carried out with the compounds according to the invention and their salts. Compounds of the present invention showed inhibition of c-Met kinase at doses less than 2 μM.

BIOLOGICAL TESTING

The efficacy of the compounds of the invention as inhibitors of HGF related activity is demonstrated as follows.

c-Met Receptor Assay

Cloning, Expression and Purification of C-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCTAAATCCA-GAGCTGGTCCAGGCA-3' (SEQ ID NO. 1) and reverse primer 5'-ACAACAGAATTCAATACGGAGCGACA-CATTTTACGTT-3' (SEQ ID NO. 2). The PCR product is cloned into a modified pFastBac1 expression vector (harboring the gene for *S. japonicum* glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione Sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of Human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche #10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10.00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

|   |   | Final concentration |
|---|---|---|
| a) | 1 00 mM ATP (Sigma #A7699) | 25 mM |
| b) | 1.0M $MgCl_2$ (Sigma #M-0250) | 100 mM |
| c) | 200 mM Sodium Orthovanadate (Sigma #S-6508) | 15 mM |
| d) | 1.0M Tris-HCl, pH 7.00 (in house) | 50 mM |
| e) | $H_2O$ |   |
| f) | GST-cMET | 0.2-0.5 mg/mL |

After incubation, the solution is concentrated in a Vivaspin 20 ml Concentrator to a volume less than 2.00 ml. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

|  |  |  | Per 1 L |
| --- | --- | --- | --- |
| 60 mM HEPES pH 7.4 | 1M stock | 16.7 X | 60 mL |
| 50 mM NaCl | 5M stock | 100 X | 10 mL |
| 20 mM MgCl$_2$ | 1M stock | 50 X | 20 mL |
| 5 mM MnCl$_2$ | 1M stock | 200 X | 5 mL |

When the assay is carried out, freshly add:

| 2 mM DTT | 1M stock | 500 X |
| --- | --- | --- |
| 0.05% BSA | 5% stock | 100 X |
| 0.1 mM Na$_3$OV$_4$ | 0.1M stock | 1000 X |

The HTRF buffer contains:
50 mM Tris-HCl (pH 7.5), 100 mM NaCl, 0.1% BSA, 0.05% Tween 20.5 mM EDTA Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
0.1 nM final Eu-PT66
11 nM final SA-APC Methods:
1. Dilute GST-cMet (P) enzyme in kinase buffer as follows:
   Prepare 8 nM GST-cMet (P) working solution (7.32 µM to 8 nM, 915×, 10 µL to 9.15 mL). In a 96 well clear plate [Costar # 3365] add 100 µL in eleven columns, in one column add 100 µL kinase reaction buffer alone.
2. Assay plate preparation:
   Use Biomek FX to transfer 10 µL 8 nM GST-cMet (P) enzyme, 48.4 µL kinase reaction buffer, 1.6 µL compound (in DMSO) (Start concentration at 10 mM, 1 mM and 0.1 mM, sequential dilution 1:3 to reach 10 test points) in a 96 well costar clear plate [Costar # 3365], mix several times. Then incubate the plate at RT for 30 min.
3. Prepare Gastrin and ATP working solution in kinase reaction buffer as follows:

| Prepare 4 µM Gastrin and 16 µM ATP working solution | | |
| --- | --- | --- |
|  |  | Per 10 mL |
| Gastrin 4 nM stock | (500 µM to 4 µM, 125 X) | 80 µL |
| ATP 16 nM stock | (1000 µM to 16 µM, 62.5 X) | 160 µL |

Use Biomek FX to add 20 µl ATP and Gastrin working solution to the assay plate to start reaction, incubate the plate at RT for 1 h.
4. Transfer 5 µL reaction product at the end of 1 h into 80 µL HTRF buffer in black plate [Costar # 3356], read on Discover after 30 min incubation.

Assay Condition Summary:

| K$_M$ ATP * | 6 µM |
| --- | --- |
| [ATP] | 4 µM |
| K$_M$ Gastrin/p(EY) | 3.8 µM |
| [gastrin] | 1 µM |
| [enzyme] | 1 nM |

K$_M$ ATP, K$_M$ gastrin for various enzymes were determined by HTRF/$^{33}$P labeling and HTRF methods.

Examples 1-28, 30, 33-34, 36-37, and 39-48 exhibited activity with IC$_{50}$ values less than 0.5 µM.

c-Met Cell-based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. 2×10$^4$ cells in medium were plated per well in a 96 well plate and incubated at 37° C. overnight. The cells were serum-starved by replacing the growth media with basic medium (DMEM low glucose +0.1 BSA, 120 µL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 µL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 µL, Roche Protease inhibitor (Complete, # 1-697-498) 2 tablets, Phosphatase Inhibitor 11 (Sigma, #P-5726) 200 µL, and a sodium vanadate solution (containing 900 µL PBS, 100 µL 300 mM NaVO$_3$, 6 µL H$_2$O$_2$ (30% stock) and stirred at RT for 15 min) (90 µL). The cells were washed once with ice cold 1×PBS (GIBCO, #14190-136), then lysis buffer (60 µL) was added and the cells were incubated on ice for 20 min.

The IGEN assay was performed as follows: Dynabeads M-280 streptavidin beads were pre-incubated with biotinylated anti-human HGFR (240 µL anti-human-HGFR(R&D system, BAF527 or BAF328) @ 100 µg/mL+360 µL Beads (IGEN #10029+5.4 PL buffer-PBS/1% BSA/0.1% Tween20) by rotating for 30 min at RT. Antibody beads (25 µL) were transferred to a 96 well plate. Cell lysate solution (25 µL) was transferred added and the plate was shaken at RT for 1 h. Anti-phosphotyrosine 4G10 (Upstate 05-321) (19.7 µL antibody+6 mL 1×PBS) (12.5 µL) was added to each well, then incubated for 1 h at RT. Anti-mouse IgG ORI-Tag (ORIGEN #110087) (24 µL Antibody+6 mL buffer) (12.5 µL) was added to each well, then incubated at RT for 30 min. 1×PBS (175 µL) was added to each well and the electrochemiluminescence was read by an IGEN M8. Raw data was analyzed using a 4-parameter fit equation in XLFit. IC$_{50}$ values are then determined using Grafit software. Examples 2, 4, 6-8, 11, 13, 15-21, 23-26, 36-37, 39, 41, and 43-44 exhibited activity in PC3 cells with IC$_{50}$ values less than 1.0 µM. Examples 2, 4, 6-8, 11-13, 15-21, 23-26, 36-37, 41, and 43-44 exhibited activity in CT26 cells with IC$_{50}$ values less than 1.0 µM.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3.

The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+ 10% FBS+antibiotics to achieve a concentration of $3\times10^5$ cells/mL. Another cell count is performed to confirm the cell concentration. The cells are diluted to $3\times10^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+ 10% FBS+antibiotics (400× dilution). Medium containing 0.25% DMSO is also prepared for the 0 µM compound sample. At the 22 h timepoint, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 L/min oxygen+5% Isofluorane). An otoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A. G. Heinz, Irvine Calif.) mounted on a Nikon SMZ-U stereo microscope (A. G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 mL of sterile 1× phosphate buffered saline, gently shaken until fully dissolved, and filtered at 0.2 µM. Individual 1.0 mL samples were aliquoted into 25 single-use vials, and stored at −20° C. until use. For the rHu-bFGF disks, a vial of this 0.1% BSA solution was allowed to thaw at room temperature. Once thawed, 10 µL of a 100 mM stock solution of DTT was added to the 1 ml BSA vial to yield a final concentration of 1 mM DTT in 0.1% BSA.

rhu-VEGF Dilutions: Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out ≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Tumor Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Formulations

Also embraced within this invention is a class of pharmaceutical compositions comprising the active compounds of Formula I-II in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax; or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

What is claimed is:

1. A compound of formula I

R—X—W—Y—R$^1$    I an enantiomer, a diastereomer, a pharmaceutically acceptable salt, or a N-oxide thereof wherein R is

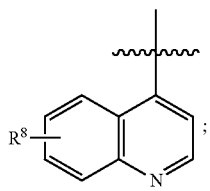

W is a substituted or unsubstituted phenyl or a substituted or unsubstituted 6-membered nitrogen-containing heteroaryl;

X is O;

Y is —NR$^a$C(=O)—(CR$^3$R$^4$)$_p$—;

R$^a$ is selected from H, alkyl, heterocyclyl, aryl, arylalkyl, heterocyclylalkyl, cycloalkyl, cycloalkylalkyl, alkenyl and alkynyl; wherein R$^a$ is optionally substituted;

R$^1$ is selected from

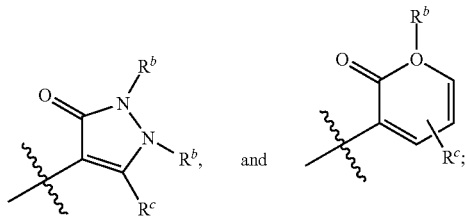

R$^b$ is independently selected at each occurrence from H, optionally substituted arylalkyl, optionally substituted 5-6-membered heterocyclyl-C$_{1-3}$ alkyl, optionally substituted C$_{1-6}$-alkyl, optionally substituted C$_{6-10}$ aryl, optionally substituted C$_{6-10}$ heteroaryl, optionally substituted 5-6 membered heterocyclyl, optionally substituted C$_{3-6}$ cycloalkyl, and R$^d$R$^{5a}$N—C$_{1-3}$alkyl;

R$^c$ is one or more substituents selected from H, methyl, isopropyl, tert-butyl, bromo, fluoro, hydroxyl, methoxymethyl, methoxyethyl, methylthiomethyl, piperidin-1-ylmethyl, pyrrolidin-1-ylmethyl, optionally substituted phenyl, optionally substituted pyridyl, optionally substituted thienyl, R$^{5a}$R$^d$N—, R$^{5a}$R$^d$N—C$_{1-3}$ alkyl and optionally substituted benzyl;

R$^d$ is selected from H, methyl, ethyl, isopropyl, butyl, sec-butyl, isobutyl, phenyl, and phenylmethyl;

R$^{5a}$ is selected from H, methyl, ethyl, isopropyl, butyl, sec-butyl, isobutyl, phenylmethyl, optionally substituted 5-6 membered heterocyclyl-C$_{1-2}$-alkyl, optionally substituted phenyl, and optionally substituted 5-6-membered heterocyclyl; C$_{6-10}$ aryl, nitrile, —C(=O)OR$^{5a}$, —C(=O)NR$^{5a}$R$^d$, —C(=O)R$^{5a}$ and optionally substituted heteroaryl;

R$^3$ and R$^4$ are each independently selected from H, alkyl, aryl, heterocyclyl, arylalkyl, heterocyclylalkyl, haloalkyl, cycloalkyl, and cycloalkylalkyl;

R$^5$ is independently selected at each occurrence from H, alkyl, haloalkyl, heterocyclylalkyl, cycloalkylalkyl, aryl, and heterocyclyl;

R$^8$ is one or more substituents independently selected at each occurrence from H, cyano, hydroxyl, halo, optionally substituted heterocyclyl, —C(=O)NR$^a$R$^5$, —OC(=O)NR$^a$R$^5$, —NR$^a$C(=O)OR$^5$, —NR$^a$C(=O)—R$^5$, R$^5$R$^a$N—O$_2$S—, R$^5$O$_2$S—, R$^5$O$_2$SR$^a$N—, R$^5$R$^a$N—, alkyl, aminoalkyl, alkylaminoalkyl, alkoxyalkyl, phenylalkyl, heterocyclylalkyl, alkoxy, haloalkoxy, alkylaminoalkoxy, arylalkoxy, heterocyclylalkoxy, cycloalkylalkoxy, heterocyclyl(hydroxyalkoxy), cycloalkyl(hydroxyalkoxy), aryl(hydroxyalkoxy), alkoxyalkoxy, aryloxyalkoxy, heterocyclyloxyalkoxy, cycloalkyloxyalkoxy, aryloxy, heterocyclyloxy, cycloalkyloxy; aryl and heteroaryl;

p is 0, 1, 2, or 3; and wherein each alkyl, aryl, heteroaryl, cycloalkyl, alkenyl, alkynyl, heterocyclyl, and alkoxy moiety of any R, R$^1$, R$^3$, R$^4$, R$^5$, R$^8$ and R$^a$ is optionally independently substituted with one or more groups independently selected at each occurrence from halo, oxo, —NR$^a$R$^5$, —(C$_1$-C$_6$)alkylamino, —NH—N=NH, (C$_1$-C$_6$)alkyl, (C$_1$-C$_6$)alkynyl, and (C$_3$-C$_6$)cycloalkyl.

2. The compound of claim 1 wherein $R^8$ is independently selected at each occurrence from H, cyano, hydroxyl, halo, alkyl, aminoalkyl, alkylaminoalkyl, alkoxyalkyl, phenylalkyl, heterocyclylalkyl, alkoxy, haloalkoxy, alkylaminoalkoxy, arylalkoxy, heterocyclylalkoxy, cycloalkylalkoxy, heterocyclyl(hydroxyalkoxy), cycloalkyl(hydroxyalkoxy), aryl(hydroxyalkoxy), alkoxyalkoxy, aryloxyalkoxy, heterocyclyloxyalkoxy, cycloalkyloxyalkoxy, aryloxy, heterocyclyloxy, cycloalkyloxy; aryl and heteroaryl, or an enantiomer, a diastereomer, a pharmaceutically acceptable salt, or a N-oxide thereof.

3. The compound of claim 2 wherein R is selected from 6,7-dimethoxy-4-quinolinyl, 7-methoxy-4 quinonlinyl, 6-methoxy-7-(dimethylaminopropoxy)-4-quinolinyl, 6-methoxy-7-(3-(morpholin-4-yl)propoxy)-4-quinolinyl, 6-methoxy-7-(3-(pyrrolidin-1-yl)propoxy)-4-quinolinyl, 6-methoxy-7-(2-hydroxy-3-(morpholin-4-yl)propoxy)-4-quinolinyl, 6-methoxy-7-(3-(1,2,4-triazol-1-yl)propoxy)-4-quinolinyl, 6-methoxy-7-(3-(4-methylpiperazin-1 -yl)propoxy)-4-quinolinyl, and 6-methoxy-7-(3-(piperidin-4-yl) propoxy)-4-quinolinyl; or an enantiomer, a diastereomer, a pharmaceutically acceptable salt, or a N-oxide thereof.

4. The compound of claim 1 wherein W is selected from substituted or unsubstituted phenyl, substituted or unsubstituted pyridyl, substituted or unsubstituted pyrimidinyl, substituted or unsubstituted pyridazinyl and substituted or unsubstituted pyrazinyl; or an enantiomer, a diastereomer, a pharmaceutically acceptable salt, or a N-oxide thereof.

5. The compound of claim 4 wherein W is substituted or unsubstituted phenyl; or an enantiomer, a diastereomer, a pharmaceutically acceptable salt, or a N-oxide thereof.

6. The compound of claim 4 wherein W is substituted or unsubstituted pyridyl; or an enantiomer, a diastereomer, a pharmaceutically acceptable salt, or a N-oxide thereof.

7. The compound according to claim 5 or 6 wherein W is substituted with one or more halogen, or an enantiomer, a diastereomer, a pharmaceutically acceptable salt, or a N-oxide thereof.

8. The compound of claim 1 wherein p is 0 or 1; or an enantiomer, a diastereomer, a pharmaceutically acceptable salt, or a N-oxide thereof.

9. The compound of claim 1 wherein Y is —NHC(=O)—; or an enantiomer, a diastereomer, a pharmaceutically acceptable salt, or a N-oxide thereof.

10. The compound of claim 1, wherein $R^b$ is selected from H, methyl, ethyl, isopropyl, butyl, sec-butyl, or isobutyl, or an enantiomer, a diastereomer, a pharmaceutically acceptable salt, or a N-oxide thereof.

11. The compound of claim 10, wherein $R^c$ is H or methyl, or an enantiomer, a diastereomer, a pharmaceutically acceptable salt, or a N-oxide thereof.

12. The compound of claim 1, wherein $R^1$ is

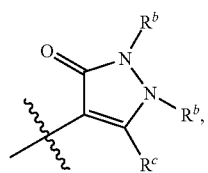

or an enantiomer, a diastereomer, a pharmaceutically acceptable salt, or a N-oxide thereof.

13. A compound selected from:
N-(4-(6,7-dimethoxyquinolin-4-yloxy)-3-fluorophenyl)-1-methyl-3-oxo-2-phenyl-5-(pyridin-4-yl)-2,3-dihydro-1H-pyrazole-4-carboxamide;
N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide;
N-(4-(6,7-dimethoxyquinolin-4-yloxy)-3-fluorophenyl)-5-((ethyl(methyl)amino)methyl)-1-methyl-3-oxo-2-phenyl-2,3-dihydro-1H-pyrazole-4-carboxamide;
N-(4-(6,7-dimethoxyquinolin-4-yloxy)-3-fluorophenyl)-5-((dimethylamino)methyl)-1-methyl-3-oxo-2-phenyl-2,3-dihydro-1H-pyrazole-4-carboxamide;
5-(aminomethyl)-N-(3-fluoro-4-(7-methoxyquinolin-4-yloxy)phenyl)-1-methyl-3-oxo-2-phenyl-2,3-dihydro-1H-pyrazole-4-carboxamide;
tert-butyl (4-((3-fluoro-4-(7-methoxyquinolin-4-yloxy) phenyl)carbamoyl)-1-methyl-3-oxo-2-phenyl-2,3-dihydro-1H-pyrazol-5-yl)methylcarbamate;
N-(5-(7-methoxyquinolin-4-yloxy)pyridin-2-yl)-1-methyl-3-oxo-2-phenyl-5-(pyrrolidin-1-ylmethyl)-2,3-dihydro-1H-pyrazole-4-carboxamide;
N-(3-fluoro-4-(7-methoxyquinolin-4-yloxy)phenyl)-1-methyl-3-oxo-2-phenyl-5-(pyrrolidin-l-ylmethyl)-2,3-dihydro-1H-pyrazole-4-carboxamide;
N-(3-fluoro-4-(7-methoxyquinolin-4-yloxy)phenyl)-5-methyl-3-oxo-2-phenyl-1-((tetrahydrofuran-2-yl)methyl)-2,3-dihydro-1H-pyrazole-4-carboxamide;
5-((ethyl(methyl)amino)methyl)-N-(3-fluoro-4-(7-methoxyquinolin-4-yloxy)phenyl)-1-methyl-3-oxo-2-phenyl-2,3-dihydro-1H-pyrazole-4-carboxamide;
2-benzyl-N-(5-(7-methoxyquinolin-4-yloxy)pyridin-2-yl)-1-methyl-3-oxo-5-(pyridin-4-yl)-2,3-dihydro-1H-pyrazole-4-carboxamide;
2-benzyl-N-(3-fluoro-4-(7-methoxyquinolin-4-yloxy) phenyl)-1-methyl-3-oxo-5-(pyridin-4-yl)-2,3-dihydro-1H-pyrazole-4-carboxamide;
(S)-N-(5-(7-methoxyquinolin-4-yloxy)pyridin-2-yl)-1-methyl-3-oxo-2-(1-phenylethyl)-5-(pyridin-4-yl)-2,3-dihydro-1H-pyrazole-4-carboxamide;
(S)-N-(3-fluoro-4-(7-methoxyquinolin-4-yloxy)phenyl)-1-methyl-3-oxo-2-(1-phenylethyl)-5-(pyridin-4-yl)-2,3-dihydro-1H-pyrazole-4-carboxamide;
N-(5-(7-methoxyquinolin-4-yloxy)pyridin-2-yl)-1-methyl-3-oxo-2-phenyl-5-(pyridin-4-yl)-2,3-dihydro-1H-pyrazole-4-carboxamide;
N-(3-fluoro-4-(7-methoxyquinolin-4-yloxy)phenyl)-1-methyl-3-oxo-2-phenyl-5-(pyridin-4-yl)-2,3-dihydro-1H-pyrazole-4-carboxamide;
N-(5-(6,7-dimethoxyquinolin-4-yloxy)pyridin-2-yl)-1-methyl-3-oxo-2-phenyl-5-(pyridin-4-yl)-2,3-dihydro-1H-pyrazole-4-carboxamide;
N-(5-(7-methoxyquinolin-4-yloxy)pyridin-2-yl)-5-methyl-3-oxo-2-phenyl-1-propyl-2,3-dihydro-1H-pyrazole-4-carboxamide;
N-(5-(7-methoxyquinolin-4-yloxy)pyridin-2-yl)-1-methyl-3-oxo-2-phenyl-5-(pyridin-3-yl)-2,3-dihydro-1H-pyrazole-4-carboxamide;
N-(5-(7-methoxyquinolin-4-yloxy)pyridin-2-yl)-1-methyl-3-oxo-2-phenyl-5-(pyridin-2-yl)-2,3-dihydro-1H-pyrazole-4-carboxamide;
N-(3-fluoro-4-(7-methoxyquinolin-4-yloxy)phenyl)-1-methyl-3-oxo-2-phenyl-5-(tetrahydro-2H-pyran-4-yl)-2,3-dihydro-1H-pyrazole-4-carboxamide;
N-(5-(7-methoxyquinolin-4-yloxy)pyridin-2-yl)-1-methyl-3-oxo-2-phenyl-5-(tetrahydro-2H-pyran-4-yl)-2,3-dihydro-1H-pyrazole-4-carboxamide;

1-Methyl-N-(5-((7-(methyloxy)-4-quinolinyl)oxy)-2-pyridinyl)-5-(2-methyl-1,3-thiazol-4-yl)-3-oxo-2-phenyl-2,3-dihydro-1H-pyrazole-4-carboxamide;

N-(5-((6,7-bis(methyloxy)-4-quinolinyl)oxy)-2-pyridinyl)-1-methyl-5-(5-methyl-3-isoxazolyl)-3-oxo-2-phenyl-2,3-dihydro-1H-pyrazole-4-carboxamide;

1-methyl-5-(5-methyl-3-isoxazolyl)-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-1-methyl-5-(5-methyl-3-isoxazolyl)-3-oxo-2-phenyl-2,3-dihydro-1H-pyrazole-4-carboxamide;

1-methyl-N-(5-((7-(methyloxy)-4-quinolinyl)oxy)-2-pyridinyl)-3-oxo-2-phenyl-5-(2-pyrazinyl)-2,3-dihydro-1H-pyrazole-4-carboxamide;

N-(3-fluoro-4-((7-(methyloxy)-4-quinolinyl)oxy)phenyl)-1-methyl-3-oxo-2-phenyl-5-(2-pyrazinyl)-2,3-dihydro-1H-pyrazole-4-carboxamide;

N-(5-((6,7-bis(methyloxy)-4-quinolinyl)oxy)-2-pyridinyl)-1-methyl-3-oxo-2-phenyl-5-(2-pyrazinyl)-2,3-dihydro-1H-pyrazole-4-carboxamide;

N-(5-((6,7-bis(methyloxy)-4-quinolinyl)oxy)-2-pyridinyl)-1-methyl-5-(2-methyl-1,3-thiazol-4-yl)-3-oxo-2-phenyl-2,3-dihydro-1H-pyrazole-4-carboxamide;

N-(3-fluoro-4-((7-(methyloxy)-4-quinolinyl)oxy)phenyl)-1-methyl-5-(2-methyl-1,3-thiazol-4-yl)-3-oxo-2-phenyl-2,3-dihydro-1H-pyrazole-4-carboxamide;

N-(4-(6,7-dimethoxyquinolin-4-yloxy)-3-fluorophenyl)-N,1,5-trimethyl-3-oxo-2-phenyl-2,3-dihydro-1H-pyrazole-4-carboxamide;

2-(3-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide;

2-(3-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide;

N-(4-(6,7-dimethoxyquinolin-4-yloxy)-3-fluorophenyl)-1,5-dimethyl-3-oxo-2-p-tolyl-2,3-dihydro-1H-pyrazole-4-carboxamide;

N-(4-(6,7-dimethoxyquinolin-4-yloxy)-3-fluorophenyl)-2-(4-fluorophenyl)-1,5-dimethyl-3-oxo-2,3-dihydro-1H-pyrazole-4-carboxamide;

N-(5-(6,7-dimethoxyquinolin-4-yloxy)pyridine-2-yl)-1,5-dimethyl-3-oxo-2-p-tolyl-2,3-dihydro-1H-pyrazole-4-carboxamide;

N-(5-(6,7-dimethoxyquinolin-4-yloxy)pyridin-2-yl)-2-(4-fluorophenyl)-1,5-dimethyl-3-oxo-2,3-dihydro-1H-pyrazole-4-carboxamide;

2-(3-chlorophenyl)-N-(5-(7-methoxyquinolin-4-yloxy)pyridin-2-yl)-1,5-dimethyl-3-oxo-2,3-dihydro-1H-pyrazole-4-carboxamide;

N-(5-(7-methoxyquinolin-4-yloxy)pyridin-2-yl)-1,5-dimethyl-3-oxo-2-p-tolyl-2,3-dihydro-1H-pyrazole-4-carboxamide;

2-(2-chlorophenyl)-N-(5-(6,7-dimethoxyquinolin-4-yloxy)pyridin-2-yl)-1,5-dimethyl-3-oxo-2,3-dihydro-1H-pyrazole-4-carboxamide;

2-(2-chlorophenyl)-N-(4-(6,7-dimethoxyquinolin-4-yloxy)-3-fluorophenyl)-1,5-dimethyl-3-oxo-2,3-dihydro-1H-pyrazole-4-carboxamide;

2-(2-chlorophenyl)-N-(3-fluoro-4-(7-methoxyquinolin-4-yloxy)phenyl)-1,5-dimethyl-3-oxo-2,3-dihydro-1H-pyrazole-4-carboxamide;

N-(3-fluoro-4-(7-methoxyquinolin-4-yloxy)phenyl)-2-(4-fluorophenyl)-1,5-dimethyl-3-oxo-2,3-dihydro-1H-pyrazole-4-carboxamide;

2-(3-chlorophenyl)-N-(3-fluoro-4-(7-methoxyquinolin-4-yloxy)phenyl)-1,5-dimethyl-3-oxo-2,3-dihydro-1H-pyrazole-4-carboxamide;

N-(6-(6,7-dimethoxyquinolin-4-yloxy)pyridin-3-yl)-1,5-dimethyl-3-oxo-2-phenyl-2,3-dihydro-1H-pyrazole-4-carboxamide;

N-(2-chloro-4-(6,7-dimethoxyquinolin-4-yloxy)phenyl)-1,5-dimethyl-3-oxo-2-phenyl-2,3-dihydro-1H-pyrazole-4-carboxamide;

2-benzyl-N-(4-(6,7-dimethoxyquinolin-4-yloxy)-3-fluorophenyl)-1,5-dimethyl-3-oxo-2,3-dihydro-1H-pyrazole-4-carboxamide;

2-benzyl-N-(5-(6,7-dimethoxyquinolin-4-yloxy)pyridin-2-yl)-1,5-dimethyl-3-oxo-2,3-dihydro-1H-pyrazole-4-carboxamide;

N-(5-(7-methoxyquinolin-4-yloxy)pyridin-2-yl)-1-methyl-3-oxo-2-phenyl-2,3-dihydro-1H-pyrazole-4-carboxamide;

N-(4-(6,7-dimethoxyquinolin-4-yloxy)-3-fluorophenyl)-1-(2-hydroxy-2-methylpropyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-3-oxo-1-(2-oxobutyl)-2-phenyl-2,3-dihydro-1H-pyrazole-4-carboxamide;

N-(3-fluoro-4-(7-methoxyquinolin-4-yloxy)phenyl)-5-methyl-1-(3-methyl-2-oxobutyl)-3-oxo-2-phenyl-2,3-dihydro-1H-pyrazole-4-carboxamide;

(R)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide;

N-(3-fluoro-4-(7-methoxyquinolin-4-yloxy)phenyl)-1-((2R,3R)-3-hydroxybutan-2-yl)-5-methyl-3-oxo-2-phenyl-2,3-dihydro-1H-pyrazole-4-carboxamide;

1-((2R,3R)-3-hydroxybutan-2-yl)-N-(5-(7-methoxyquinolin-4-yloxy)pyridin-2-yl)-5-methyl-3-oxo-2-phenyl-2,3-dihydro-1H-pyrazole-4-carboxamide;

(S)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

(R)-1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

(S)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

(R)-N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-1-((3-methyl-2-oxooxazolidin-5-yl)methyl)-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-(methylamino)propyl)-5-methyl-3-oxo-2-phenyl-2,3-dihydro-1H-pyrazole-4-carboxamide;

1-(3-chloro-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-2-methylbutyl)-5-methyl-3-oxo-2-phenyl-2,3-dihydro-1H-pyrazole-4-carboxamide;

1-(2-hydroxy-3-methylbutyl)-N-(5-(7-methoxyquinolin-4-yloxy)pyridin-2-yl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-methylbutyl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-3-morpholinopropyl)-5-methyl-3-oxo-2-phenyl-2,3-dihydro-1H-pyrazole-4-carboxamide;

N-(3-fluoro-4-(7-methoxyquinolin-4-yloxy)phenyl)-5-methyl-1-(oxazolidin-5-ylmethyl)-3-oxo-2-phenyl-2,3-dihydro-1H-pyrazole-4-carboxamide;

(S)-N-(3-fluoro-4-(7-methoxyquinolin-4-yloxy)phenyl)-1-(2-hydroxybutyl)-5-methyl-3-oxo-2-phenyl-2,3-dihydro-1H-pyrazole-4-carboxamide;

1-(3-amino-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

1-(2-hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide;

N-(3-fluoro-4-(7-methoxyquinolin-4-yloxy)phenyl)-1-(2-hydroxy-2-methylpropyl)-5-methyl-3-oxo-2-phenyl-2,3-dihydro-1H-pyrazole-4-carboxamide;

(R)-1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide;

1-(3-(dimethylamino)-2-hydroxypropyl)-N-(3-fluoro-4-(7-methoxyquinolin-4-yloxy)phenyl)-5-methyl-3-oxo-2-phenyl-2,3-dihydro-1H-pyrazole-4-carboxamide;

(R)-N-(3-fluoro-4-(7-methoxyquinolin-4-yloxy)phenyl)-1-(2-hydroxypropyl)-5-methyl-3-oxo-2-phenyl-2,3-dihydro-1H-pyrazole-4-carboxamide;

(R)-N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide;

1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide;

N-(5-(6,7-dimethoxyquinolin-4-yloxy)pyridin-2-yl)-1-(2-hydroxy-2-methylpropyl)-5-methyl-3-oxo-2-phenyl-2,3-dihydro-1H-pyrazole-4-carboxamide;

(R)-2-(3-chlorophenyl)-N-(3-fluoro-4-(7-methoxyquinolin-4-yloxy)phenyl)-1-(2-hydroxypropyl)-5-methyl-3-oxo-2,3-dihydro-1H-pyrazole-4-carboxamide;

(R)-2-(3-chlorophenyl)-1-(2-hydroxypropyl)-N-(5-(7-methoxyquinolin-4-yloxy)pyridin-2-yl)-5-methyl-3-oxo-2,3-dihydro-1H-pyrazole-4-carboxamide;

(R)-N-(3-fluoro-4-(7-methoxyquinolin-4-yloxy)phenyl)-2-(4-fluorophenyl)-1-(2-hydroxypropyl)-5-methyl-3-oxo-2,3-dihydro-1H-pyrazole-4-carboxamide;

1-(2-hydroxy-2-methylpropyl)-N-(5-(1-oxo-7-methoxyquinolin-4-yloxy)pyridin-2-yl)-5-methyl-3-oxo-2-phenyl-2,3-dihydro-1H-pyrazole-4-carboxamide;

N-(3-Fluoro-4-(7-hydroxyquinolin-4-yloxy)phenyl)-1-(2-hydroxy-2-methylpropyl)-5-methyl-3-oxo-2-phenyl-2,3-dihydro-1H-pyrazole-4-carboxamide;

1-(2-hydroxy-2-methylpropyl)-N-(5-(7-hydroxyquinolin-4-yloxy)pyridin-2-yl)-5-methyl-3-oxo-2-phenyl-2,3-dihydro-1H-pyrazole-4-carboxamide;

N-(4-(6-Ethyl-7-methoxyquinolin-4-yloxy)-3-fluorophenyl)-1,5-dimethyl-3-oxo-2-phenyl-2,3-dihydro-1H-pyrazole-4-carboxamide;

N-(3-Fluoro-4-(7-methoxyquinolin-4-yloxy)phenyl)-1,5-dimethyl-3-oxo-2-phenyl-2,3-dihydro-1H-pyrazole-4-carboxamide;

N-(3-fluoro-4-(7-Methoxyquinolin-4-yloxy)phenyl)-1,2-dimethyl-3-oxo-5-phenyl-2,3-dihydro-1H-pyrazole-4-carboxamide;

N-(5-(7-Methoxyquinolin-4-yloxy)pyridin-2-yl)-1,2-dimethyl-3-oxo-5-phenyl-2,3-dihydro-1H-pyrazole-4-carboxamide;

N-(4-(6,7-Dimethoxyquinolin-4-yloxy)-3-fluorophenyl)-1,2-dimethyl-3-oxo-5-phenyl-2,3-dihydro-1H-pyrazole-4-carboxamide;

N-(5-(7-Methoxyquinolin-4-yloxy)pyridin-2-yl)-1,5-dimethyl-3-oxo-2-phenyl-2,3-dihydro-1H-pyrazole-4-carboxamide;

(R)-1-(2-Hydroxypropyl)-N-(5-(7-methoxyquinolin-4-yloxy)pyridin-2-yl)-2-methyl-3-oxo-5-phenyl-2,3-dihydro-1H-pyrazole-4-carboxamide;

(R)-N-(3-Fluoro-4-(7-methoxyquinolin-4-yloxy)phenyl)-1-(2-hydroxypropyl)-2-methyl-3-oxo-5-phenyl-2,3-dihydro-1H-pyrazole-4-carboxamide (S)-N-(3-fluoro-4-(6-methoxyquinolin-4-yloxy)phenyl)-1-(2-hydroxypropyl)-5-methyl-3-oxo-2-phenyl-2,3-dihydro-1H-pyrazole-4-carboxamide;

1-(2-aminoethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide 1-(2-(1,3-dioxo-1,3-dihydro-2H-isoindol-2-yl)ethyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-(2-aminoethyl)-N-(3-fluoro-4((7-(methyloxy)-4-quinolinyl)oxy)phenyl)-5-methyl-3-oxo-2-phenyl-2,3-dihydro-1H-pyrazole-4-carboxamide;

5-methyl-N-(5-((7-(methyloxy)-4-quinolinyl)oxy)-2-pyridinyl)-3-oxo-2-phenyl-1-(phenylmethyl)-2,3-dihydro-1H-pyrazole-4-carboxamide 1-benzyl-N-(3-fluoro-4-(7-methoxyquinolin-4-yloxy)phenyl)-5-methyl-3-oxo-2-phenyl-2,3-dihydro-1H-pyrazole-4-carboxamide;

5-methyl-1-(2-(methyloxy)ethyl)-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-5-methyl-1-(2-(methyloxy)ethyl)-3-oxo-2-phenyl-2,3-dihydro-1H-pyrazole-4-carboxamide;

1-(2-hydroxyethyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

1-((2R)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

(S)-1-(2-(dimethylamino)propyl)-N-(3-fluoro-4-(7-methoxyquinolin-4-yloxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-3-oxo-2-phenyl-1-(2-(1-pyrrolidinyl)ethyl)-2,3-dihydro-1H-pyrazole-4-carboxamide;

1-((2S)-2-fluoropropyl)-5-methyl-N-(5-((7-(methyloxy)-4-quinolinyl)oxy)-2-pyridinyl)-3-oxo-2-phenyl-2,3-dihydro-1H-pyrazole-4-carboxamide;

N-(3-fluoro-4-((7-(methyloxy)-4-quinolinyl)oxy)phenyl)-1-((2S)-2-fluoropropyl)-5-methyl-3-oxo-2-phenyl-2,3-dihydro-1H-pyrazole-4-carboxamide;

1-((2S)-2-(acetylamino)propyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-((2S)-2-aminopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

1-((2S)-2-azidopropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-1-(2-hydroxyethyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-3-oxo-2-phenyl-1-propyl-2,3-dihydro-1H-pyrazole-4-carboxamide;

N-(4-((6,7-bis(methyloxy)-4-quinolinyl)oxy)-3-fluorophenyl)-1-((2R)-2-hydroxypropyl)-5-methyl-3-oxo-2-phenyl-2,3-dihydro-1H-pyrazole-4-carboxamide;

N-(4-((6,7-bis(methyloxy)-4-quinolinyl)oxy)-3-fluorophenyl)-1-((2 S)-2-hydroxypropyl)-5-methyl-3-oxo-2-phenyl-2,3-dihydro-1H-pyrazole-4-carboxamide;

5-methyl-N-(5-((7-(methyloxy)-4-quinolinyl)oxy)-2-pyridinyl)-1-(2-methylpropyl)-3-oxo-2-phenyl-2,3-dihydro-1H-pyrazole-4-carboxamide;

5-methyl-N-(5-((7-(methyloxy)-4-quinolinyl)oxy)-2-pyridinyl)-3-oxo-2-phenyl-1-propyl-2,3-dihydro-1H-pyrazole-4-carboxamide;

N-(3-fluoro-4-((7-(methyloxy)-4-quinolinyl)oxy)phenyl)-5-methyl-3-oxo-1-(2-oxopropyl)-2-phenyl-2,3-dihydro-1H-pyrazole-4-carboxamide;

1-(2,3-dihydroxy-2-methylpropyl)-N-(3-fluoro-4-((7-(methyloxy)-4-quinolinyl)oxy)phenyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-1-(2-hydroxypropyl)-5-methyl-3-oxo-2-phenyl-2,3-dihydro-1H-pyrazole-4-carboxamide;

N-(3-fluoro-4-((7-(methyloxy)-4-quinolinyl)oxy)phenyl)-5-methyl-1-(2-methyl-2-propen-1-yl)-3-oxo-2-phenyl-2,3-dihydro-1H-pyrazole-4-carboxamide;

N-(4-((6,7-bis(methyloxy)-4-quinolinyl)oxy)-3-fluorophenyl)-1-((2S)-2-hydroxypropyl)-5-methyl-3-oxo-2-phenyl-2,3-dihydro-1H-pyrazole-4-carboxamide;

N-(4-4-((6,7-bis(methyloxy)-4-quinolinyl)oxy)-3-fluorophenyl)-5-methyl-3-oxo-1-(2-oxopropyl)-2-phenyl-2,3-dihydro-1H-pyrazole-4-carboxamide;

N-(4-((6,7-bis(methyloxy)-4-quinolinyl)oxy)-3-fluorophenyl)-1-(2,3-dihydroxy-2-methylpropyl)-5-methyl-3-oxo-2-phenyl-2,3-dihydro-1H-pyrazole-4-carboxamide;

N-(4-((6,7-bis(methyloxy)-4-quinolinyl)oxy)-3-fluorophenyl)-5-methyl-1-(2-methyl-2-propen-1-yl)-3-oxo-2-phenyl-2,3-dihydro-1H-pyrazole-4-carboxamide;

N-(5-((6,7-bis(methyloxy)-4-quinolinyl)oxy)-2-pyridinyl)-5-methyl-3-oxo-2-phenyl-1-propyl-2,3-dihydro-1H-pyrazole-4-carboxamide;

N-(4-((6,7-bis(methyloxy)-4-quinolinyl)oxy)-3-fluorophenyl)-5-methyl-3-oxo-2-phenyl-2,3-dihydro-1H-pyrazole-4-carboxamide;

N-(5-((6,7-bis(methyloxy)-4-quinolinyl)oxy)-2-pyridinyl)-5-methyl-3-oxo-2-phenyl-1-(2-propen-1-yl)-2,3-dihydro-1H-pyrazole-4-carboxamide;

N-(4-((6,7-bis(methyloxy)-1-oxido-4-quinolinyl)oxy)-3-fluorophenyl)-5-methyl-3-oxo-2-phenyl-1-(2-propen-1-yl)-2,3-dihydro-1H-pyrazole-4-carboxamide;

N-(4-((6,7-bis(methyloxy)-4-quinolinyl)oxy)-3-fluorophenyl)-5-methyl-3-oxo-2-phenyl-1-(phenylmethyl)-2,3-dihydro-1H-pyrazole-4-carboxamide;

4-(6,7-Dimethoxyquinolin-4-yloxy)-3-fluoro-N-(5-oxo-1-phenyl-2,5-dihydro-1H-pyrazol-3-yl)benzamide;

4-(6,7-Dimethoxyquinolin-4-yloxy)-N-((1,2-dimethyl-5-oxo-3-phenyl-2,5-dihydro-1H-pyrazol-4-yl)methyl)-3-fluorobenzamide;

4-(6,7-Dimethoxyquinolin-4-yloxy)-N-(2,3-dimethyl-5-oxo-1-phenyl-2,5-dihydro-1H-pyrazol-4-yl)-3-fluorobenzamide;

4-(6,7-Dimethoxyquinolin-4-yloxy)-N-((2,3-dimethyl-5-oxo-1-phenyl-2,5-dihydro-1H-pyrazol-4-yl)methyl)-3-fluorobenzamide;

1-Benzyl-N-(5-(7-methoxyquinolin-4-yloxy)pyridin-2-yl)-2-oxo-1 ,2-dihydropyrazolo[1,5-a]pyridine-3-carboxamide;

1,5-dimethyl-N-(5-((7-(methyloxy)-4-quinolinyl)oxy)-2-pyrimidinyl)-3-oxo-2-phenyl-2,3-dihydro-1H-pyrazole-4-carboxamide;

5-methyl-N-(5-((7-(methyloxy)-4-quinolinyl)oxy)-2-pyrimidinyl)-3-oxo-2-phenyl-1-propyl-2,3-dihydro-1H-pyrazole-4-carboxamide;

N-(3-fluoro-4-((7-(methyloxy)-4-quinolinyl)amino)phenyl)-1-(2-hydroxy-2-methylpropyl)-5-methyl-3-oxo-2-phenyl-2,3-dihydro-1H-pyrazole-4-carboxamide;

N-(4-(6,7-dimethoxyquinolin-4-yloxy)-3-fluorophenyl)-3-hydroxy-2-(1-oxoisoindolin-2-yl)propanamide;

N-(4-(6,7-dimethoxyquinolin-4-yloxy)-3-fluorophenyl)-2-(1-oxoisoindolin-2-yl)acetamide;

N-(4-(6,7-dimethoxyquinolin-4-yloxy)-3-fluorophenyl)-2-oxo-1,5-diphenyl-1,2-dihydropyridine-3-carboxamide;

N-(5-((6,7-bis(methyloxy)-4-quinolinyl)oxy)-2-pyridinyl)-6-oxo-1-(phenylmethyl)-1,1',2',3',6,6'-hexahydro-3,4'-bipyridine-5-carboxamide;

N-(5-((6,7-bis(methyloxy)-4-quinolinyl)oxy)-2-pyridinyl)-6-oxo-1-(phenylmethyl)-1,6-dihydro-3,3'-bipyridine-5-carboxamide;

N-(5-((6,7-bis(methyloxy)-4-quinolinyl)oxy)-2-pyridinyl)-6'-oxo-1'-(phenylmethyl)-1',6'-dihydro-2,3'-bipyridine-5'-carboxamide;

N-(5-((6,7-bis(methyloxy)-4-quinolinyl)oxy)-2-pyridinyl)-2-oxo-1-(phenylmethyl)-5-(2-thienyl)-1,2-dihydro-3-pyridinecarboxamide;

N-(5-((6,7-bis(methyloxy)-4-quinolinyl)oxy)-2-pyridinyl)-2-oxo-1-(phenylmethyl)-5-(2-pyrazinyl)-1,2-dihydro-3-pyridinecarboxamide;

N-(5-((6,7-bis(methyloxy)-4-quinolinyl)oxy)-2-pyridinyl)-5-methyl-2-oxo-1-(phenylmethyl)-1,2-dihydro-3-pyridinecarboxamide;

N-(4-((6,7-bis(methyloxy)-4-quinolinyl)oxy)-3-fluorophenyl)-5-bromo-1-(3-methylphenyl)-2-oxo-1,2-dihydro-3-pyridinecarboxamide;

N-(4-((6,7-bis(methyloxy)-4-quinolinyl)oxy)-3-fluorophenyl)-5-(1-methyl-1H-pyrazol-4-yl)-2-oxo-1-phenyl-1,2-dihydro-3-pyridinecarboxamide;

N-(3-fluoro-4-((6-(methyloxy)-7-((3-(4-morpholinyl)propyl)oxy)-4-quinolinyl)oxy)phenyl)-2-oxo-5-phenyl-1-(phenylmethyl)-1,2-dihydro-3-pyridinecarboxamide;

1,1-dimethylethyl 5-(((5((6,7-bis(methyloxy)-4-quinolinyl)oxy)-2-pyridinyl)amino)carbonyl)-6-oxo-1-(phenylmethyl)-1,3',6,6'-tetrahydro-3,4'-bipyridine-1'(2'H)-carboxylate;

N-(4-((6,7-bis(methyloxy)-4-quinolinyl)oxy)-3-fluorophenyl)-2-oxo-1-(phenylmethyl)-5-(2-pyrimidinyl)-1,2-dihydro-3-pyridinecarboxamide;

N-(4-((6,7-bis(methyloxy)-4-quinolinyl)oxy)-3-fluorophenyl)-2-oxo-1-phenyl-5-(1H-pyrazol-4-yl)-1,2-dihydro-3-pyridinecarboxamide;

1-benzyl-5-bromo-N-(2-chloro-4-(6,7-dimethoxyquinolin-4-yloxy)phenyl)-2-oxo-1,2-dihydropyridine-3-carboxamide;

N-(5-(7-methoxyquinolin-4-yloxy)pyridin-2-yl)-2-oxo-1-phenyl-5-(pyridin-3-yl)-1,2-dihydropyridine-3-carboxamide;

N-(5-(7-methoxyquinolin-4-yloxy)pyridin-2-yl)-2-oxo-1-phenyl-5-(pyrazin-2-yl)-1,2-dihydropyridine-3-carboxamide;
N-(5-(6,7-dimethoxyquinolin-4-yloxy)pyridin-2-yl)-2-oxo-1-phenyl-5-(pyridin-3-yl)-1,2-dihydropyridine-3-carboxamide;
N-(5-(6,7-dimethoxyquinolin-4-yloxy)pyridin-2-yl)-2-oxo-1-phenyl-5-(pyrazin-2-yl)-1,2-dihydropyridine-3-carboxamide;
N-(5-(6,7-dimethoxyquinolin-4-yloxy)pyridin-2-yl)-2-oxo-1-phenyl-5-(thiophen-2-yl)-1,2-dihydropyridine-3-carboxamide;
5-benzyl-N-(5-(6,7-dimethoxyquinolin-4-yloxy)pyridin-2-yl)-2-oxo-1-phenyl-1,2-dihydropyridine-3-carboxamide;
tert-butyl 4-(5-((5-(6,7-dimethoxyquinolin-4-yloxy)pyridin-2-yl)carbamoyl)-6-oxo-1-phenyl-1,6-dihydropyridin-3-yl)-5,6-dihydropyridine-1(2H)-carboxylate;
5-bromo-N-(2-chloro-4-(6,7-dimethoxyquinolin-4-yloxy)phenyl)-2-oxo-1-phenyl-1,2-dihydropyridine-3-carboxamide;
N-(5-(6,7-dimethoxyquinolin-4-yloxy)pyridin-2-yl)-4-(2-methoxyethylamino)-2-oxo-1-phenyl-1,2-dihydropyridine-3-carboxamide;
N-(5-(6,7-dimethoxyquinolin-4-yloxy)pyridin-2-yl)-2-oxo-1-phenyl-4-(tetrahydro-2H-pyran-4-ylamino)-1,2-dihydropyridine-3-carboxamide;
N-(5-(6,7-dimethoxyquinolin-4-yloxy)pyridin-2-yl)-2-oxo-1-phenyl-4-(phenylamino)-1,2-dihydropyridine-3-carboxamide;
N-(5-(6,7-dimethoxyquinolin-4-yloxy)pyridin-2-yl)-4-(4-methylpiperazin-1-yl)-2-oxo-1-phenyl-1,2-dihydropyridine-3-carboxamide;
N-(5-(6,7-dimethoxyquinolin-4-yloxy)pyridin-2-yl)-4-(methylamino)-2-oxo-1-phenyl-1,2-dihydropyridine-3-carboxamide;
N-(5-(6,7-dimethoxyquinolin-4-yloxy)pyridin-2-yl)-4-(dimethylamino)-2-oxo-1-phenyl-1,2-dihydropyridine-3-carboxamide;
4-(2-methoxyethylamino)-N-(5-(7-methoxyquinolin-4-yloxy)pyridin-2-yl)-2-oxo-1-phenyl-1,2-dihydropyridine-3-carboxamide;
N-(3-fluoro-4-(7-methoxyquinolin-4-yloxy)phenyl)-4-(2-methoxyethylamino)-2-oxo-1-phenyl-1,2-dihydropyridine-3-carboxamide;
N-(4-((6,7-bis(methyloxy)-4-quinolinyl)oxy)-3-fluorophenyl)-1-cyclopentyl-6-oxo-5-(2-oxo-1-pyrrolidinyl)-1,6-dihydro-3-pyridinecarboxamide;
1-benzyl-N-(5-(6,7-dimethoxyquinolin-4-yloxy)pyridin-2-yl)-4-(2-methoxyethylamino)-2-oxo-1,2-dihydropyridine-3-carboxamide;
1-benzyl-N-(5-(6,7-dimethoxyquinolin-4-yloxy)pyridin-2-yl)-4-(dimethylamino)-2-oxo-1,2-dihydropyridine-3-carboxamide;
1-benzyl-N-(5-(6,7-dimethoxyquinolin-4-yloxy)pyridin-2-yl)-4-(methylamino)-2-oxo-1,2-dihydropyridine-3-carboxamide;
1-benzyl-N-(5-(6,7-dimethoxyquinolin-4-yloxy)pyridin-2-yl)-2-oxo-4-(phenylamino)-1,2-dihydropyridine-3-carboxamide;
1-benzyl-N-(5-(6,7-dimethoxyquinolin-4-yloxy)pyridin-2-yl)-2-oxo-4-(pyridin-4-ylamino)-1,2-dihydropyridine-3-carboxamide;
1-benzyl-N-(5-(6,7-dimethoxyquinolin-4-yloxy)pyridin-2-yl)-4-(4-methylpiperazin-1-yl)-2-oxo-1,2-dihydropyridine-3-carboxamide;
1-benzyl-N-(5-(6,7-dimethoxyquinolin-4-yloxy)pyridin-2-yl)-2-oxo-4-(tetrahydro-2H-pyran-4-ylamino)-1,2-dihydropyridine-3-carboxamide;
1-benzyl-N-(5-(6,7-dimethoxyquinolin-4-yloxy)pyridin-2-yl)-2-oxo-4-(4-(trifluoromethyl)phenylamino)-1,2-dihydropyridine-3-carboxamide;
1-cyclopentyl-N-(4-(6,7-dimethoxyquinolin-4-yloxy)-3-fluorophenyl)-6-oxo-5-(2-oxopyrrolidin-1-yl)-1,6-dihydropyridine-3-carboxamide;
N-(3-fluoro-4-(2-(pyrrolidine-1-carboxamido)pyridin-4-yloxy)phenyl)-3-oxo-2-phenyl-2,3-dihydropyridazine-4-carboxamide;
6-((diethylamino)methyl)-N-(4-(6,7-dimethoxyquinolin-4-yloxy)-3-fluorophenyl)-3-oxo-2-phenyl-2,3-dihydropyridazine-4-carboxamide;
N-(5-(7-methoxyquinolin-4-yloxy)pyridin-2-yl)-1-methyl-3-oxo-2-phenyl-2,3-dihydro-1H-pyrazole-4-carboxamide;

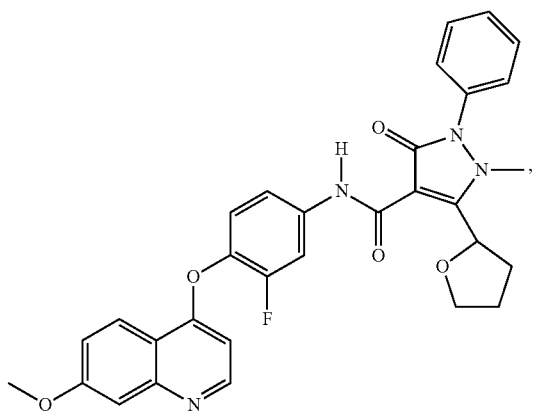

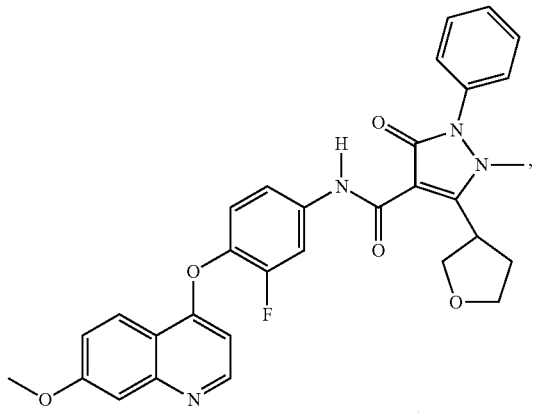

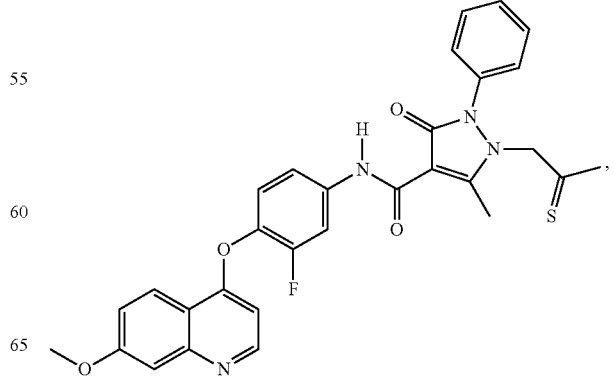

265
-continued
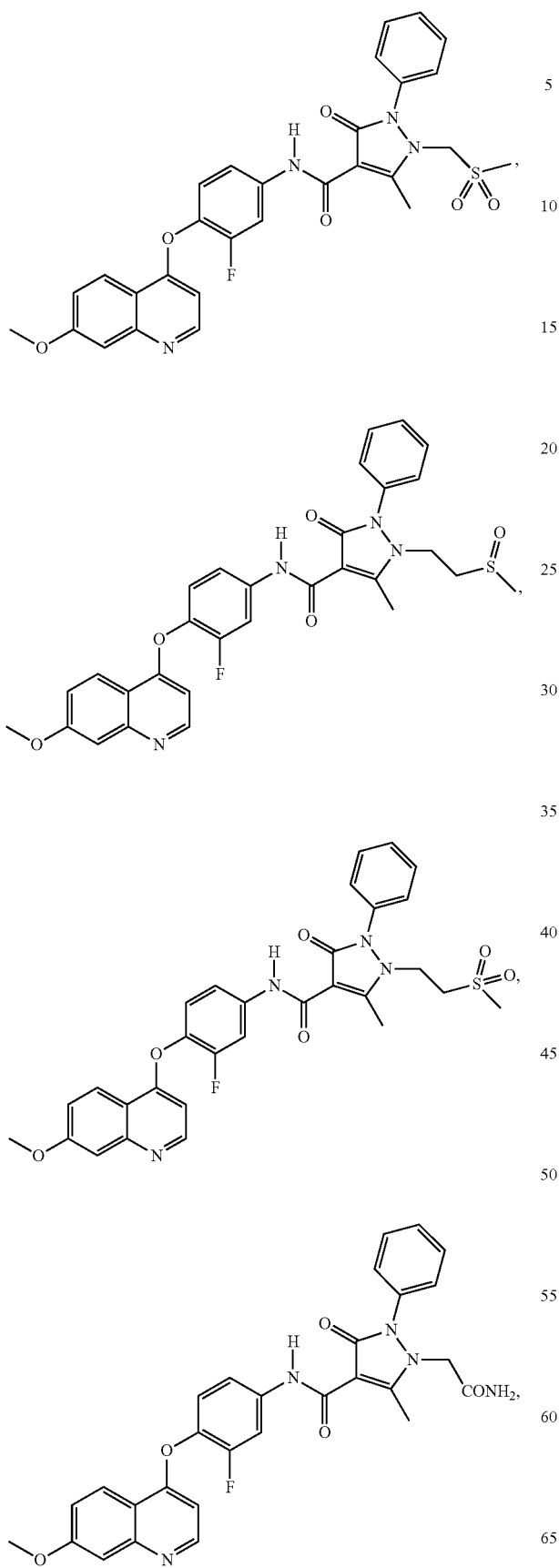
266
-continued
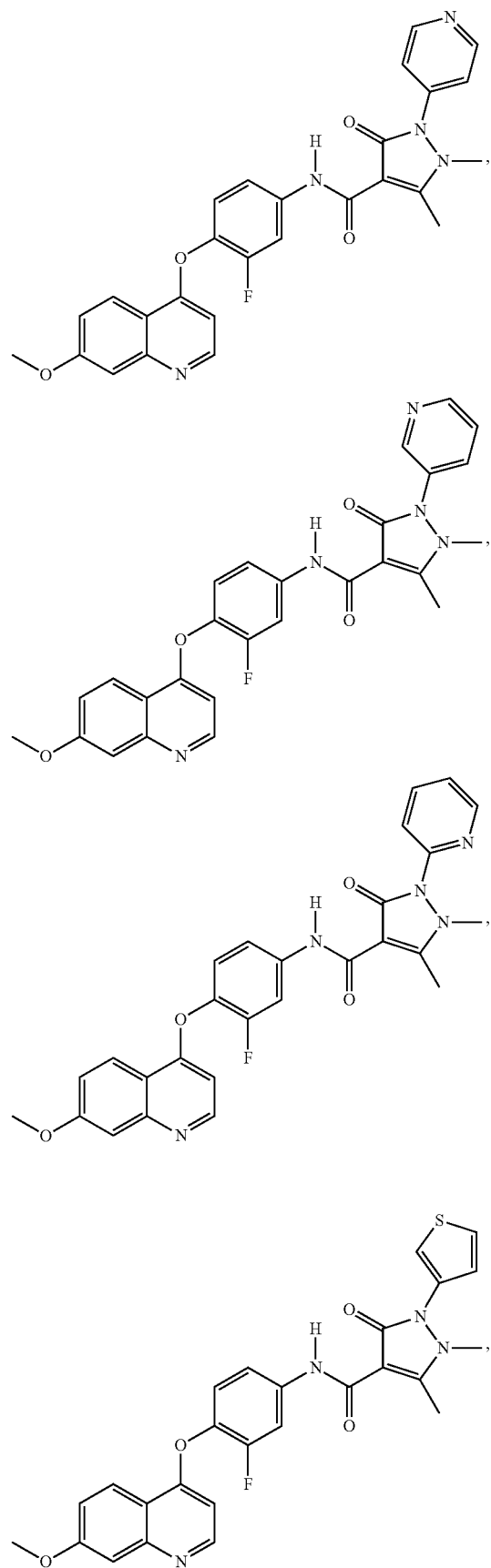

267
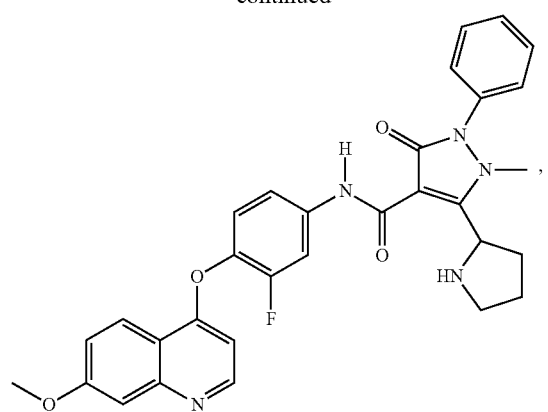
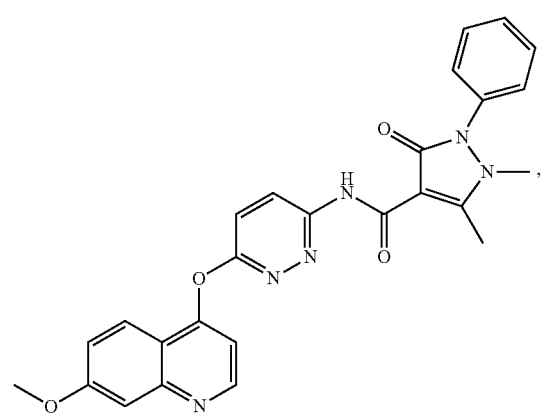
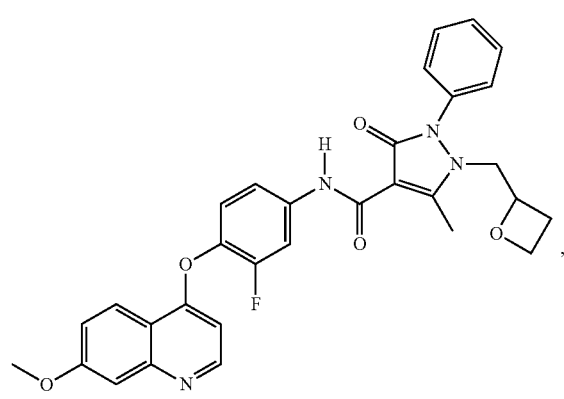
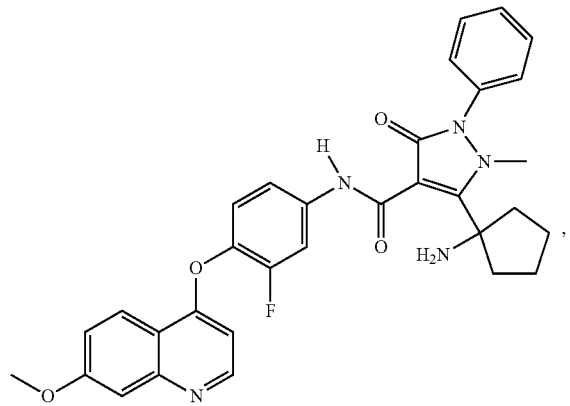
268
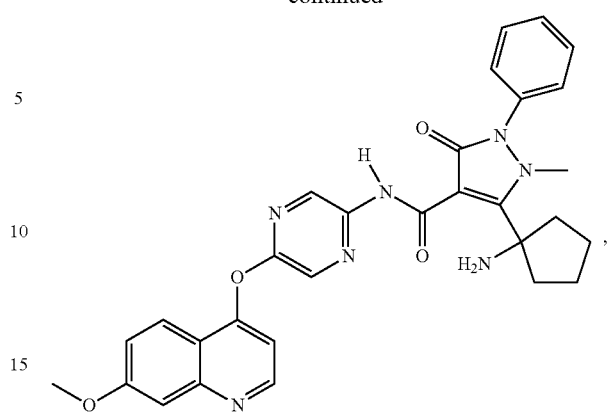
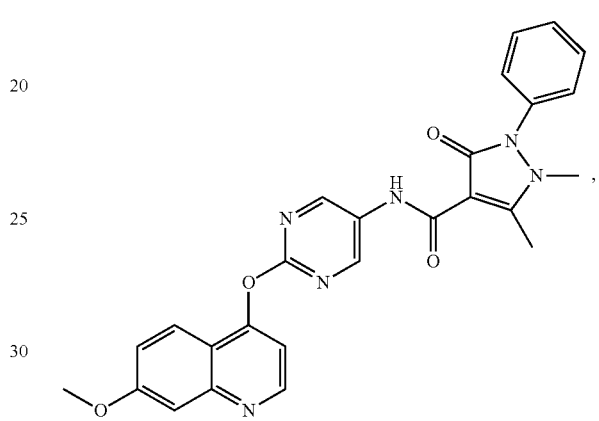
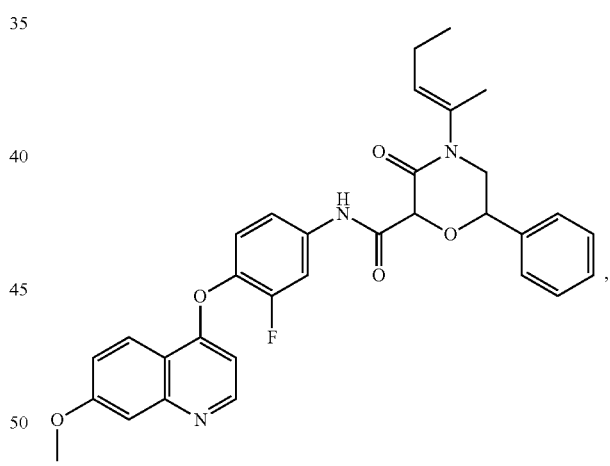
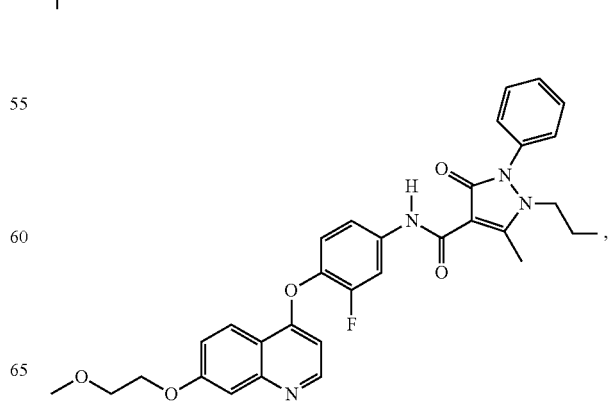

269
-continued
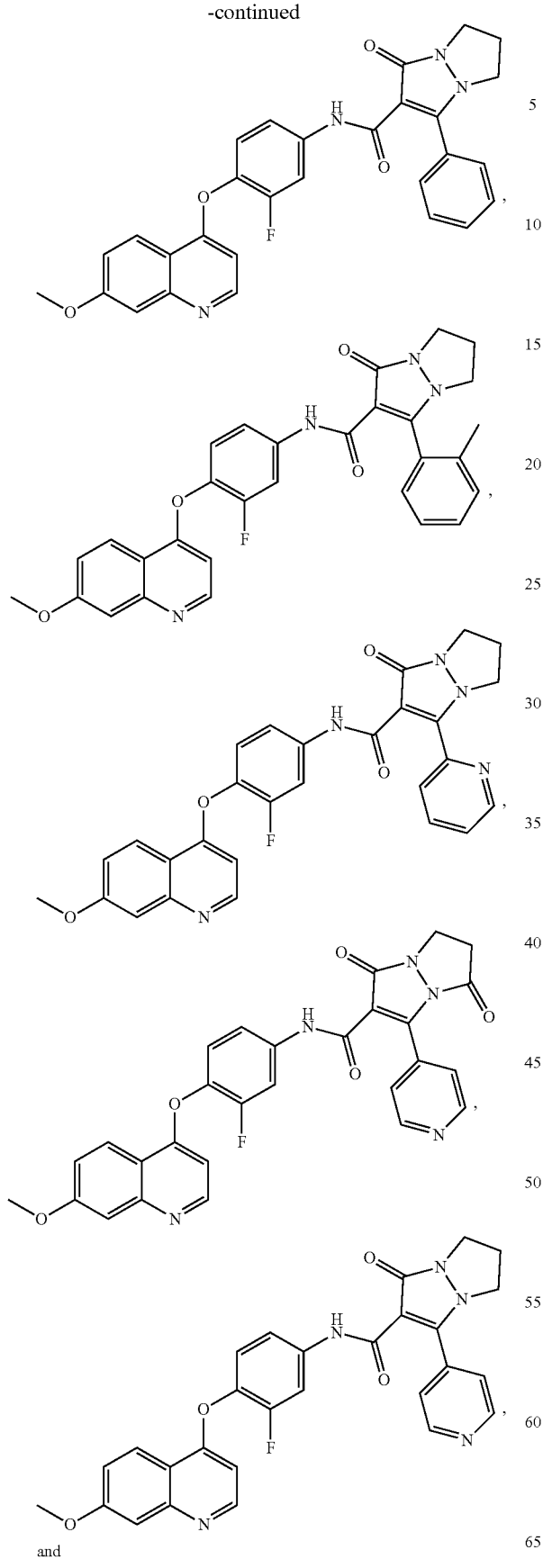
270
-continued
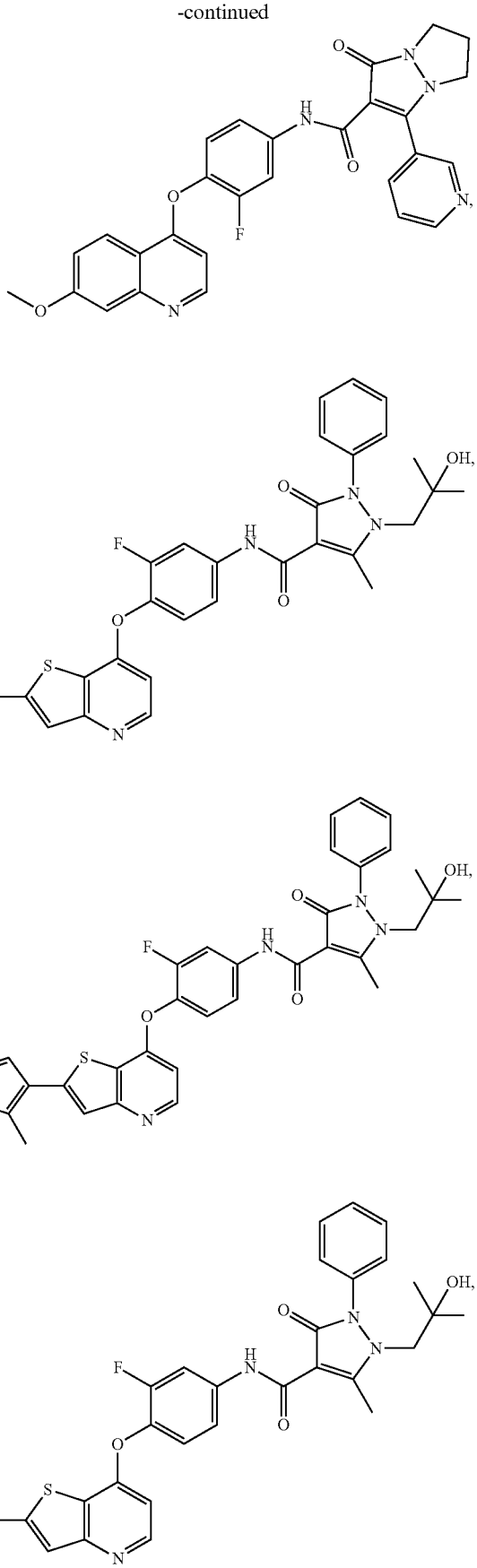
and

271
-continued
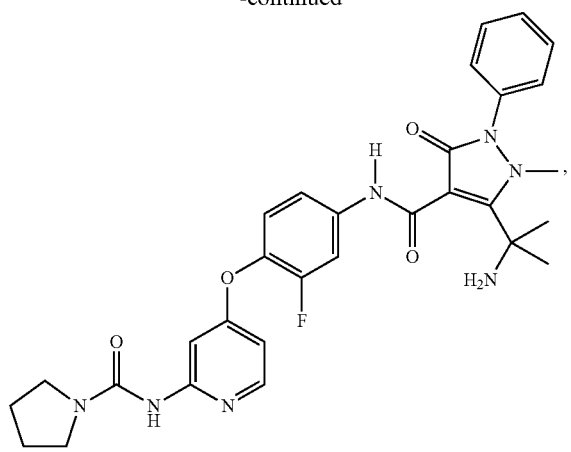
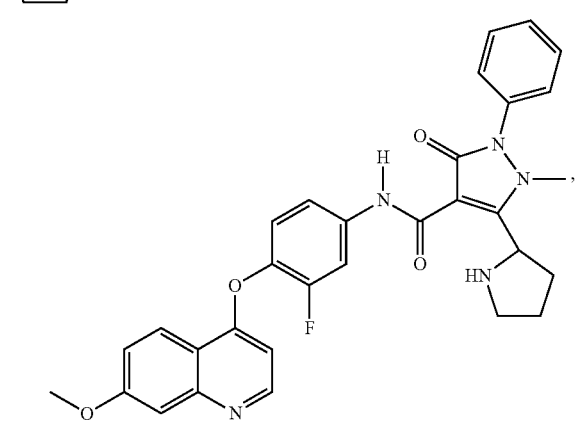
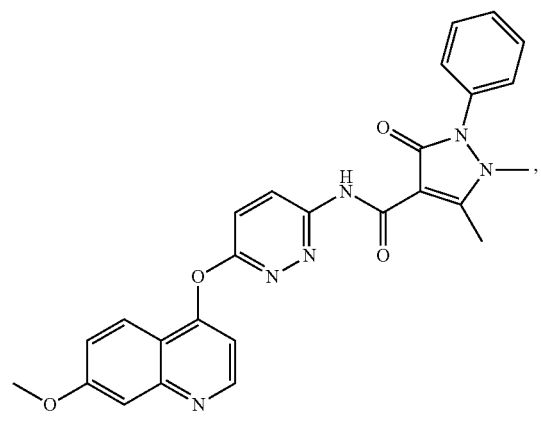
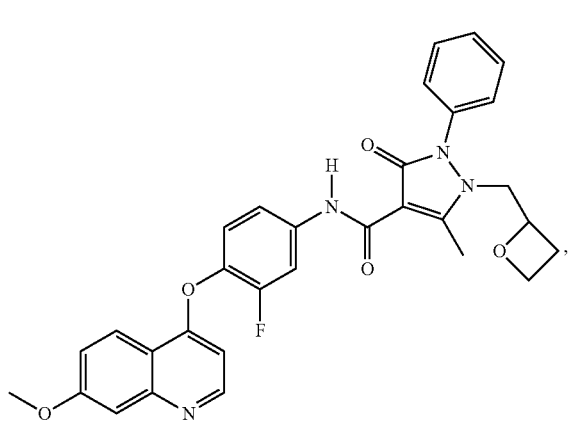
272
-continued
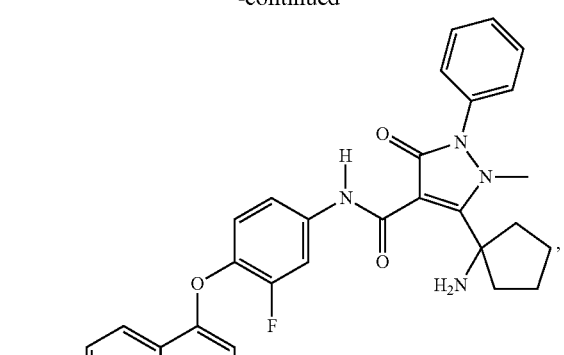
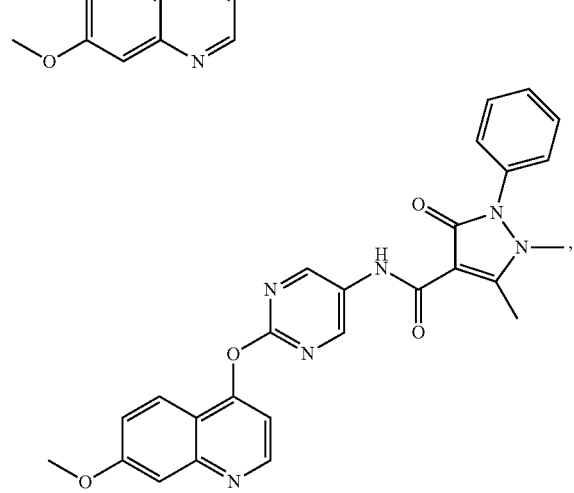
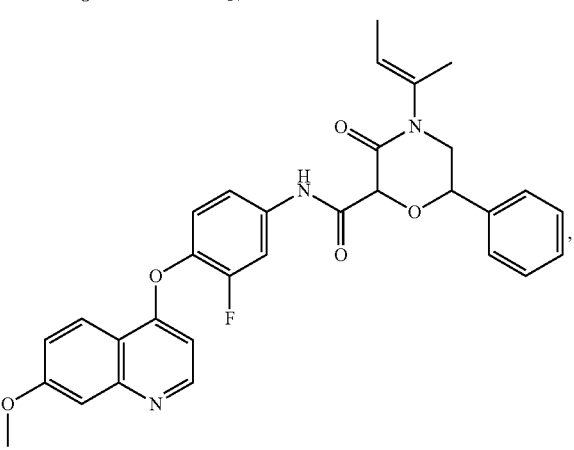
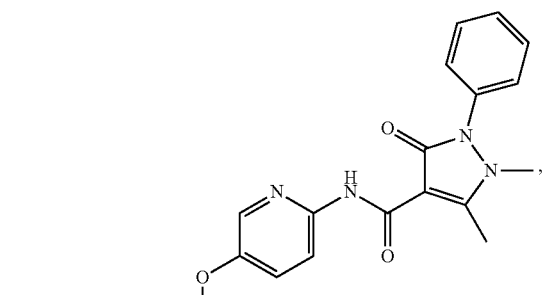

273
-continued
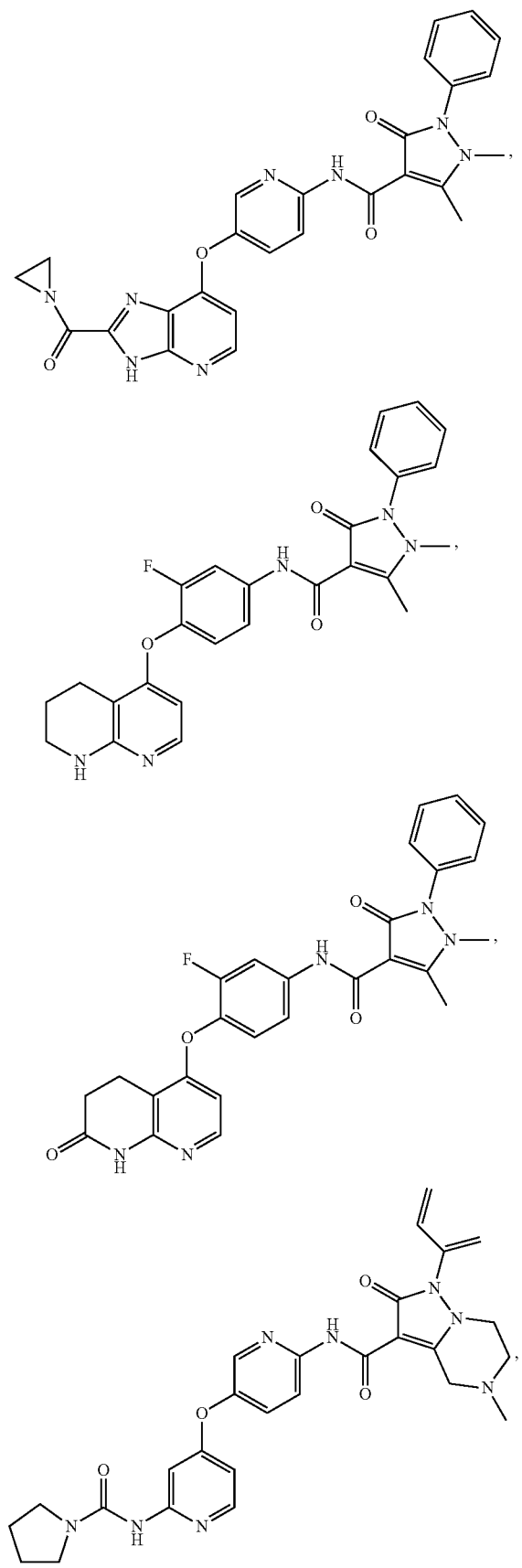
274
-continued
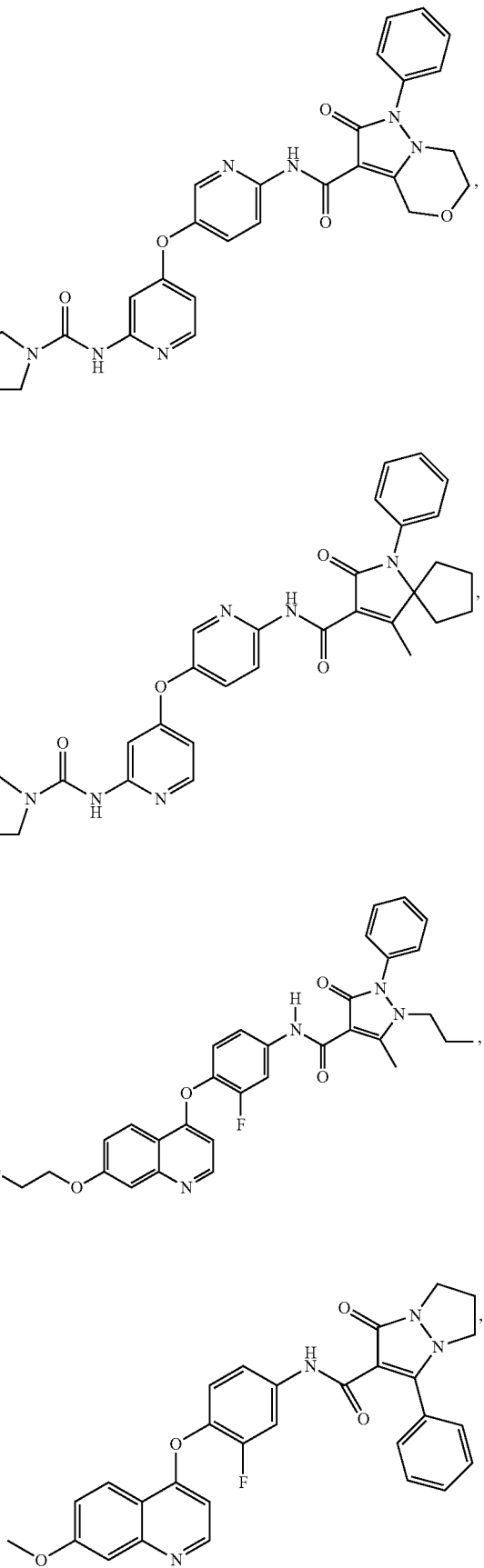

275
-continued
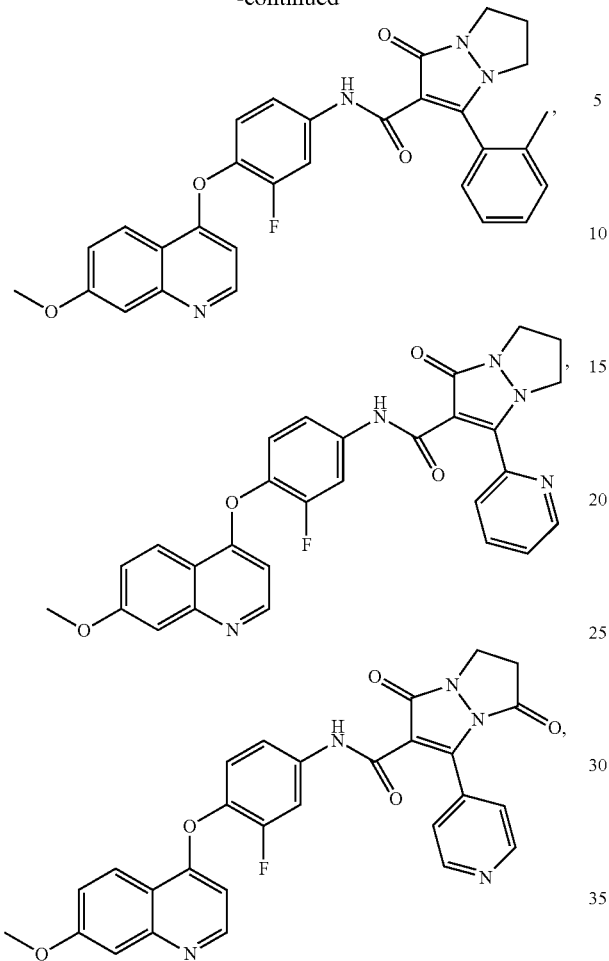
276
-continued
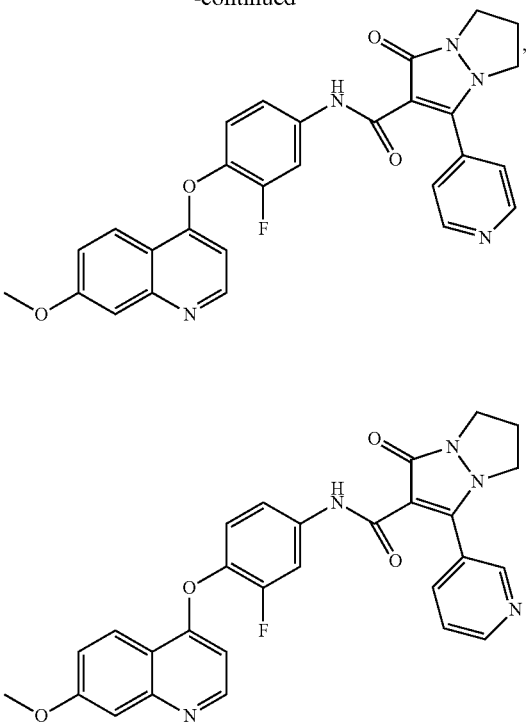
or an enantiomer, a diastereomer, a pharmaceutically acceptable salt, or a N-oxide thereof.
14. A pharmaceutical composition comprising a pharmaceutically-acceptable carrier and a compound according to claim 1 or 13, or a pharmaceutically acceptable salt thereof.
* * * * *